United States Patent
Tsukagoshi et al.

(10) Patent No.: US 7,781,483 B2
(45) Date of Patent: Aug. 24, 2010

(54) BENZOPYRAN COMPOUND

(75) Inventors: Toru Tsukagoshi, Funabashi (JP); Takayuki Nagatsuka, Funabashi (JP); Tomoyuki Matsuda, Minamisaitama-gun (JP); Norio Hashimoto, Minamisaitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 560 days.

(21) Appl. No.: 10/590,207

(22) PCT Filed: Feb. 25, 2005

(86) PCT No.: PCT/JP2005/003690

§ 371 (c)(1), (2), (4) Date: Oct. 26, 2006

(87) PCT Pub. No.: WO2005/080368

PCT Pub. Date: Sep. 1, 2005

(65) Prior Publication Data

US 2007/0299130 A1    Dec. 27, 2007

(30) Foreign Application Priority Data

Feb. 25, 2004   (JP) ............... 2004-048842

(51) Int. Cl.
  *A61K 31/353* (2006.01)
  *C07D 311/68* (2006.01)
  *C07D 311/70* (2006.01)

(52) U.S. Cl. ............ 514/456; 549/399; 549/404

(58) Field of Classification Search ......... 549/399, 549/404; 514/456
See application file for complete search history.

(56) References Cited

U.S. PATENT DOCUMENTS

| 4,481,214 A | 11/1984 | Evans |
| 4,568,692 A | 2/1986 | Evans |
| 6,066,631 A | 5/2000 | Tanikawa et al. |

FOREIGN PATENT DOCUMENTS

| EP | 0 095 316 A | 11/1983 |
| JP | A 58-067683 | 4/1983 |
| JP | A-09-235227 | 9/1997 |
| KR | 2000-0023843 | 4/2005 |
| WO | WO 99/62867 | 12/1999 |
| WO | WO 00/12492 | 3/2000 |
| WO | WO 00/58300 | 10/2000 |
| WO | WO 01/21609 A1 | 3/2001 |
| WO | WO 01/21610 A1 | 3/2001 |
| WO | WO 01/25224 A1 | 4/2001 |
| WO | WO 02/064581 A1 | 8/2002 |
| WO | WO 03/000675 A1 | 1/2003 |
| WO | WO 03/014113 A1 | 2/2003 |

*Primary Examiner*—Bernard Dentz
(74) *Attorney, Agent, or Firm*—Oliff & Berridge, PLC

(57) ABSTRACT

This invention relates to benzopyran compounds of formula (I)

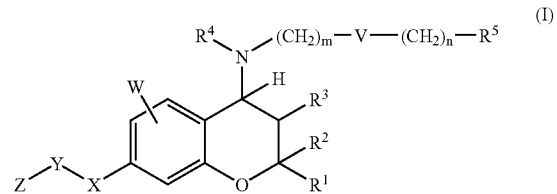

wherein X is $NR^6$, Y is a bond, SO or $SO_2$, Z is $C_{1-4}$alkyl group or phenyl group, W is hydrogen atom, hydroxy group, $C_{1-6}$ alkoxy group, a halogen atom, $C_{1-4}$alkyl group or $C_{1-6}$alkylsulfonylamino group, $R^1$ and $R^2$ are independently of each other $C_{1-3}$alkyl group, $R^3$ is hydrogen atom, hydroxy group or methoxy group, m is an integer of 0 to 4, n is an integer of 0 to 4, V is a single bond, $CR^7R^8$, $NR^9$, O, S, SO or $SO_2$, $R^4$ is hydrogen atom or $C_{1-6}$alkyl group, $R^5$ is hydrogen atom, $C_{1-6}$alkyl group, $C_{3-8}$cycloalkyl group, $C_{3-8}$cycloalkenyl group, $C_{6-14}$aryl group or $C_{2-9}$heteroaryl group. These compounds are useful as an anti-arrhythmic agent.

43 Claims, No Drawings

BENZOPYRAN COMPOUND

TECHNICAL FIELD

The present invention relates to benzopyran compounds having the prolongation effect on the refractory period, which are used for the treatment of arrhythmia in mammals including human being.

BACKGROUND ART

As benzopyran derivatives, 4-acylaminobenzopyran derivatives exemplified by Cromakalim have been known (Japanese Patent Laid-open No. Sho 58-67683). These 4-acylaminobenzopyran derivatives exemplified by Cromakalim are known to open ATP sensitive $K^+$ channel so as to be effective for the treatment of hypertension and asthma, but there has not been any mention as to the treatment of arrhythmia based on the prolongation effect on the refractory period.

At present, conventional anti-arrhythmic agents having the prolongation effect on the refractory period as a main mechanism (such as Class I drugs of anti-arrhythmic agent classification according to Vaughan Williams, or d-sotalol or dofetilide belonging to Class III) have the therapeutic problems in inducing highly dangerous arrhythmia leading to the sudden death from such as torsades de pointes among others due to prolongation of action potential in ventricular muscle correlated to the prolongation effect on the refractory period. Thus, treating agents with less adverse effect have been highly desired.

DISCLOSURE OF INVENTION

The inventors have eagerly investigated benzopyran compounds, and surprisingly found that the compound of formula (I) has the prolongation effect on the refractory period selective for atrium muscle without any influence on the refractory period and action potential in ventricular muscle. Thus, the present invention has been accomplished.

The present invention relates to the following aspects:
(1) A benzopyran compound of formula (I)

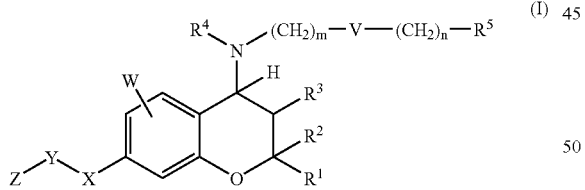

wherein
X is $NR^6$ wherein $R^6$ is hydrogen atom or $C_{1-4}$ alkyl group;
Y is a bond, SO or $SO_2$;
Z is $C_{1-4}$ alkyl group (wherein the $C_{1-4}$ alkyl group may be arbitrarily substituted with 1 to 5 halogen atoms or phenyl group (wherein the phenyl group may be arbitrarily substituted with $C_{1-4}$ alkyl group)) or phenyl group (wherein the phenyl group may be arbitrarily substituted with $C_{1-4}$ alkyl group);
W is hydrogen atom, hydroxy group, $C_{1-6}$ alkoxy group (wherein the $C_{1-6}$ alkoxy group may be arbitrarily substituted with halogen atom), halogen atom, $C_{1-4}$ alkyl group or $C_{1-6}$ alkylsulfonylamino group;

$R^1$ and $R^2$ are independently of each other $C_{1-3}$ alkyl group (wherein the $C_{1-3}$ alkyl group may be arbitrarily substituted with hydroxy group, methoxy group, halogen atom or trifluoromethoxy group);
$R^3$ is hydrogen atom, hydroxy group or methoxy group;
m is an integer of 0 to 4;
n is an integer of 0 to 4;
V is a single bond, $CR^7R^8$ wherein $R^7$ is
$C_{1-6}$ alkyl group (wherein the $C_{1-6}$ alkyl group may be arbitrarily substituted with halogen atom, hydroxy group, $C_{1-6}$ alkoxy group (wherein the $C_{1-6}$ alkoxy group may be arbitrarily substituted with halogen atom), $C_{6-14}$ aryl group or $C_{2-9}$ heteroaryl group (wherein each of the $C_{6-14}$ aryl group or $C_{2-9}$ heteroaryl group may be arbitrarily substituted with 1 to 3 $R^{10}$ wherein $R^{10}$ is halogen atom; hydroxy group; $C_{1-6}$ alkyl group (wherein the $C_{1-6}$ alkyl group may be arbitrarily substituted with halogen atom, hydroxy group or $C_{1-6}$ alkoxy group (wherein the $C_{1-6}$ alkoxy group may be arbitrarily substituted with halogen atom)); $C_{1-6}$ alkoxy group (wherein the $C_{1-6}$ alkoxy group may be arbitrarily substituted with halogen atom); nitro group; cyano group; formyl group; formamide group; sulfonylamino group; sulfonyl group; amino group; $C_{1-6}$ alkylamino group; di-$C_{1-6}$ alkylamino group; $C_{1-6}$ alkylcarbonylamino group; $C_{1-6}$ alkylsulfonylamino group; aminocarbonyl group; $C_{1-6}$ alkylaminocarbonyl group; di-$C_{1-6}$ alkylaminocarbonyl group; $C_{1-6}$ alkylcarbonyl group; $C_{1-6}$ alkoxycarbonyl group; aminosulfonyl group; $C_{1-6}$ alkylsulfonyl group; carboxy group or $C_{6-14}$ arylcarbonyl group, and when a plurality of $R^{10}$ are present, they may be identical or different from each other),
—$C_{6-14}$ aryl group or $C_{2-9}$ heteroaryl group (wherein each of the $C_{6-14}$ aryl group or $C_{2-9}$ heteroaryl group may be arbitrarily substituted with 1 to 3 $R^{10}$ wherein $R^{10}$ has the above-mentioned meaning));
hydroxy group or
$C_{1-6}$ alkoxy group (wherein the $C_{1-6}$ alkoxy group may be arbitrarily substituted with halogen atom), and $R^8$ is
hydrogen atom,
$C_{1-6}$ alkyl group (wherein the $C_{1-6}$ alkyl group may be arbitrarily substituted with halogen atom, hydroxy group, $C_{1-6}$ alkoxy group (wherein the $C_{1-6}$ alkoxy group may be arbitrarily substituted with halogen atom)),
$C_{6-14}$ aryl group or $C_{2-9}$ heteroaryl group (wherein each of the $C_{6-14}$ aryl group or $C_{2-9}$ heteroaryl group may be arbitrarily substituted with 1 to 3 $R^{11}$ wherein $R^{11}$ is halogen atom; hydroxy group; $C_{1-6}$ alkyl group (wherein the $C_{1-6}$ alkyl group may be arbitrarily substituted with halogen atom, hydroxy group or $C_{1-6}$ alkoxy group (wherein the $C_{1-6}$ alkoxy group may be arbitrarily substituted with halogen atom));
$C_{1-6}$ alkoxy group (wherein the $C_{1-6}$ alkoxy group may be arbitrarily substituted with halogen atom); nitro group; cyano group; formyl group; formamide group; sulfonylamino group; sulfonyl group; amino group; $C_{1-6}$ alkylamino group; di-$C_{1-6}$ alkylamino group; $C_{1-6}$ alkylcarbonylamino group; $C_{1-6}$ alkylsulfonylamino group; aminocarbonyl group; $C_{1-6}$ alkylaminocarbonyl group; di-$C_{1-6}$ alkylaminocarbonyl group; $C_{1-6}$ alkylcarbonyl group; $C_{1-6}$ alkoxycarbonyl group; aminosulfonyl group; $C_{1-6}$ alkylsulfonyl group; carboxy group or $C_{6-14}$ arylcarbonyl group, and when a plurality of $R^{11}$ are present, they may be identical or different from each other),
hydroxy group or
$C_{1-6}$ alkoxy group (wherein the $C_{1-6}$ alkoxy group may be arbitrarily substituted with halogen atom), or $R^7$ together with $R^8$ may represent O or S, or V is NR$^9$ wherein R$^9$ is hydrogen or C$_{1-6}$ alkyl group (wherein the C$_{1-6}$ alkyl group may be arbitrarily substituted with halogen atom, C$_{1-6}$ alkoxy group (wherein the C$_{1-6}$ alkoxy group may be arbitrarily substituted with halogen atom), hydroxy group, C$_{6-14}$ aryl group or C$_{2-9}$ heteroaryl group (wherein each of the C$_{6-14}$ aryl group or C$_{2-9}$ heteroaryl group may be arbitrarily substituted with 1 to 3 R$^{11}$ wherein R$^{11}$ has the above-mentioned meaning)); or O, S, SO or SO$_2$;

R$^4$ is hydrogen or C$_{1-6}$ alkyl group (wherein the C$_{1-6}$ alkyl group may be arbitrarily substituted with halogen atom, C$_{1-6}$ alkoxy group (wherein the C$_{1-6}$ alkoxy group may be arbitrarily substituted with halogen atom), or hydroxy group); and R$^5$ is hydrogen atom, C$_{1-6}$ alkyl group (wherein the C$_{1-6}$ alkyl group may be arbitrarily substituted with halogen atom, C$_{1-6}$ alkoxy group (wherein the C$_{1-6}$ alkoxy group may be arbitrarily substituted with halogen atom), amino group, carboxy group or hydroxy group), C$_{3-8}$ cycloalkyl group or C$_{3-8}$ cycloalkenyl group (wherein the C$_{3-8}$ cycloalkyl group or C$_{3-8}$ cycloalkenyl group may be arbitrarily substituted with halogen atom, C$_{1-6}$ alkyl group (wherein the C$_{1-6}$ alkyl group may be arbitrarily substituted with halogen atom, C$_{1-6}$ alkoxy group (wherein the C$_{1-6}$ alkoxy group may be arbitrarily substituted with halogen atom), amino group, carboxy group or hydroxy group), C$_{1-6}$ alkoxy group (wherein the C$_{1-6}$ alkoxy group may be arbitrarily substituted with halogen atom), amino, carboxy group or hydroxy group), or C$_{6-14}$ aryl group or C$_{2-9}$ heteroaryl group (wherein each of the C$_{6-14}$ aryl group or C$_{2-9}$ heteroaryl group may be arbitrarily substituted with 1 to 3 R$^{12}$ wherein R$^{12}$ is halogen atom; hydroxy group; C$_{1-6}$ alkyl group (wherein the C$_{1-6}$ alkyl group may be arbitrarily substituted with halogen atom, hydroxy group or C$_{1-6}$ alkoxy group (wherein the C$_{1-6}$ alkoxy group may be arbitrarily substituted with halogen atom)); C$_{1-6}$ alkoxy group (wherein the C$_{1-6}$ alkoxy group may be arbitrarily substituted with halogen atom); nitro group; cyano group; formyl group; formamide group; sulfonylamino group; sulfonyl group; amino group; C$_{1-6}$ alkylamino group; di-C$_{1-6}$ alkylamino group; C$_{1-6}$ alkylcarbonylamino group; C$_{1-6}$ alkylsulfonylamino group; aminocarbonyl group; C$_{1-6}$ alkylaminocarbonyl group; di-C$_{1-6}$ alkylaminocarbonyl group; C$_{1-6}$ alkylcarbonyl group; C$_{1-6}$ alkoxycarbonyl group; aminosulfonyl group; C$_{1-6}$ alkylsulfonyl group; carboxy group, C$_{6-14}$ arylcarbonyl group, ureido group, C$_{1-6}$ alkylureilene group, C$_{6-14}$ aryl C$_{1-6}$ alkylamino group, C$_{1-6}$ alkoxycarbonylamino group, C$_{6-14}$ aryloxy group or C$_{6-14}$ arylcarbonylamino group, when a plurality of R$^{12}$ are present, they may be identical or different from each other);

(2) The benzopyran compound as set forth in (1), wherein both R$^1$ and R$^2$ are methyl group, R$^3$ is hydroxy group, and V is a single bond;

(3) The benzopyran compound as set forth in (1), wherein both R$^1$ and R$^2$ are methyl group, R$^3$ is hydroxy group, and V is CR$^7$R$^8$;

(4) The benzopyran compound as set forth in (1), wherein both R$^1$ and R$^2$ are methyl group, R$^3$ is hydroxy group, and V is NR$^9$;

(5) The benzopyran compound as set forth in (2), wherein R$^5$ is C$_{1-6}$ alkyl group, C$_{3-8}$ cycloalkyl group or C$_{6-14}$ aryl group;

(6) The benzopyran compound as set forth in (3), wherein R$^5$ is C$_{1-6}$ alkyl group, C$_{3-8}$ cycloalkyl group or C$_{6-14}$ aryl group;

(7) The benzopyran compound as set forth in (4), wherein R$^5$ is C$_{1-6}$ alkyl group, C$_{3-8}$ cycloalkyl group or C$_{6-14}$ aryl group;

(8) The benzopyran compound as set forth in (5), wherein W is hydrogen atom, hydroxy group, methoxy group, chlorine atom, bromine atom, methyl group, ethyl group or methylsulfonylamino group;

(9) The benzopyran compound as set forth in (6), wherein W is hydrogen atom, hydroxy group, methoxy group, chlorine atom, bromine atom, methyl group, ethyl group or methylsulfonylamino group;

(10) The benzopyran compound as set forth in (8), wherein R$^5$ is C$_{1-6}$ alkyl group or C$_{6-14}$ aryl group, R$^6$ is hydrogen atom or methyl group, Y is SO$_2$, and Z is C$_{1-4}$ alkyl group;

(11) The benzopyran compound as set forth in (8), wherein R$^5$ is C$_{1-6}$ alkyl group or C$_{6-14}$ aryl group, R$^6$ is hydrogen atom or methyl group, Y is a bond, and Z is C$_{1-4}$ alkyl group;

(12) A benzopyran compound which is N-{(3R*,4S*)-3-hydroxy-6-methoxy-2,2-dimethyl-4-[(2-phenylethyl)amino]-3,4-dihydro-2H-1-benzopyran-7-yl}-methanesulfonamide;

(13) A benzopyran compound which is N-{(3R*,4S*)-3,6-dihydroxy-2,2-dimethyl-4-[(2-phenylethyl)amino]-3,4-dihydro-2H-1-benzopyran-7-yl}methanesulfonamide;

(14) A benzopyran compound which is N-{(3R*,4S*)-3-hydroxy-6-methoxy-2,2-dimethyl-4-[(2-phenylethyl)amino]-3,4-dihydro-2H-1-benzopyran-7-yl}-N-methyl-methanesulfonamide;

(15) A benzopyran compound which is N-{(3R*,4S*)-4-[(2-cyclohexylethyl)amino]-3-hydroxy-6-methoxy-2,2-dimethyl-3,4-dihydro-2H-1-benzopyran-7-yl}methanesulfonamide;

(16) A benzopyran compound which is N-{(3R*,4S*)-3-hydroxy-6-methoxy-2,2-dimethyl-4-(pentylamino)-3,4-dihydro-2H-1-benzopyran-7-yl}methanesulfonamide;

(17) A benzopyran compound which is N-{(3R*,4S*)-3-hydroxy-2,2,8-trimethyl-4-[(2-phenylethyl)amino]-3,4-dihydro-2H-1-benzopyran-7-yl}methanesulfonamide;

(18) A benzopyran compound which is N-{(3R*,4S*)-3-hydroxy-2,2-dimethyl-4-[(2-phenylethyl)amino]-3,4-dihydro-2H-benzopyran-7-yl}methanesulfonamide;

(19) A benzopyran compound which is N-{(3R*,4S*)-3-hydroxy-2,2-dimethyl-4-[(2-phenylethyl)amino]-3,4-dihydro-2H-benzopyran-7-yl}ethanesulfonamide;

(20) A benzopyran compound which is 1,1,1-trifluoro-N-{(3R*,4S*)-3-hydroxy-2,2-dimethyl-4-[(2-phenylethyl)amino]-3,4-dihydro-2H-benzopyran-7-yl}-methanesulfonamide;

(21) A benzopyran compound which is N-{(3R*,4S*)-3-hydroxy-2,2-dimethyl-4-[(2-phenylethyl)amino]-3,4-dihydro-2H-benzopyran-7-yl}-N-methylmethanesulfonamide;

(22) A benzopyran compound which is N-{(3R*,4S*)-6-bromo-3-hydroxy-2,2-dimethyl-4-[(2-phenylethyl)amino]-3,4-dihydro-2H-benzopyran-7-yl}-methanesulfonamide;

(23) A benzopyran compound which is (3R*,4S*)-2,2-dimethyl-7-dimethylamino-4-[(2-phenylethyl)amino]-3-chromanol;

(24) A benzopyran compound which is (3R*,4S*)-2,2-dimethyl-7-methylamino-4-[(2-phenylethyl)amino]-3-chromanol;

(25) A benzopyran compound which is (3R*,4S*)-4-{[2-(4-fluorophenyl)ethyl]amino}-2,2-dimethyl-7-dimethylamino-3-chromanol;

(26) A benzopyran compound which is (3R*,4S*)-6-methoxy-2,2-dimethyl-7-dimethylamino-4-[(2-phenylethyl)amino]-3-chromanol;

(27) A benzopyran compound which is (3R*,4S*)-6-methoxy-2,2-dimethyl-7-methylamino-4-[(2-phenylethyl)amino]-3-chromanol;

(28) A benzopyran compound which is N-{(3R*,4S*)-3-hydroxy-2,2-dimethyl-4-[(2-phenylethyl)amino]-3,4-dihydro-2H-benzopyran-7-yl}-4-methylbenzenesulfonamide.

(29) A benzopyran compound which is N-{(3R*,4S*)-3-hydroxy-2,2-dimethyl-6-[(methylsulfonyl)amino]-4-[(2-phenylethyl)amino]-3,4-dihydro-2H-benzopyran-7-yl}-methanesulfonamide.

(30) A benzopyran compound which is (3R*,4S*)-2,2-dimethyl-7-methylethylamino-4-[(2-phenylethyl)amino]-3-chromanol.

(31) A benzopyran compound which is N-{(3R*,4S*)-3-hydroxy-2,2-dimethyl-4-[(2-phenylethyl)amino]-3,4-dihydro-2H-chromen-7-yl}-N-isopropylmethanesulfonamide.

(32) A pharmaceutical characterized by comprising the benzopyran compound as set forth in any one of (1) to (31) or pharmaceutically acceptable salt thereof as an active ingredient; and

(33) A pharmaceutical for treating arrhythmia characterized by comprising the benzopyran compound as set forth in any one of (1) to (31) or pharmaceutically acceptable salt thereof as an active ingredient.

The compound according to the present invention has a strong prolongation effect on the refractory period and it can be used as a drug for treating arrhythmia.

BEST MODE FOR CARRYING OUT THE INVENTION

Respective substituents of compounds (1) according to the present invention are concretely defined below.

In the meanwhile, "n" means normal, "i" means iso, "s" means secondary, "t" means tertiary, "c" means cyclo, "o" means ortho, "m" means meta, "p" means para, "Me" means methyl, "Et" means ethyl, "Pr" means propyl, "Ms" means methylsulfonyl, "Ts" means p-tolylsulfonyl, "Ph" means phenyl and "Ac" means acetyl in this specification.

Examples of $C_{1-3}$ alkyl group are such as methyl, ethyl, n-propyl, i-propyl and the like.

Examples of $C_{1-4}$ alkyl group are such as methyl, ethyl, n-propyl, i-propyl, n-butyl, i-butyl, s-butyl, t-butyl and the like.

Examples of $C_{1-6}$ alkyl group are such as methyl, ethyl, n-propyl, i-propyl, n-butyl, i-butyl, s-butyl, t-butyl, 1-pentyl, 2-pentyl, 3-pentyl, i-pentyl, neopentyl, 1-hexyl, 2-hexyl, 3-hexyl, 1,1,2-trimethyl-n-propyl, 1,2,2-trimethyl-n-propyl, 3,3-dimethyl-n-butyl and the like.

Preferably, methyl, ethyl, n-propyl, i-propyl and n-butyl may be mentioned.

Examples of halogen atom are such as fluorine atom, chlorine atom, bromine atom and iodine atom. Preferably, fluorine atom and chlorine atom may be mentioned.

Examples of $C_{1-6}$ alkoxy group are such as methoxy, ethoxy, n-propoxy, i-propoxy, n-butoxy, i-butoxy, s-butoxy, t-butoxy, 1-pentyloxy, 2-pentyloxy, 3-pentyloxy, i-pentyloxy, neopentyloxy, 1-hexyloxy, 2-hexyloxy, 3-hexyloxy, 1,1,2-trimethyl-n-propoxy, 1,2,2-trimethyl-n-propoxy, 3,3-dimethyl-n-butoxy and the like.

Preferably, methoxy, ethoxy, n-propoxy and i-propoxy may be mentioned.

Examples of $C_{6-14}$ aryl group are such as phenyl, o-biphenylyl, m-biphenylyl, p-biphenylyl, α-naphthyl, β-naphthyl, 1-anthryl, 2-anthryl, 9-anthryl, 1-phenanthryl, 2-phenanthryl, 3-phenanthryl, 4-phenanthryl, 9-phenanthryl and the like.

Preferably, phenyl may be mentioned.

$C_{2-9}$ heteroaryl group includes $C_{2-6}$ single-ring heterocyclic group with 5- to 7-member ring and $C_{5-9}$ fused double-ring heterocyclic group with member atom number of 8 to 10, which may contain 1 to 3 hetero atoms selected from the group consisting of oxygen atom, nitrogen atom and sulfur atom alone or in a combination.

Examples of the $C_{2-6}$ single-ring heterocyclic group with 5- to 7-member ring are such as 2-thienyl group, 3-thienyl group, 2-furyl group, 3-furyl group, 2-pyranyl group, 3-pyranyl group, 4-pyranyl group, 1-pyrrolyl group, 2-pyrrolyl group, 3-pyrrolyl group, 1-imidazolyl group, 2-imidazolyl group, 4-imidazolyl group, 1-pyrazolyl group, 3-pyrazolyl group, 4-pyrazolyl group, 2-thiazolyl group, 4-thiazolyl group, 5-thiazolyl group, 3-isothiazolyl group, 4-isothiazolyl group, 5-isothiazolyl group, 2-oxazolyl group, 4-oxazolyl group, 5-oxazolyl group, 3-isooxazolyl group, 4-isooxazolyl group, 5-isooxazolyl group, 2-pyridyl group, 3-pyridyl group, 4-pyridyl group, 2-pyradinyl group, 2-pyrimidinyl group, 4-pyrimidinyl group, 5-pyrimidinyl group, 3-pyridazinyl group, 4-pyridazinyl group, 2-1,3,4-oxadiazolyl group, 2-1,3,4-thiadiazolyl group, 3-1,2,4-oxadiazolyl group, 5-1,2,4-oxadiazolyl group, 3-1,2,4-thiadiazolyl group, 5-1,2,4-thiadiazolyl group, 3-1,2,5-oxadiazolyl group, 3-1,2,5-thiadiazolyl group and the like.

Examples of the $C_{5-9}$ fused double-ring heterocyclic group with member atom number of 8 to 10 are 2-benzofuranyl group, 3-benzofuranyl group, 4-benzofuranyl group, 5-benzofuranyl group, 6-benzofuranyl group, 7-benzofuranyl group, 1-isobenzofuranyl group, 4-isobenzofuranyl group, 5-isobenzofuranyl group, 2-benzothienyl group, 3-benzothienyl group, 4-benzothienyl group, 5-benzothienyl group, 6-benzothienyl group, 7-benzothienyl group, 1-isobenzothienyl group, 4-isobenzothienyl group, 5-isobenzothienyl group, 2-chromenyl group, 3-chromenyl group, 4-chromenyl group, 5-chromenyl group, 6-chromenyl group, 7-chromenyl group, 8-chromenyl group, 1-indolizinyl group, 2-indolizinyl group, 3-indolizinyl group, 5-indolizinyl group, 6-indolizinyl group, 7-indolizinyl group, 8-indolizinyl group, 1-isoindolyl group, 2-isoindolyl group, 4-isoindolyl group, 5-isoindolyl group, 1-indolyl group, 2-indolyl group, 3-indolyl group, 4-indolyl group, 5-indolyl group, 6-indolyl group, 7-indolyl group, 1-indazolyl group, 2-indazolyl group, 3-indazolyl group, 4-indazolyl group, 5-indazolyl group, 6-indazolyl group, 7-indazolyl group, 1-purinyl group, 2-purinyl group, 3-purinyl group, 6-purinyl group, 7-purinyl group, 8-purinyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 1-phthalazinyl group, 5-phthalazinyl group, 6-phthalazinyl group, 1-2,7-naphthyridinyl group, 3-2,7-naphthyridinyl group, 4-2,7-naphthyridinyl group, 1-2,6-naphthyridinyl group, 3-2,6-naphthyridinyl group, 4-2,6-naphthyridinyl group, 2-1,8-naphthyridinyl group, 3-1,8-naphthyridinyl group, 4-1,8-naphthyridinyl group, 2-1,7-naphthyridinyl group, 3-1,7-naphthyridinyl group, 4-1,7-naphthyridinyl group, 5-1,7-naphthyridinyl group, 6-1,7-naphthyridinyl group, 8-1,7-naphthyridinyl group, 2-1,6-naphthyridinyl group, 3-1,6-naphthyridinyl group, 4-1,6-naphthyridinyl group, 5-1,6-naphthyridinyl group, 7-1,6-naphthyridinyl group, 8-1,6-naphthyridinyl group, 2-1,5-naphthyridinyl group, 3-1,5-naphthyridinyl group, 4-1,5-naphthyridinyl group, 6-1,5-naphthyridinyl group, 7-1,5-naphthyridinyl group, 8-1,5-naphthyridinyl group, 2-quinoxalinyl group, 5-quinoxalinyl group, 6-quinoxalinyl group, 2-quinazolinyl group, 4-quinazolinyl group, 5-quinazolinyl group, 6-quinazolinyl group, 7-quinazolinyl group, 8-quinazolinyl group, 3-cinnolinyl group, 4-cinnolinyl group, 5-cinnolinyl group, 6-cinnolinyl group, 7-cinnolinyl group, 8-cinnolinyl group, 2-pteridinyl group, 4-pteridinyl group, 6-pteridinyl group, 7-pteridinyl group, and the like.

Preferably, 2-pyridyl group, 3-pyridyl group and 4-pyridyl group may be mentioned.

Examples of $C_{1-6}$ alkylamino group are such as methylamino, ethylamino, n-propylamino, i-propylamino, c-propylamino, n-butylamino, i-butylamino, s-butylamino, t-butylamino, c-butylamino, 1-pentylamino, 2-pentylamino, 3-pentylamino, i-pentylamino, neopentylamino, t-pentylamino, c-pentylamino, 1-hexylamino, 2-hexylamino, 3-hexylamino, c-hexylamino, 1,1,2-trimethyl-n-propylamino, 1,2,2-trimethyl-n-propylamino, 3,3-dimethyl-n-butylamino and the like.

Preferably, methylamino, ethylamino, n-propylamino, i-propylamino and n-butylamino may be mentioned.

Examples of di-$C_{1-6}$alkylamino group are such as dimethylamino, diethylamino, di-n-propylamino, di-i-propylamino, di-c-propylamino, di-n-butylamino, di-i-butylamino, di-s-butylamino, di-t-butylamino, di-c-butylamino, di-1-pentylamino, di-2-pentylamino, di-3-pentylamino, di-1-pentylamino, di-neopentylamino, di-t-pentylamino, di-c-pentylamino, di-1-hexylamino, di-2-hexylamino, di-3-hexylamino, di-c-hexylamino, di-(1-methyl-n-pentyl)amino, di-(1,1,2-trimethyl-n-propyl)amino, di-(1,2,2-trimethyl-n-propyl)amino, di-(3,3-dimethyl-n-butyl)amino, methyl(ethyl)amino, methyl(n-propyl)amino, methyl(i-propyl)amino, methyl(c-propyl)amino, methyl(n-butyl) amino, methyl(i-butyl)amino, methyl(s-butyl)amino, methyl(t-butyl)amino, methyl(c-butyl)amino, ethyl(n-propyl)amino, ethyl(i-propyl)amino, ethyl(c-propyl) amino, ethyl(n-butyl)amino, ethyl(i-butyl)amino, ethyl(s-butyl)amino, ethyl(t-butyl) amino, ethyl(c-butyl)amino, n-propyl(i-propyl)amino, n-propyl(c-propyl)amino, n-propyl(n-butyl)amino, n-propyl(i-butyl)amino, n-propyl(s-butyl)amino, n-propyl(t-butyl) amino, n-propyl(c-butyl)amino, i-propyl(c-propyl)amino, i-propyl (n-butyl)amino, i-propyl(i-butyl)amino, i-propyl(s-butyl) amino, i-propyl(t-butyl) amino, i-propyl(c-butyl) amino, c-propyl(n-butyl)amino, c-propyl(i-butyl)amino, c-propyl(s-butyl)amino, c-propyl(t-butyl)amino, c-propyl(c-butyl) amino, n-butyl(i-butyl)amino, n-butyl(s-butyl) amino, n-butyl(t-butyl)amino, n-butyl(c-butyl)amino, i-butyl(s-butyl) amino, i-butyl (t-butyl)amino, i-butyl(c-butyl)amino, s-butyl (t-butyl)amino, s-butyl(c-butyl)amino, t-butyl(c-butyl)amino and the like.

Preferably, dimethylamino, diethylamino, di-n-propylamino, di-i-propylamino and di-n-butylamino may be mentioned.

Examples of $C_{1-6}$alkylcarbonylamino group are such as methylcarbonylamino, ethylcarbonylamino, n-propylcarbonylamino, i-propylcarbonylamino, n-butylcarbonylamino, i-butylcarbonylamino, s-butylcarbonylamino, t-butylcarbonylamino, 1-pentylcarbonylamino, 2-pentylcarbonylamino, 3-phenylcarbonylamino, i-pentylcarbonylamino, neopentylcarbonylamino, t-pentylcarbonylamino, 1-hexylcarbonylamino, 2-hexylcarbonylamino, 3-hexylcarbonylamino and the like.

Preferably, methylcarbonylamino, ethylcarbonylamino, n-propylcarbonylamino, i-propylcarbonylamino and n-butylcarbonylamino may be mentioned.

Examples of $C_{1-6}$alkylsulfonylamino group are such as methylsulfonylamino, ethylsulfonylamino, n-propylsulfonylamino, i-propylsulfonylamino, n-butylsulfonylamino, i-butylsulfonylamino, s-butylsulfonylamino, t-butylsulfonylamino, 1-pentylsulfonylamino, 2-pentylsulfonylamino, 3-pentylsulfonylamino, i-pentylsulfonylamino, neopentylsulfonylamino, t-pentylsulfonylamino, 1-hexylsulfonylamino, 2-hexylsulfonylamino, 3-hexylsulfonylamino and the like.

Preferably, methylsulfonylamino, ethylsulfonylamino, n-propylsulfonylamino, i-propylsulfonylamino and n-butylsulfonylamino may be mentioned.

Examples of $C_{1-6}$ alkylaminocarbonyl group are such as methylaminocarbonyl, ethylaminocarbonyl, n-propylaminocarbonyl, i-propyl-aminocarbonyl, n-butylaminocarbonyl, i-butylaminocarbonyl, s-butylaminocarbonyl, t-butylaminocarbonyl, 1-pentylaminocarbonyl, 2-pentylaminocarbonyl, 3-pentyl-aminocarbonyl, i-pentylaminocarbonyl, neopentylaminocarbonyl, t-pentylamino-carbonyl, 1-hexylaminocarbonyl, 2-hexylaminocarbonyl, 3-hexylaminocarbonyl and the like.

Preferably, methylaminocarbonyl, ethylaminocarbonyl, n-propylaminocarbonyl, i-propylaminocarbonyl and n-butylaminocarbonyl may be mentioned.

Examples of di-$C_{1-6}$ alkylaminocarbonyl group are such as dimethylaminocarbonyl, diethylaminocarbonyl, di-n-propylaminocarbonyl, di-i-propylaminocarbonyl, di-c-propylaminocarbonyl, di-n-butylaminocarbonyl, di-i-butylaminocarbonyl, di-s-butylaminocarbonyl, di-t-butylaminocarbonyl, di-c-butylaminocarbonyl, di-1-pentylaminocarbonyl, di-2-pentylaminocarbonyl, di-3-pentylaminocarbonyl, di-1-pentylaminocarbonyl, di-neopentylaminocarbonyl, di-t-pentylaminocarbonyl, di-c-pentylaminocarbonyl, di-1-hexylaminocarbonyl, di-2-hexylaminocarbonyl, di-3-hexylaminocarbonyl and the like.

Preferably, dimethylaminocarbonyl, diethylaminocarbonyl, di-n-propylaminocarbonyl, di-i-propylaminocarbonyl, di-c-propylaminocarbonyl and di-n-butylaminocarbonyl may be mentioned.

Examples of $C_{1-6}$alkylcarbonyl group are such as methylcarbonyl, ethylcarbonyl, n-propylcarbonyl, i-propylcarbonyl, n-butylcarbonyl, i-butylcarbonyl, s-butylcarbonyl, t-butylcarbonyl, 1-pentylcarbonyl, 2-pentylcarbonyl, 3-pentylcarbonyl, i-pentylcarbonyl, neopentylcarbonyl, t-pentylcarbonyl, 1-hexylcarbonyl, 2-hexylcarbonyl, 3-hexylcarbonyl and the like.

Preferably, methylcarbonyl, ethylcarbonyl, n-propylcarbonyl, i-propylcarbonyl and n-butylcarbonyl may be mentioned.

Examples of $C_{1-6}$alkoxycarbonyl group are such as methoxycarbonyl, ethoxycarbonyl, n-propoxycarbonyl, i-propoxycarbonyl, n-butoxycarbonyl, i-butoxycarbonyl, s-butoxycarbonyl, t-butoxycarbonyl, 1-pentyloxycarbonyl, 2-pentyloxycarbonyl, 3-pentyloxycarbonyl, i-pentyloxycarbonyl, neopentyloxycarbonyl, t-pentyloxycarbonyl, 1-hexyloxycarbonyl, 2-hexyloxycarbonyl, 3-hexyloxycarbonyl and the like.

Preferably, methoxycarbonyl, ethoxycarbonyl, n-propoxycarbonyl, i-propoxycarbonyl, n-butoxycarbonyl, i-butoxycarbonyl, s-butoxycarbonyl and t-butoxycarbonyl may be mentioned.

Examples of $C_{1-6}$ alkylsulfonyl group are such as methanesulfonyl, ethanesulfonyl and the like.

Examples of $C_{6-14}$ arylcarbonyl group are such as benzoyl, p-methylbenzoyl, p-t-butylbenzoyl, p-methoxybenzoyl, p-chlorobenzoyl, p-nitrobenzoyl, p-cyanobenzoyl, o-biphenylylcarbonyl, m-biphenylylcarbonyl, p-biphenylylcarbonyl, □-naphthylcarbonyl, □-naphthylcarbonyl, 1-anthrylcarbonyl, 2-anthrylcarbonyl, 9-anthrylcarbonyl, 1-phenanthrylcarbonyl, 2-phenanthrylcarbonyl, 3-phenanthrylcarbonyl, 4-phenanthrylcarbonyl, 9-phenanthrylcarbonyl and the like.

Preferably, benzoyl, p-nitrobenzoyl and p-cyanobenzoyl may be mentioned.

Examples of $C_{1-6}$ alkylureylene group are such as methylureylene, ethylureylene, n-propylureylene, i-propylureylene, n-butylureylene, i-butylureylene, s-butylureylene, t-butylureylene, 1-pentylureylene, 2-pentylureylene, 3-pentylureylene, i-pentylureylene, neopentylureylene, 1-hexylureylene, 2-hexylureylene, 3-hexylureylene, 1,1,2-trimethyl-n-pentylureylene, 1,2,2-trimethyl-n-pentylureylene, 3,3-dimethyl-n-butylureylene and the like.

Examples of $C_{6-14}$ aryl $C_{1-6}$ alkyl group are such as benzyl, 1-phenethyl, 2-phenethyl, 1-phenylpropyl, 2-phenylpropyl, 3-phenylpropyl, 4-phenylbutyl, 5-phenylpentyl, 6-phenylhexyl, 1-naphthylmethyl, 2-naphthimethyl and the like.

Preferably, benzyl, 2-phenethyl and 3-phenylpropyl may be mentioned.

Examples of $C_{1-6}$ alkoxycarbonylamino group are such as methoxycarbonylamino, ethoxycarbonylamino, n-propoxycarbonylamino, i-propoxycarbonylamino, n-butoxycarbonylamino, i-butoxycarbonylamino, s-butoxycarbonylamino, t-butoxycarbonylamino, 1-pentyloxycarbonylamino, 2-pentyloxycarbonylamino, 3-pentyloxycarbonylamino, i-pentyloxycarbonylamino, neopentyloxycarbonylamino, t-pentyloxycarbonylamino, 1-hexyloxycarbonylamino, 2-hexyloxycarbonylamino, 3-hexyloxycarbonylamino and the like.

Examples of $C_{6-14}$ aryloxy group are such as phenoxy, p-methylphenoxy, p-t-butylphenoxy, p-methoxyphenoxy, p-chlorophenoxy, p-nitrophenoxy, p-cyanophenoxy, o-biphenylyloxy, m-biphenylyloxy, p-biphenylyloxy, α-naphthoxy, β-naphthoxy, 1-anthoryloxy, 2-anthoryloxy, 9-anthoryloxy, 1-phenanthryloxy, 2-phenanthryloxy, 3-phenanthryloxy, 4-phenanthryloxy, 9-phenanthryloxy and the like.

Examples of $C_{6-14}$ arylcarbonylamino group are such as benzoylamino, p-methylbenzoylamino, p-t-butylbenzoylamino, p-methoxybenzoylamino, p-chlorobenzoylamino, p-nitrobenzoylamino, p-cyanobenzoylamino, o-biphenylylcarbonylamino, m-biphenylylcarbonylamino, p-biphenylylcarbonylamino, α-naphthylcarbonylamino, β-naphthylcarbonylamino, 1-anthrylcarbonylamino, 2-anthrylcarbonylamino, 9-anthrylcarbonylamino, 1-phenanthrylcarbonylamino, 2-phenanthrylcarbonylamino, 3-phenanthrylcarbonylamino, 4-phenanthrylcarbonylamino, 9-phenanthrylcarbonylamino and the like.

Examples of $C_{3-8}$ cycloalkyl group are such as cyclopropyl, cyclobutyl, cyclopentyl, cyclohexyl, cycloheptyl, cyclooctyl and the like.

Preferably, cyclopropyl, cyclobutyl and cyclohexyl may be mentioned.

Examples of $C_{3-8}$ cycloalkenyl group are such as 1-c-pentenyl, 2-c-pentenyl, 3-c-pentenyl, 1-methyl-2-c-pentenyl, 1-methyl-3-c-pentenyl, 2-methyl-1-c-pentenyl, 2-methyl-2-c-pentenyl, 2-methyl-3-c-pentenyl, 2-methyl-4-c-pentenyl, 2-methyl-5-c-pentenyl, 2-methylene-c-pentyl, 3-methyl-1-c-pentenyl, 3-methyl-2-c-pentenyl, 3-methyl-3-c-pentenyl, 3-methyl-4-c-pentenyl, 3-methyl-5-c-pentenyl, 3-methylene-c-pentyl, 1-c-hexenyl, 2-c-hexenyl, 3-c-hexenyl, 1-c-heptenyl, 2-c-heptenyl, 3-c-heptenyl, 4-c-heptenyl, 1-c-octenyl, 2-c-octenyl, 3-c-octenyl, 4-c-octenyl and the like.

Preferably, 1-c-pentenyl, 2-c-pentenyl, 3-c-pentenyl, 1-c-hexenyl, 2-c-hexenyl and 3-c-hexenyl may be mentioned.

Concrete examples of substituents on the compounds used in the present invention are as follows.

Concrete examples of $R^1$ and $R^2$ are preferably methyl.

Concrete examples of $R^3$ are preferably hydroxy group.

Concrete examples of $R^4$ are preferably hydrogen atom.

Concrete examples of —X—Y—Z are preferably —NHSO$_2$Me, —NMeSO$_2$Me, —NHSO$_2$Et, —NHSO$_2$CF$_3$, —NHTs, —NMe$_2$ and —NHMe, and more preferably —NHSO$_2$Me and —NMeSO$_2$Me.

Concrete examples of W are preferably hydrogen atom, methyl, ethyl, i-propyl, fluorine atom, chlorine atom, bromine atom, hydroxy group, methoxy and NHSO$_2$Me. In case where W is present at 5-position of the benzopyran ring, W is preferably hydrogen atom. In case where W is present at 6-position, W is preferably hydrogen atom, methyl, ethyl, i-propyl, fluorine atom, chlorine atom, bromine atom, hydroxy group, methoxy and NHSO$_2$Me. In addition, in case where W is present at 8-position, W is preferably hydrogen atom and methyl.

More preferably, concrete examples of W are hydrogen atom, bromine atom, hydroxyl group, methoxy and NHSO$_2$Me at 6-position, and hydrogen atom and methyl at 8-position, and further preferably hydrogen atom, hydroxy group and methoxy at 6-position.

Concrete examples of N—(CH$_2$)$_m$—V—(CH$_2$)$_n$—R$^5$ are preferably as follows.

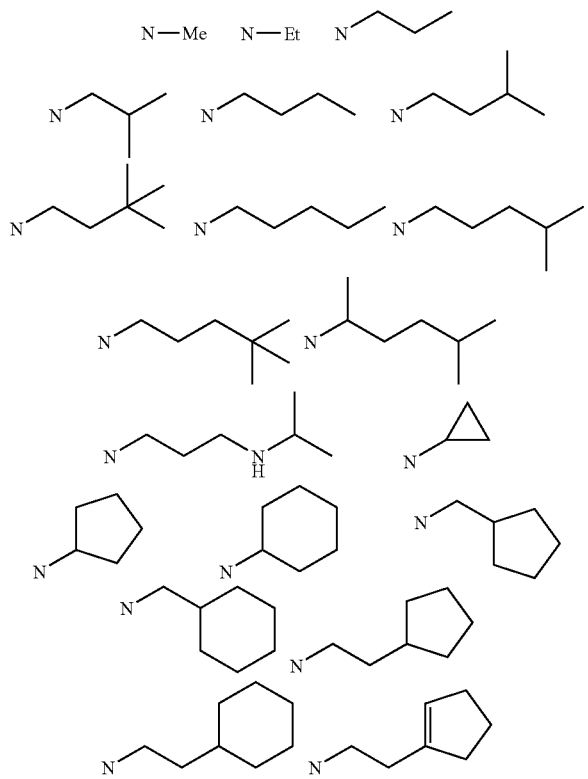

-continued
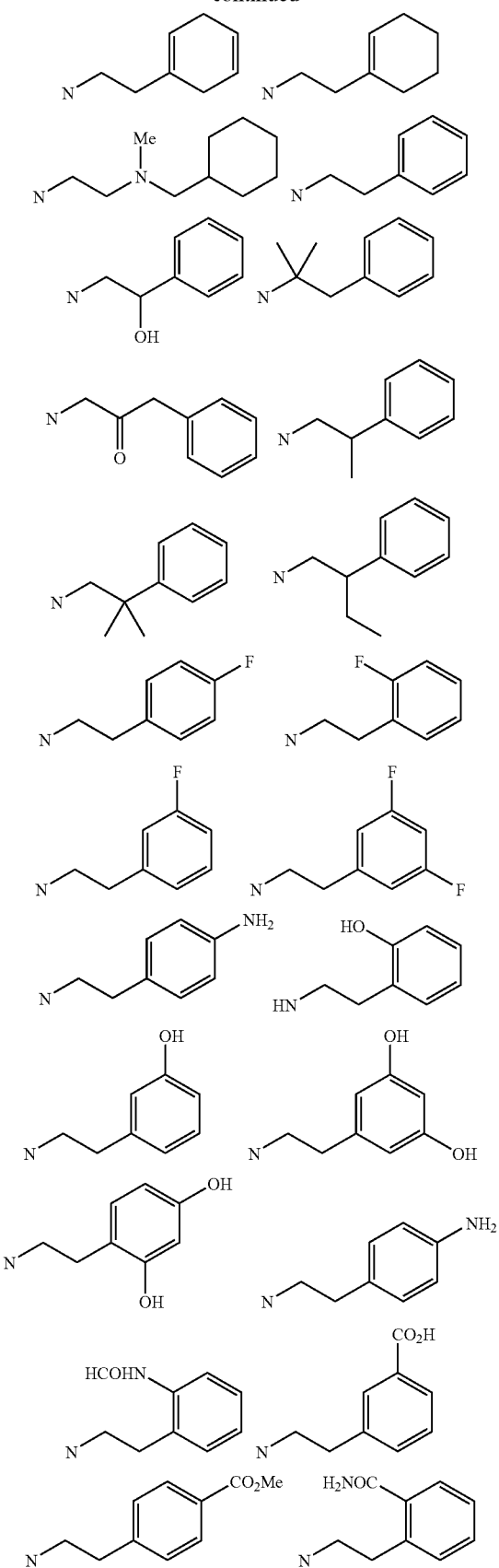
-continued
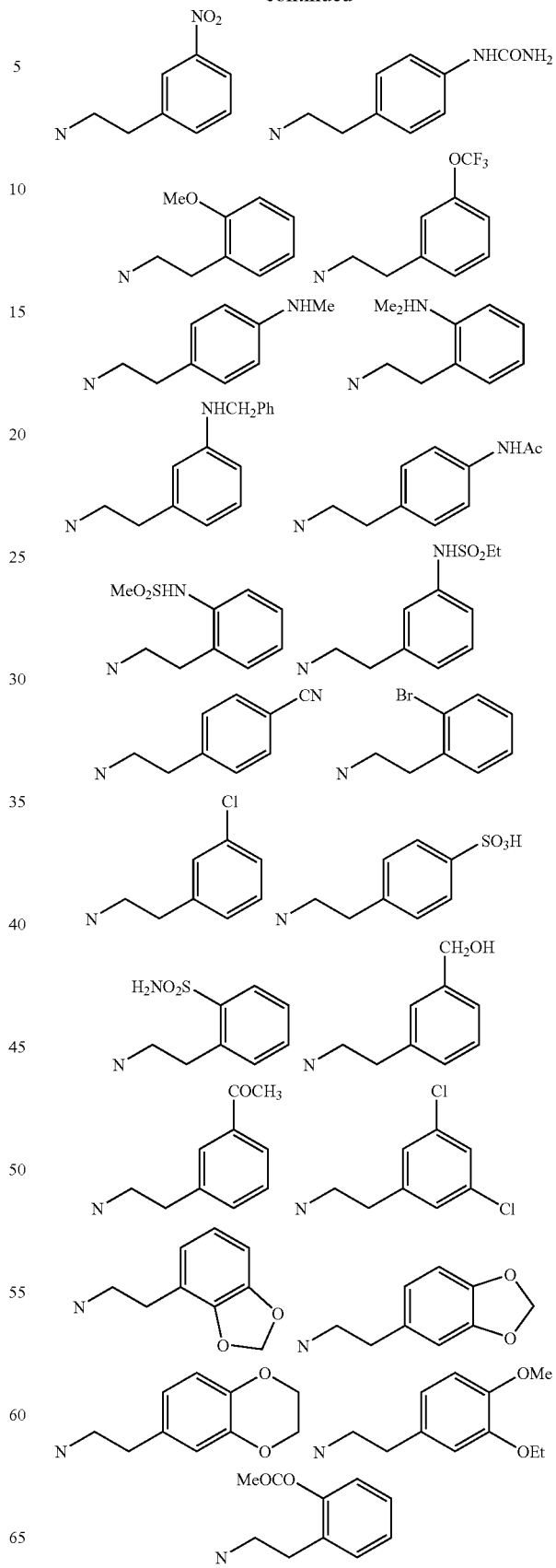

-continued
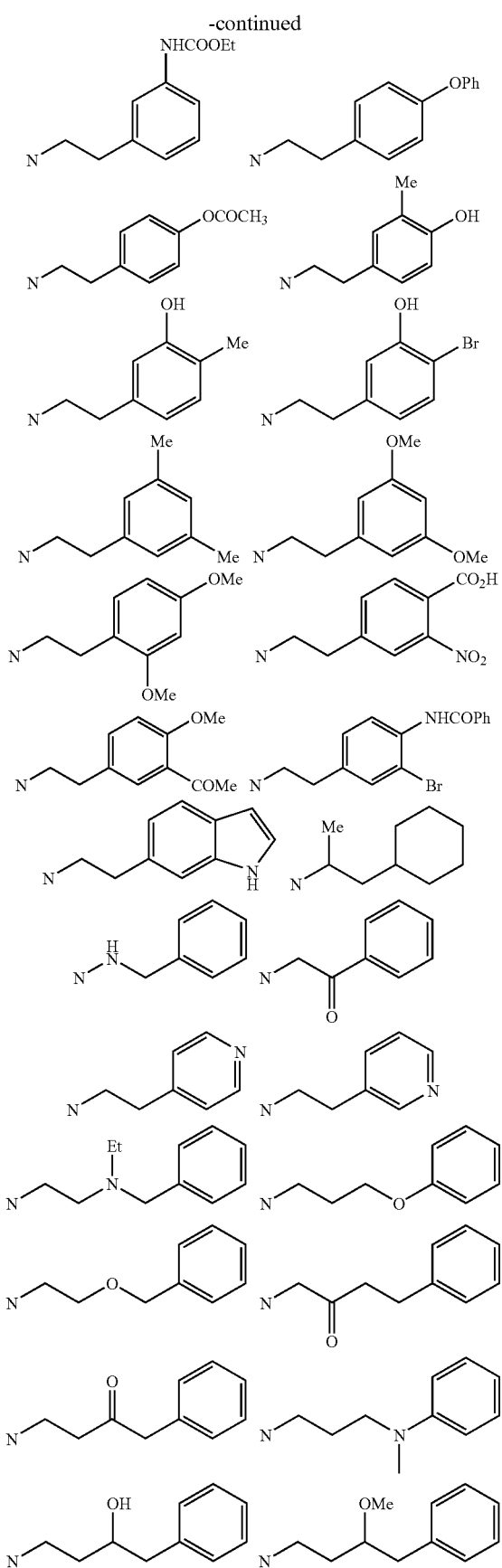
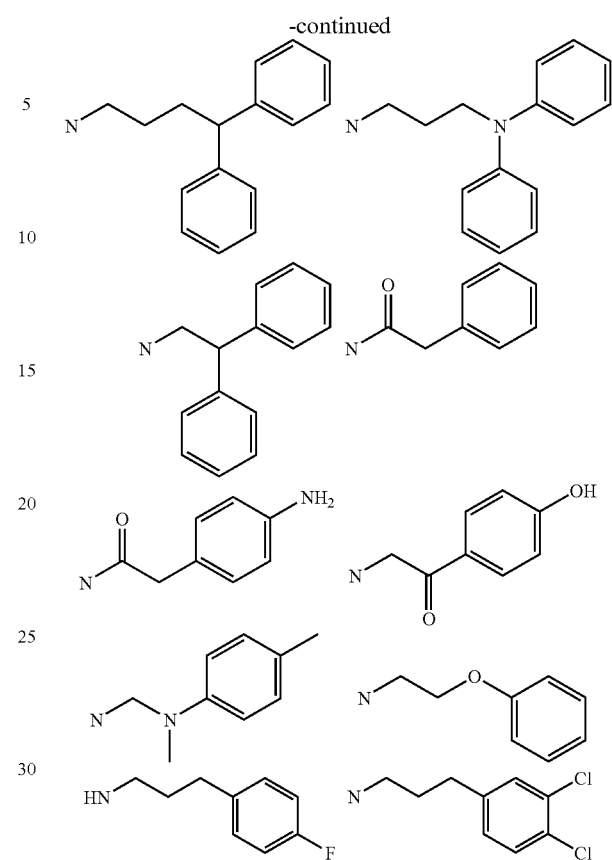
Concrete examples of N—(CH$_2$)$_m$—V—(CH$_2$)$_n$—R$^5$ are more preferably as follows.
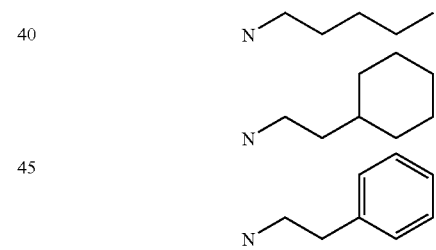
Concrete examples of preferable compounds that can be used in the present invention are shown in Tables 1 to 59 below, but the present invention is not limited thereto.
TABLE 1
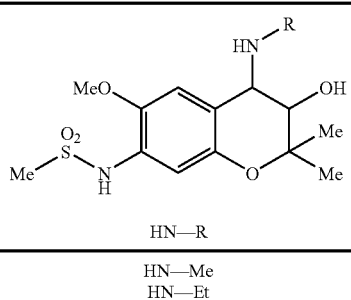
| HN—R |
|---|
| HN—Me |
| HN—Et |

TABLE 1-continued
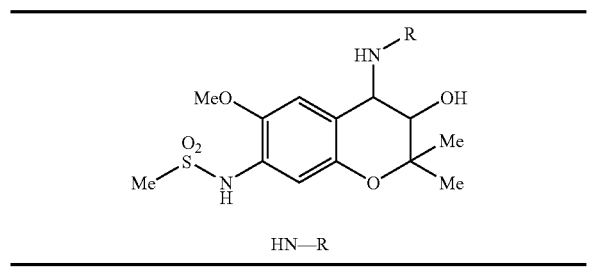
HN—R
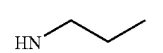
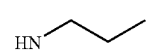
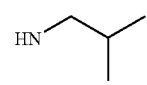
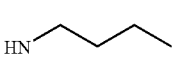
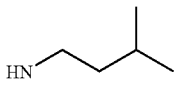
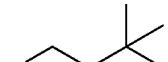
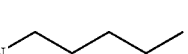
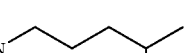
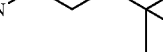
TABLE 1-continued
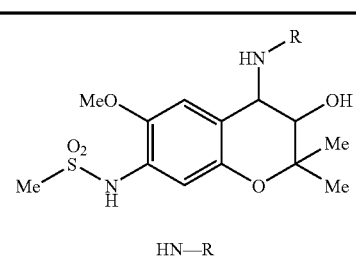
HN—R
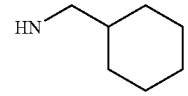
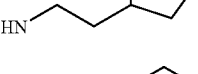
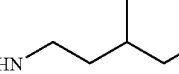

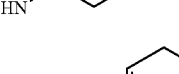
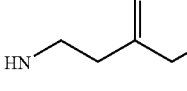
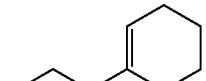
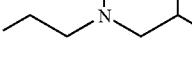
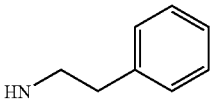

TABLE 1-continued
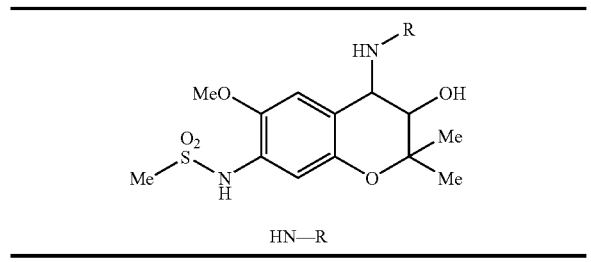
HN—R
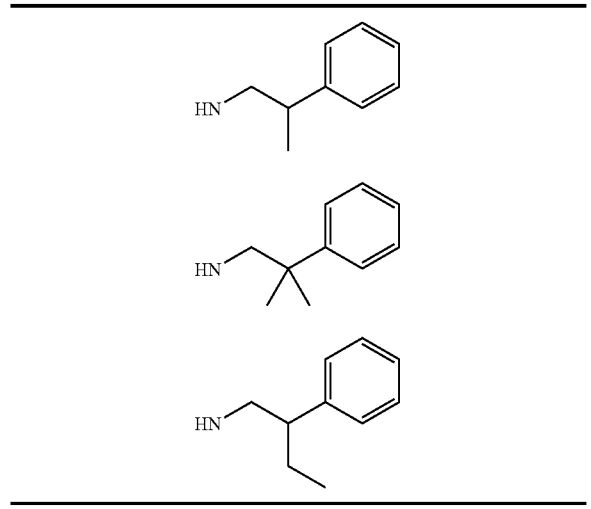
TABLE 2
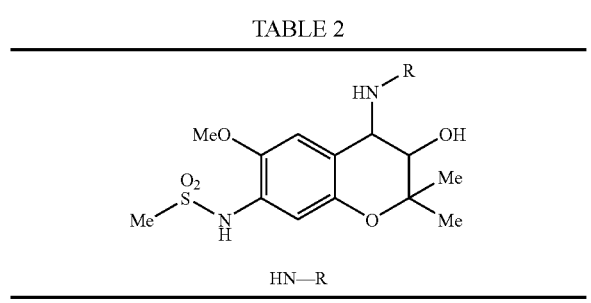
HN—R
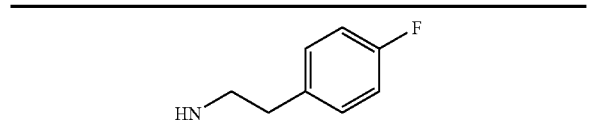
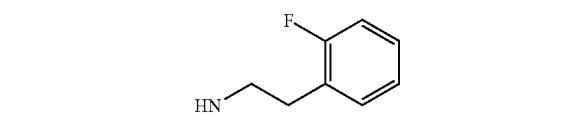
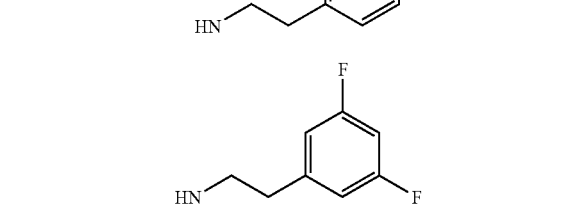
TABLE 2-continued
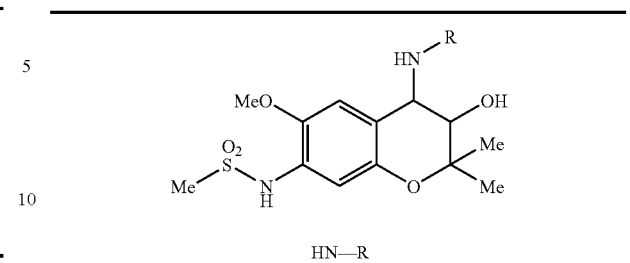
HN—R
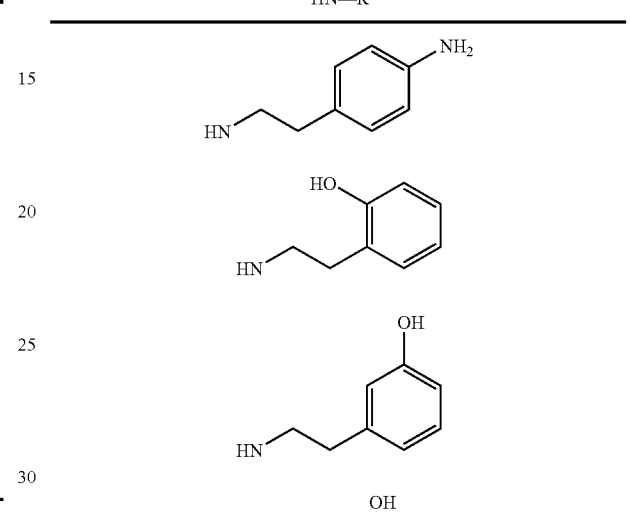
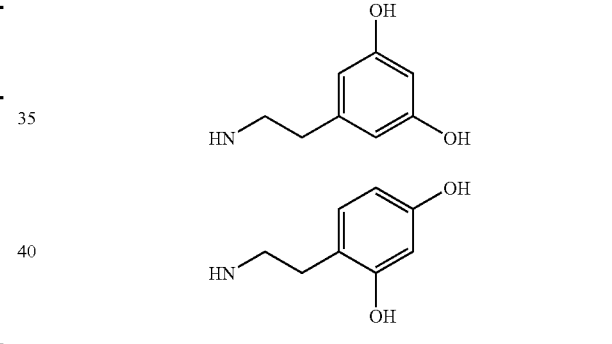
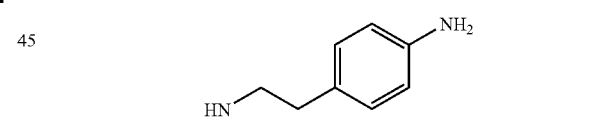
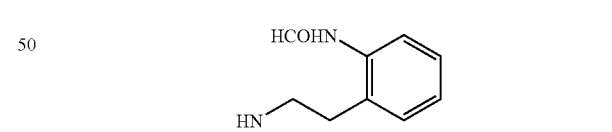
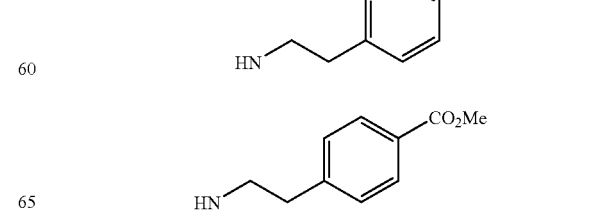

TABLE 2-continued
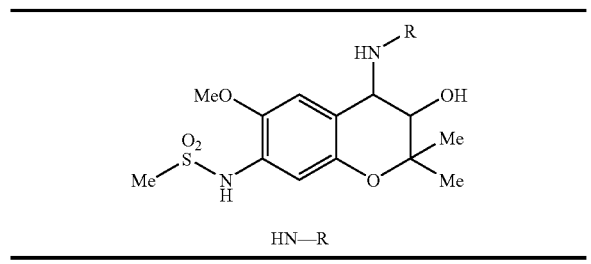
HN—R
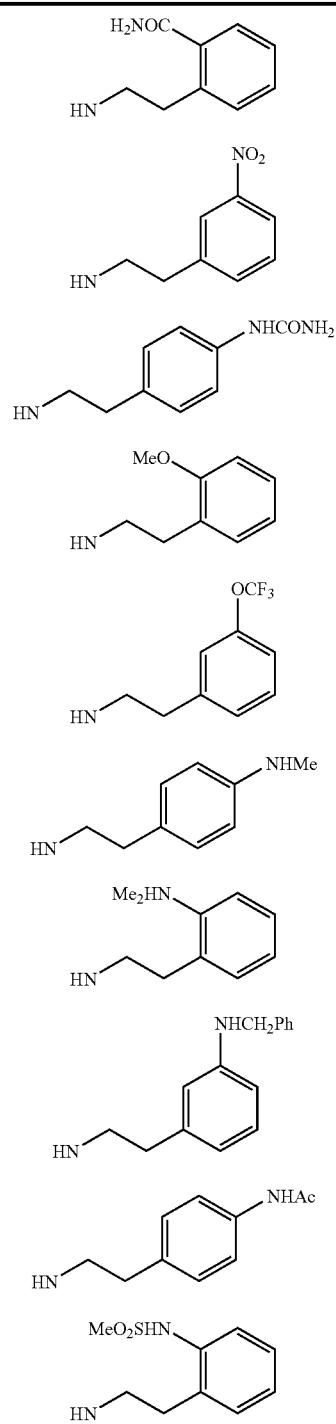
TABLE 2-continued
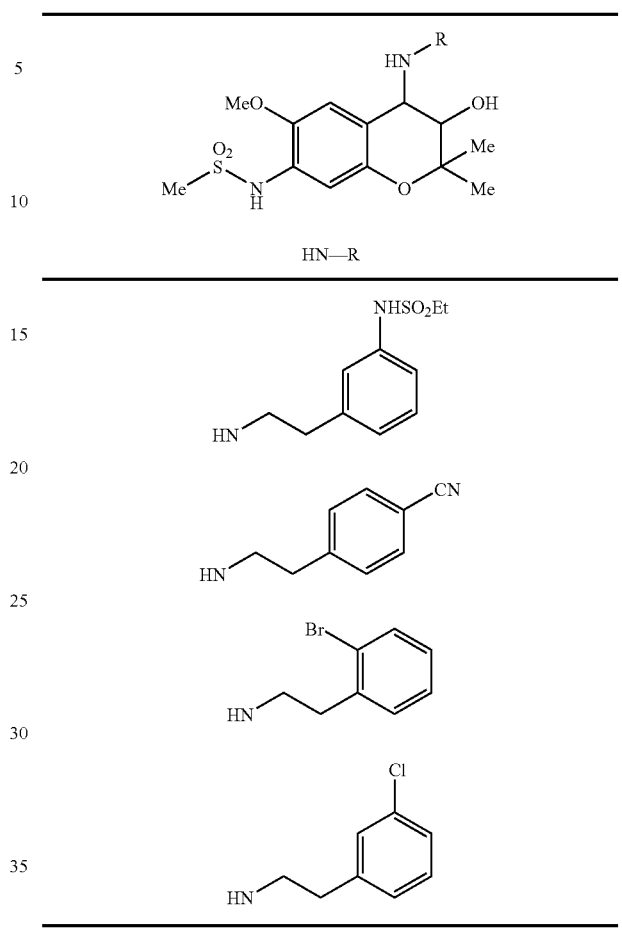
TABLE 3
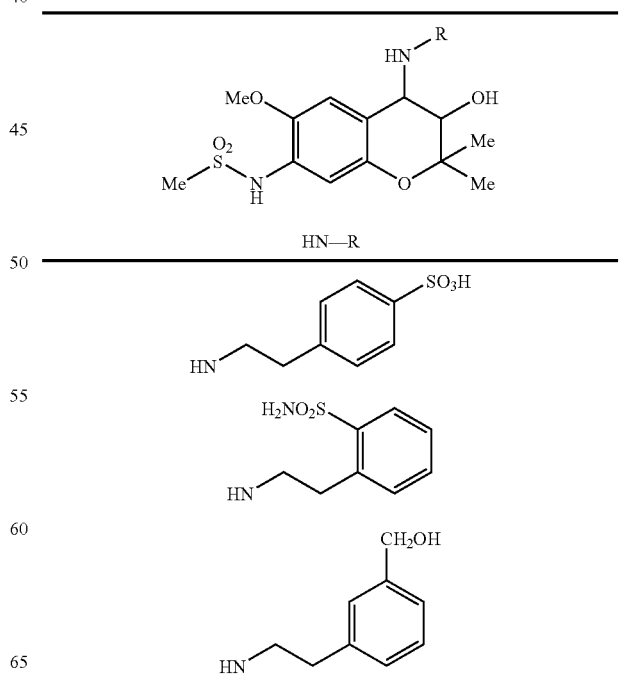

TABLE 3-continued
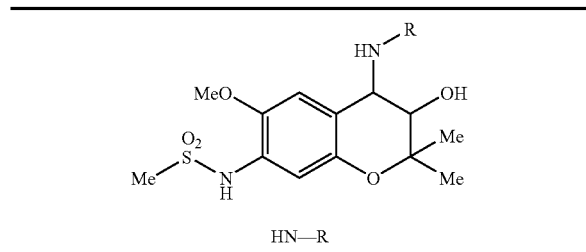
HN—R
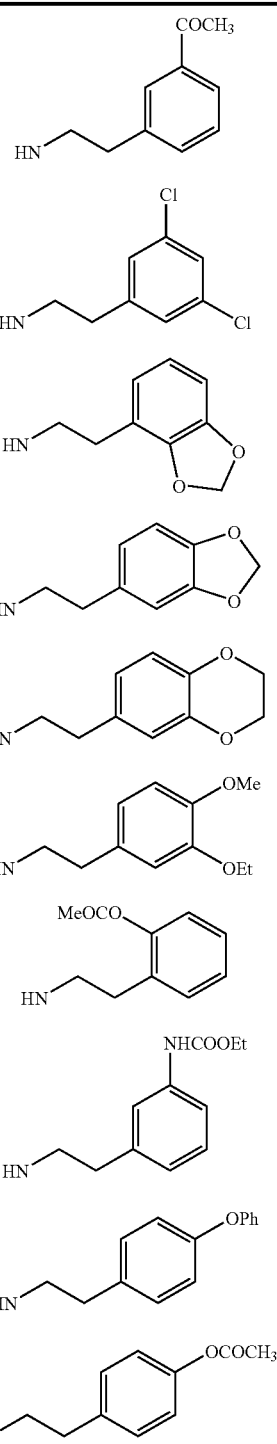
TABLE 3-continued
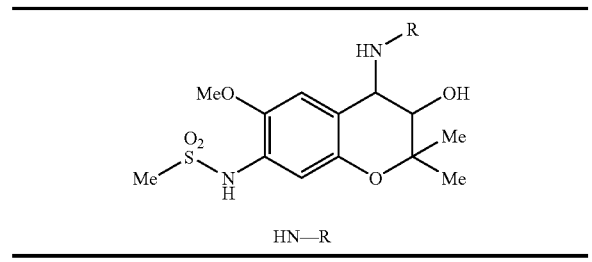
HN—R
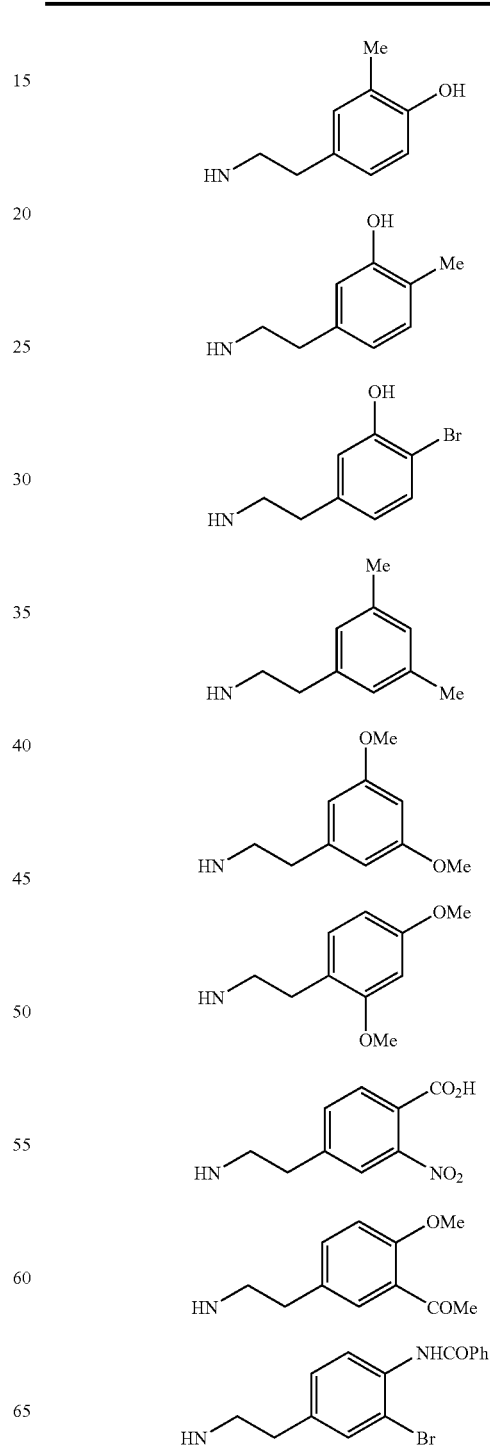

TABLE 3-continued
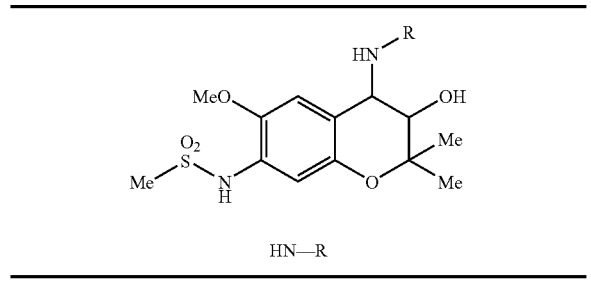
HN—R
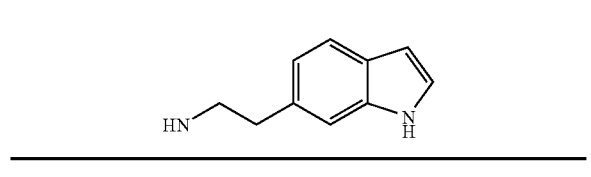
TABLE 4
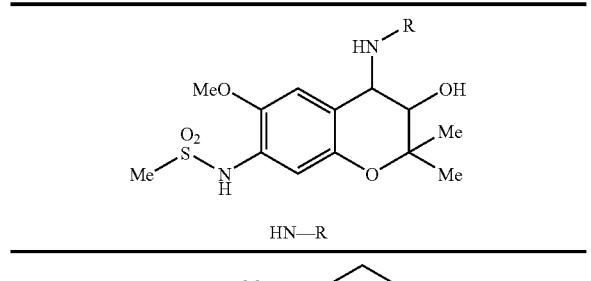
HN—R
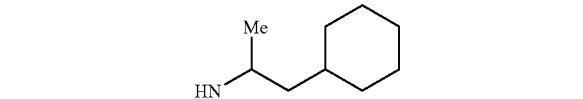
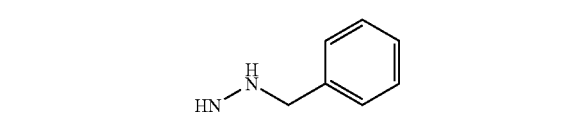
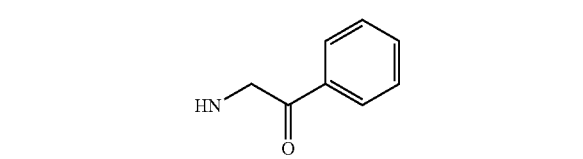
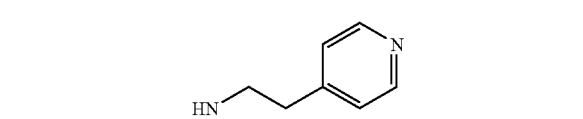
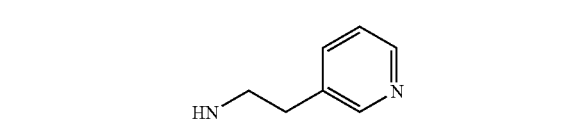
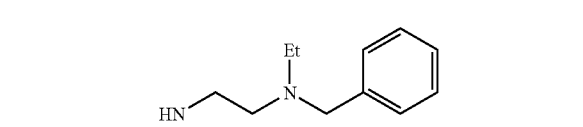
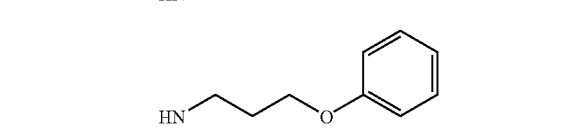
TABLE 4-continued
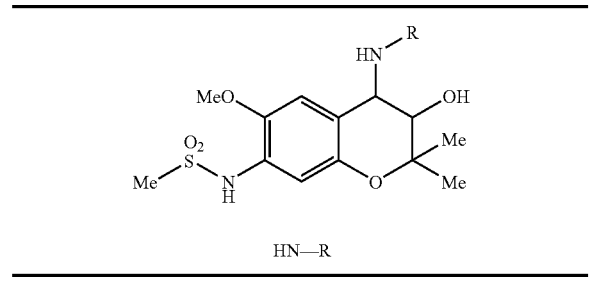
HN—R
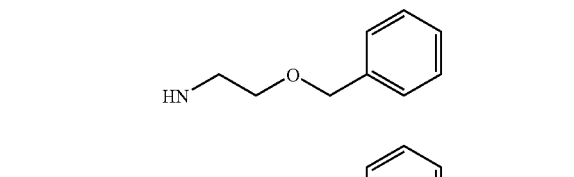
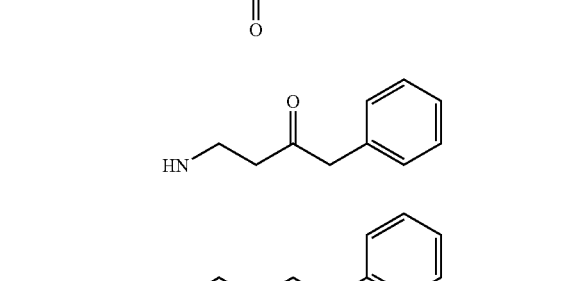
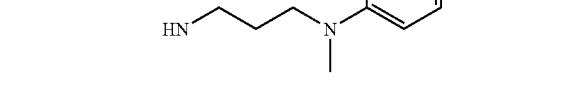
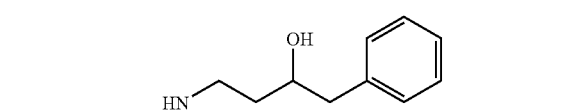
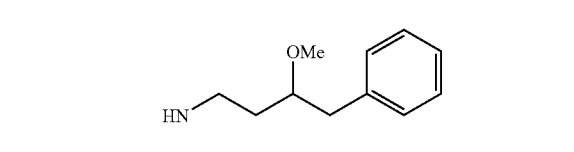
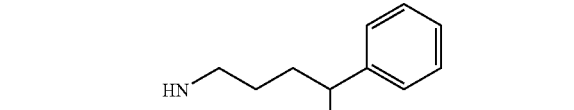
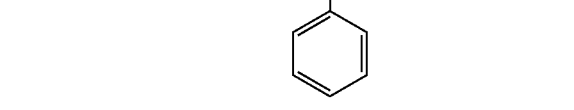
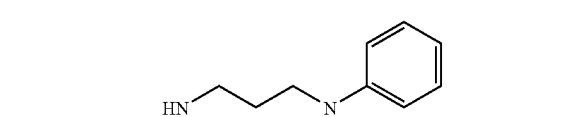
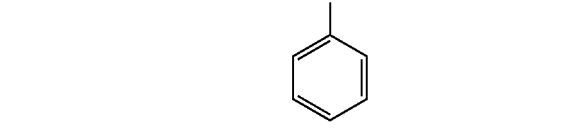

TABLE 4-continued
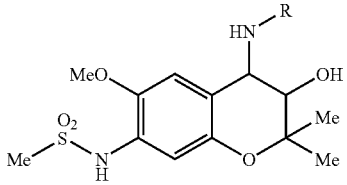
HN—R
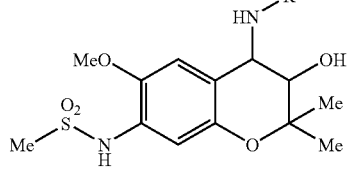
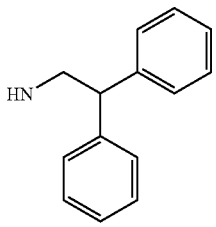
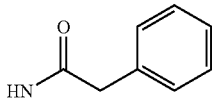
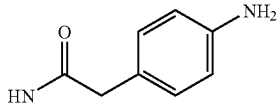
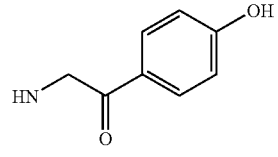
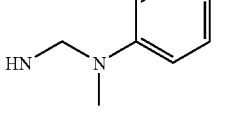
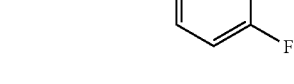
TABLE 5
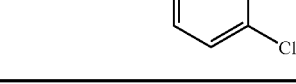
HN—R
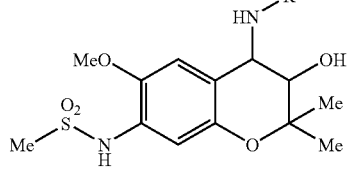
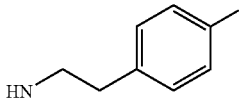
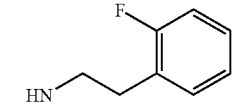
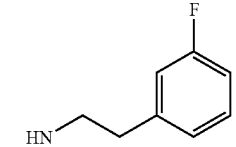
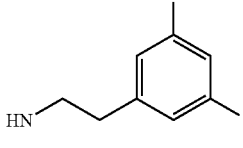
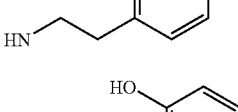
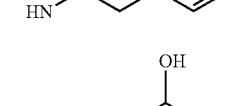
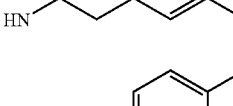

TABLE 5-continued
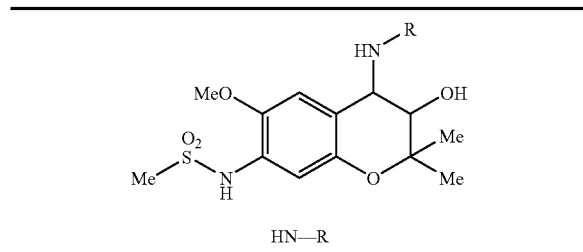
HN—R
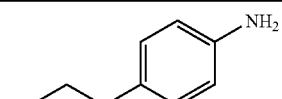
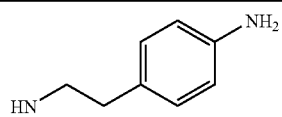
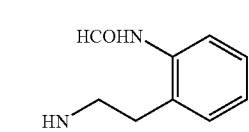
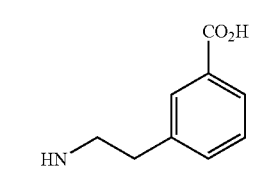
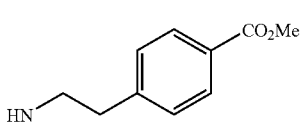
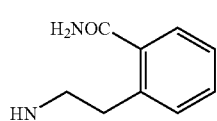
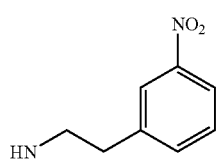
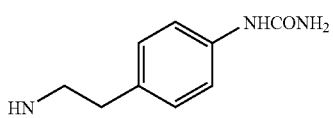
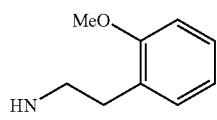
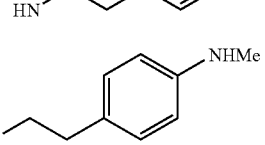
TABLE 5-continued
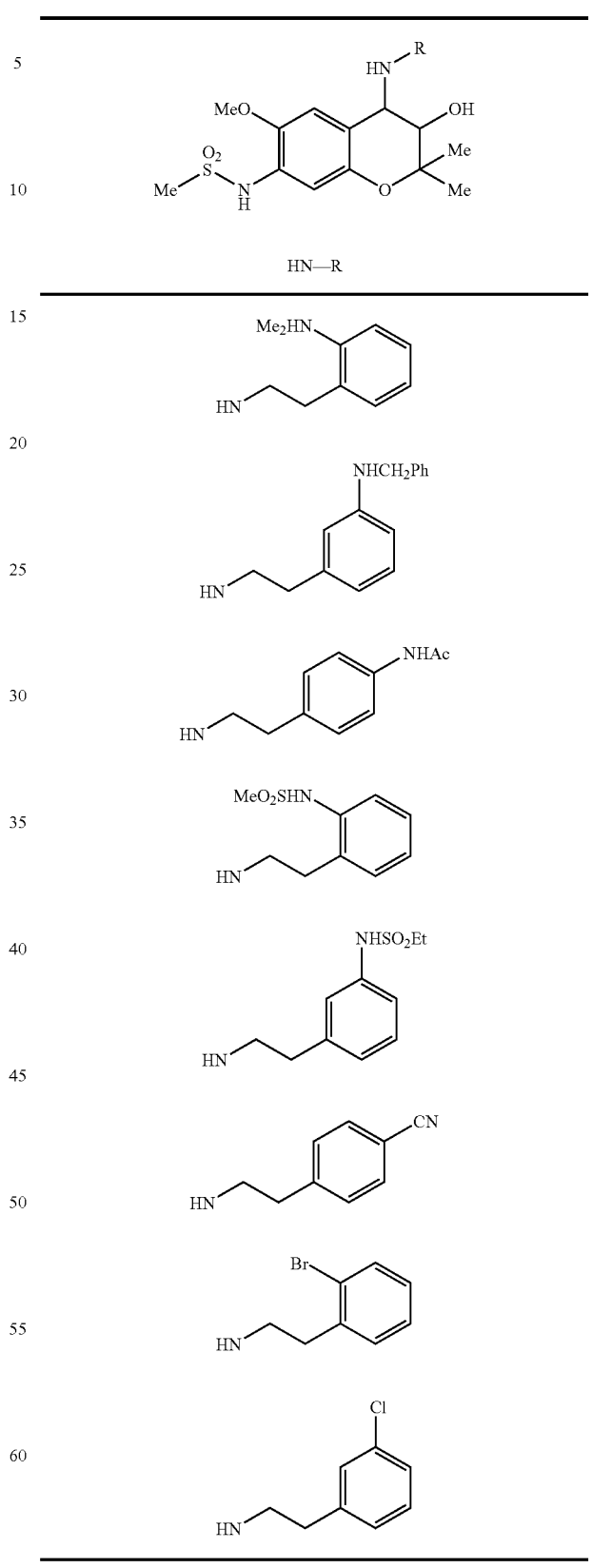

TABLE 6
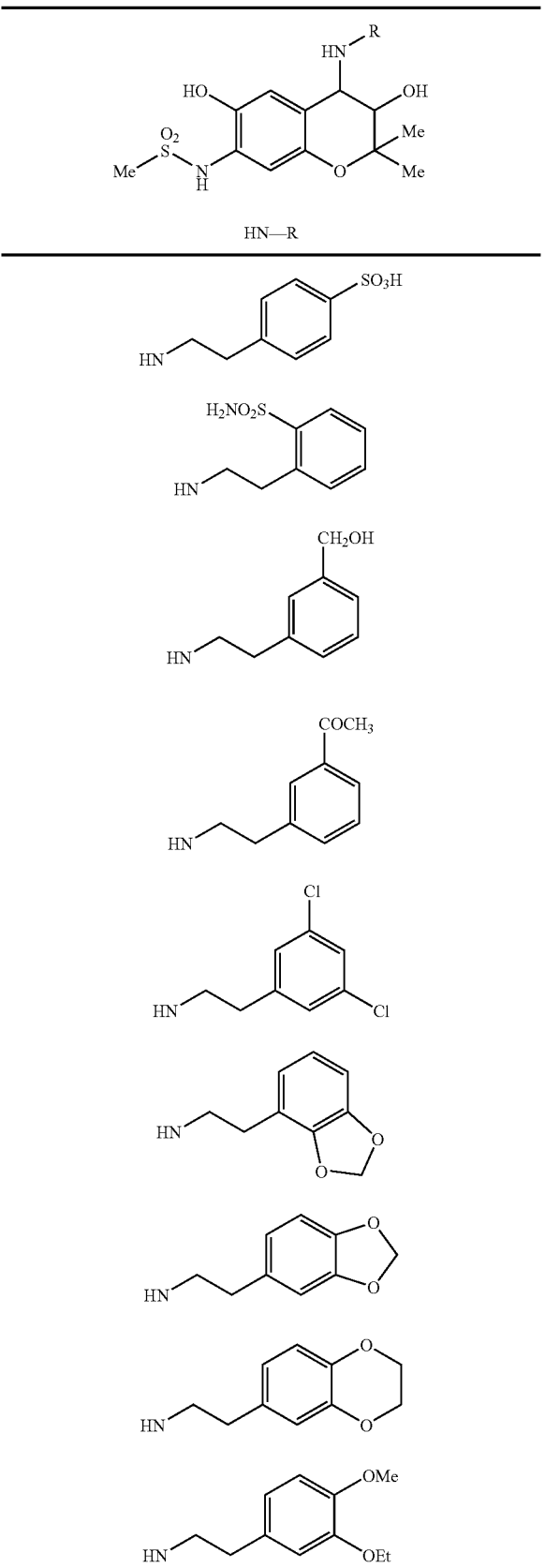
TABLE 6-continued
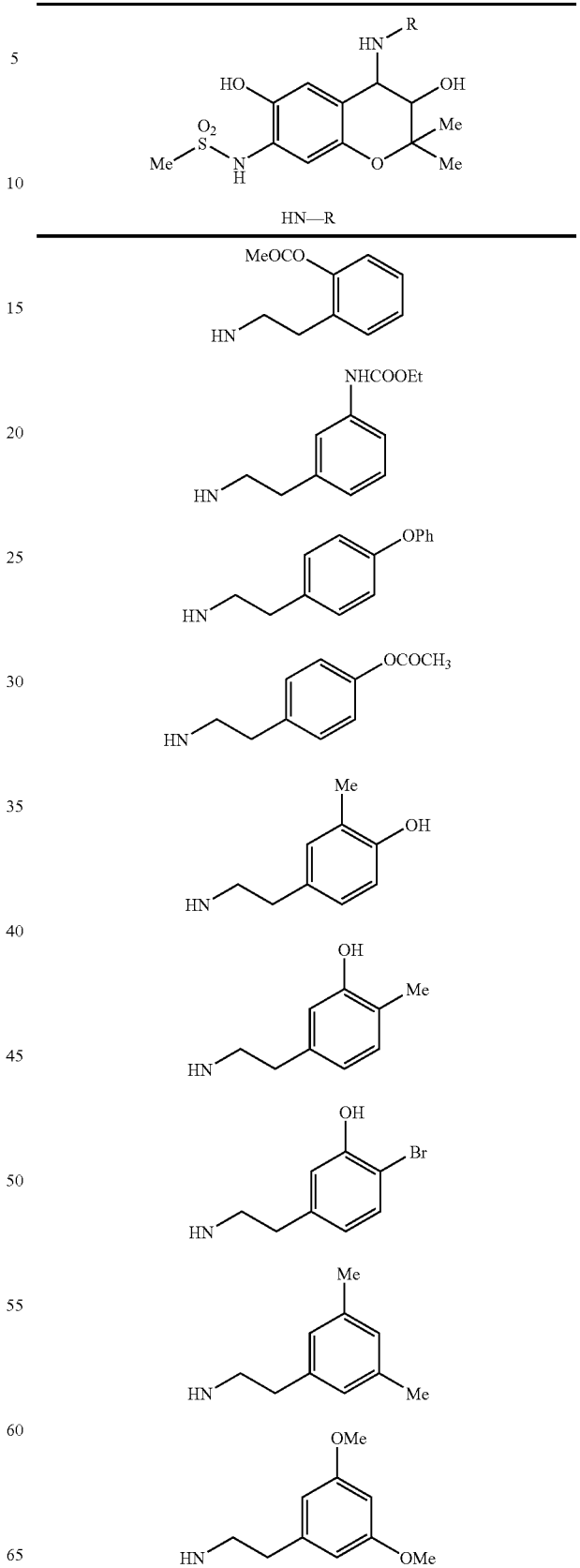

TABLE 6-continued

[Structure: chromane core with HN-R at position 4, OH at position 3, HO at position 6, MeSO2NH at position 7, and 2,2-dimethyl]

| HN—R |
|---|
| [2,4-dimethoxyphenethylamine] |
| [4-(2-aminoethyl)-2-nitrobenzoic acid] |
| [2-methoxy-5-(2-aminoethyl)benzaldehyde / COMe derivative] |
| [2-bromo-4-(2-aminoethyl)-N-benzoyl aniline] |
| [6-(2-aminoethyl)-1H-indole] |

TABLE 7

[Structure: same chromane core with HN-R at position 4, OH at position 3, HO at position 6, MeSO2NH at position 7, and 2,2-dimethyl]

| HN—R |
|---|
| [1-cyclohexyl-2-aminopropane] |
| [benzylhydrazine] |
| [2-amino-1-phenylethanone] |

TABLE 7-continued

[Structure: same chromane core]

| HN—R |
|---|
| [2-(pyridin-4-yl)ethylamine] |
| [2-(pyridin-3-yl)ethylamine] |
| [N-benzyl-N-ethyl ethylenediamine] |
| [3-phenoxypropylamine] |
| [2-(benzyloxy)ethylamine] |
| [1-amino-4-phenylbutan-2-one] |
| [1-amino-3-phenylpropan-2-one / 4-amino-1-phenylbutan-2-one] |
| [N-methyl-N-phenyl-1,3-propanediamine] |
| [1-amino-3-phenyl-2-propanol (with OH)] |
| [3-amino-1-methoxy-1-phenylpropane / OMe derivative] |

TABLE 7-continued
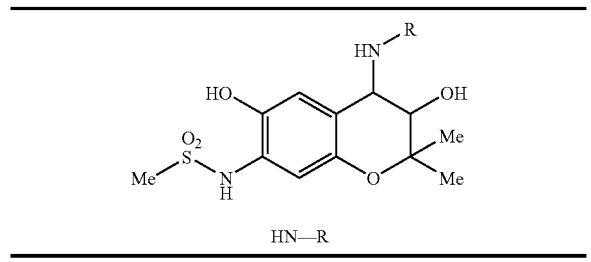
| HN—R |
|---|
| 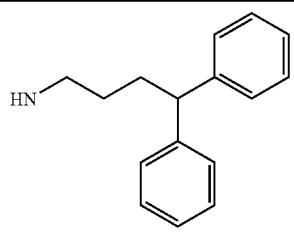 |
| 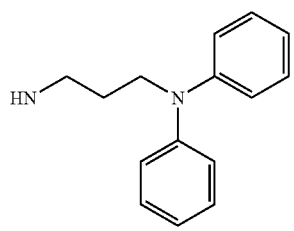 |
| 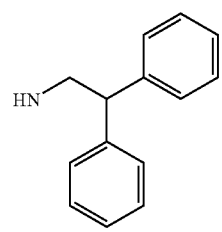 |
| 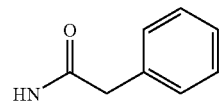 |
| 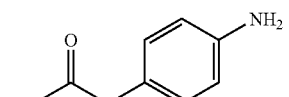 |
| 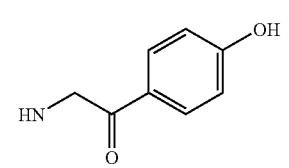 |
| 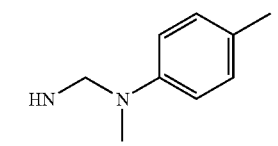 |
| 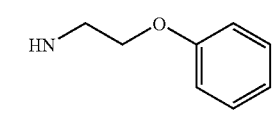 |
TABLE 7-continued
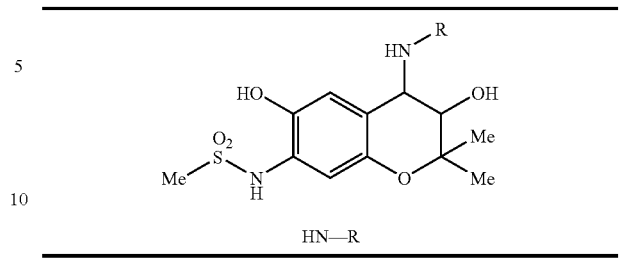
| HN—R |
|---|
| 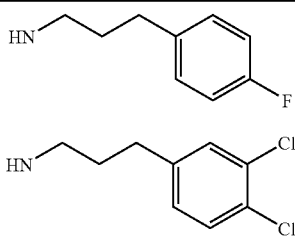 |
| 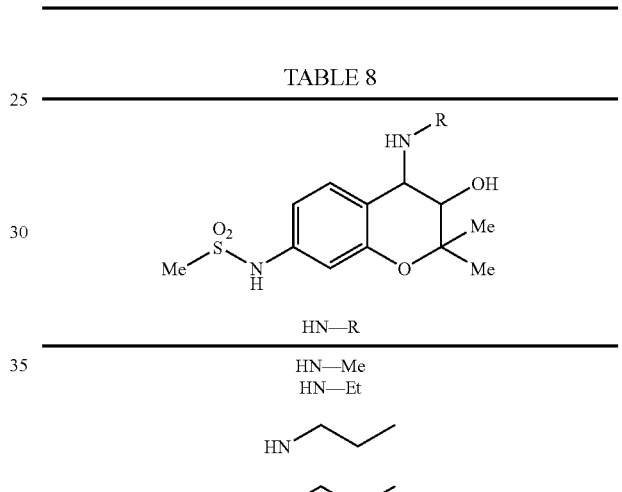 |
TABLE 8
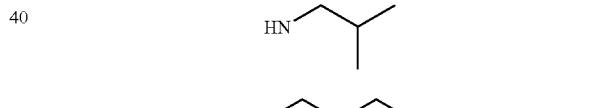
| HN—R |
|---|
| HN—Me |
| HN—Et |
| 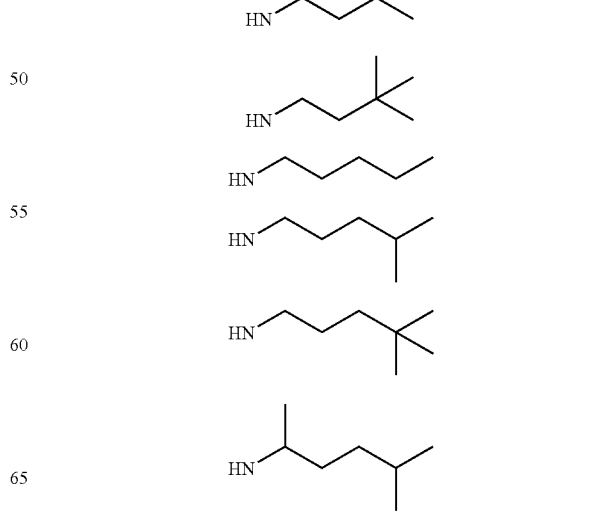 |

TABLE 8-continued
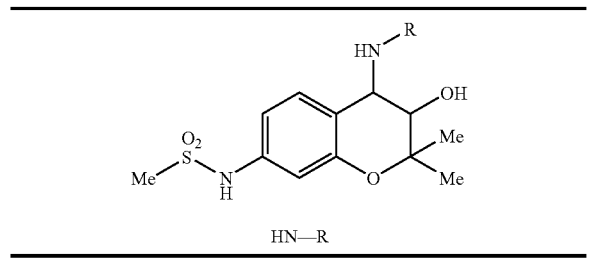
HN—R
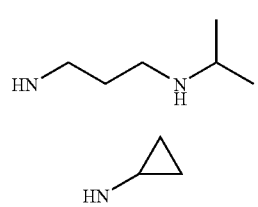
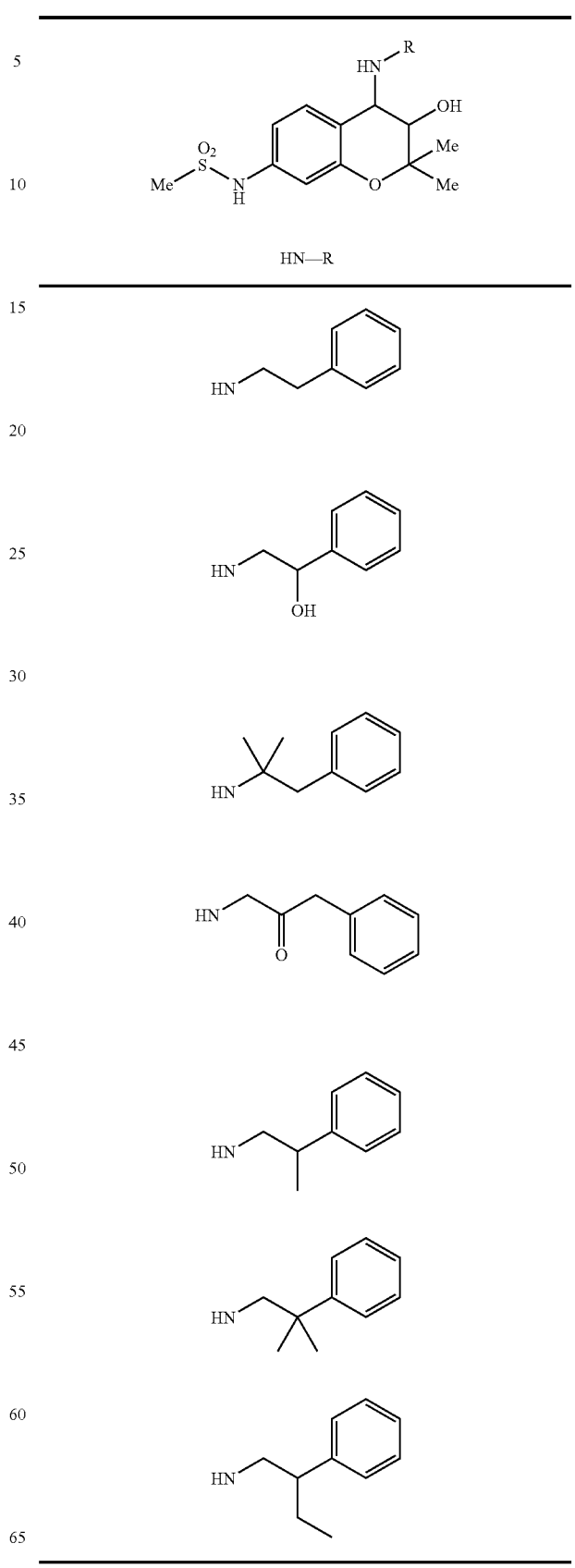

TABLE 9
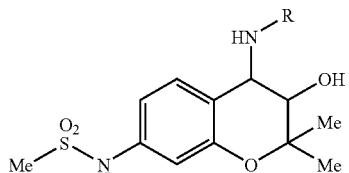
HN—R
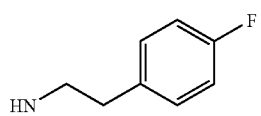
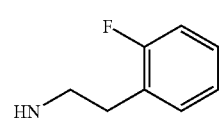
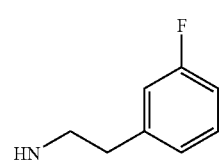
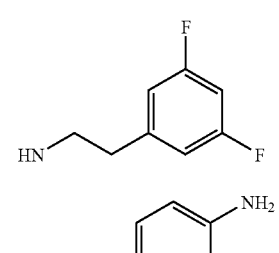
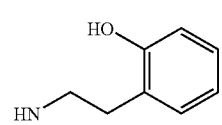
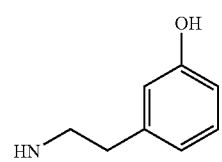
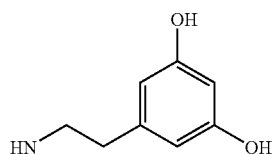
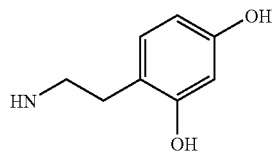
TABLE 9-continued
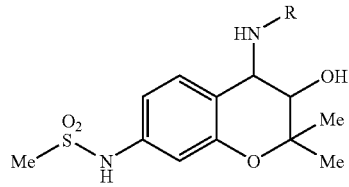
HN—R
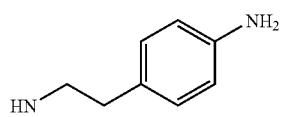
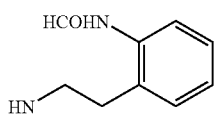
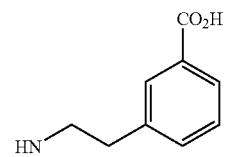
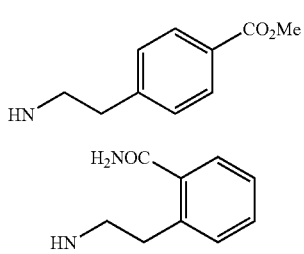
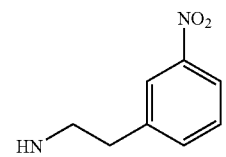
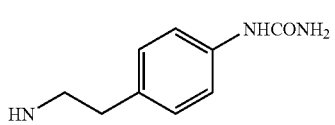
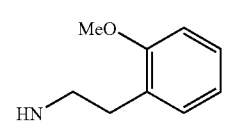
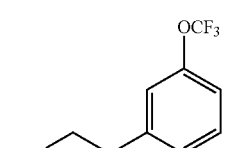
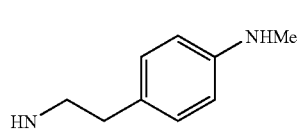

TABLE 9-continued

[Structure: chroman-4-amine with 7-methylsulfonamido, 3-OH, 2,2-dimethyl, 4-NHR]

HN—R

- 2-(NMe₂)-phenethylamine
- 3-(NHCH₂Ph)-phenethylamine
- 4-(NHAc)-phenethylamine
- 2-(NHSO₂Me)-phenethylamine
- 3-(NHSO₂Et)-phenethylamine
- 4-CN-phenethylamine
- 2-Br-phenethylamine
- 3-Cl-phenethylamine

TABLE 10

[Structure: chroman-4-amine with 7-methylsulfonamido, 3-OH, 2,2-dimethyl, 4-NHR]

HN—R

- 4-(SO₃H)-phenethylamine
- 2-(SO₂NH₂)-phenethylamine
- 3-(CH₂OH)-phenethylamine
- 3-(COCH₃)-phenethylamine
- 3,5-dichloro-phenethylamine
- 2-(2,3-methylenedioxyphenyl)ethylamine (benzo[1,3]dioxole)
- 2-(3,4-methylenedioxyphenyl)ethylamine
- 2-(2,3-dihydro-1,4-benzodioxin-6-yl)ethylamine
- 2-(4-methoxy-3-ethoxyphenyl)ethylamine TABLE 10-continued
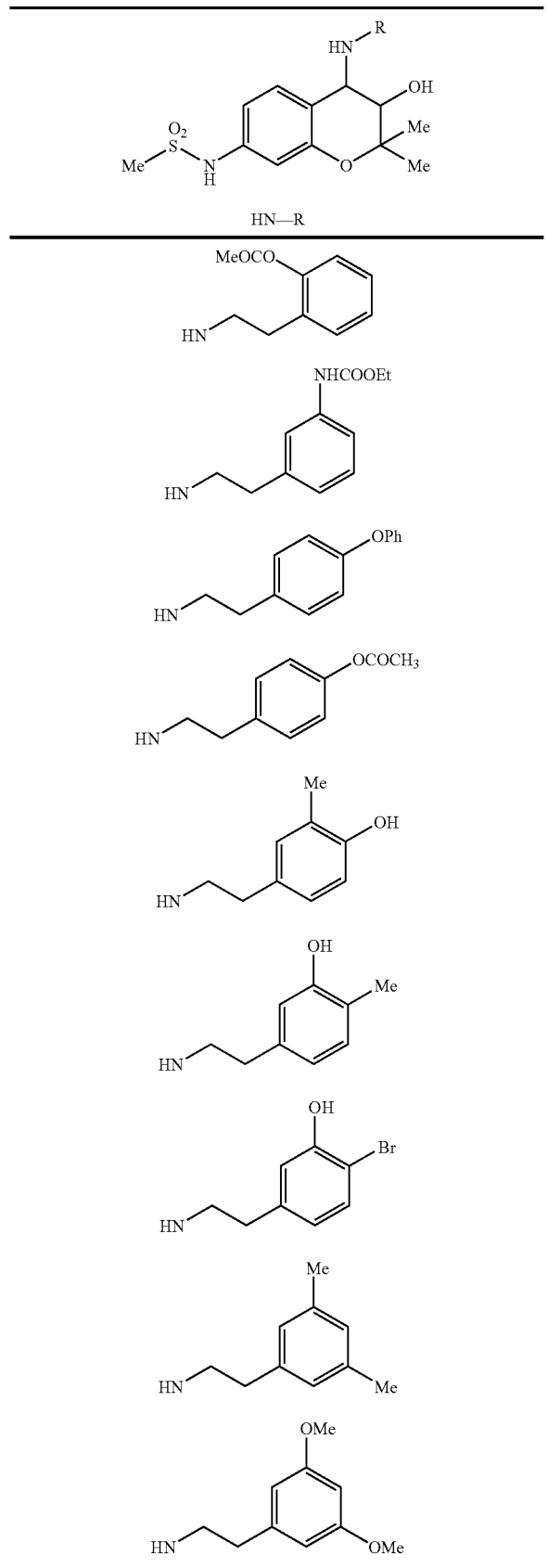
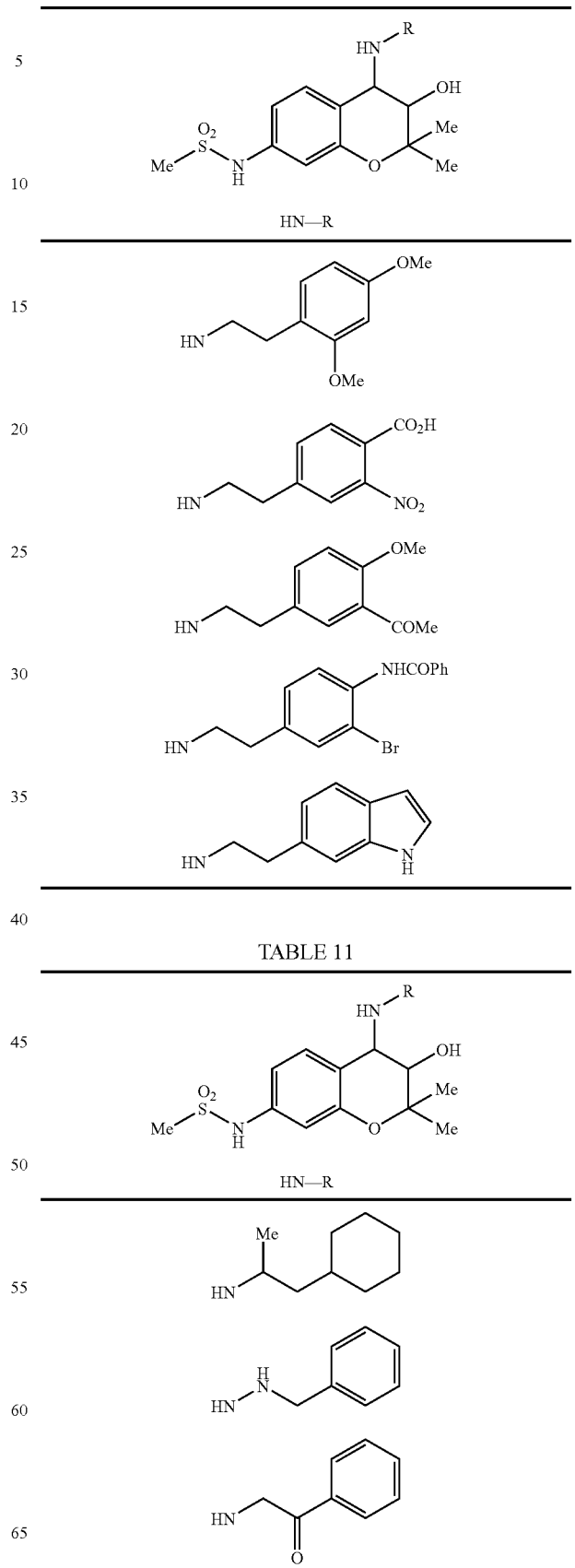

TABLE 11-continued
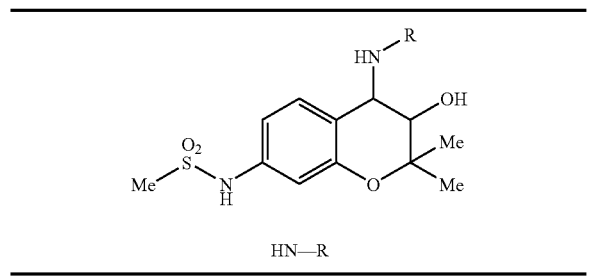
HN—R
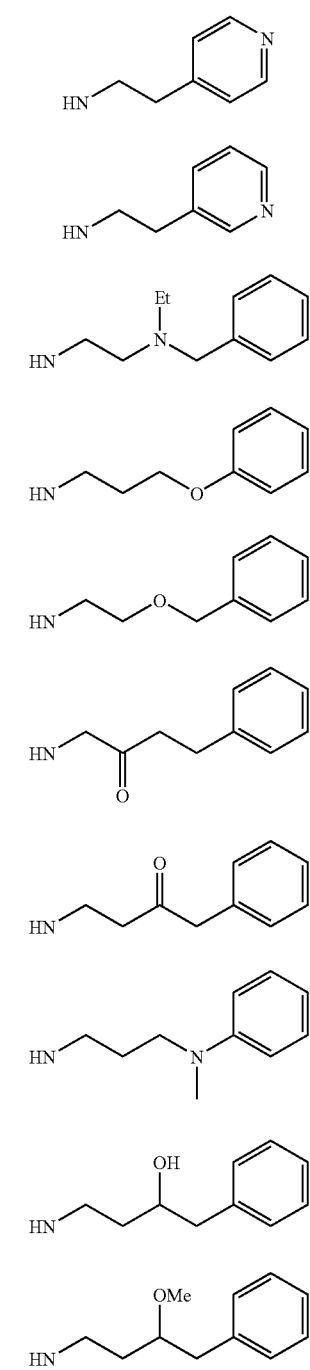
TABLE 11-continued
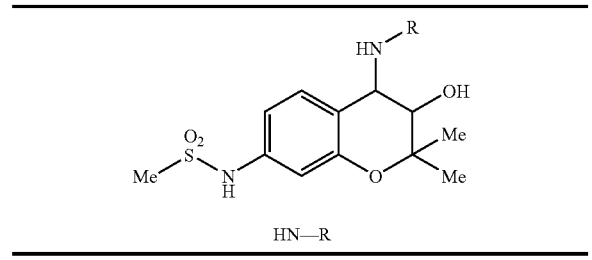
HN—R
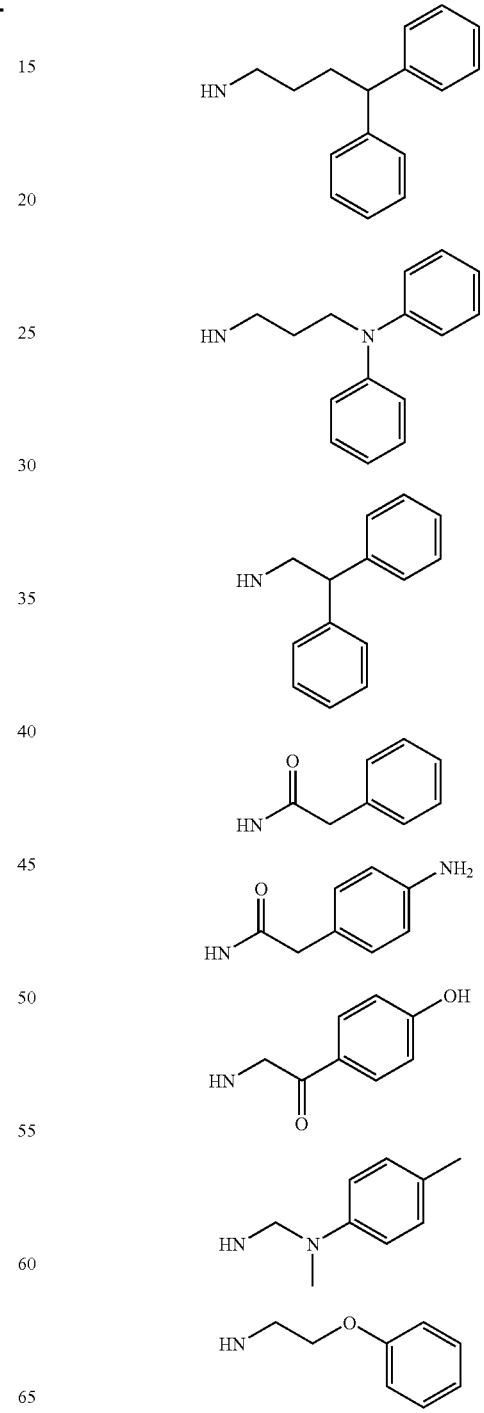

TABLE 11-continued
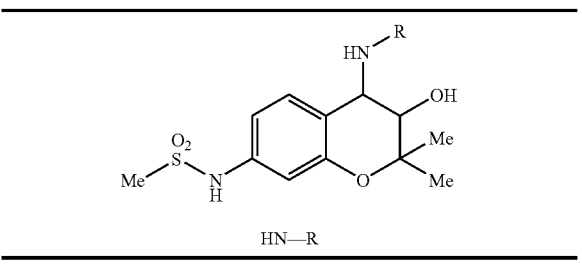
| HN—R |
|---|
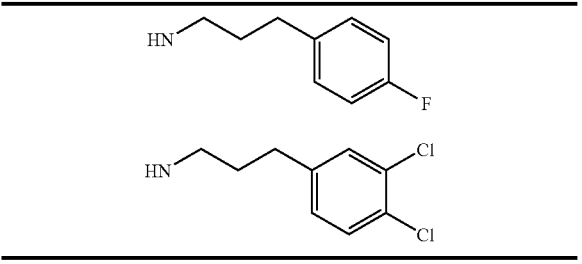
TABLE 12
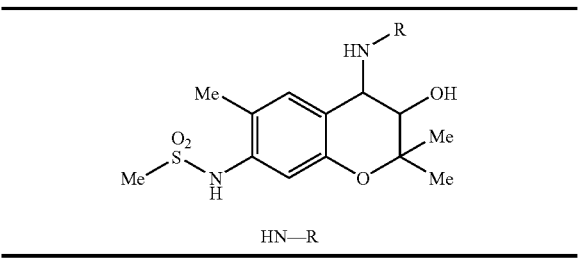
| HN—R |
|---|
| HN—Me |
| HN—Et |
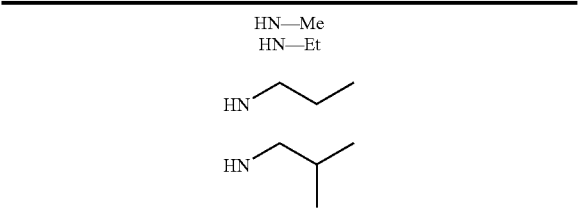
TABLE 12-continued
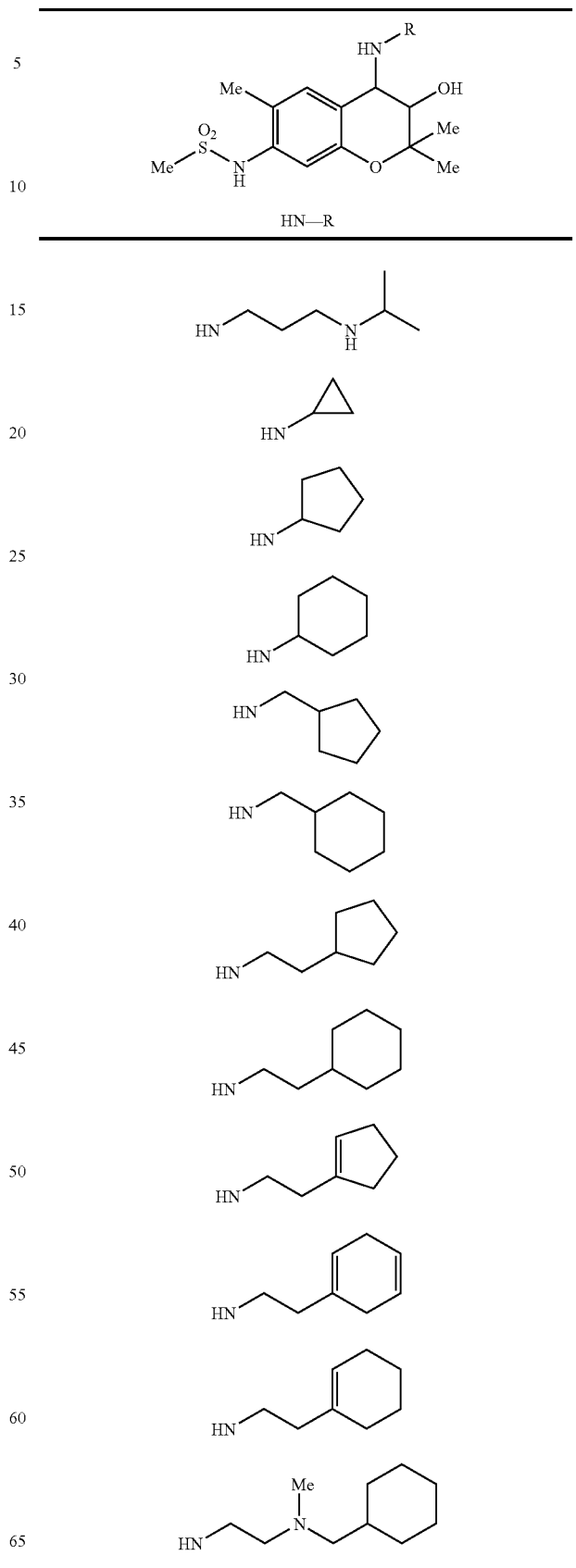

TABLE 12-continued
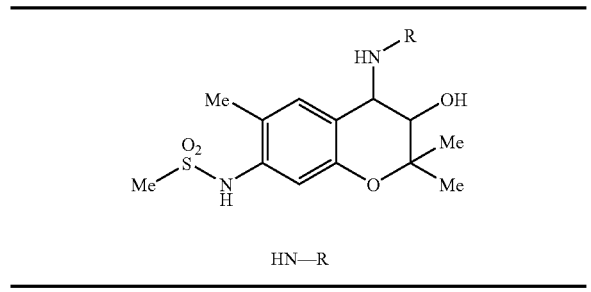
HN—R
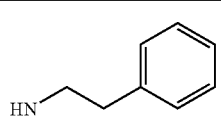
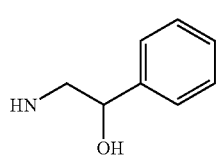
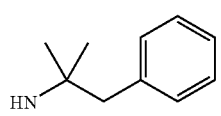
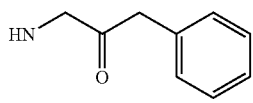
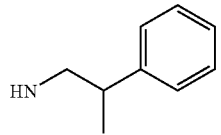
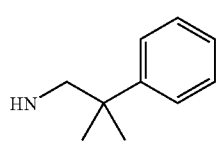
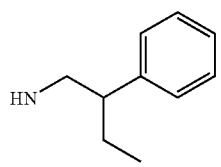
TABLE 13
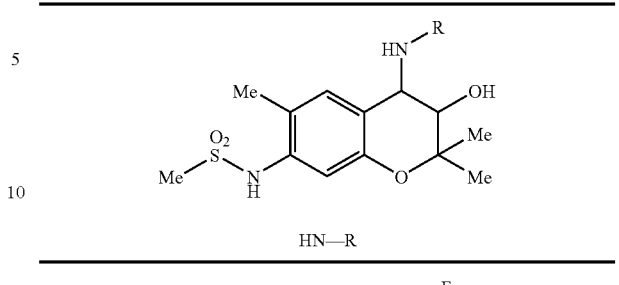
HN—R
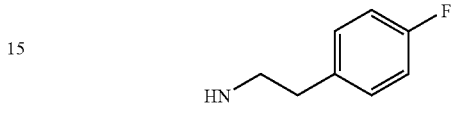
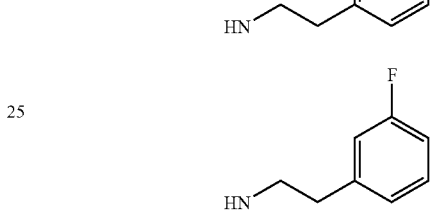
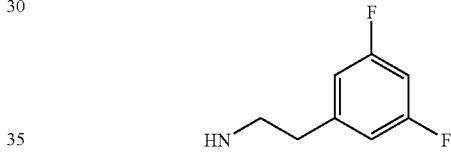
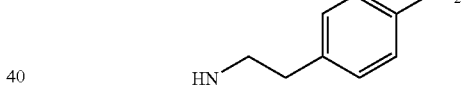
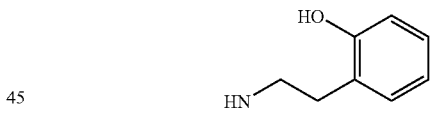
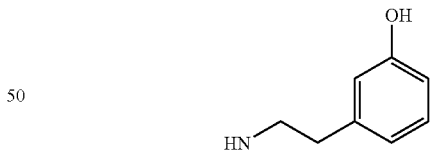
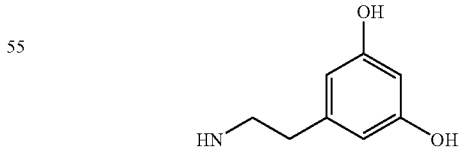
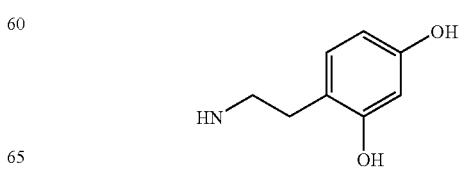

TABLE 13-continued
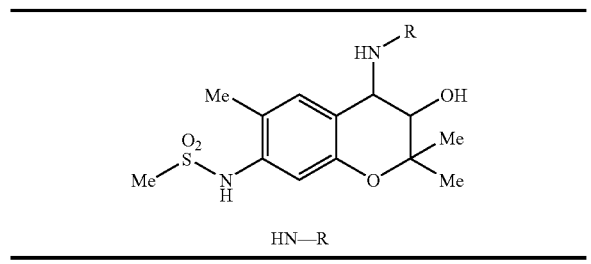
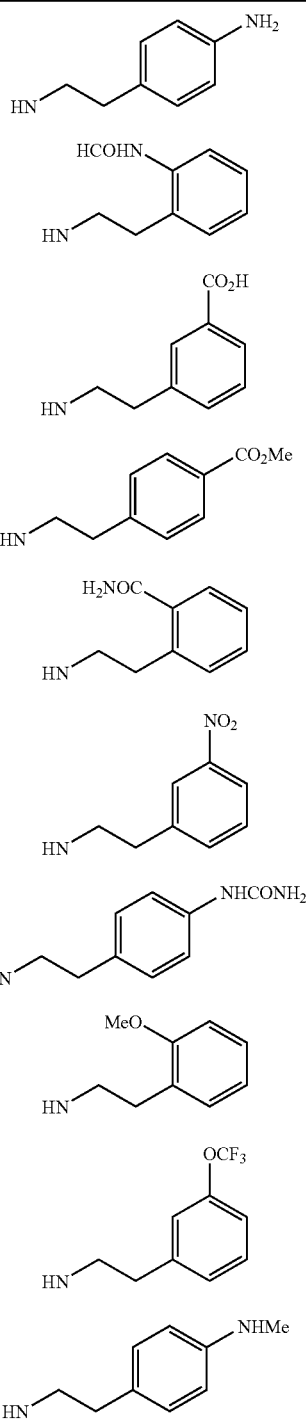
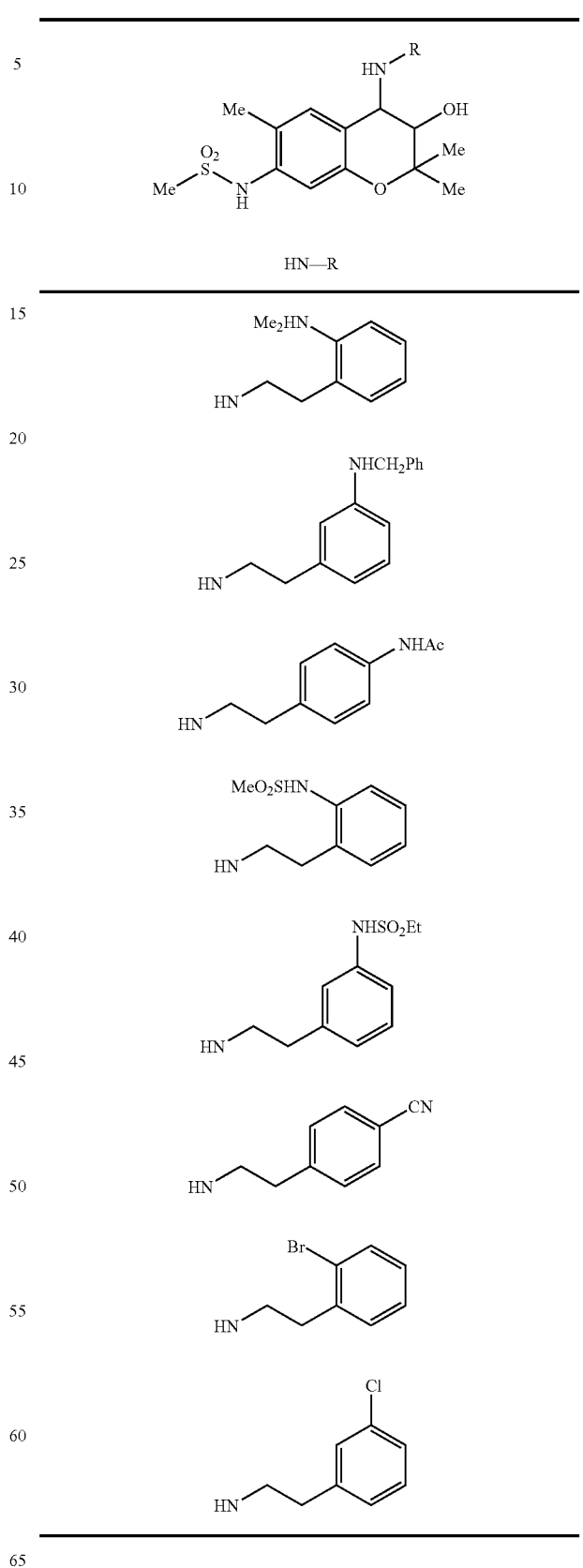

TABLE 14
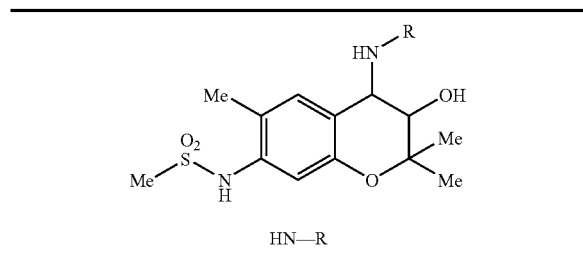
| HN—R |
|---|
| 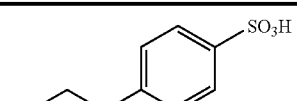 |
| 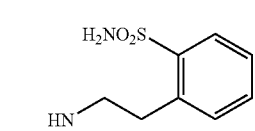 |
| 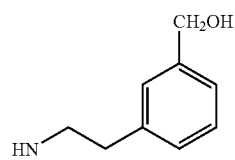 |
| 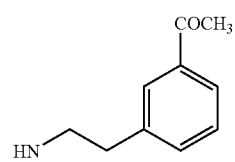 |
| 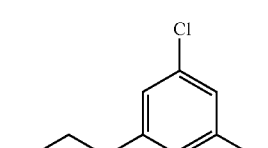 |
| 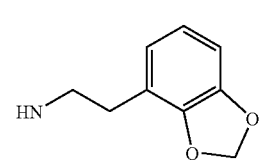 |
| 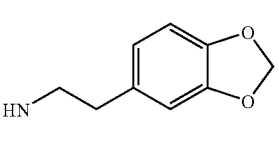 |
| 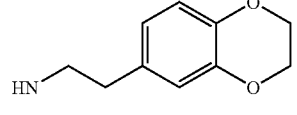 |
| 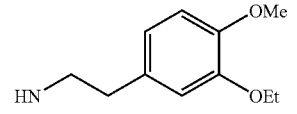 |
| 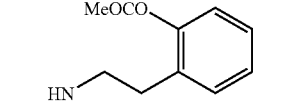 |
TABLE 14-continued
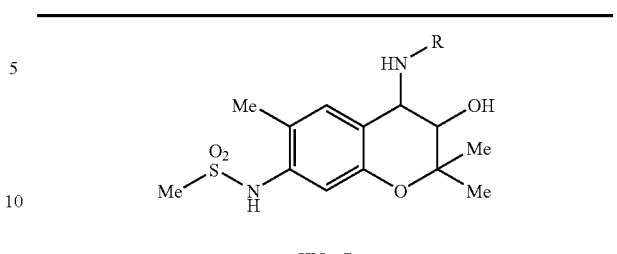
| HN—R |
|---|
| 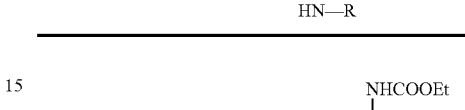 |
| 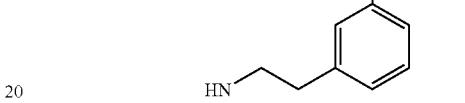 |
| 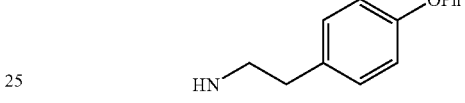 |
| 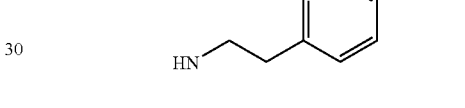 |
| 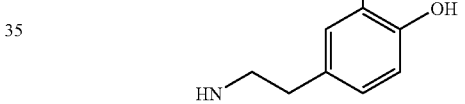 |
| 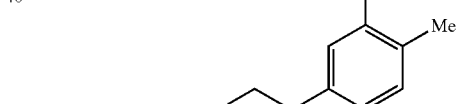 |
|  |
| 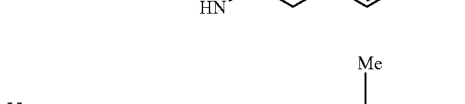 |
| 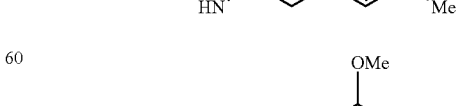 |
| 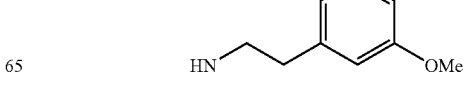 |

TABLE 14-continued
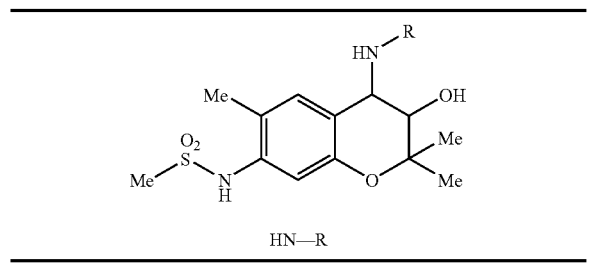
HN—R
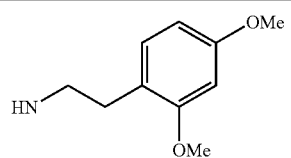
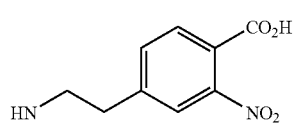
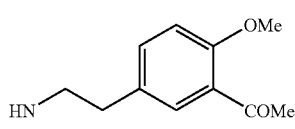
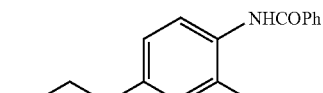
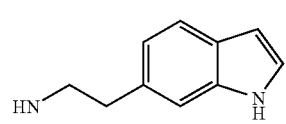
TABLE 15
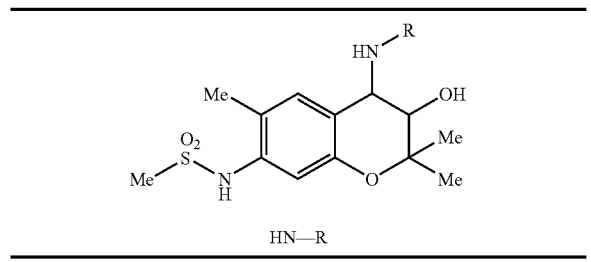
HN—R
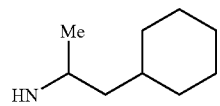
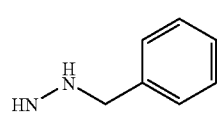
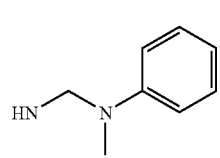
TABLE 15-continued
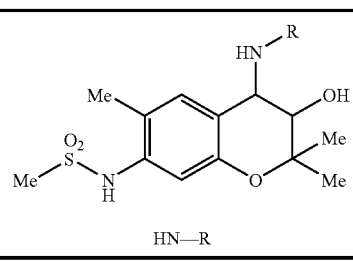
HN—R
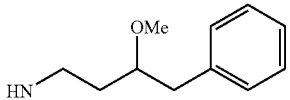
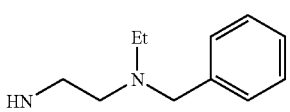
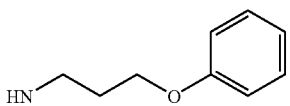
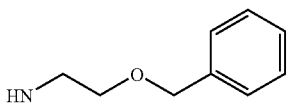
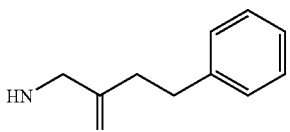
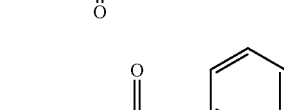
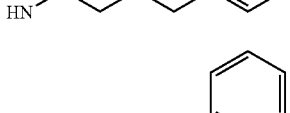
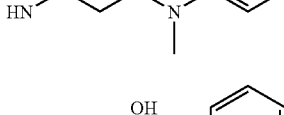
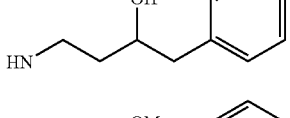
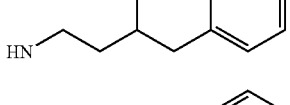
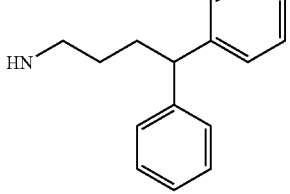

TABLE 15-continued
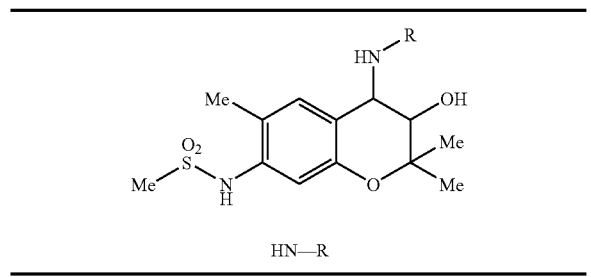
HN—R
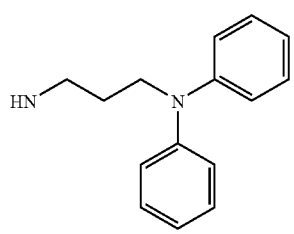
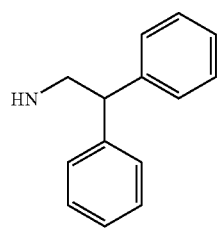
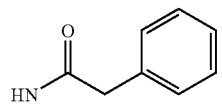
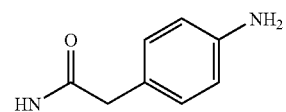
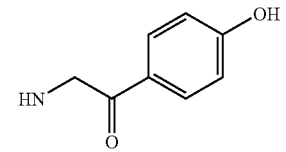
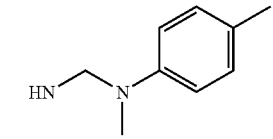
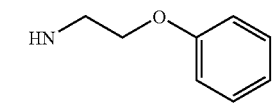
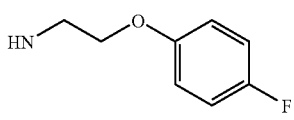
TABLE 15-continued
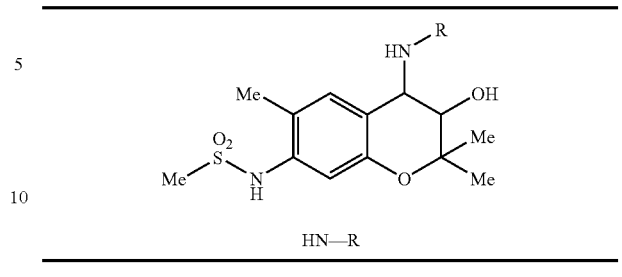
HN—R
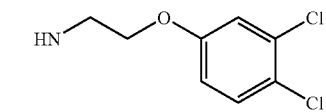
TABLE 16
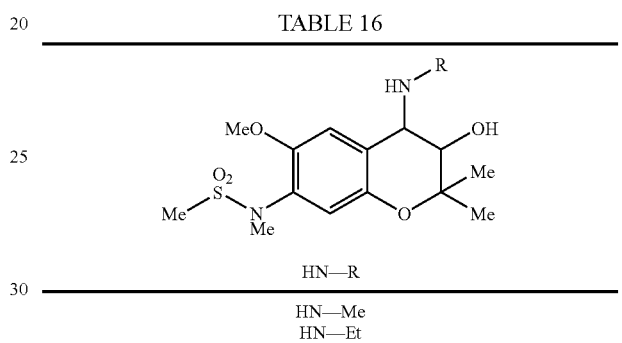
HN—R
HN—Me
HN—Et
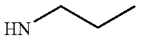
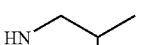
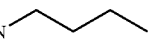
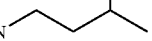
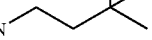
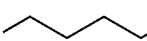

TABLE 16-continued
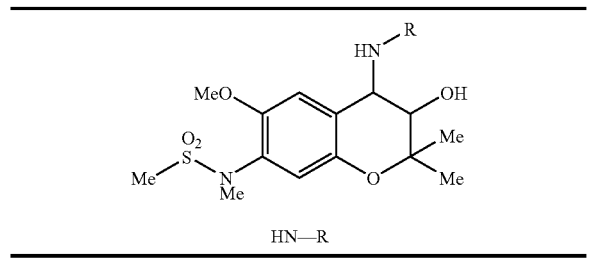
HN—R
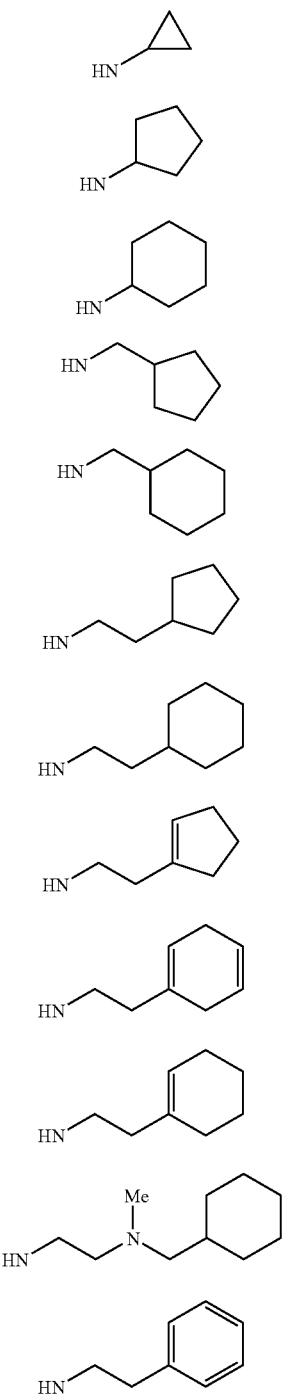
TABLE 16-continued
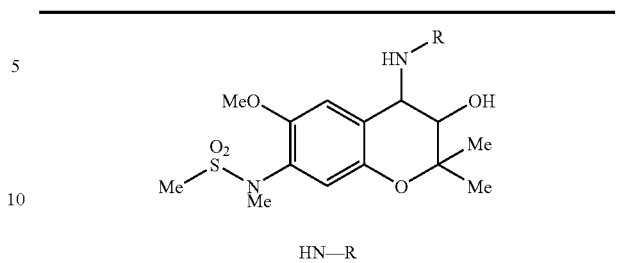
HN—R
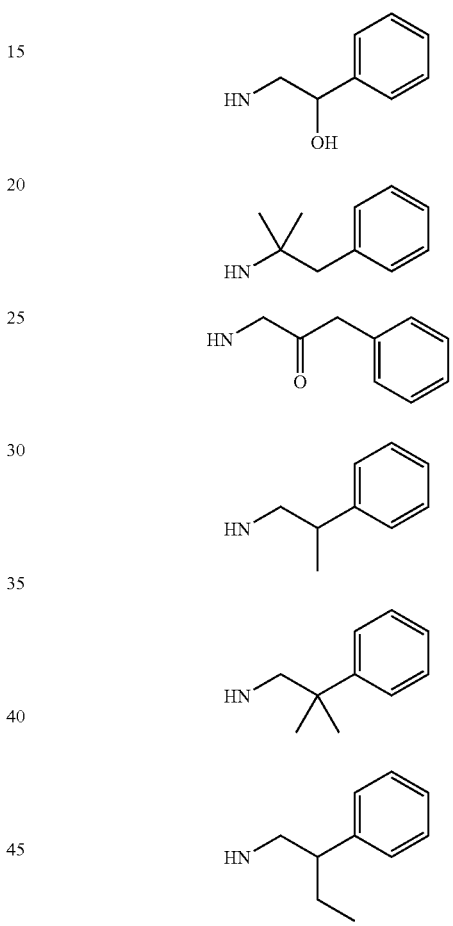
TABLE 17
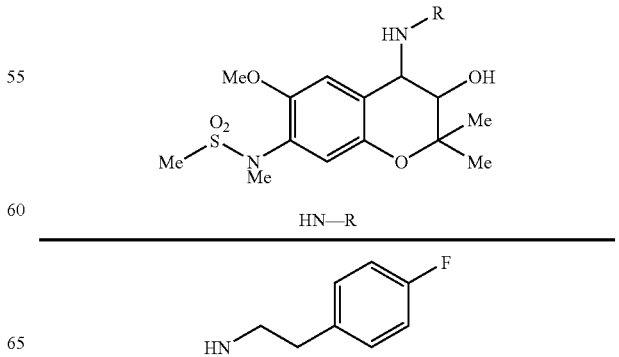
HN—R TABLE 17-continued

TABLE 17-continued

[Structure: chroman with HN-R at 4-position, OH at 3-position, 2,2-dimethyl, 6-OMe, 7-N(Me)SO2Me]

HN—R

- HN-CH2CH2-C6H4(3-NHCH2Ph)
- HN-CH2CH2-C6H4(4-NHAc)
- HN-CH2CH2-C6H4(2-NHSO2Me)
- HN-CH2CH2-C6H4(3-NHSO2Et)
- HN-CH2CH2-C6H4(4-CN)
- HN-CH2CH2-C6H4(2-Br)
- HN-CH2CH2-C6H4(3-Cl)

TABLE 18

[Structure: chroman with HN-R at 4-position, OH at 3-position, 2,2-dimethyl, 6-OMe, 7-N(Me)SO2Me]

HN—R

- HN-CH2CH2-C6H4(4-SO3H)
- HN-CH2CH2-C6H4(2-SO2NH2)
- HN-CH2CH2-C6H4(3-CH2OH)
- HN-CH2CH2-C6H4(3-COCH3)
- HN-CH2CH2-C6H3(3,5-Cl2)
- HN-CH2CH2-(benzo[1,3]dioxol-4-yl)
- HN-CH2CH2-(benzo[1,3]dioxol-5-yl)
- HN-CH2CH2-(2,3-dihydrobenzo[1,4]dioxin-6-yl)
- HN-CH2CH2-C6H3(4-OMe, 3-OEt)
- HN-CH2CH2-C6H4(2-CO2Me)

TABLE 18-continued
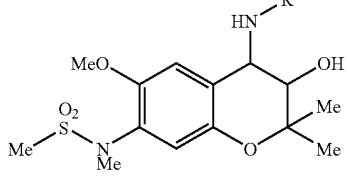
HN—R
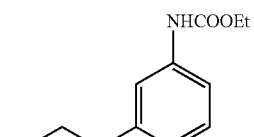
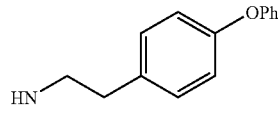
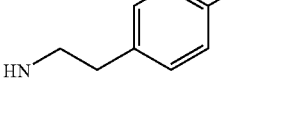
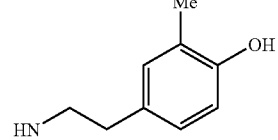
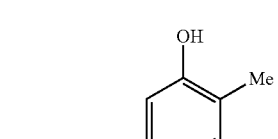
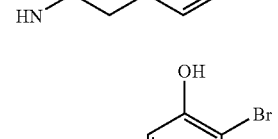
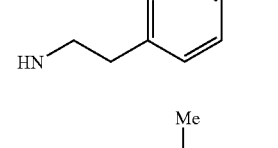
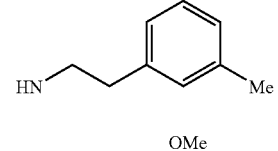
TABLE 18-continued
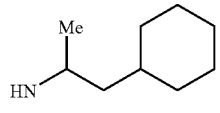
HN—R
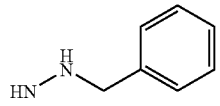
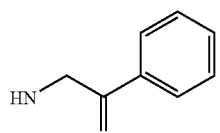
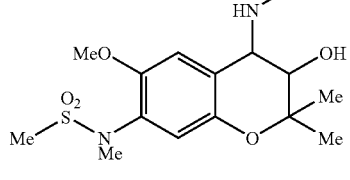
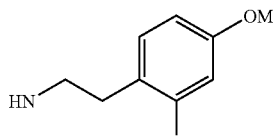
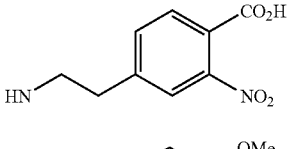
TABLE 19
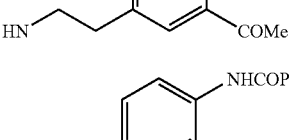
HN—R
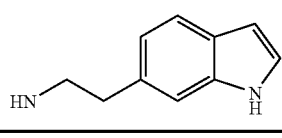
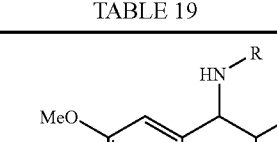
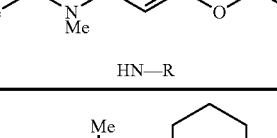

TABLE 19-continued
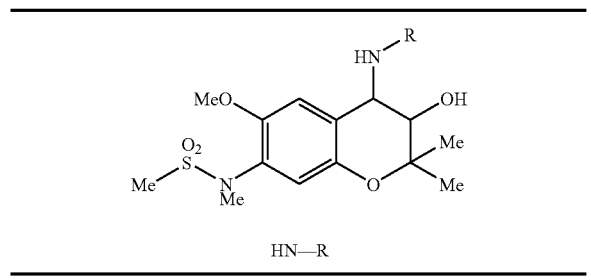
HN—R
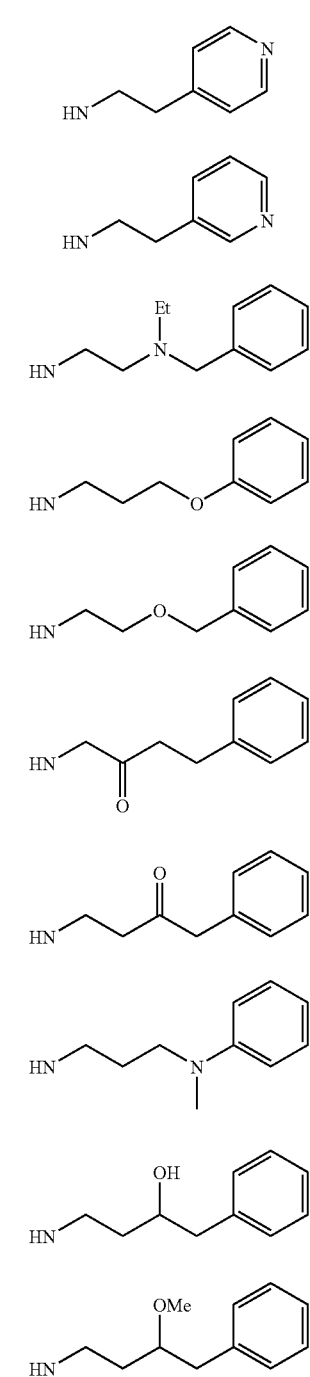
TABLE 19-continued
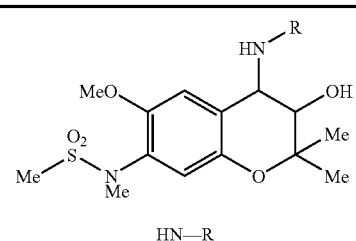
HN—R
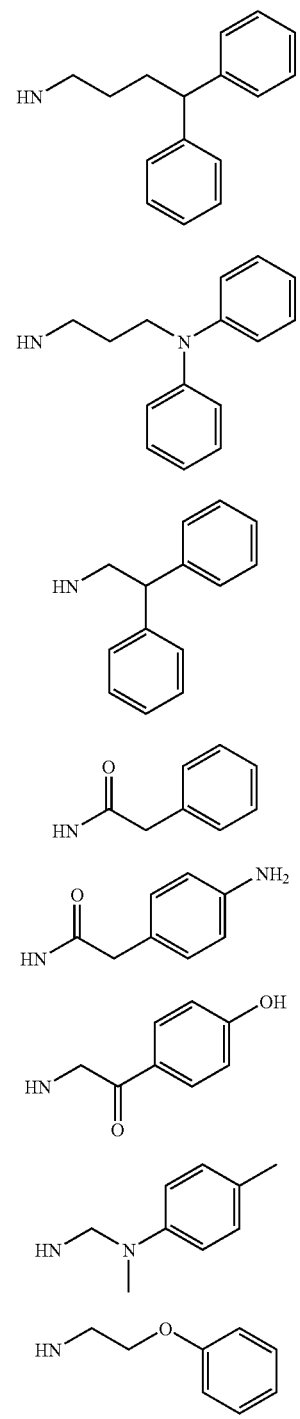

TABLE 19-continued
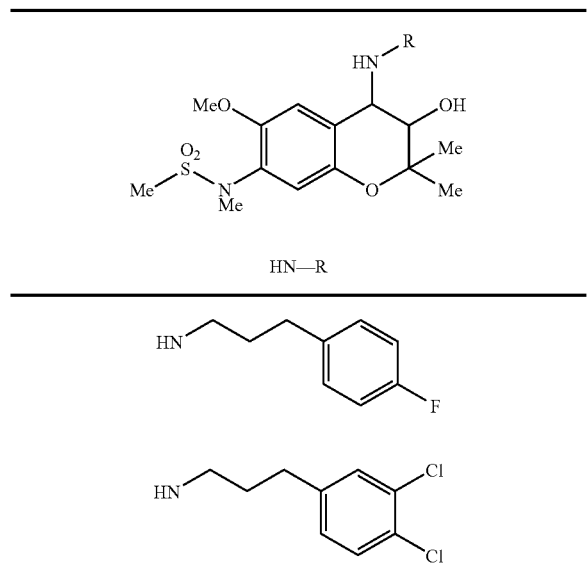
| HN—R |
|---|
| 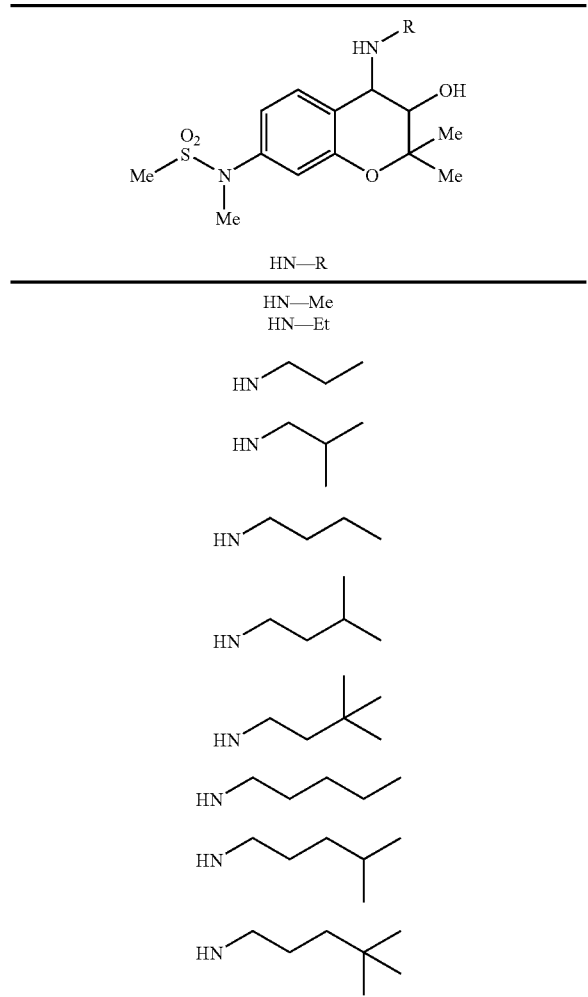 |
TABLE 20
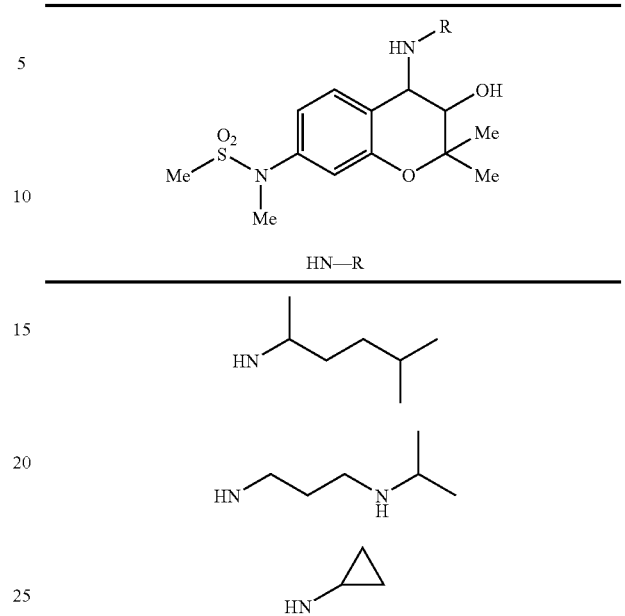
| HN—R |
|---|
| HN—Me |
| HN—Et |

TABLE 20-continued
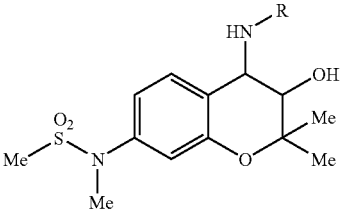
HN—R
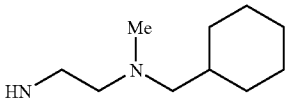
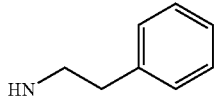
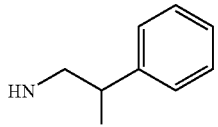
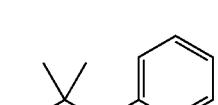
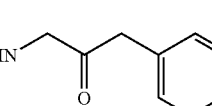
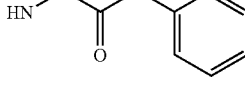
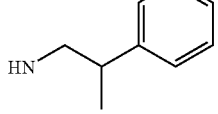
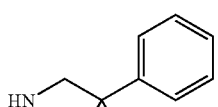
TABLE 21
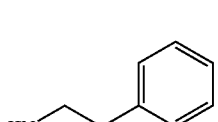
HN—R
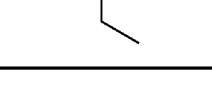
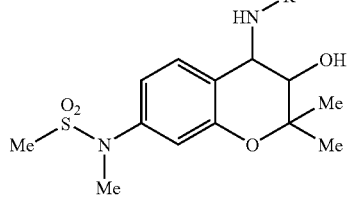
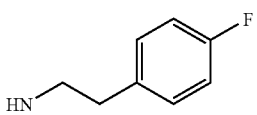
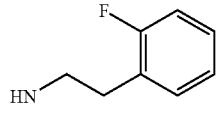
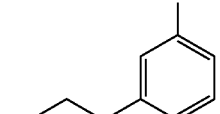
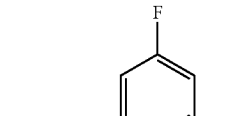
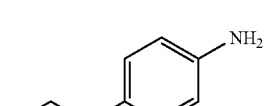
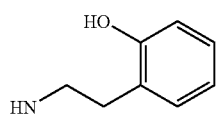

TABLE 21-continued
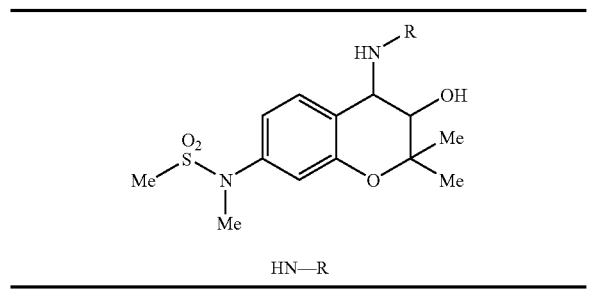
HN—R
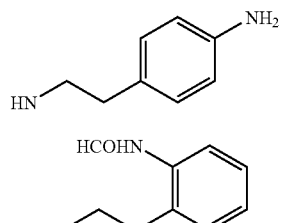
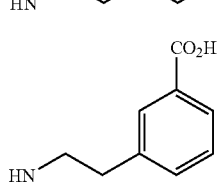
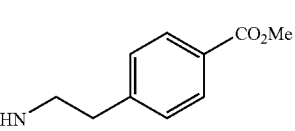
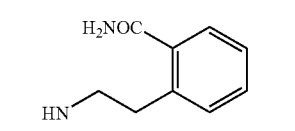
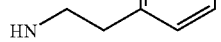
TABLE 21-continued
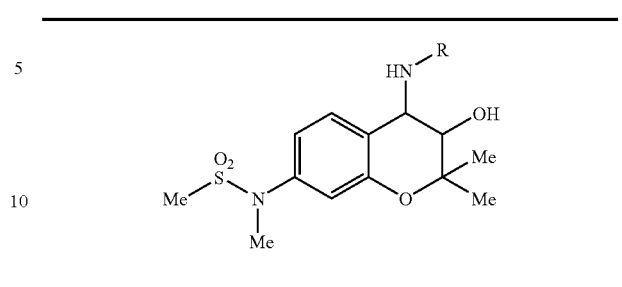
HN—R
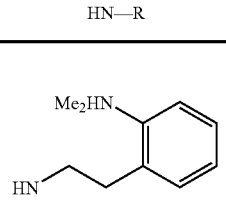
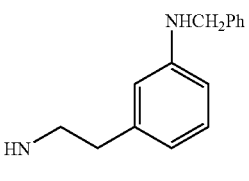
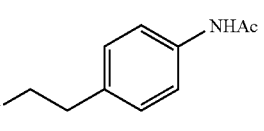
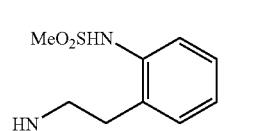
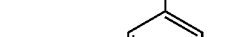
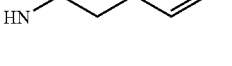
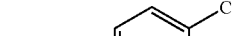
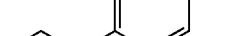

TABLE 22
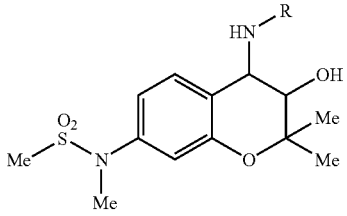
| HN—R |
|---|
| 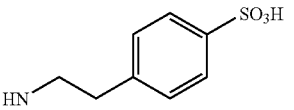 |
| 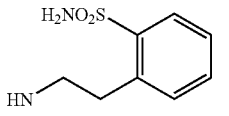 |
| 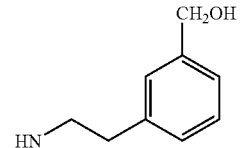 |
| 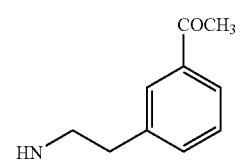 |
| 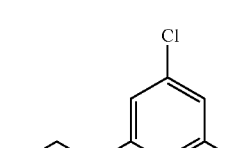 |
| 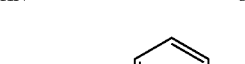 |
| 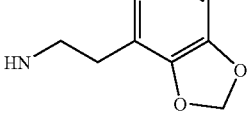 |
| 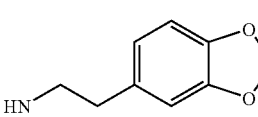 |
| 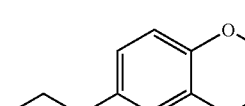 |
TABLE 22-continued
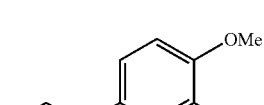
| HN—R |
|---|
|  |
| 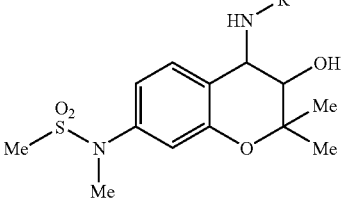 |
| 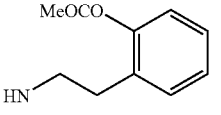 |
| 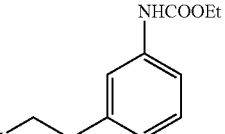 |
| 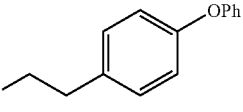 |
| 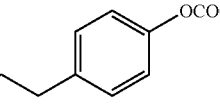 |
| 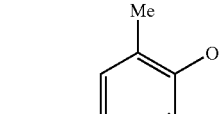 |
| 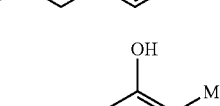 |
| 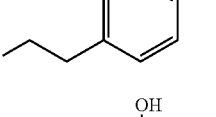 |

TABLE 22-continued
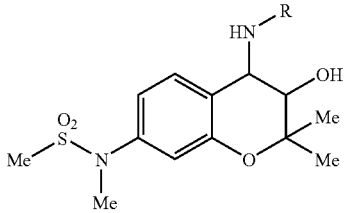
HN—R
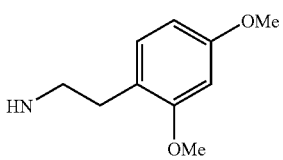
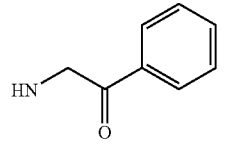
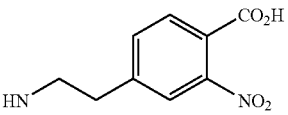
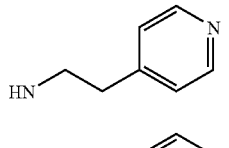
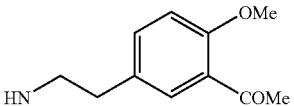
TABLE 23
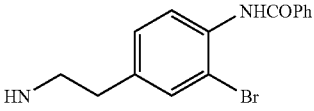
HN—R
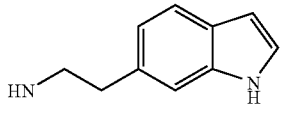
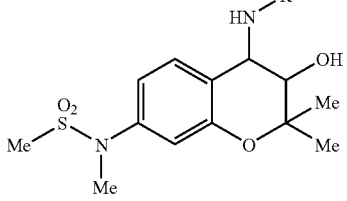
TABLE 23-continued
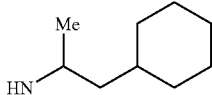
HN—R
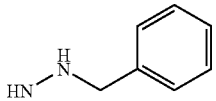
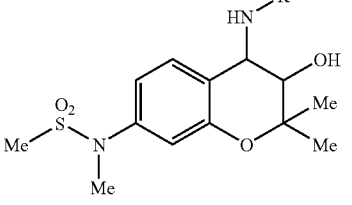
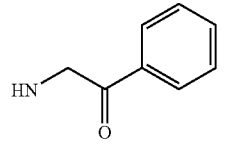
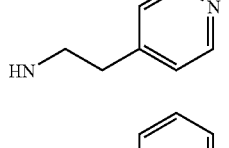
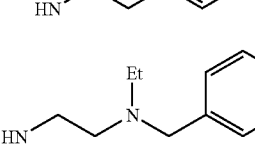
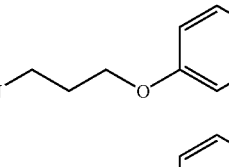
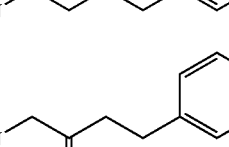
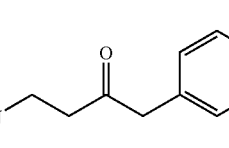
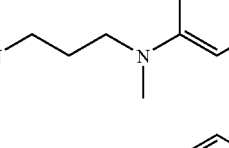
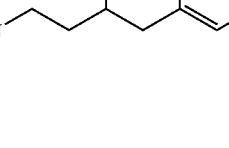

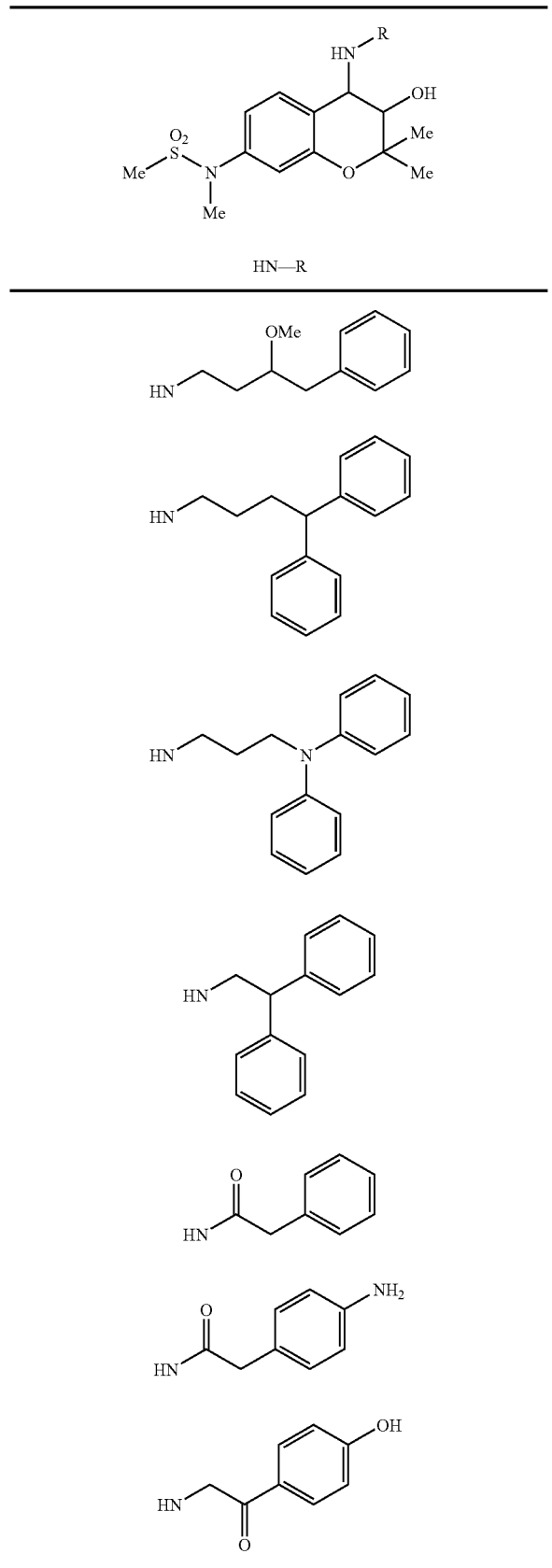
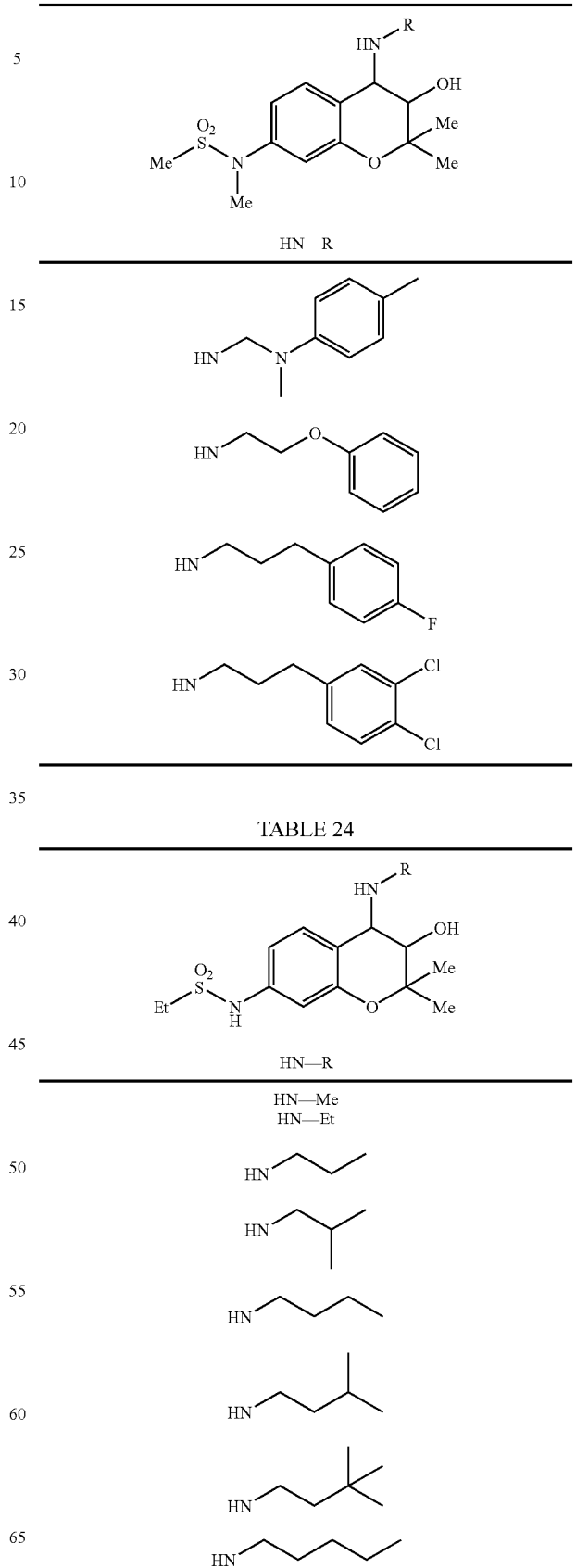

TABLE 24-continued
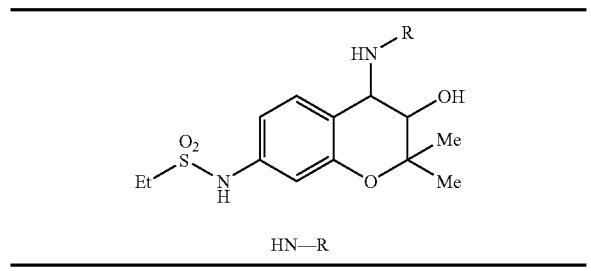
HN—R
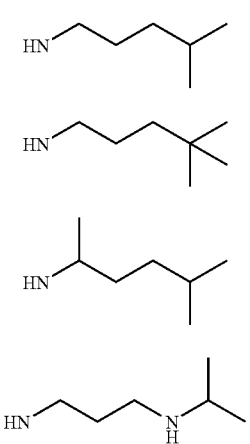
TABLE 24-continued
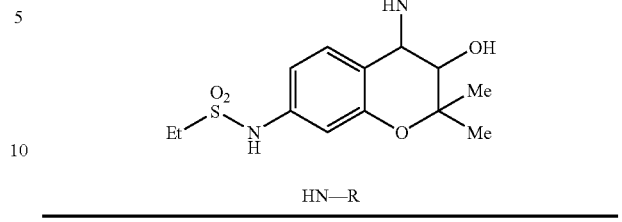
HN—R
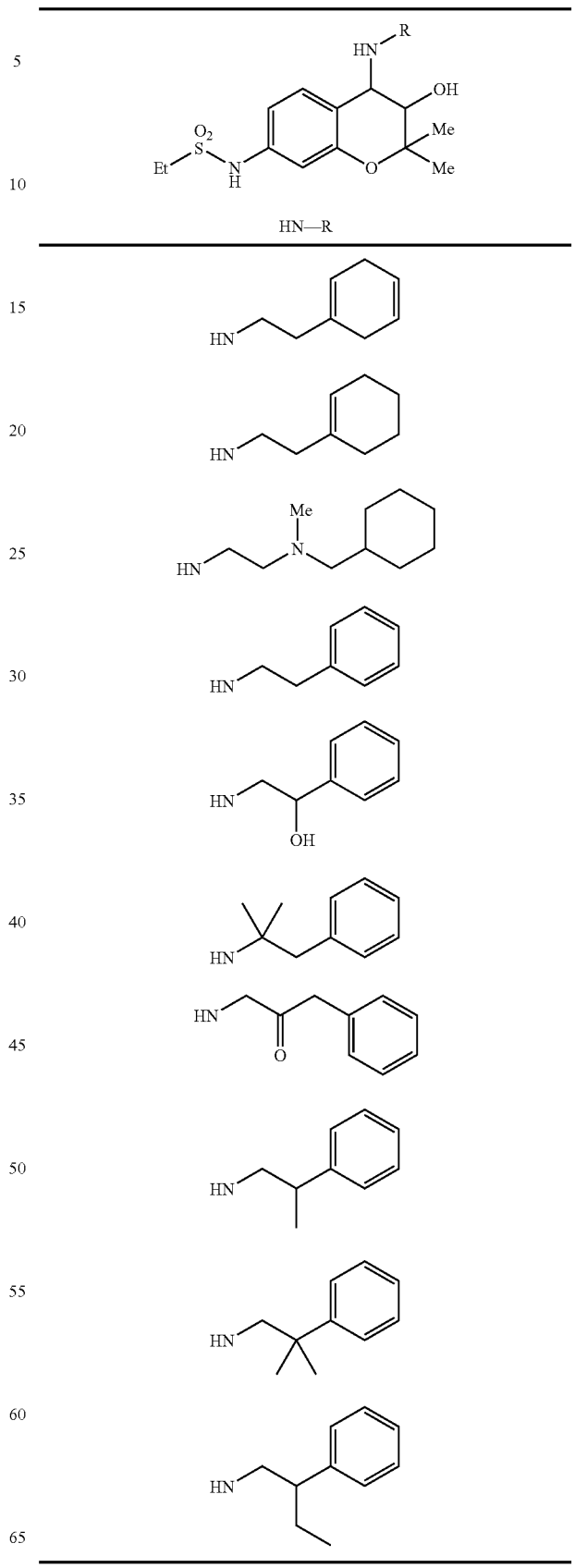

TABLE 25
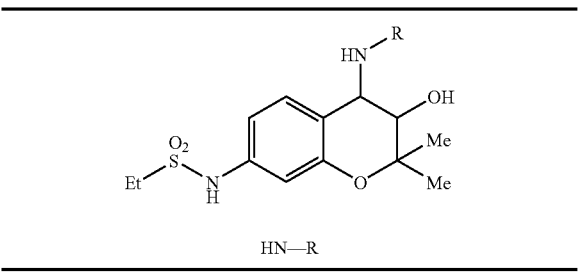
| HN—R |
|---|
| 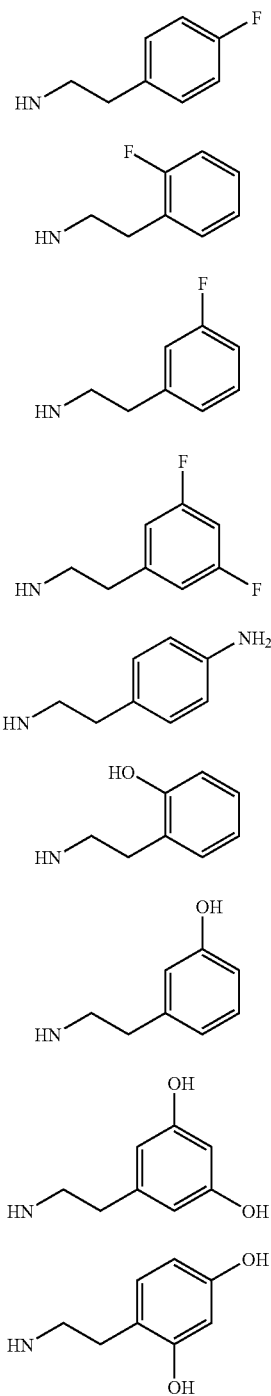 |
TABLE 25-continued
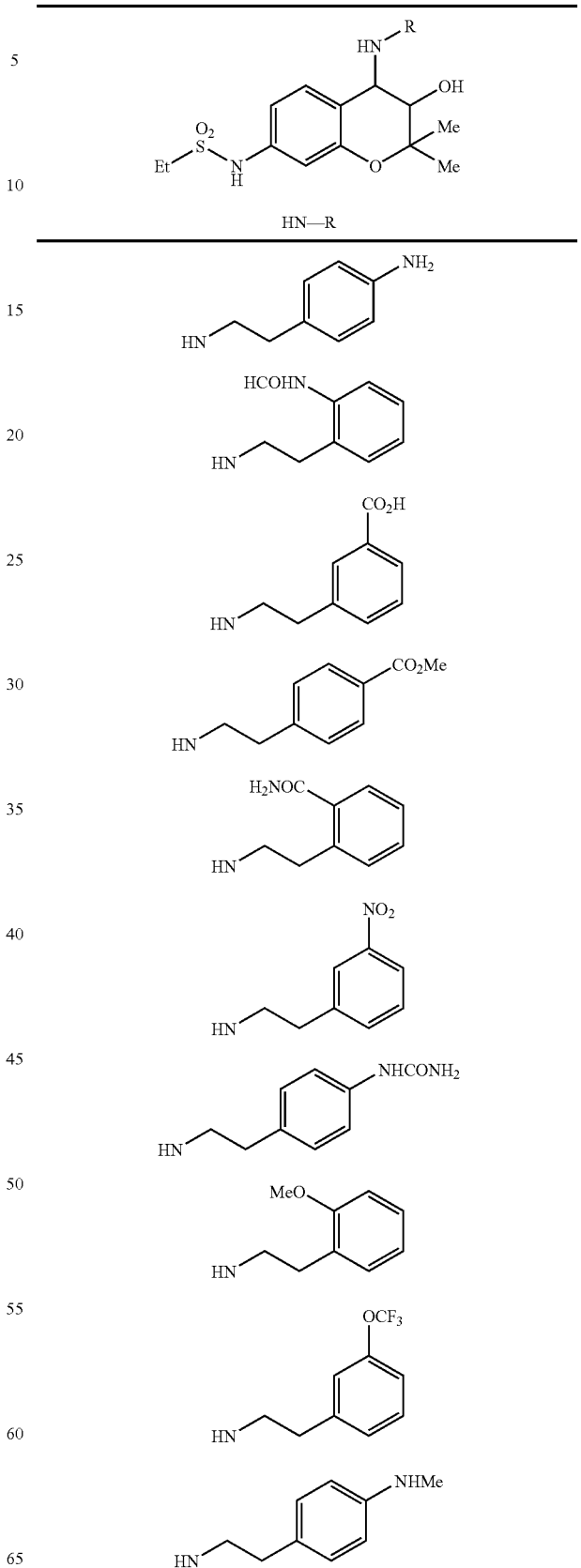

TABLE 25-continued

[Structure: chroman core with HN-R at 4-position, OH at 3-position, 2,2-dimethyl, and 7-EtSO2NH substituent]

HN—R

- 2-(Me2N)-C6H4-CH2CH2-NH-
- 3-(PhCH2NH)-C6H4-CH2CH2-NH-
- 4-(AcNH)-C6H4-CH2CH2-NH-
- 2-(MeO2SNH)-C6H4-CH2CH2-NH-
- 3-(EtSO2NH)-C6H4-CH2CH2-NH-
- 4-CN-C6H4-CH2CH2-NH-
- 2-Br-C6H4-CH2CH2-NH-
- 3-Cl-C6H4-CH2CH2-NH-

TABLE 26

[Structure: chroman core with HN-R at 4-position, OH at 3-position, 2,2-dimethyl, and 7-EtSO2NH substituent]

HN—R

- 4-(SO3H)-C6H4-CH2CH2-NH-
- 2-(H2NO2S)-C6H4-CH2CH2-NH-
- 3-(CH2OH)-C6H4-CH2CH2-NH-
- 3-(COCH3)-C6H4-CH2CH2-NH-
- 3,5-di-Cl-C6H3-CH2CH2-NH-
- 4-yl-benzo[1,3]dioxole-CH2CH2-NH-
- 6-yl-benzo[1,3]dioxole-CH2CH2-NH-
- 2,3-dihydro-benzo[1,4]dioxin-6-yl-CH2CH2-NH-
- 3-OEt-4-OMe-C6H3-CH2CH2-NH-
- 2-(MeOCO)-C6H4-CH2CH2-NH- TABLE 26-continued
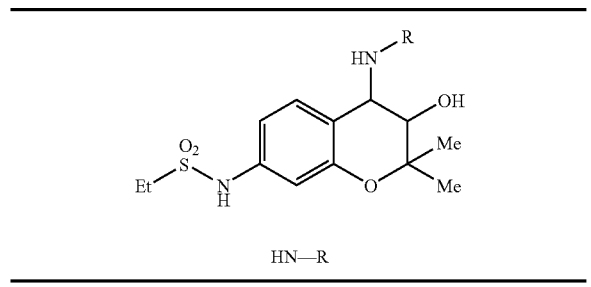
HN—R
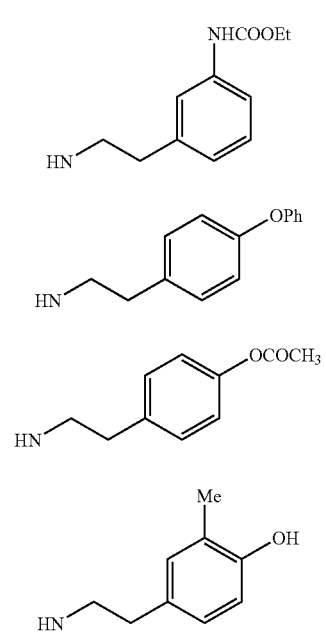
TABLE 26-continued
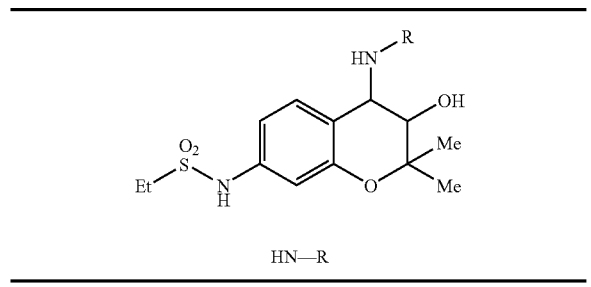
HN—R
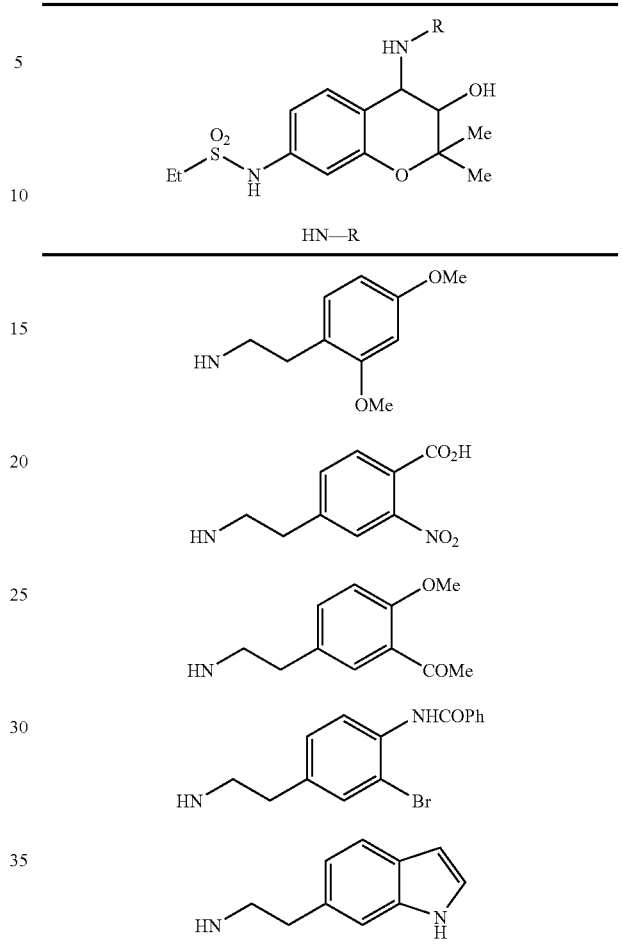
TABLE 27
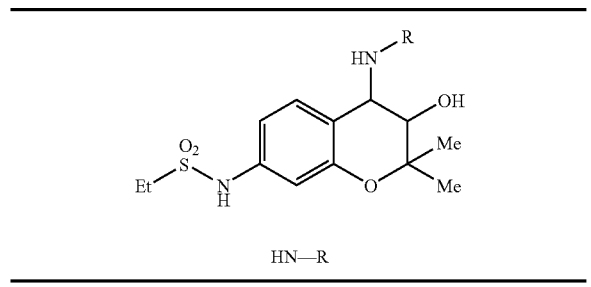
HN—R
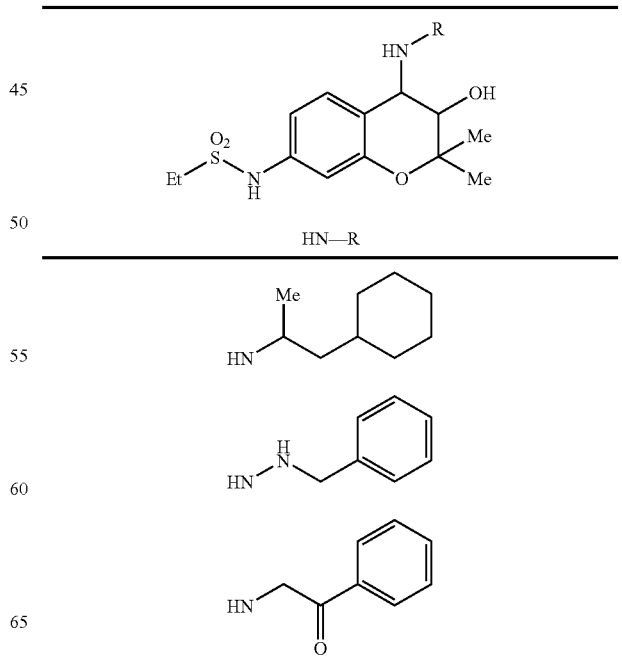

TABLE 27-continued
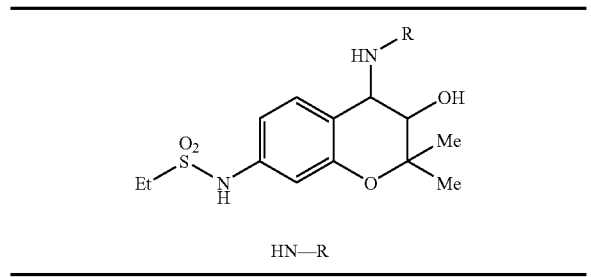
HN—R
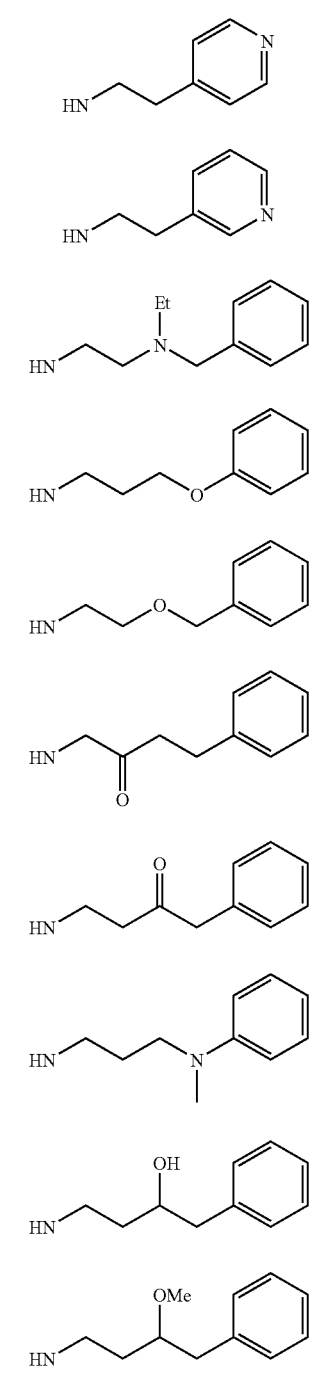
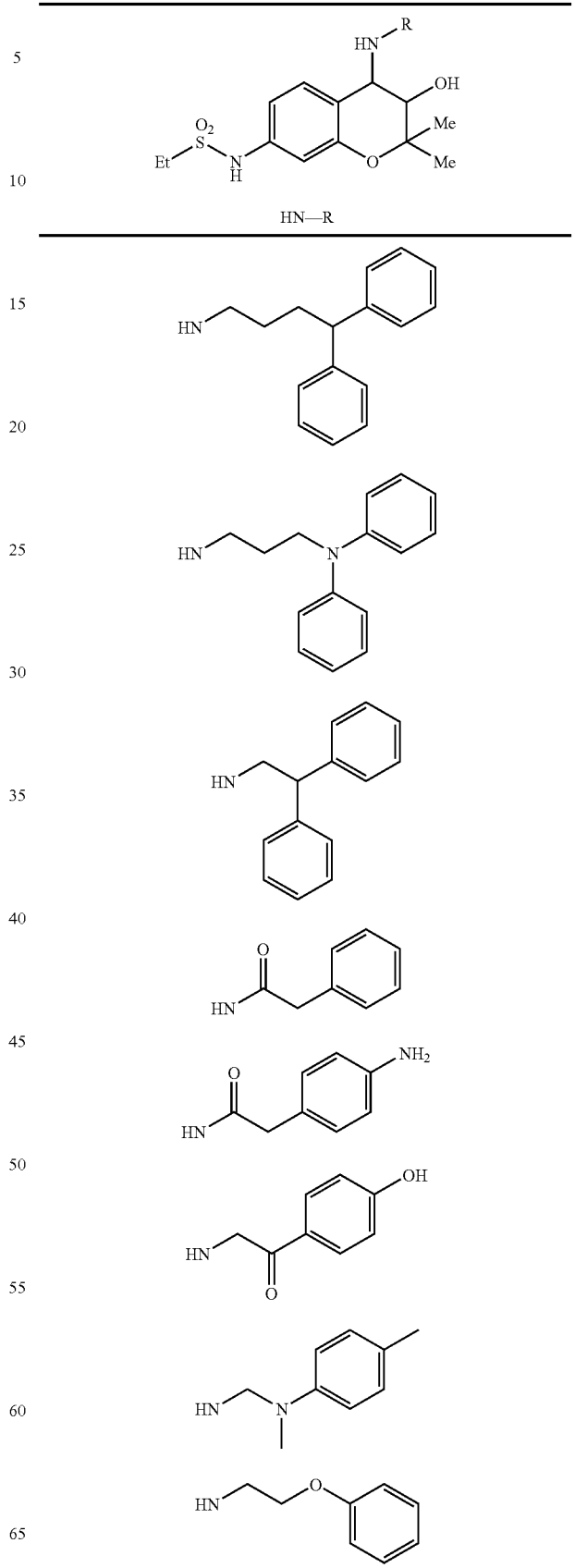

TABLE 27-continued
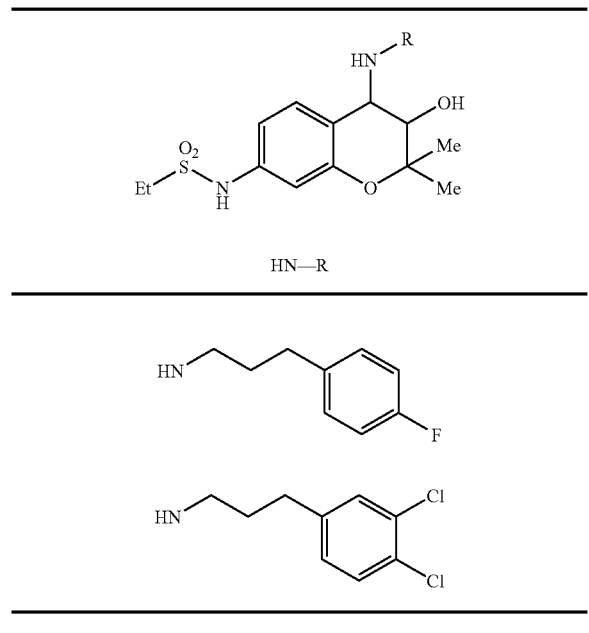
TABLE 28
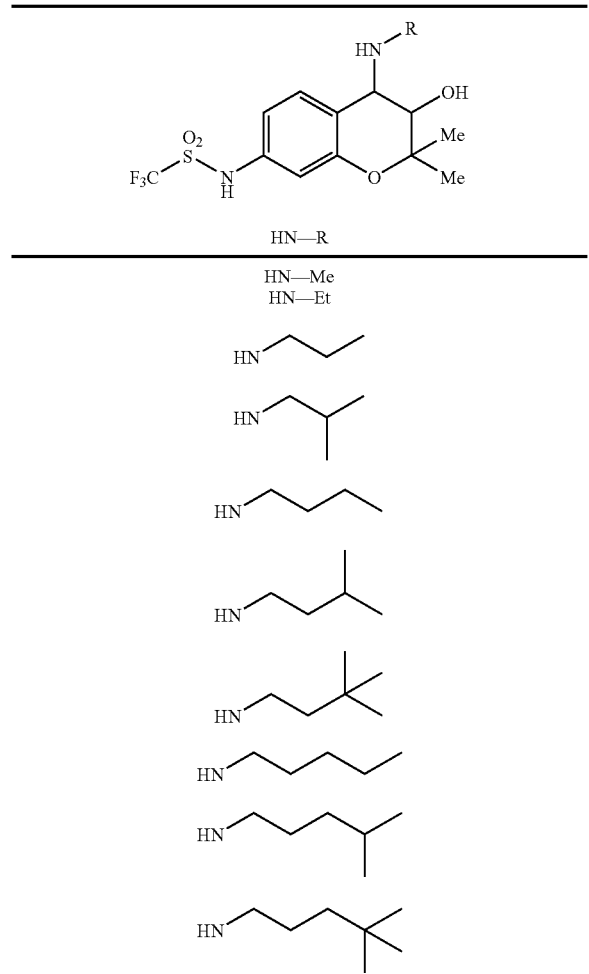
TABLE 28-continued
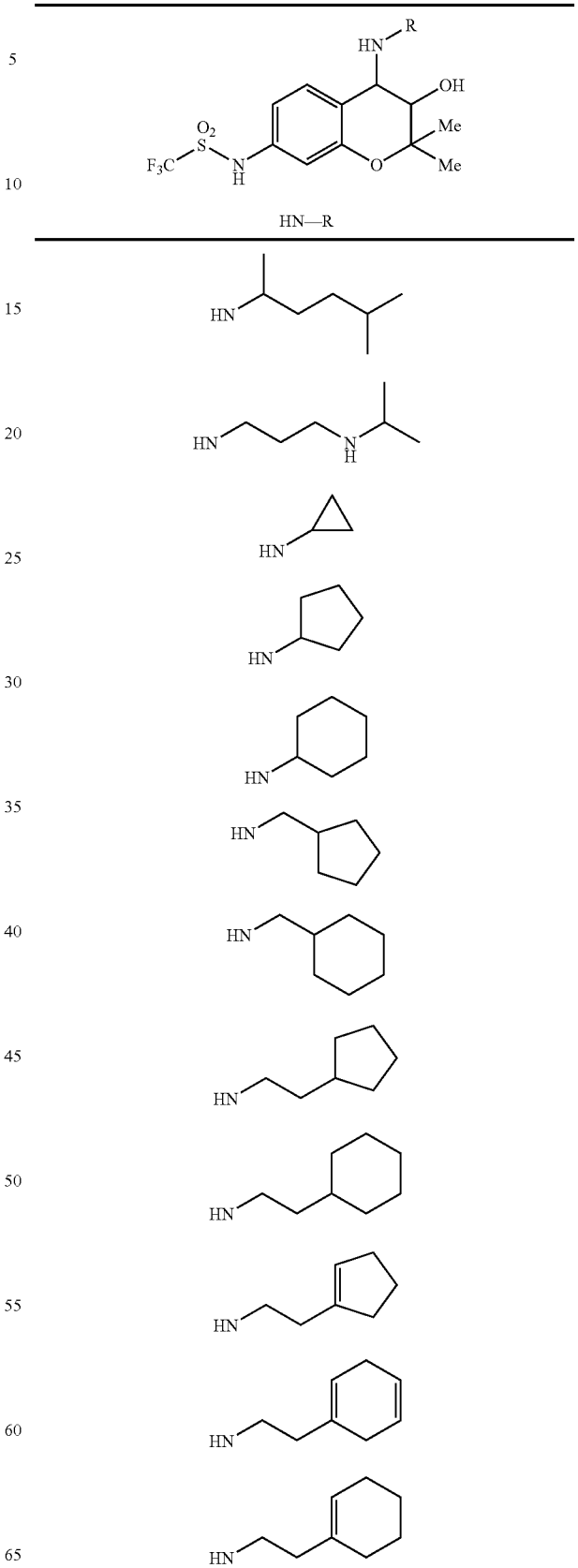

TABLE 28-continued
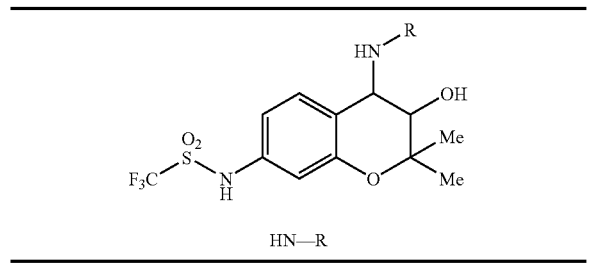
| HN—R |
|---|
| 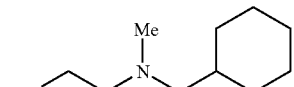 |
| 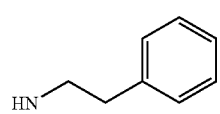 |
| 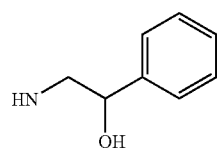 |
| 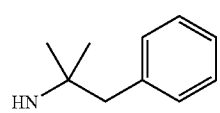 |
| 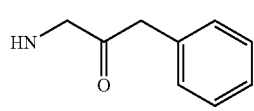 |
| 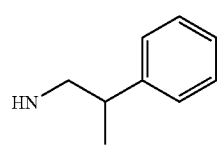 |
| 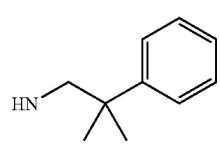 |
| 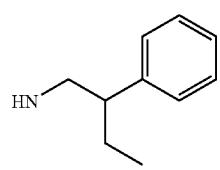 |
TABLE 29
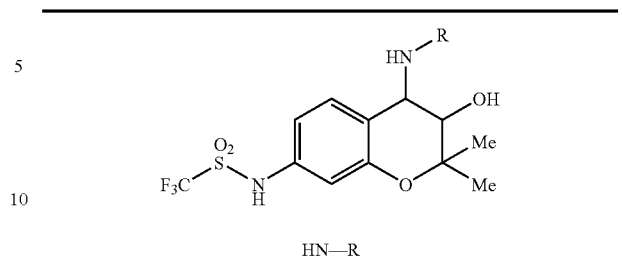
| HN—R |
|---|
|  |
| 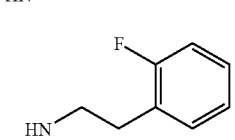 |
| 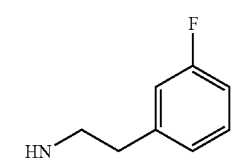 |
| 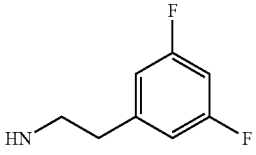 |
| 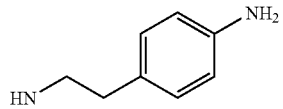 |
| 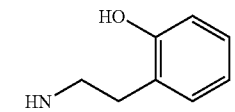 |
| 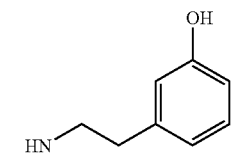 |
| 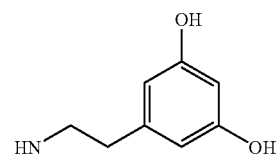 |
| 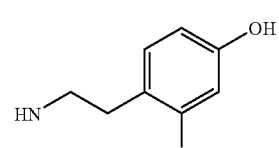 |

TABLE 29-continued
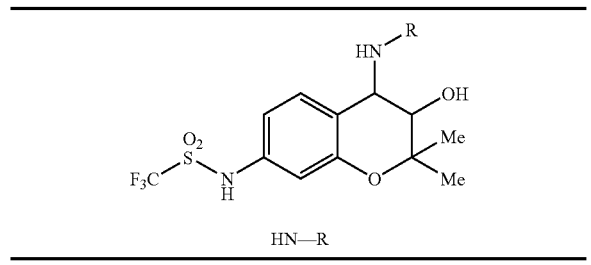
HN—R
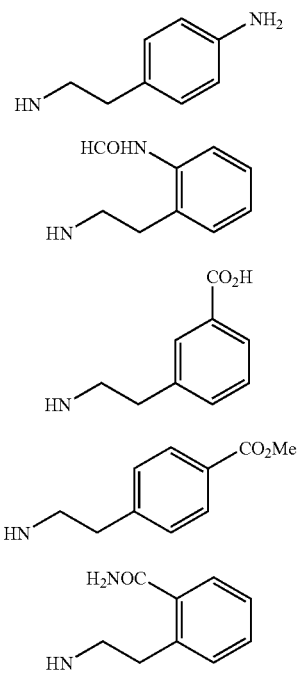
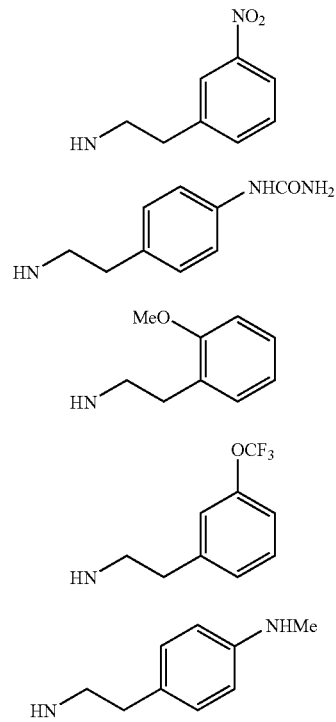
TABLE 29-continued
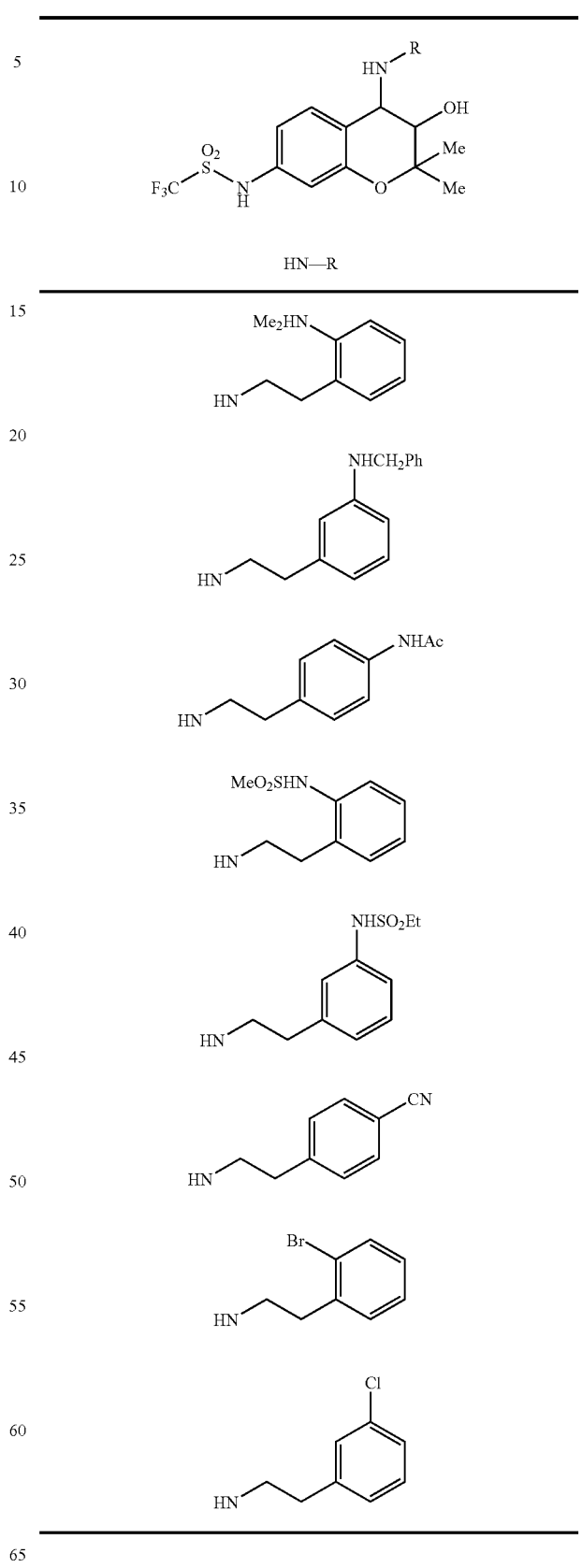

TABLE 30
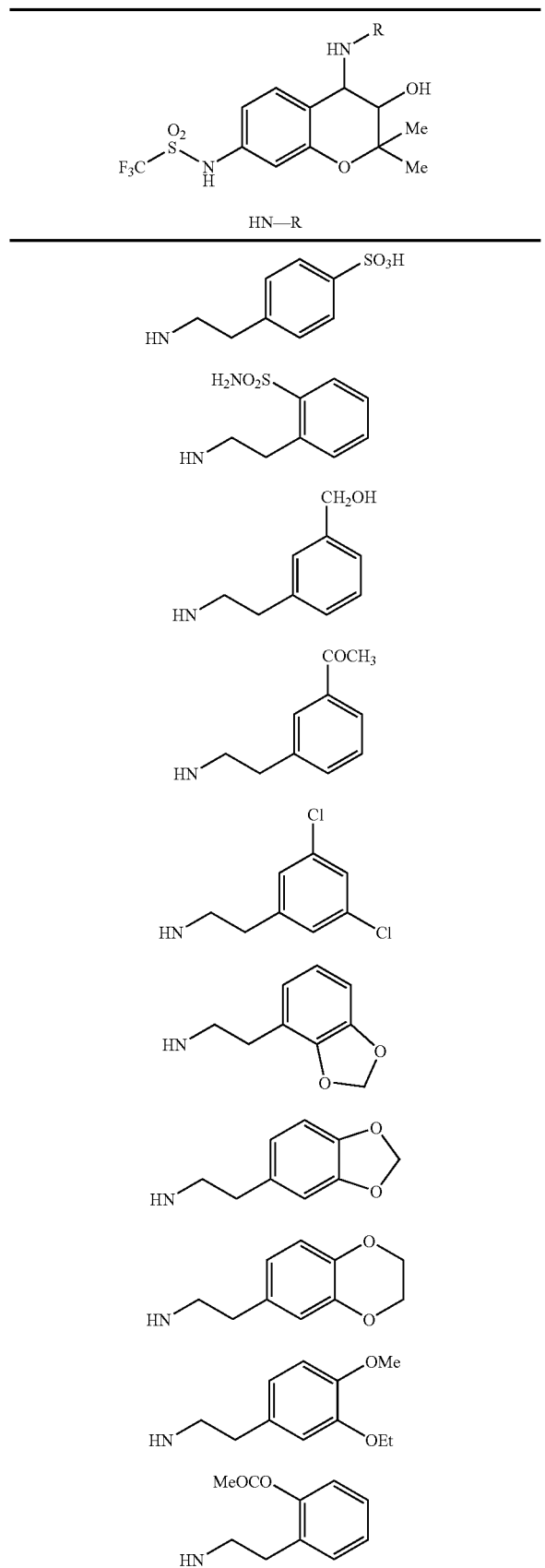
TABLE 30-continued
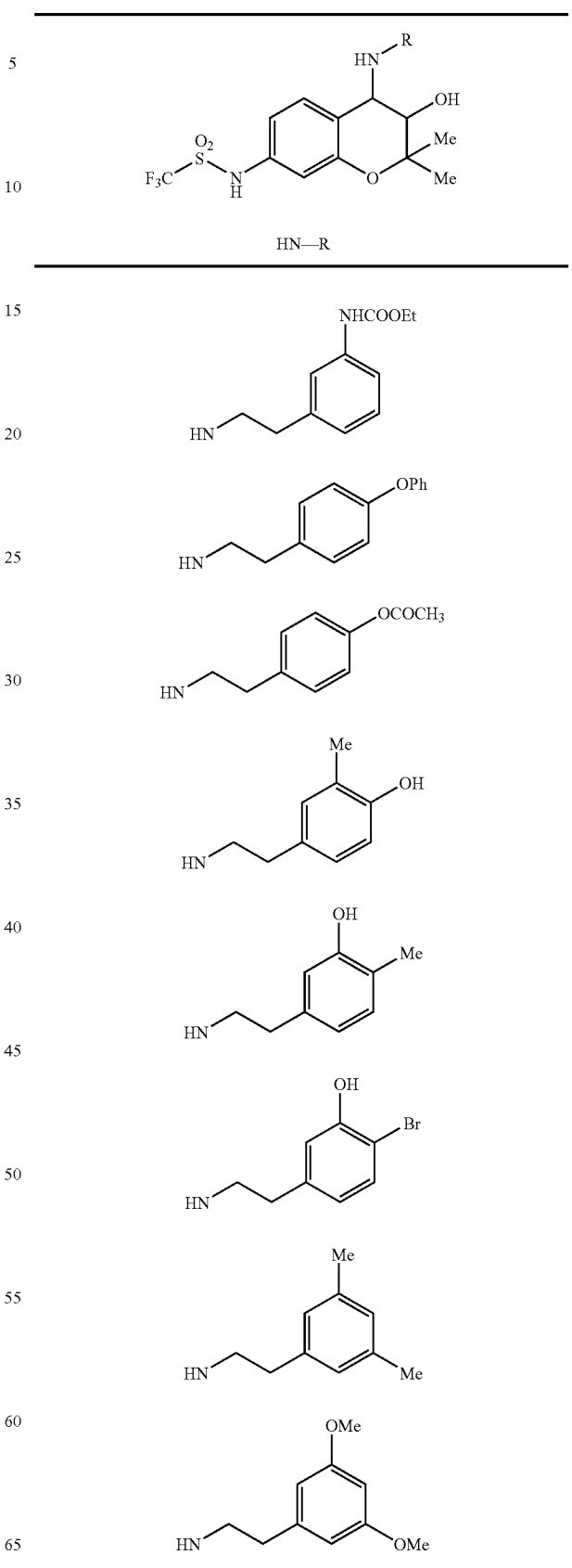

TABLE 30-continued
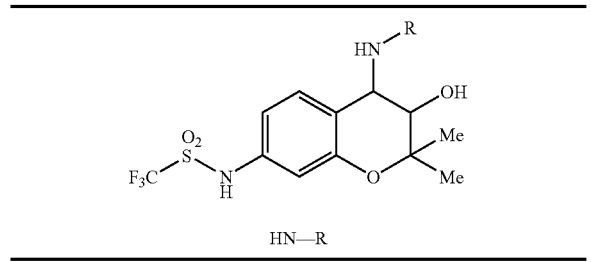
| HN—R |
|---|
| 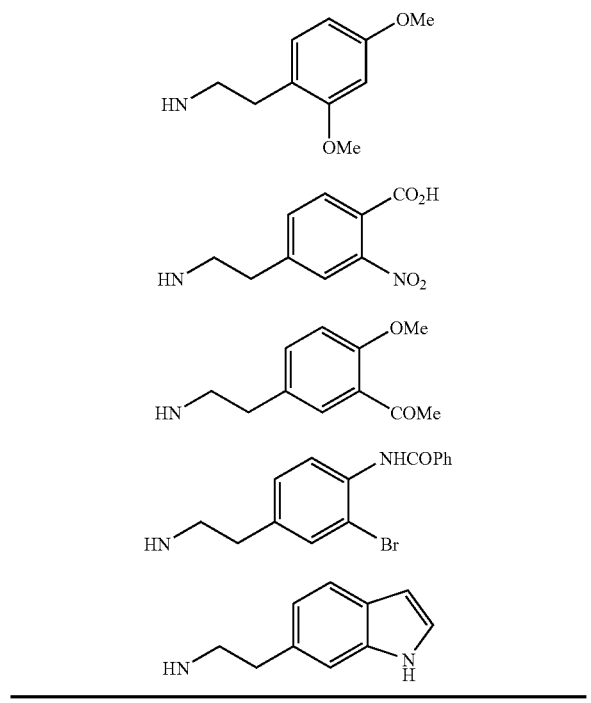 |
TABLE 31
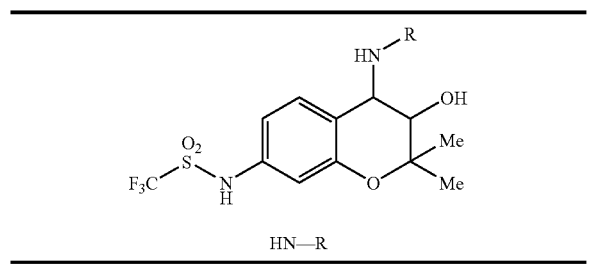
| HN—R |
|---|
| 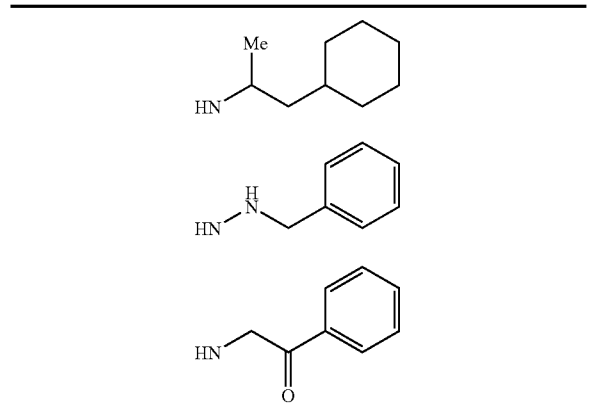 |
TABLE 31-continued
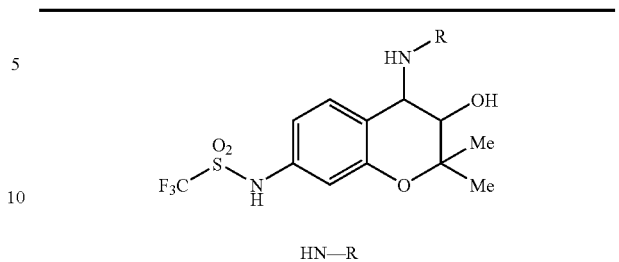
| HN—R |
|---|
| 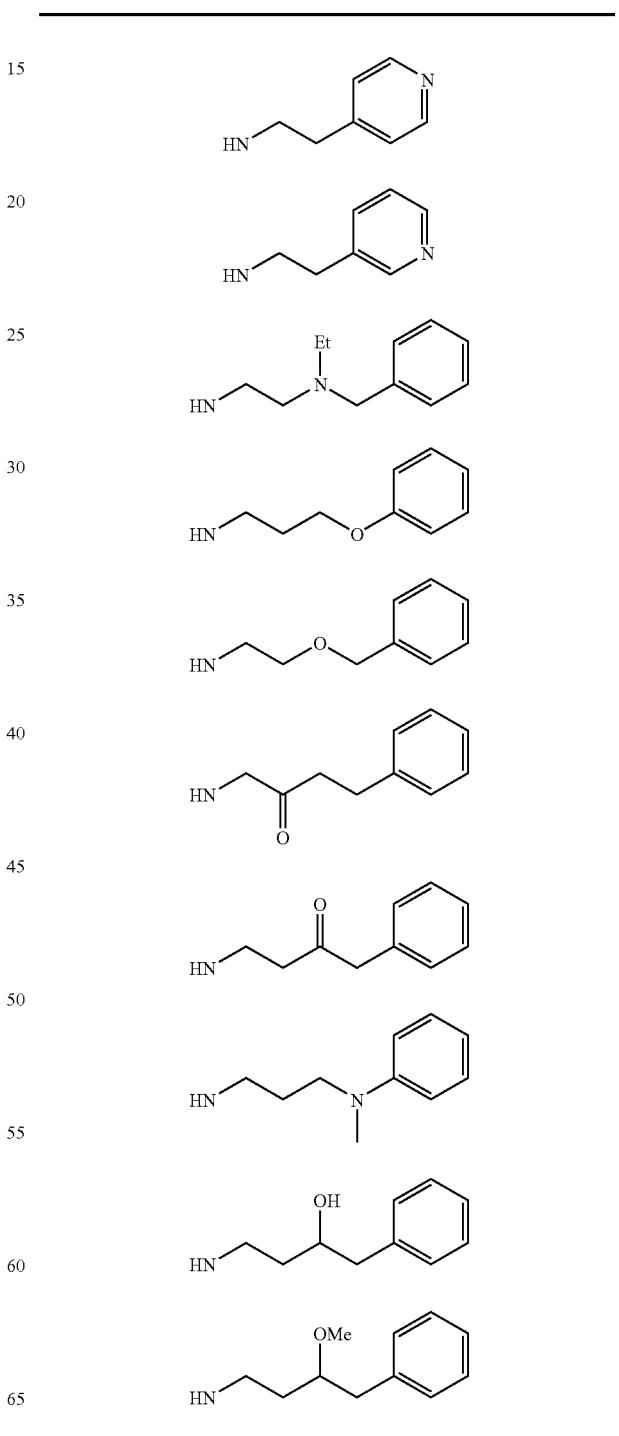 |

TABLE 31-continued
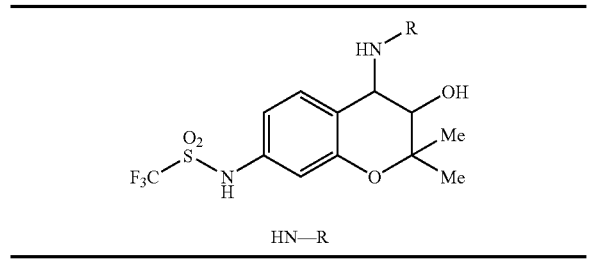
HN—R
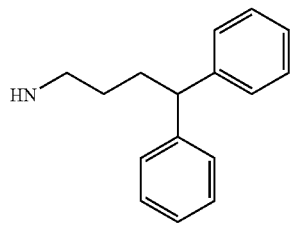
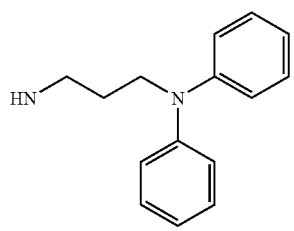
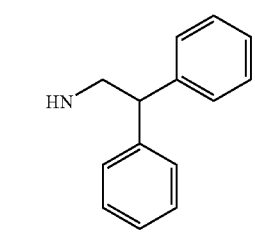
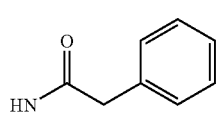
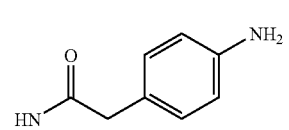
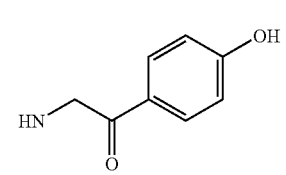
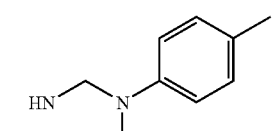
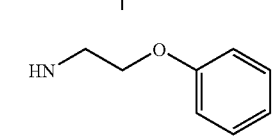
TABLE 31-continued
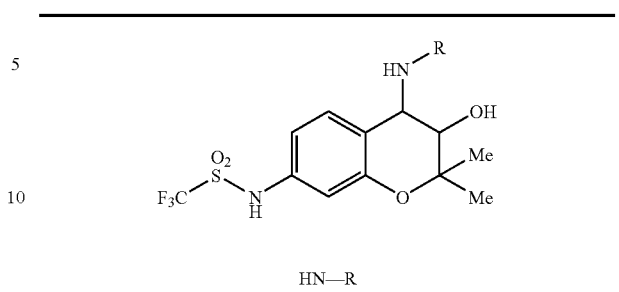
HN—R
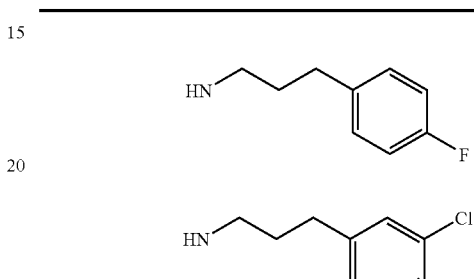
TABLE 32
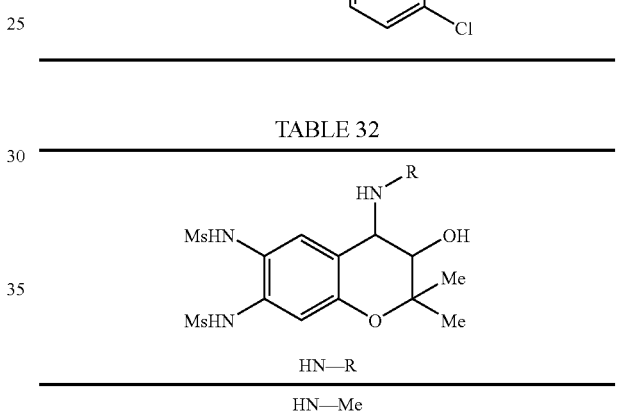
HN—R
HN—Me
HN—Et
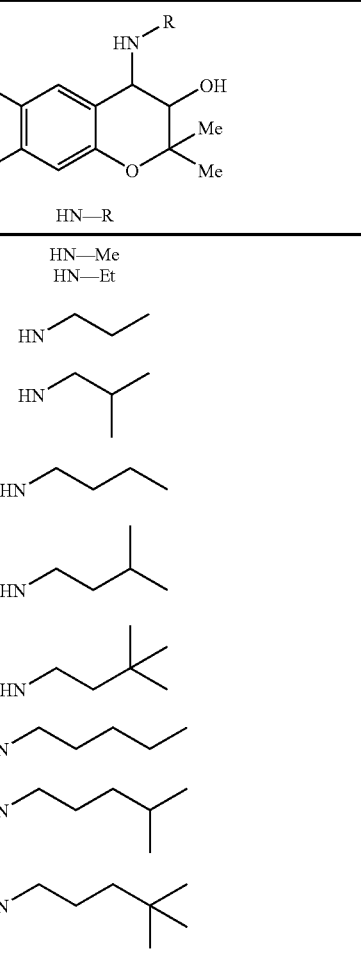

TABLE 32-continued
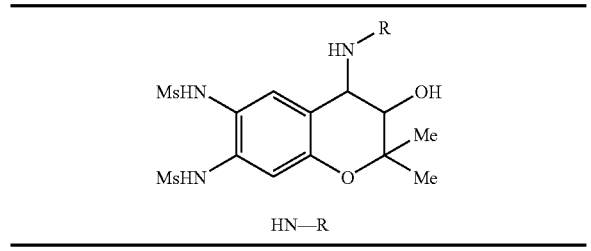
HN—R
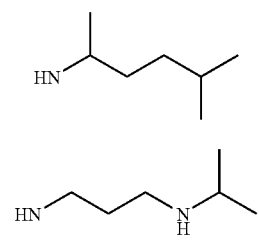
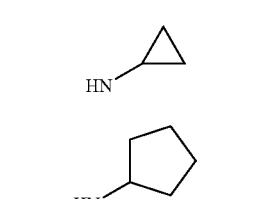
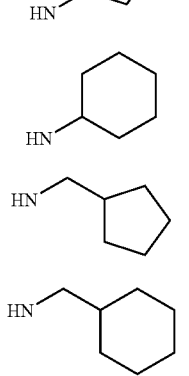
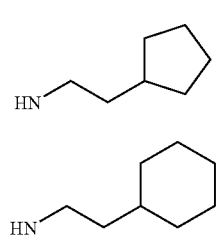
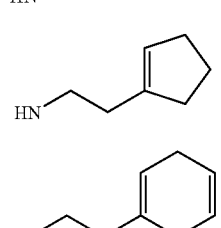
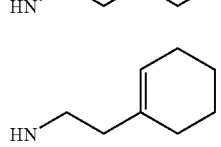
TABLE 32-continued
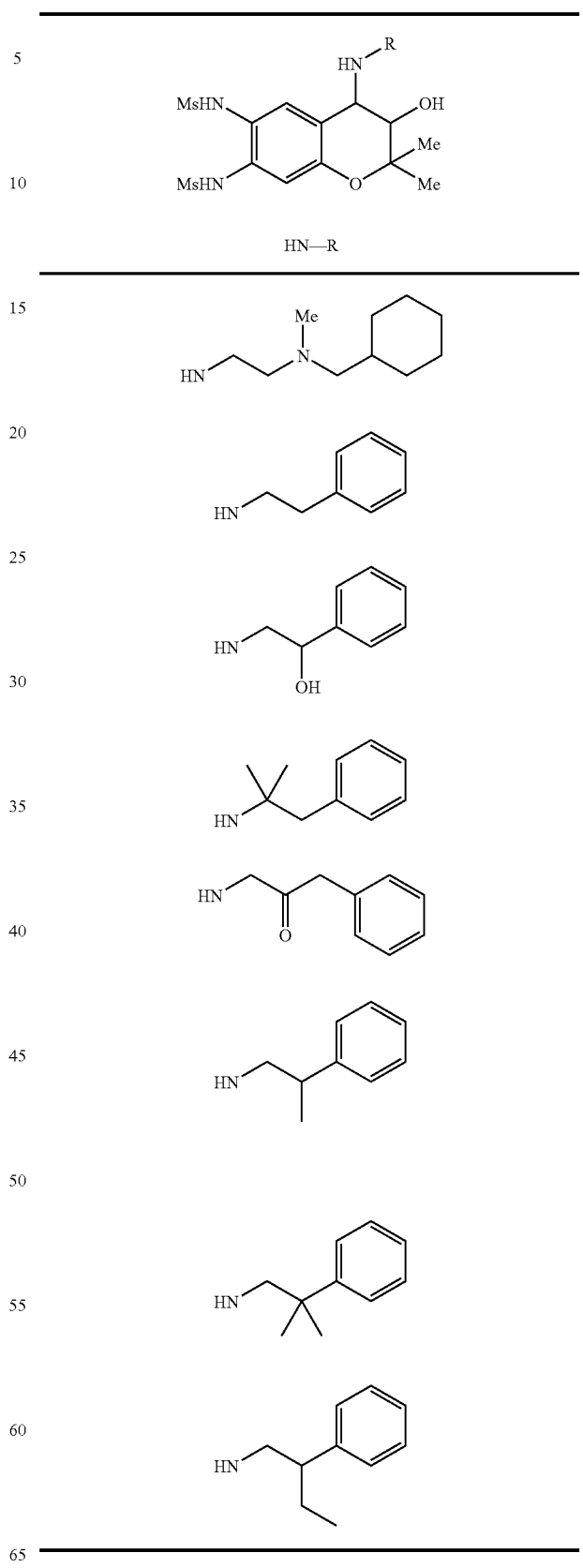

TABLE 33
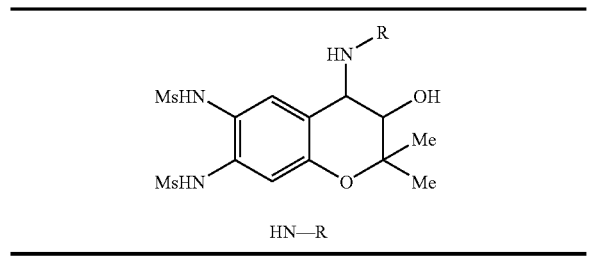
HN—R
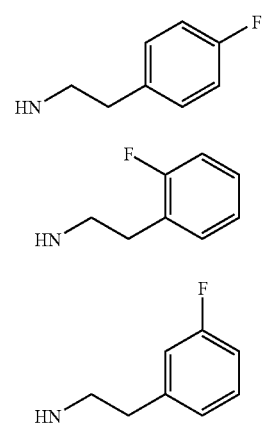
TABLE 33-continued
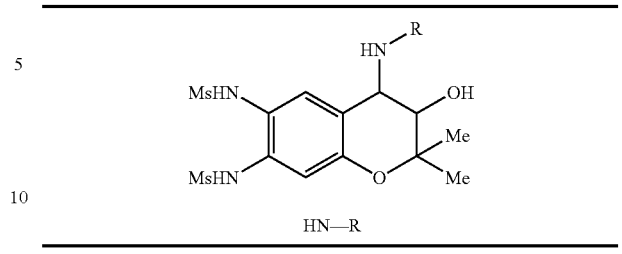
HN—R
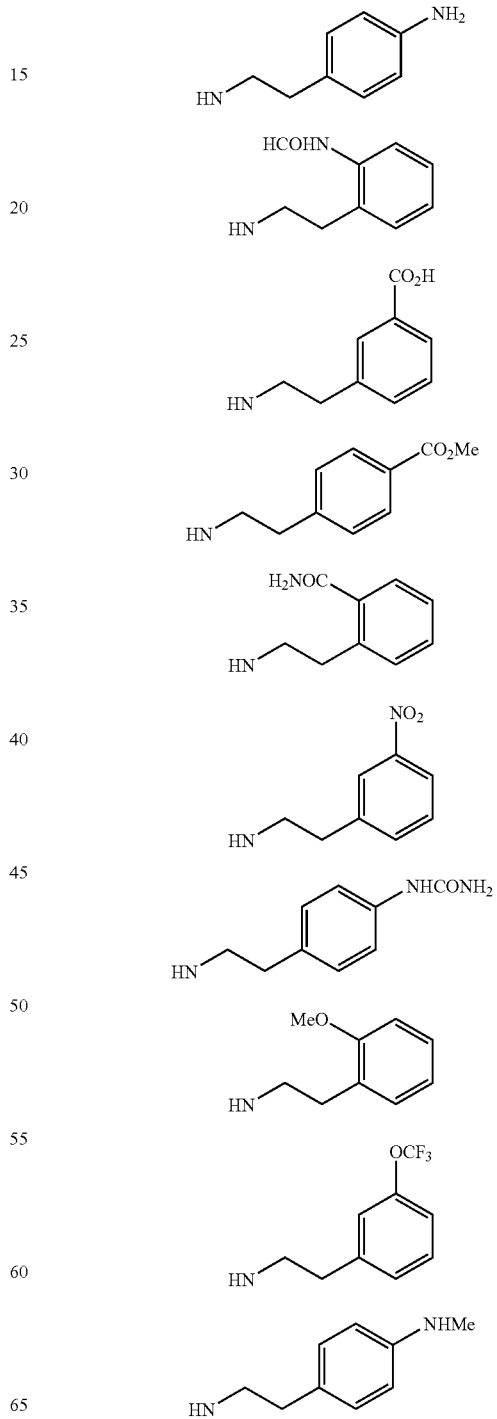

TABLE 33-continued

[Structure: chroman with MsHN groups at 6,7-positions, 3-OH, 4-NHR, 2,2-dimethyl]

HN—R

- 2-(Me₂N)-C₆H₄-CH₂CH₂-NH—
- 3-(PhCH₂NH)-C₆H₄-CH₂CH₂-NH—
- 4-(NHAc)-C₆H₄-CH₂CH₂-NH—
- 2-(MeO₂SHN)-C₆H₄-CH₂CH₂-NH—
- 3-(EtSO₂NH)-C₆H₄-CH₂CH₂-NH—
- 4-CN-C₆H₄-CH₂CH₂-NH—
- 2-Br-C₆H₄-CH₂CH₂-NH—
- 3-Cl-C₆H₄-CH₂CH₂-NH—

TABLE 34

[Structure: chroman with MsHN groups at 6,7-positions, 3-OH, 4-NHR, 2,2-dimethyl]

HN—R

- 4-(SO₃H)-C₆H₄-CH₂CH₂-NH—
- 2-(H₂NO₂S)-C₆H₄-CH₂CH₂-NH—
- 3-(CH₂OH)-C₆H₄-CH₂CH₂-NH—
- 3-(COCH₃)-C₆H₄-CH₂CH₂-NH—
- 3,5-Cl₂-C₆H₃-CH₂CH₂-NH—
- (2,3-methylenedioxyphenyl-4-yl)-CH₂CH₂-NH—
- (benzo[1,3]dioxol-5-yl)-CH₂CH₂-NH—
- (2,3-dihydrobenzo[1,4]dioxin-6-yl)-CH₂CH₂-NH—
- 3-OEt-4-OMe-C₆H₃-CH₂CH₂-NH—
- 2-(MeOCO)-C₆H₄-CH₂CH₂-NH—

TABLE 34-continued
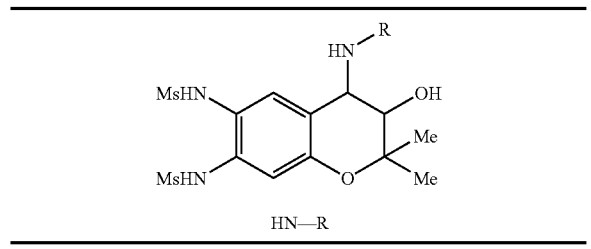
| HN—R |
|---|
| 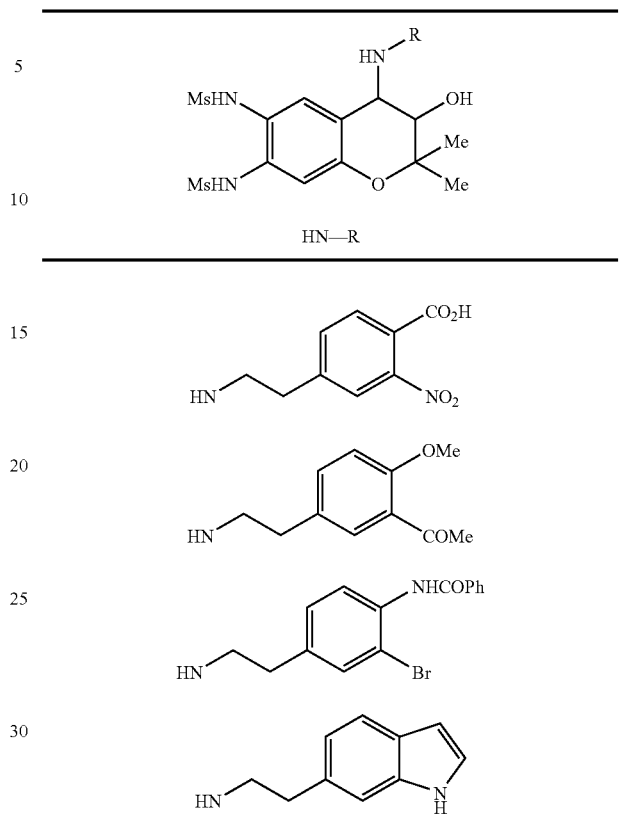 |
TABLE 34-continued
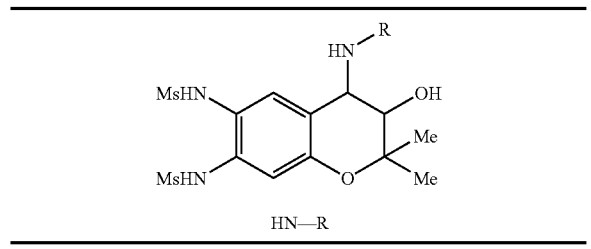
| HN—R |
|---|
| 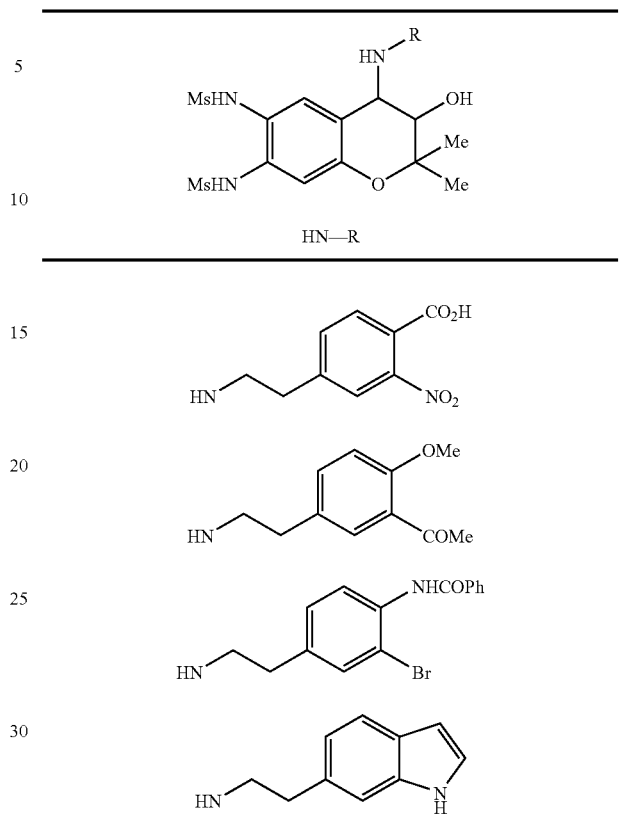 |
TABLE 35
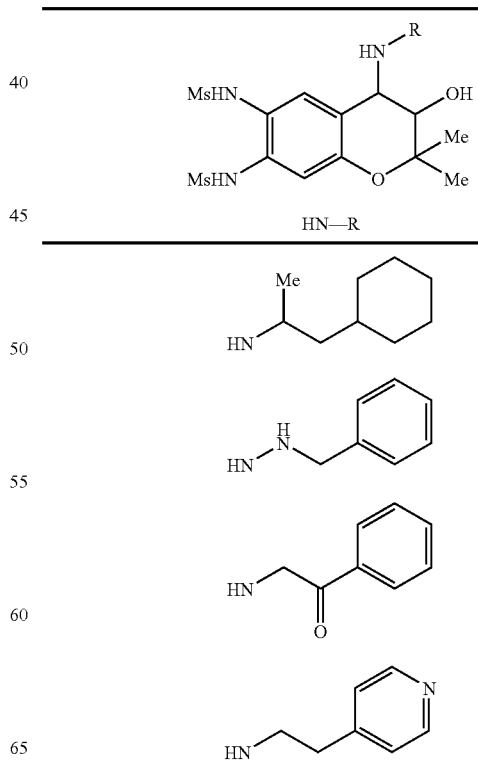

TABLE 35-continued
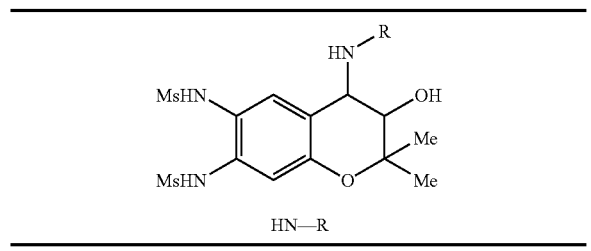
HN—R
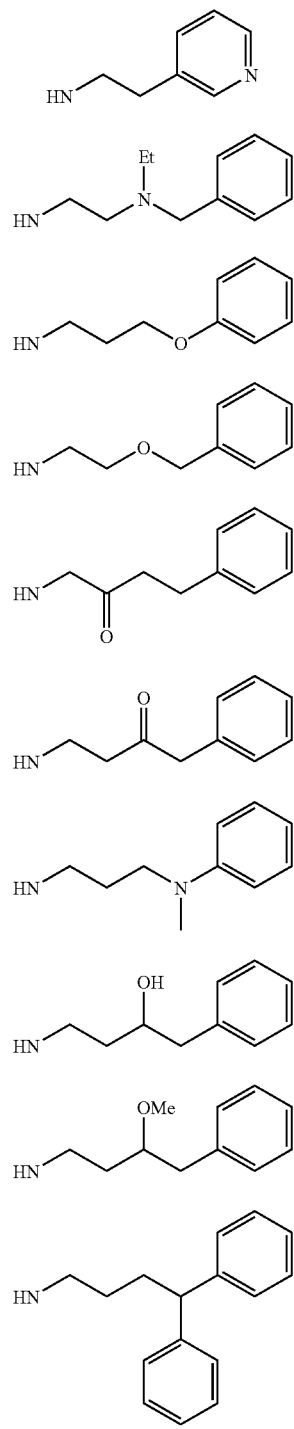
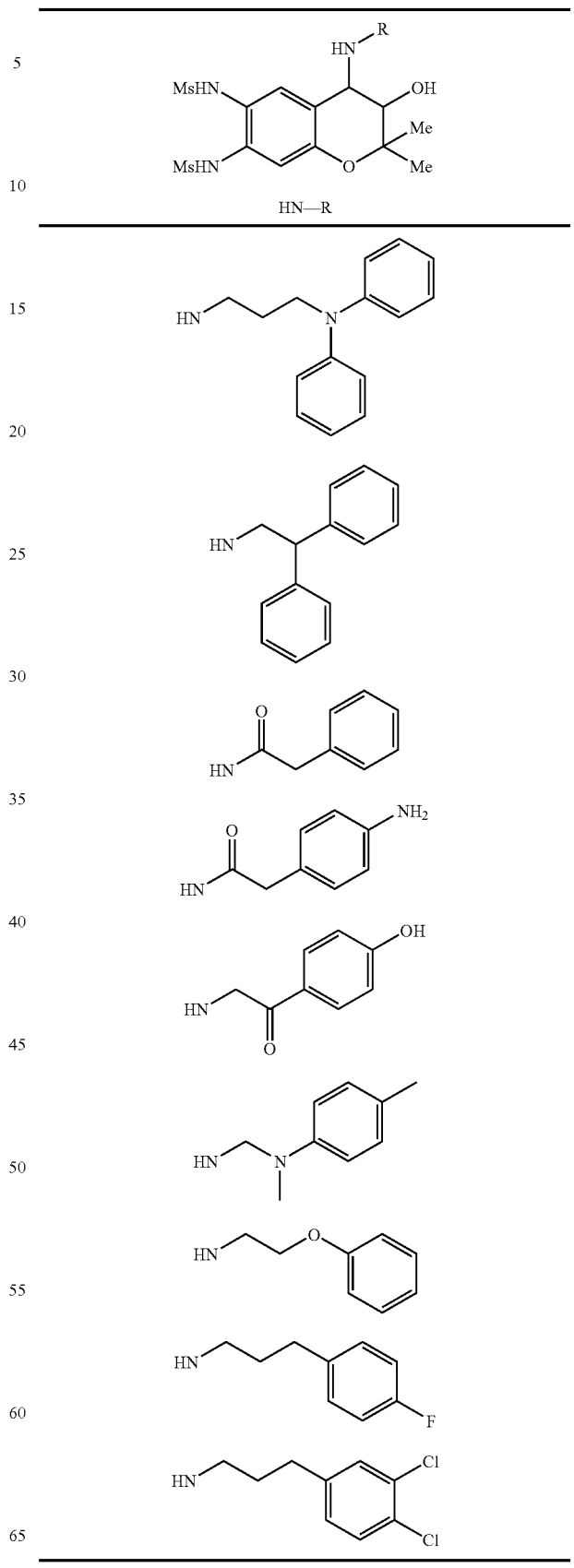

TABLE 36
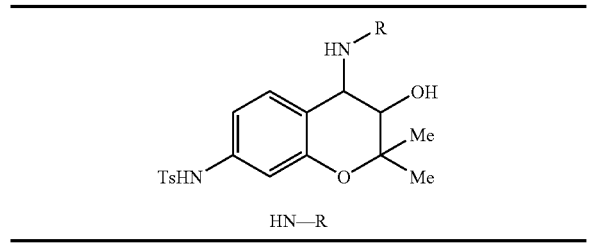
| HN—R |
|---|
| HN—Me |
| HN—Et |
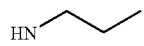
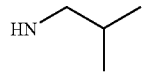
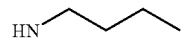
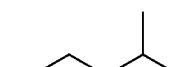
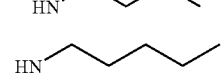
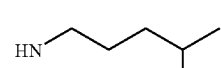
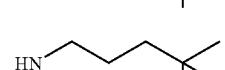
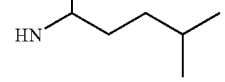
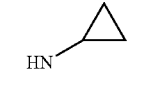
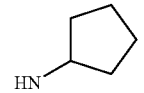
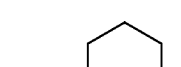
TABLE 36-continued
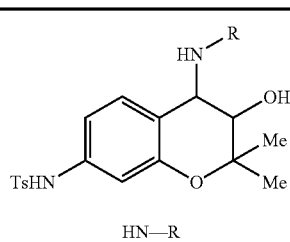
| HN—R |
|---|
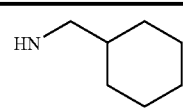
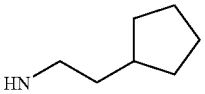
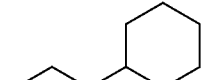
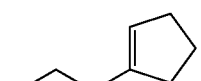
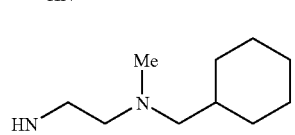
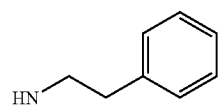
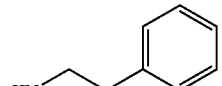
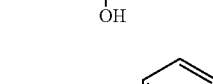
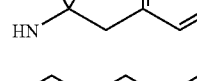
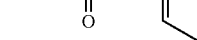

TABLE 36-continued
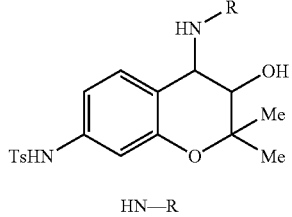
HN—R
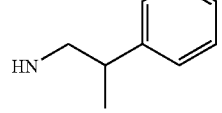
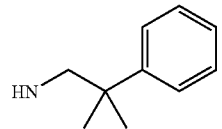
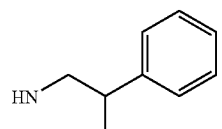
TABLE 37
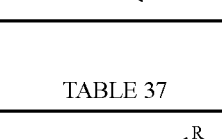
HN—R
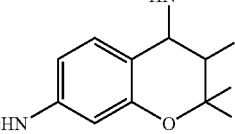
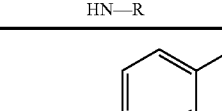
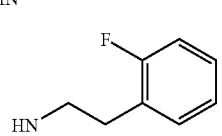
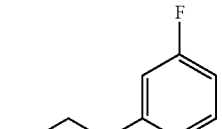
TABLE 37-continued
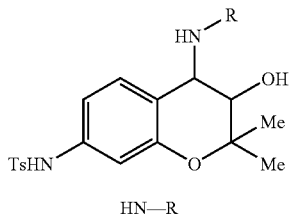
HN—R
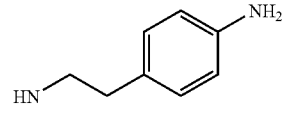
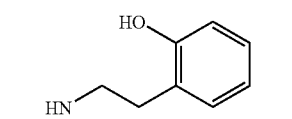
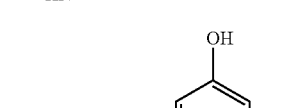
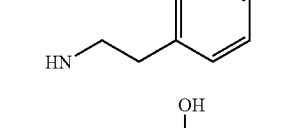
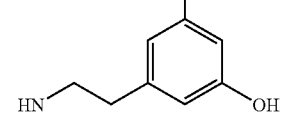
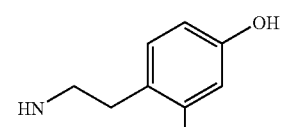
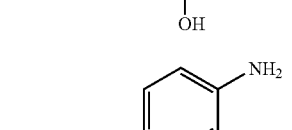
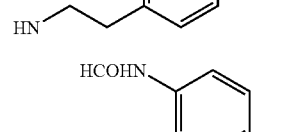
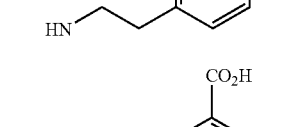
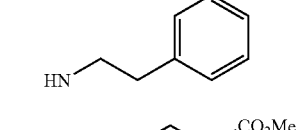
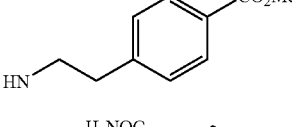
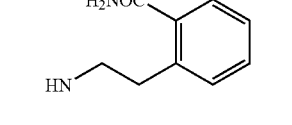

TABLE 37-continued
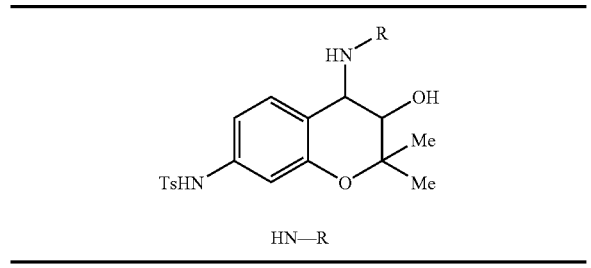
HN—R
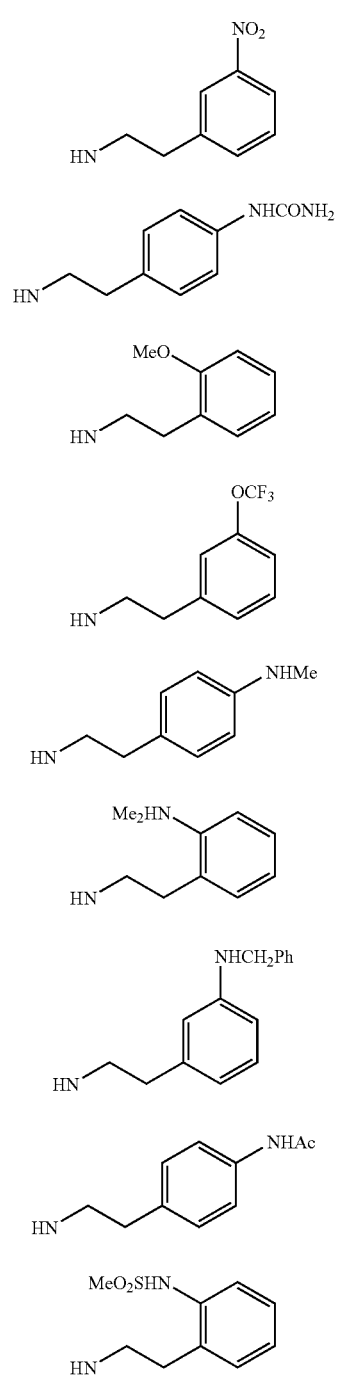
TABLE 37-continued
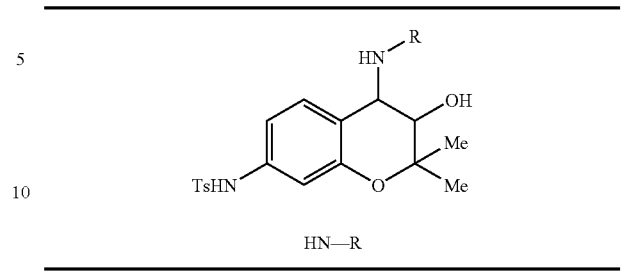
HN—R
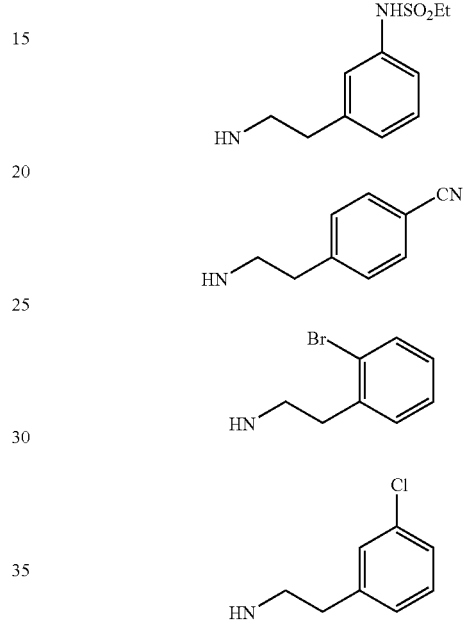
TABLE 38
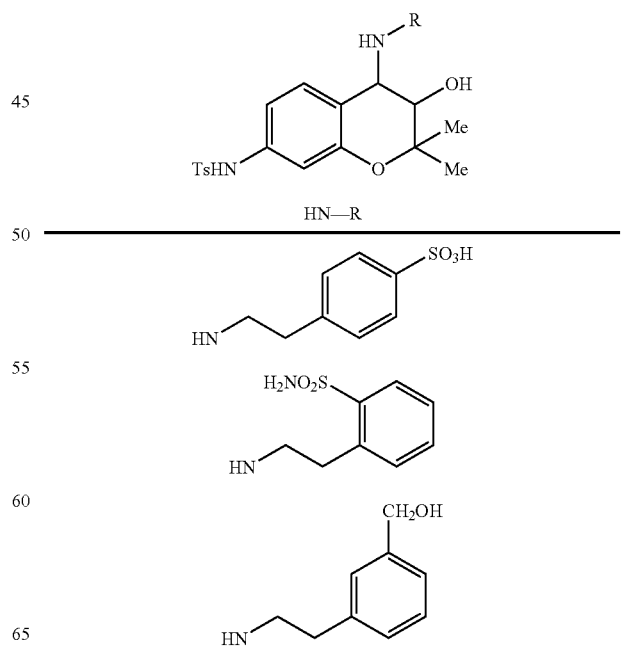

TABLE 38-continued (structure: 4-(R-amino)-3-hydroxy-2,2-dimethyl-7-(tosylamino)chroman)

HN—R

TABLE 38-continued
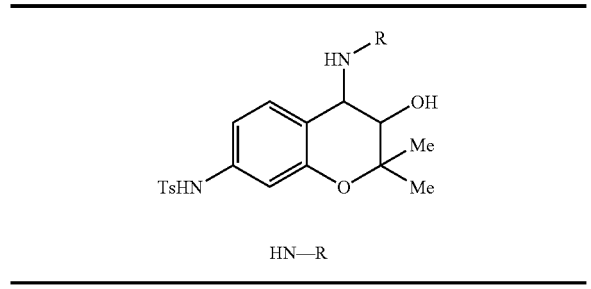
HN—R
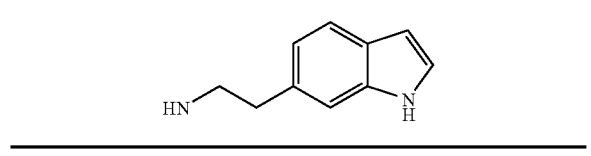
TABLE 39
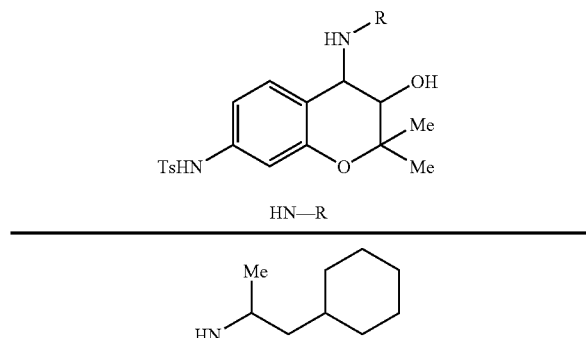
HN—R
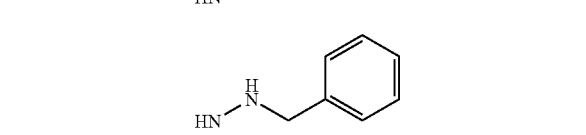
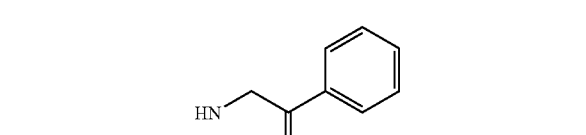
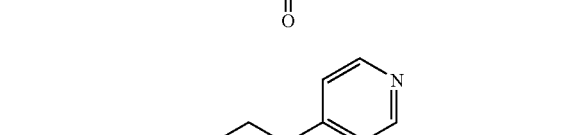
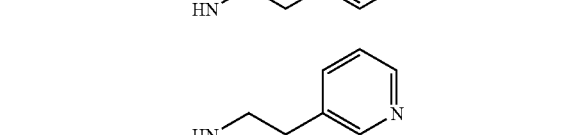
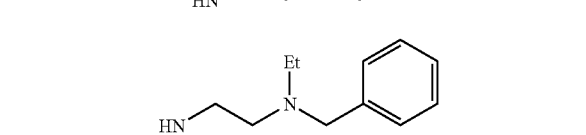
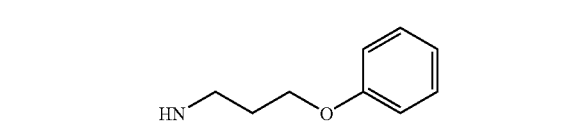
TABLE 39-continued
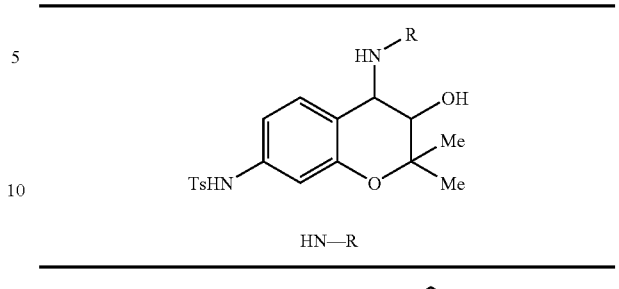
HN—R
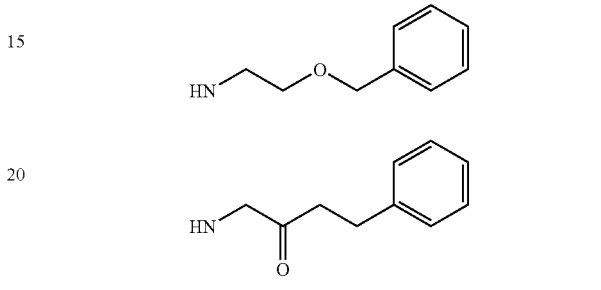
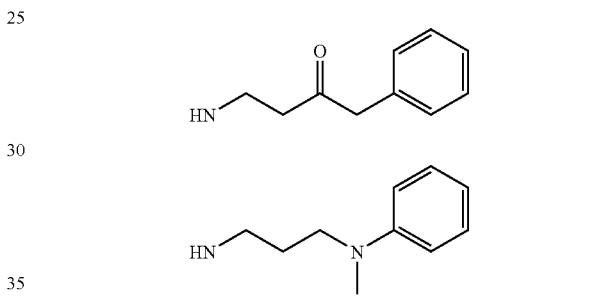
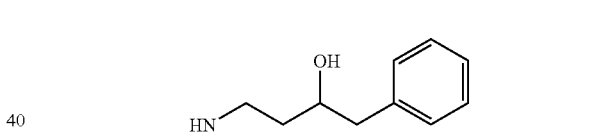
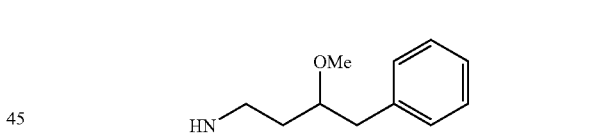
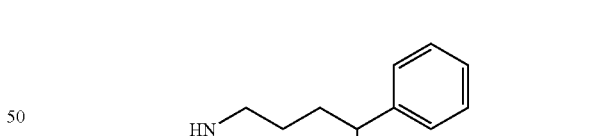
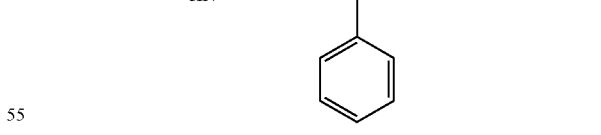
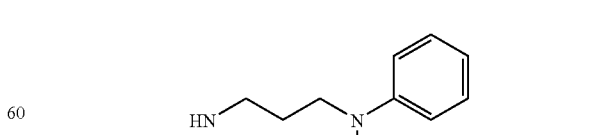
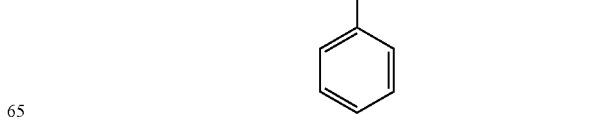

TABLE 39-continued
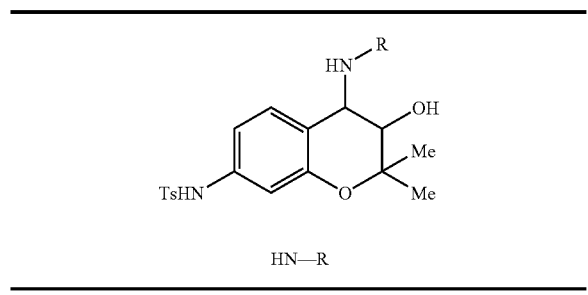
HN—R
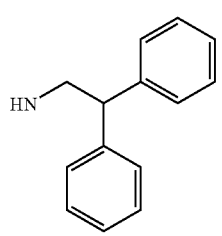
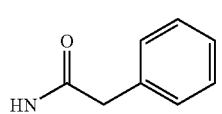
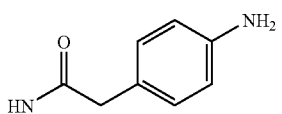
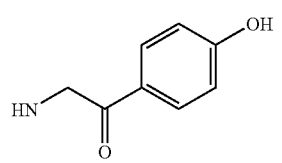
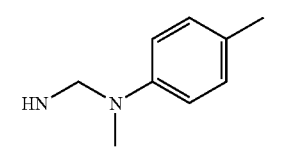
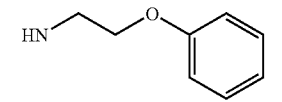
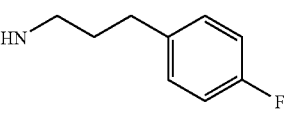
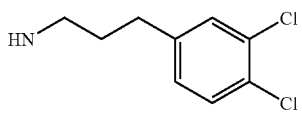
TABLE 40
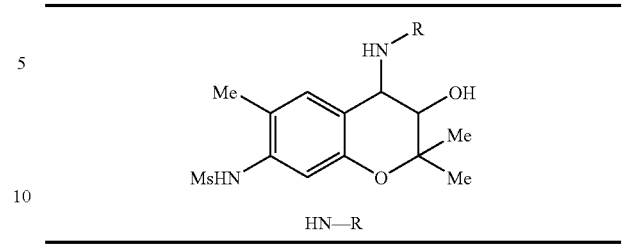
HN—R
HN—Me
HN—Et
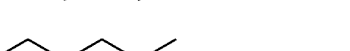

TABLE 40-continued
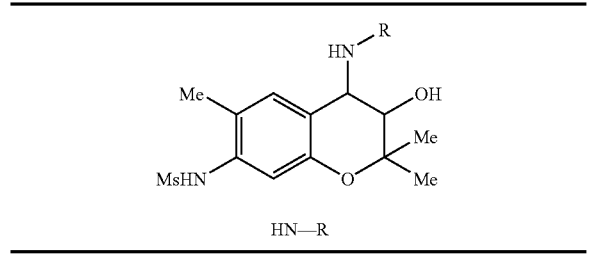
HN—R
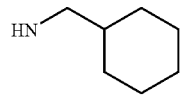
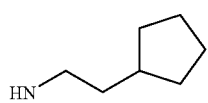
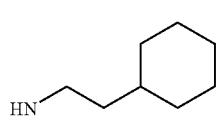
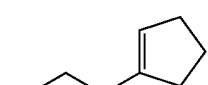
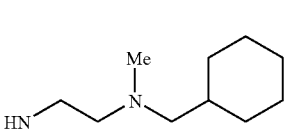
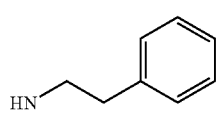
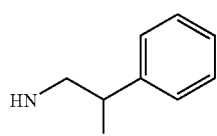
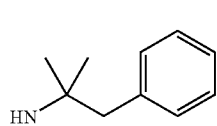
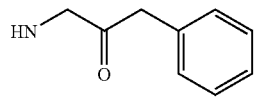
TABLE 40-continued
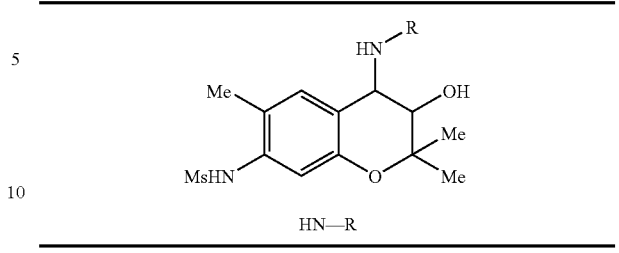
HN—R
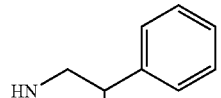
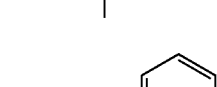
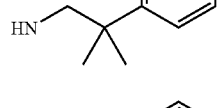
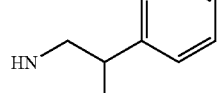
TABLE 41
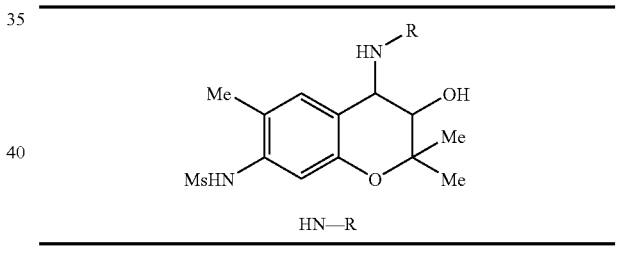
HN—R
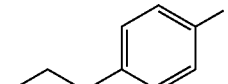
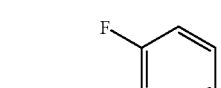
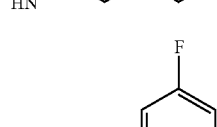
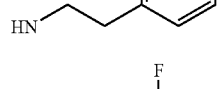
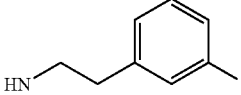

TABLE 41-continued

[Structure: chroman with Me at 6, MsHN at 7, OH at 3, NHR at 4, 2,2-diMe]

| HN—R |
|---|

- 4-aminophenethylamine (HN-CH2CH2-C6H4-NH2)
- 2-hydroxyphenethylamine
- 3-hydroxyphenethylamine
- 3,5-dihydroxyphenethylamine
- 2,4-dihydroxyphenethylamine
- 4-aminophenethylamine
- 2-(formylamino)phenethylamine (HCOHN-)
- 3-carboxyphenethylamine (CO2H)
- 4-(methoxycarbonyl)phenethylamine (CO2Me)
- 2-(aminocarbonyl)phenethylamine (H2NOC-)

TABLE 41-continued

[Structure: chroman with Me at 6, MsHN at 7, OH at 3, NHR at 4, 2,2-diMe]

| HN—R |
|---|

- 3-nitrophenethylamine (NO2)
- 4-(ureido)phenethylamine (NHCONH2)
- 2-methoxyphenethylamine (MeO)
- 3-(trifluoromethoxy)phenethylamine (OCF3)
- 4-(methylamino)phenethylamine (NHMe)
- 2-(dimethylamino)phenethylamine (Me2N)
- 3-(benzylamino)phenethylamine (NHCH2Ph)
- 4-(acetamido)phenethylamine (NHAc)
- 2-(methanesulfonylamino)phenethylamine (MeO2SHN-)

TABLE 41-continued
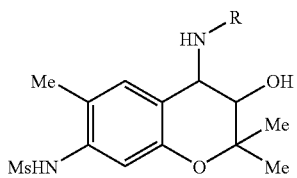
HN—R
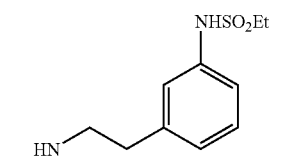
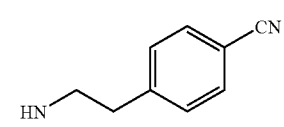
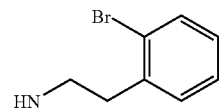
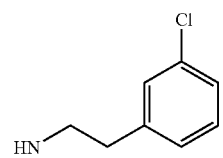
TABLE 42
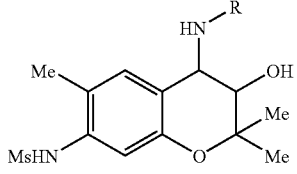
HN—R
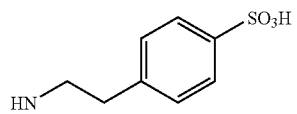
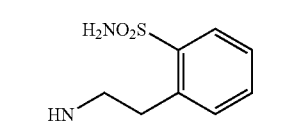
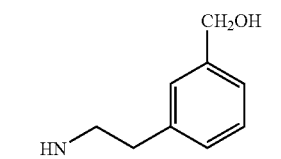
TABLE 42-continued
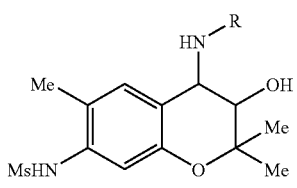
HN—R
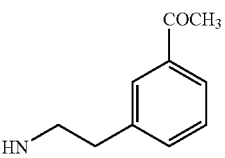
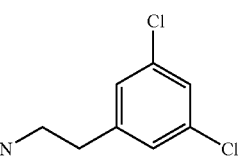
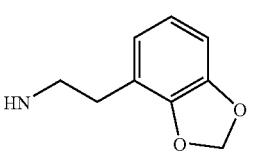
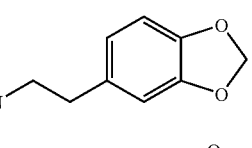
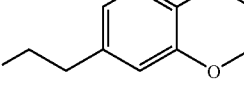
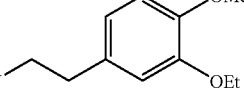
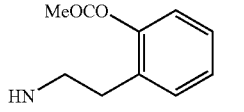
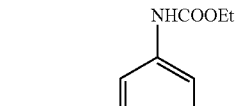
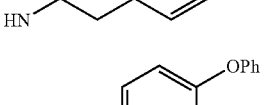
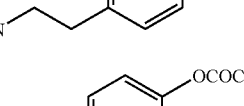
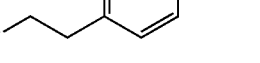

TABLE 42-continued
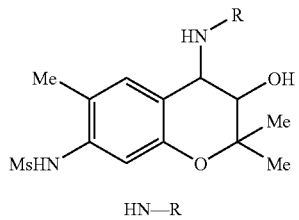
HN—R
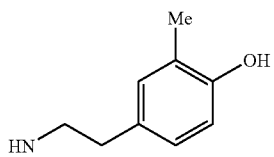
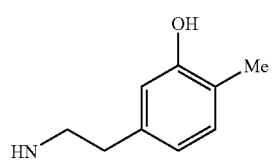
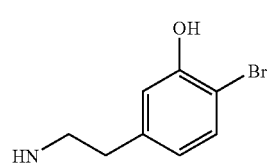
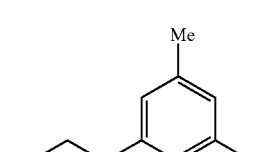
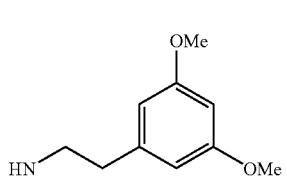
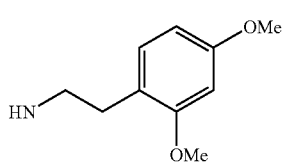
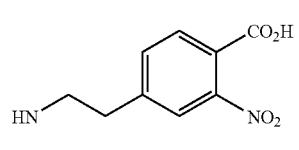
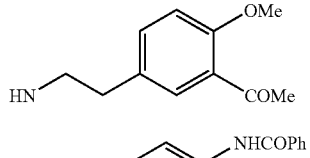
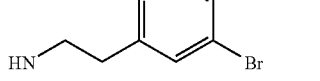
TABLE 42-continued
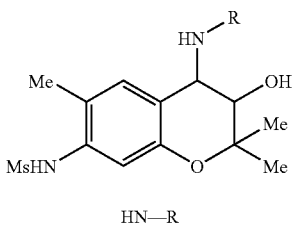
HN—R
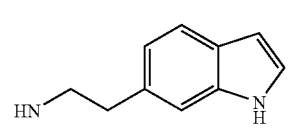
TABLE 43
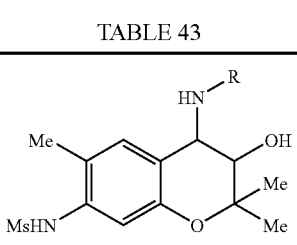
HN—R
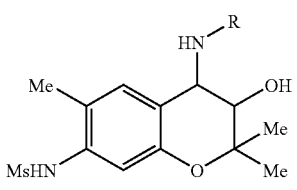
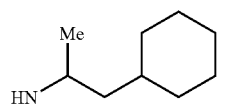
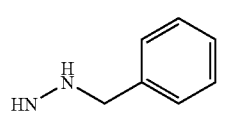
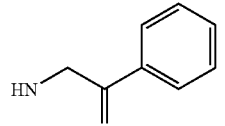
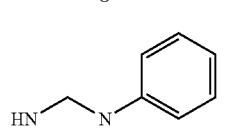
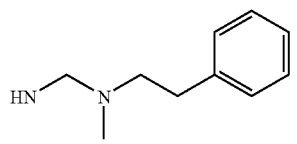
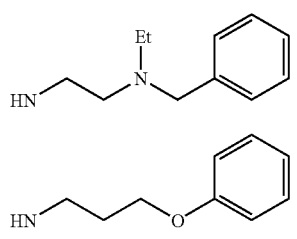

TABLE 43-continued
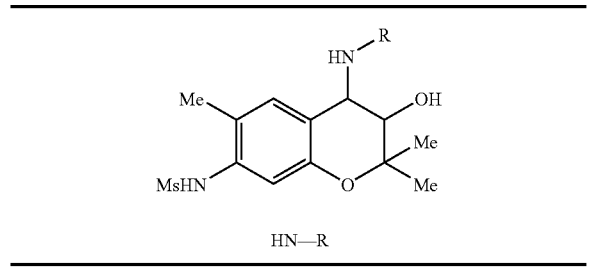
HN—R
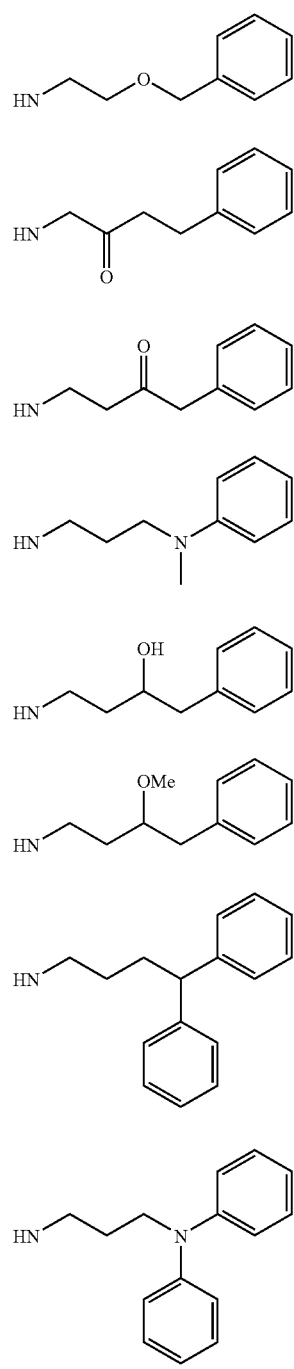
TABLE 43-continued
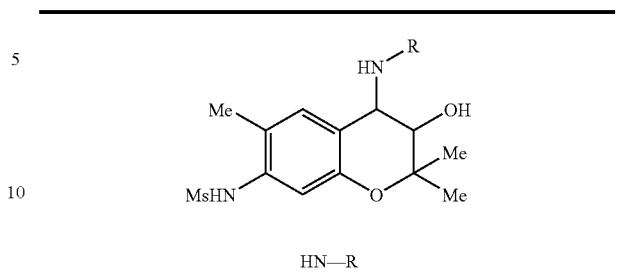
HN—R
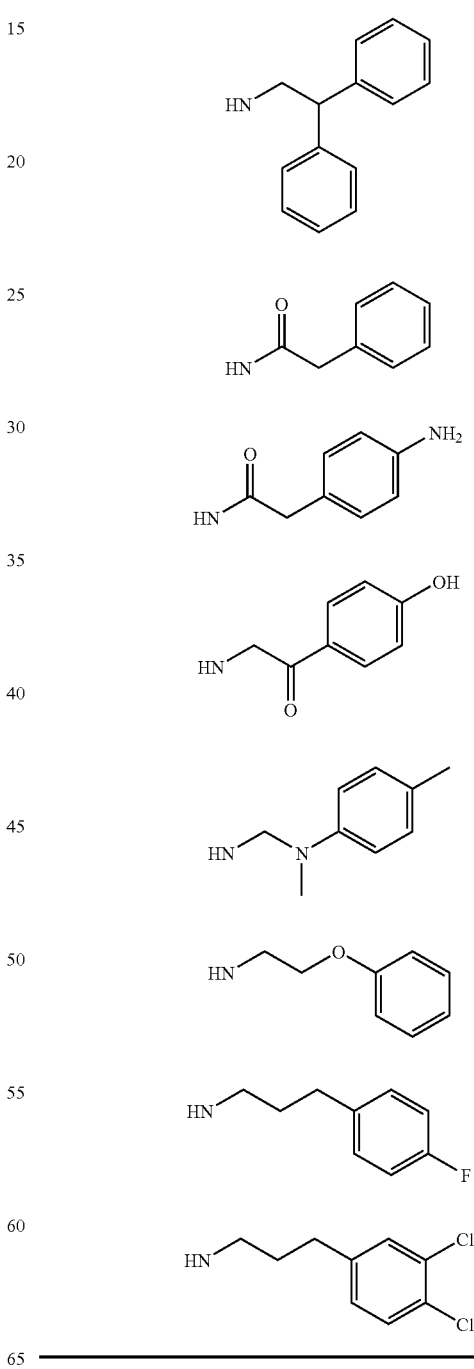

TABLE 44
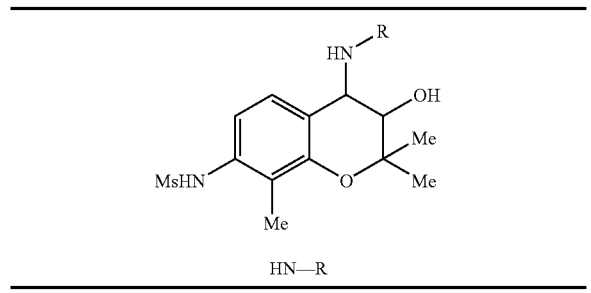
| HN—R |
|---|
| HN—Me |
| HN—Et |
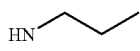
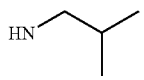
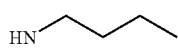
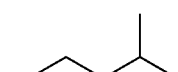
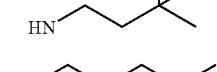
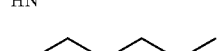
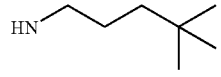
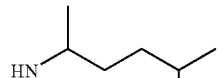
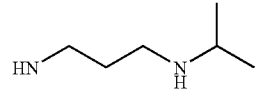
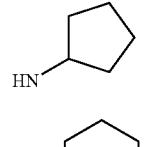
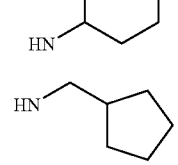
TABLE 44-continued
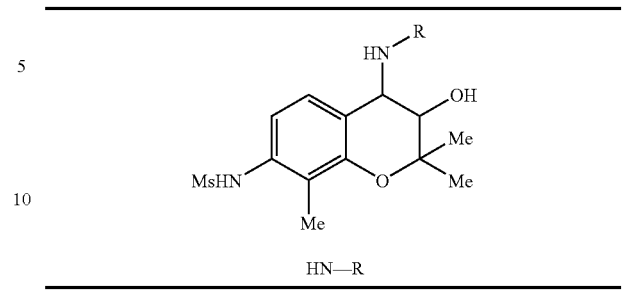
| HN—R |
|---|
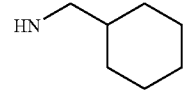
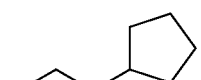
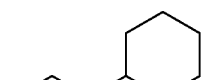
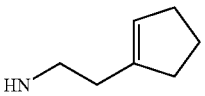
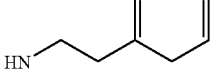
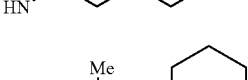
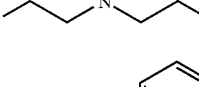
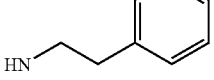
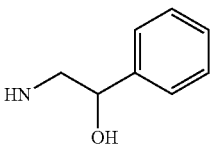
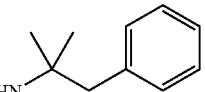
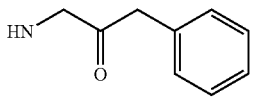

TABLE 44-continued
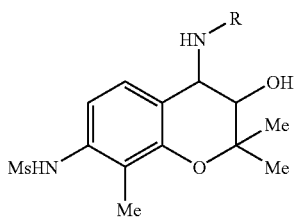
HN—R
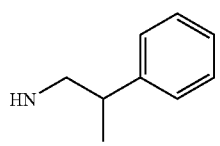
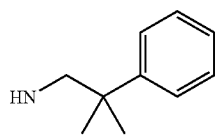
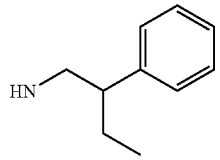
TABLE 45
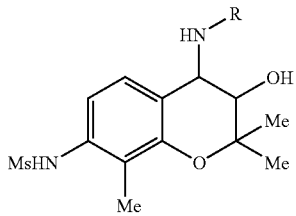
HN—R
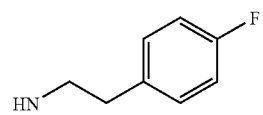
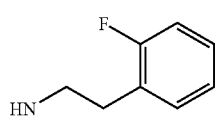
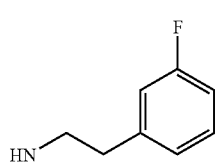
TABLE 45-continued
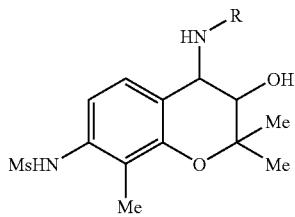
HN—R
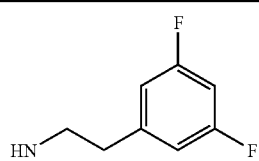
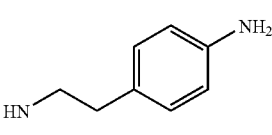
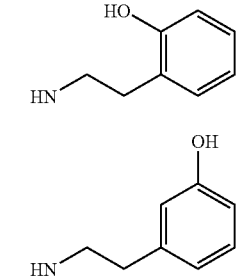
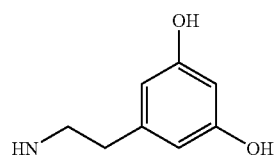
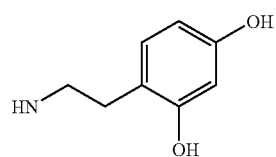
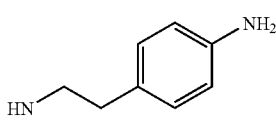
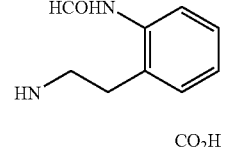
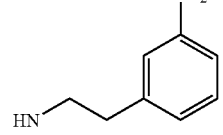

TABLE 45-continued
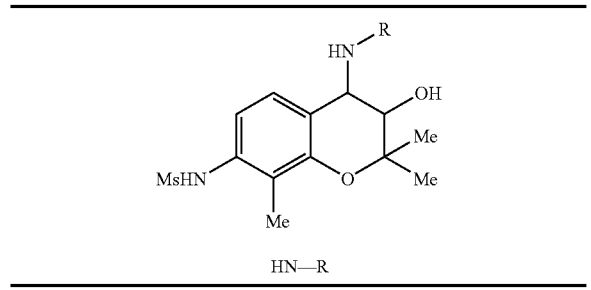
HN—R
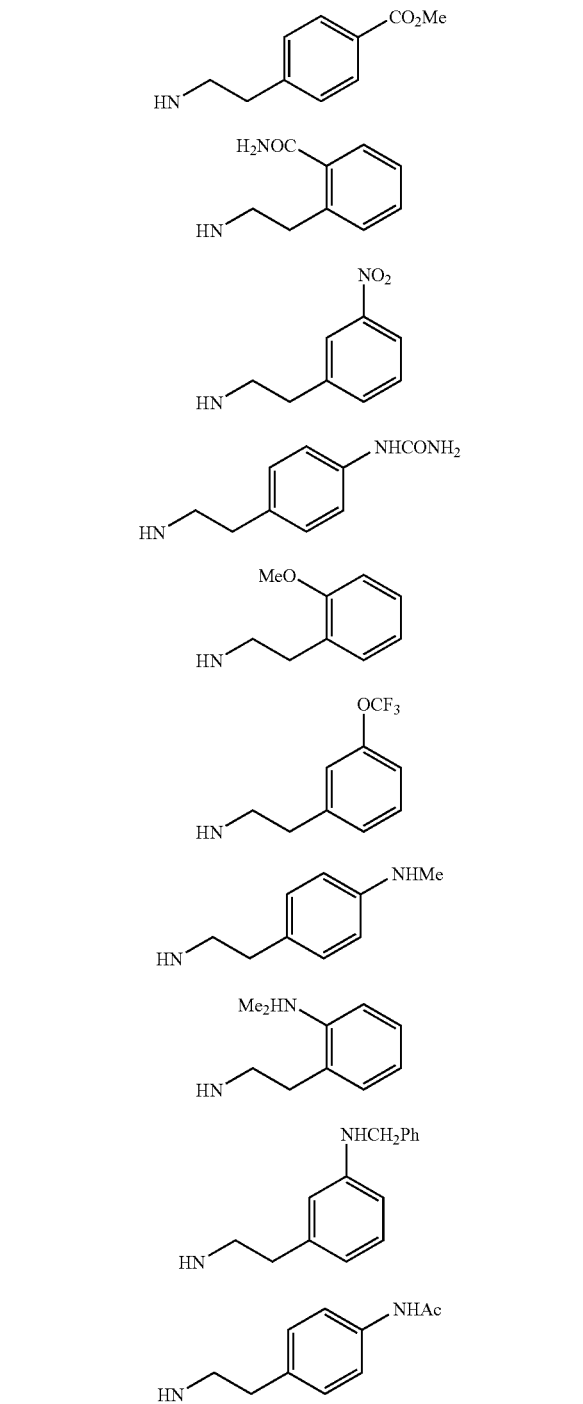
TABLE 45-continued
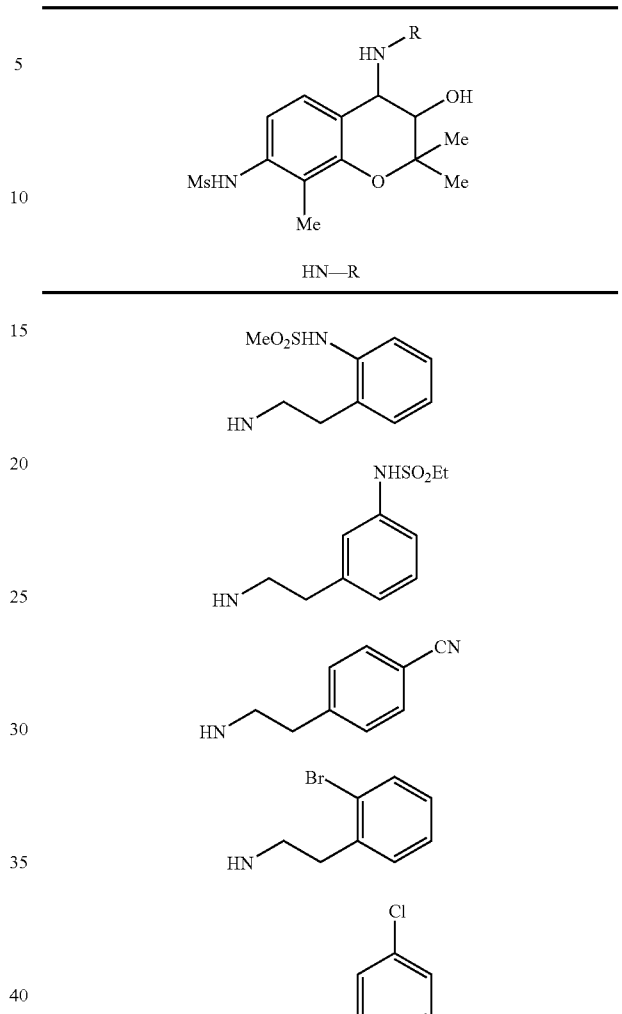
TABLE 46
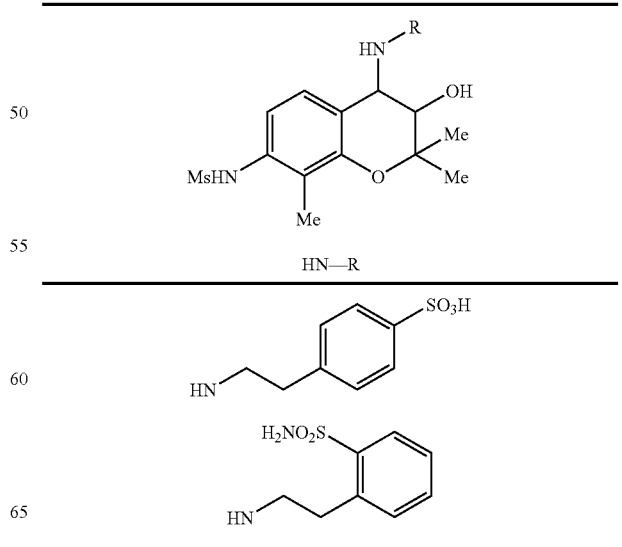

TABLE 46-continued

[Structures with core: 4-(NHR)-3-OH-2,2,8-trimethyl-7-(MsHN)-chroman]

HN—R (Column 139)
- 3-(hydroxymethyl)phenethylamine
- 3-acetylphenethylamine
- 3,5-dichlorophenethylamine
- 2-(benzo[d][1,3]dioxol-4-yl)ethylamine
- 2-(benzo[d][1,3]dioxol-5-yl)ethylamine
- 2-(2,3-dihydrobenzo[b][1,4]dioxin-6-yl)ethylamine
- 2-(3-ethoxy-4-methoxyphenyl)ethylamine
- 2-(2-(methoxycarbonyloxy)phenyl)ethylamine
- 2-(3-(ethoxycarbonylamino)phenyl)ethylamine (Column 140)
- 2-(4-phenoxyphenyl)ethylamine
- 2-(4-acetoxyphenyl)ethylamine
- 2-(4-hydroxy-3-methylphenyl)ethylamine
- 2-(3-hydroxy-4-methylphenyl)ethylamine
- 2-(4-bromo-3-hydroxyphenyl)ethylamine
- 2-(3,5-dimethylphenyl)ethylamine
- 2-(3,5-dimethoxyphenyl)ethylamine
- 2-(2,4-dimethoxyphenyl)ethylamine TABLE 46-continued
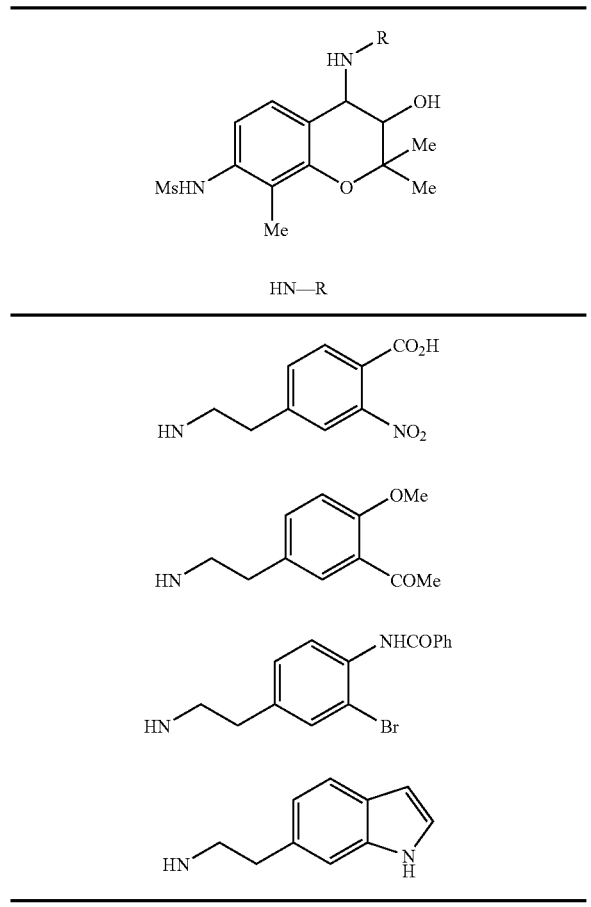
TABLE 47
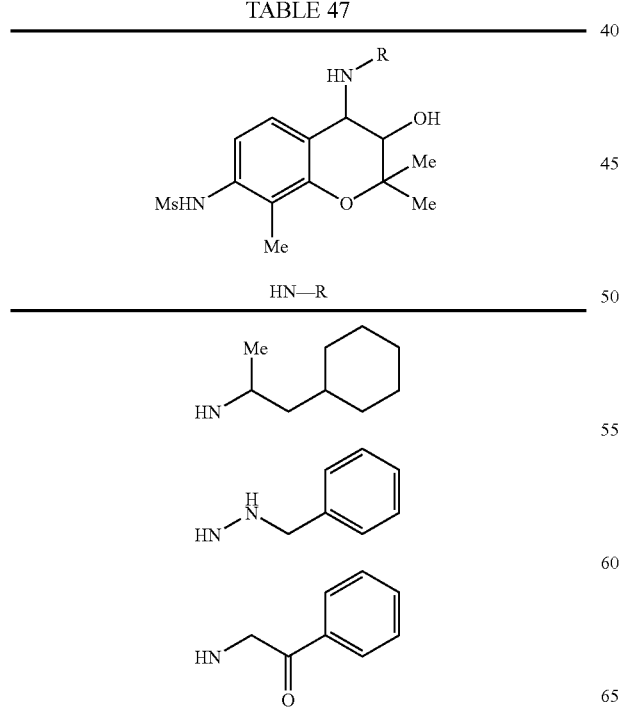
TABLE 47-continued
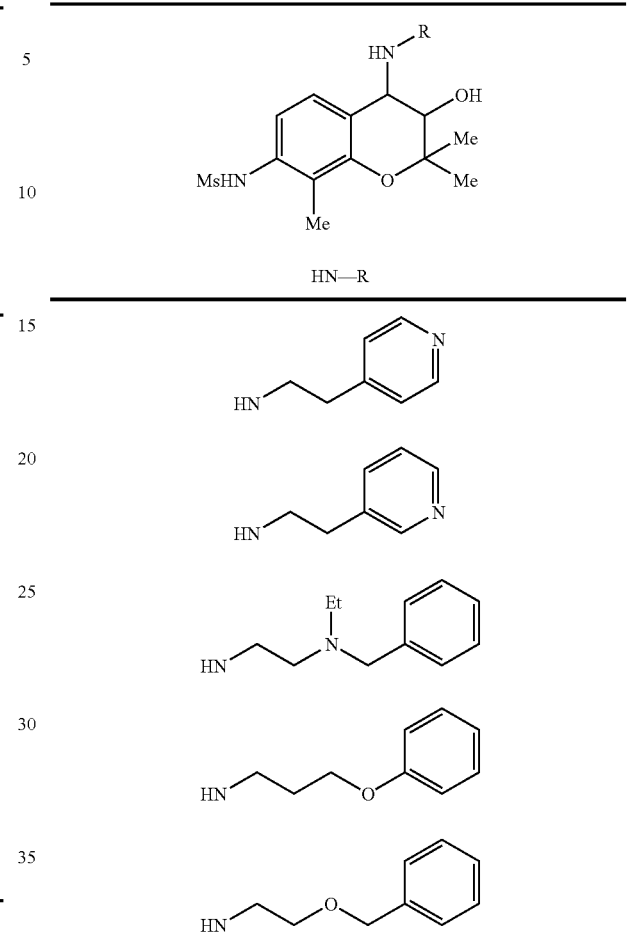
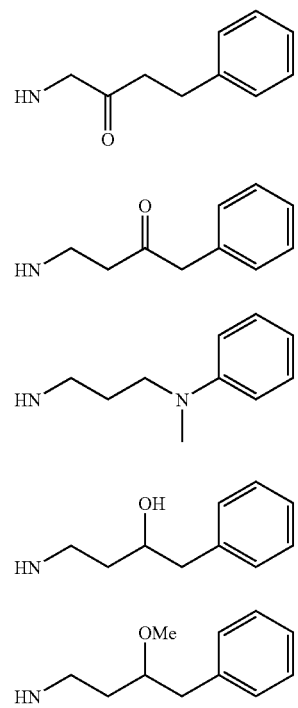

TABLE 47-continued
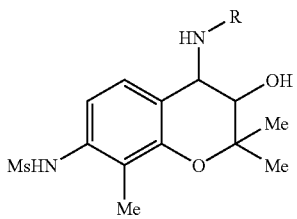
HN—R
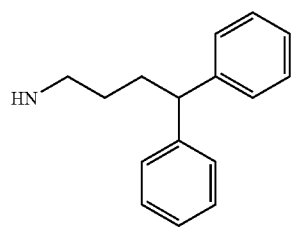
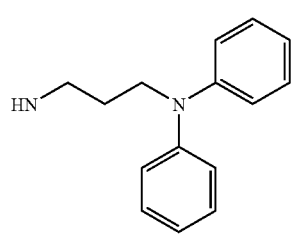
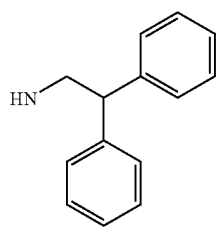
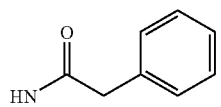
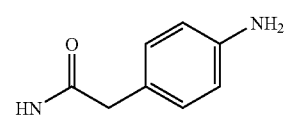
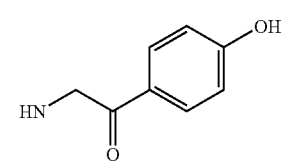
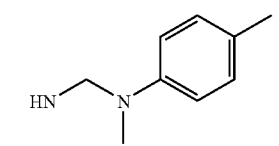
TABLE 47-continued
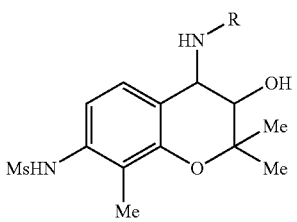
HN—R
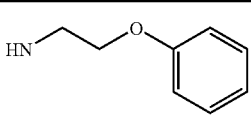
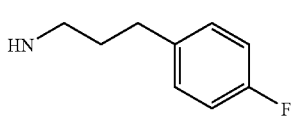
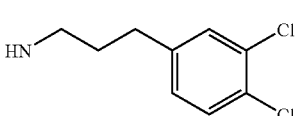
TABLE 48
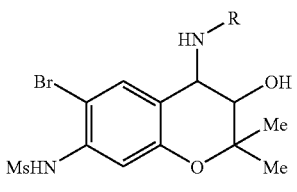
HN—R
HN—Me
HN—Et
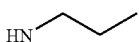
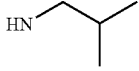
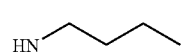
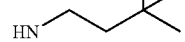

TABLE 48-continued
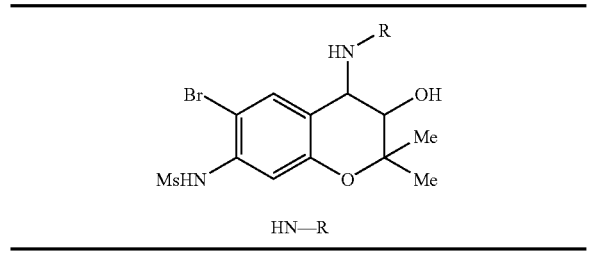
HN—R
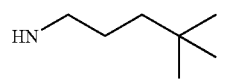
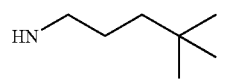
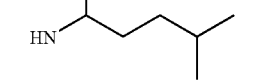
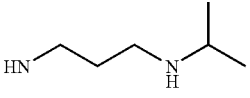
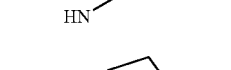
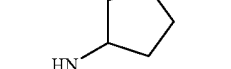
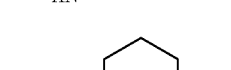
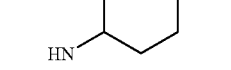
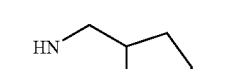
TABLE 48-continued
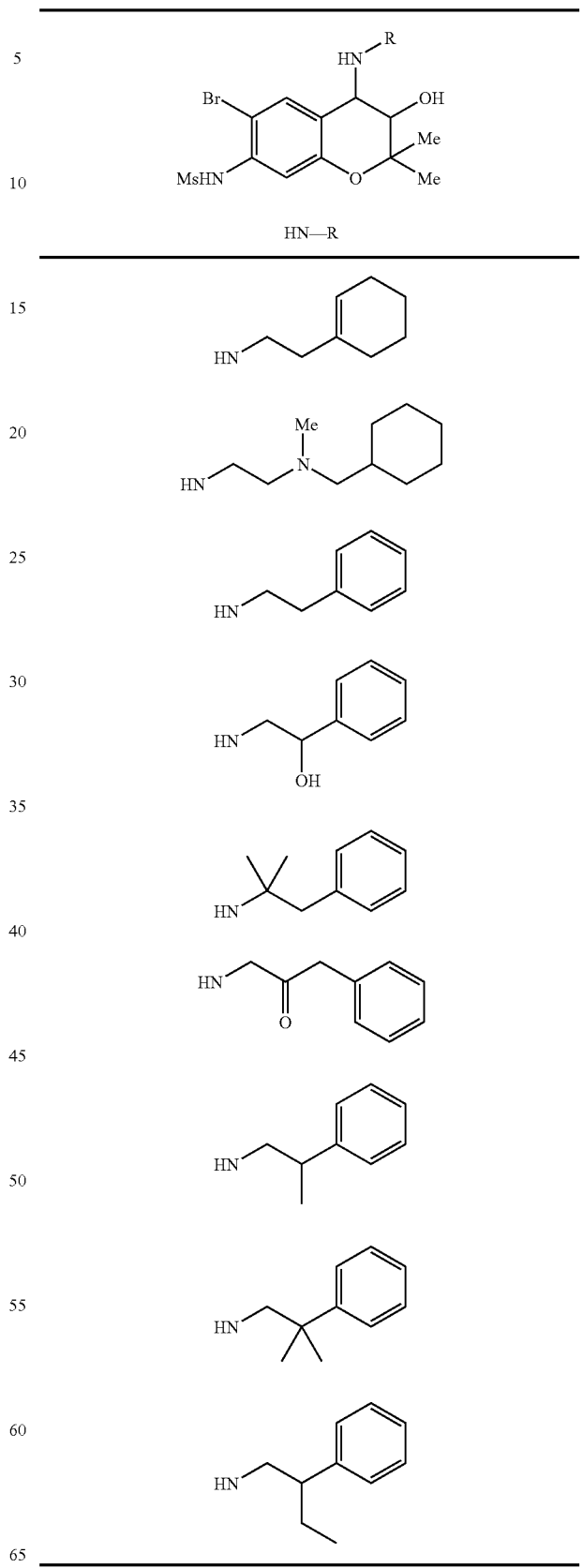

TABLE 49
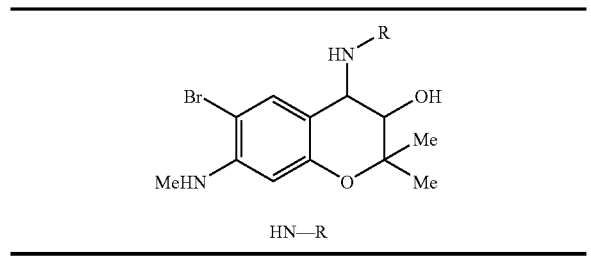
HN—R
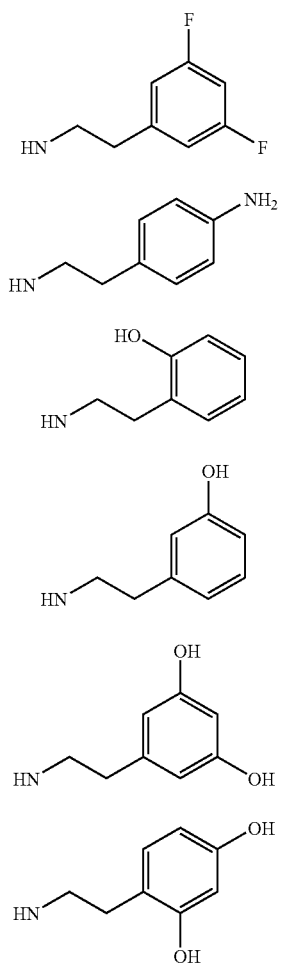
TABLE 49-continued
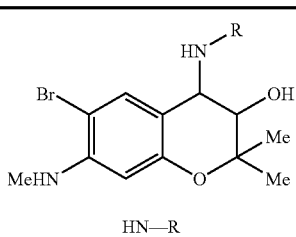
HN—R
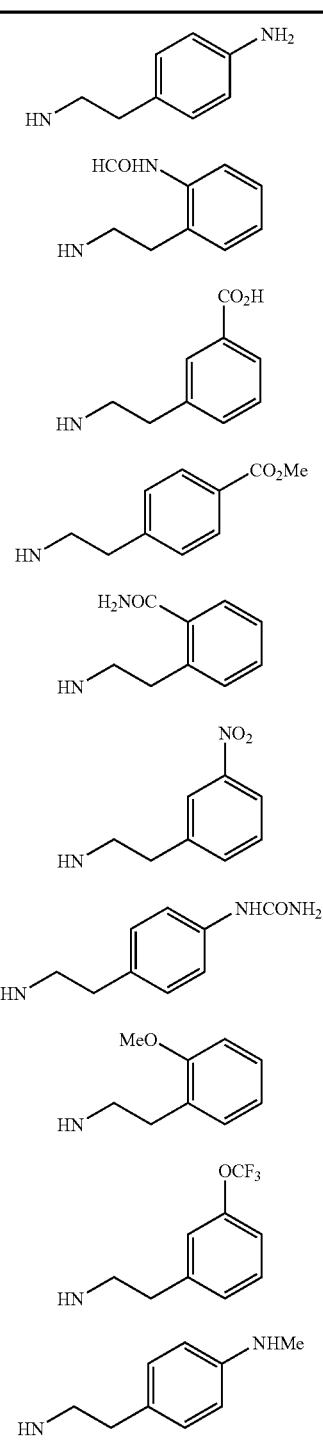

TABLE 49-continued

[Structure: 6-bromo-7-(methylamino)-2,2-dimethyl-4-(NHR)-chroman-3-ol]

HN—R

[Structures of R-NH groups shown:]
- 2-(2-(dimethylamino)phenyl)ethylamine
- 2-(3-(benzylamino)phenyl)ethylamine
- 2-(4-acetamidophenyl)ethylamine
- 2-(2-(methylsulfonamido)phenyl)ethylamine
- 2-(3-(ethylsulfonamido)phenyl)ethylamine
- 2-(4-cyanophenyl)ethylamine
- 2-(2-bromophenyl)ethylamine
- 2-(3-chlorophenyl)ethylamine

TABLE 50

[Structure: 6-bromo-7-(methanesulfonamido)-2,2-dimethyl-4-(NHR)-chroman-3-ol]

HN—R

[Structures of R-NH groups shown:]
- 2-(4-sulfophenyl)ethylamine
- 2-(2-sulfamoylphenyl)ethylamine
- 2-(3-(hydroxymethyl)phenyl)ethylamine
- 2-(3-acetylphenyl)ethylamine
- 2-(3,5-dichlorophenyl)ethylamine
- 2-(benzo[d][1,3]dioxol-4-yl)ethylamine
- 2-(benzo[d][1,3]dioxol-5-yl)ethylamine
- 2-(2,3-dihydrobenzo[b][1,4]dioxin-6-yl)ethylamine
- 2-(3-ethoxy-4-methoxyphenyl)ethylamine
- 2-(2-(methoxycarbonyloxy)phenyl)ethylamine TABLE 50-continued
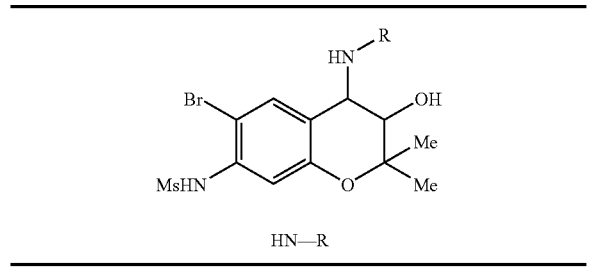
HN—R
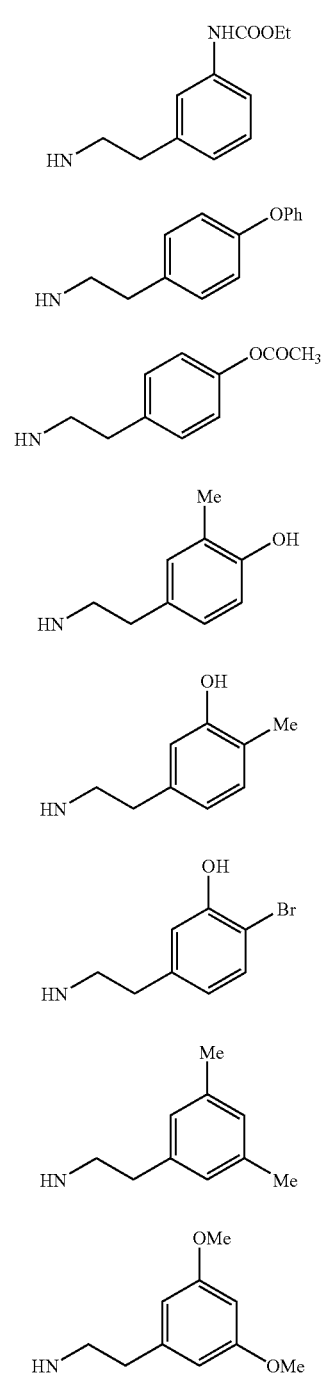
TABLE 50-continued
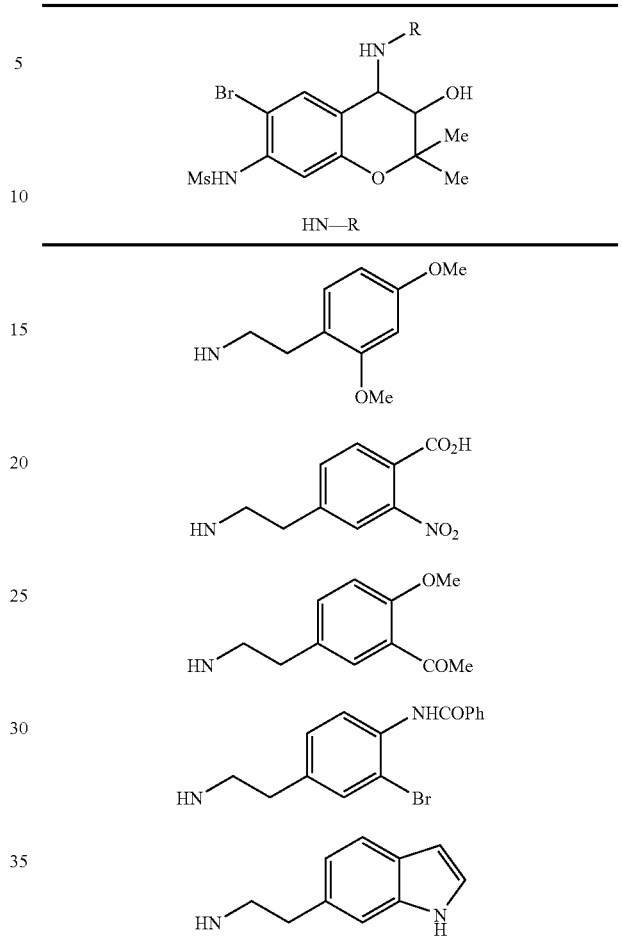
TABLE 51
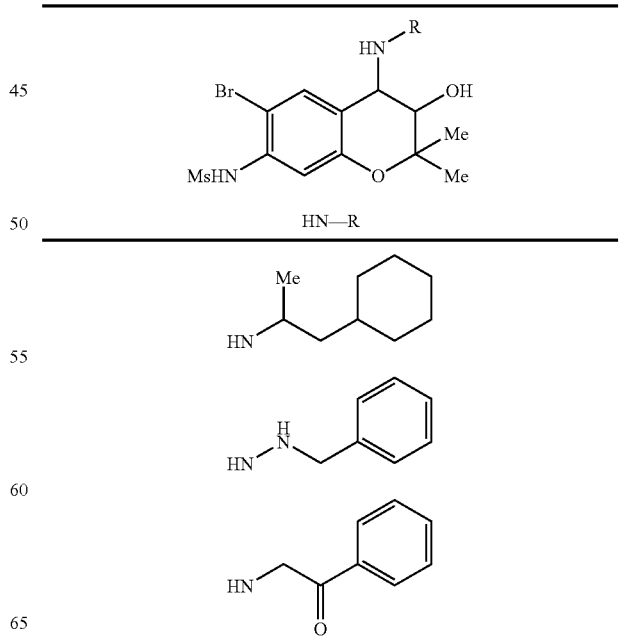

TABLE 51-continued
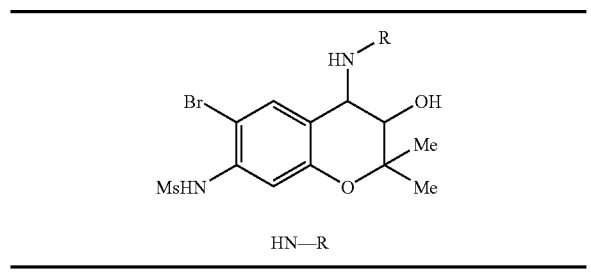
HN—R
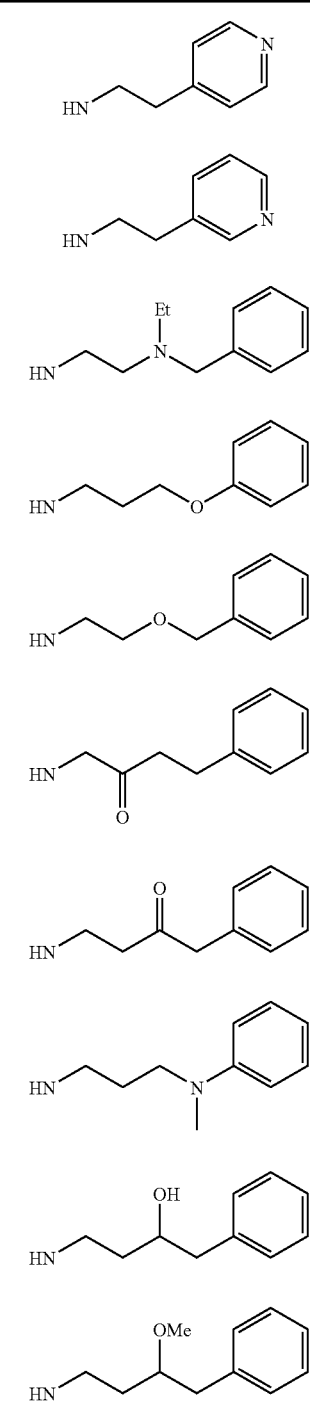
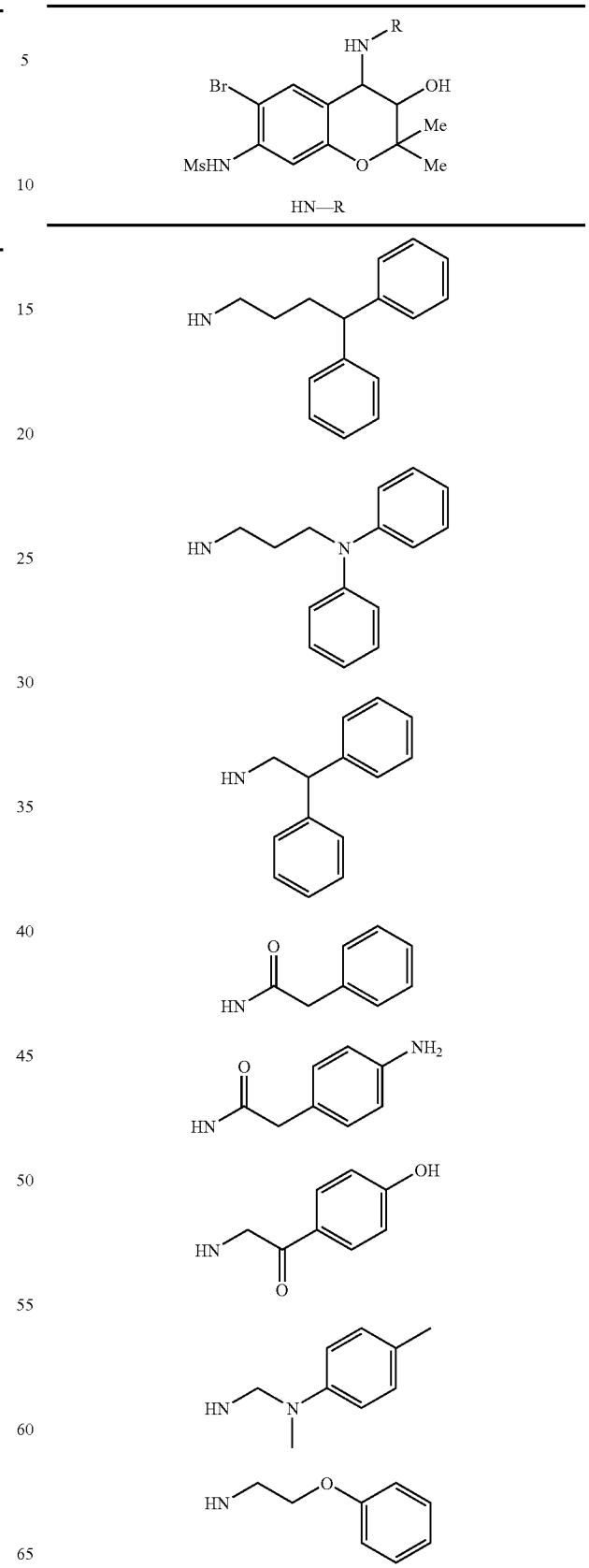

TABLE 51-continued
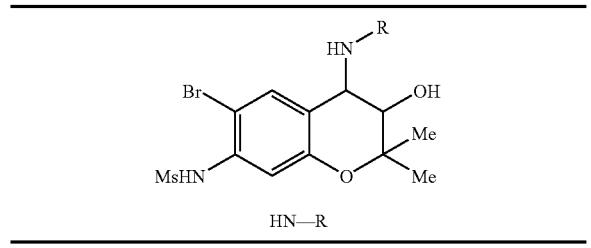
| HN—R |
|---|
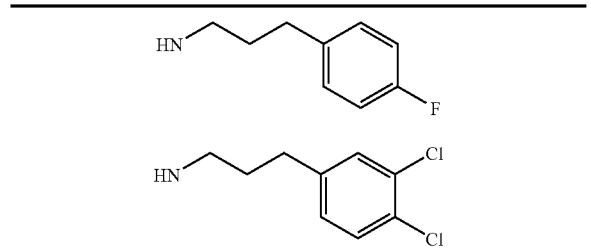
TABLE 52
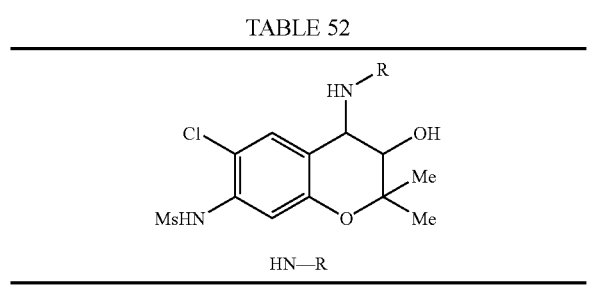
| HN—R |
|---|
| HN—Me |
| HN—Et |
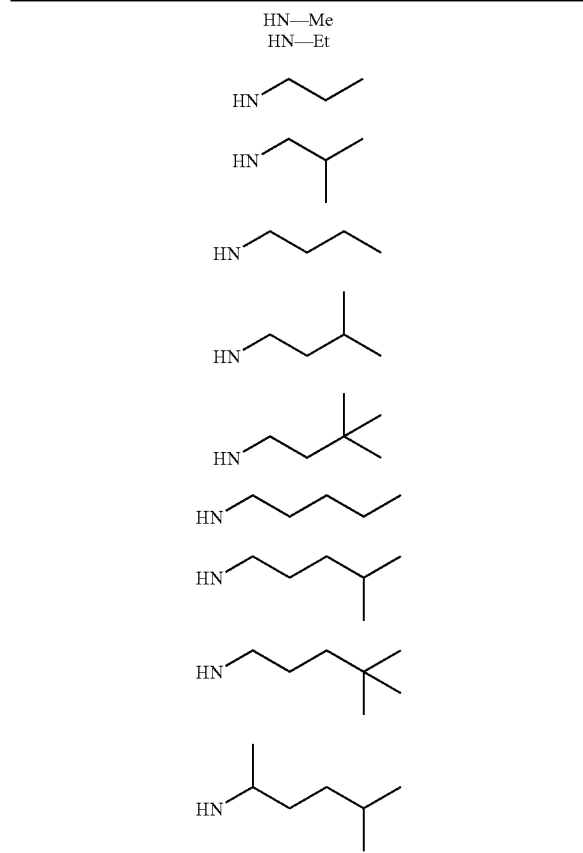
TABLE 52-continued
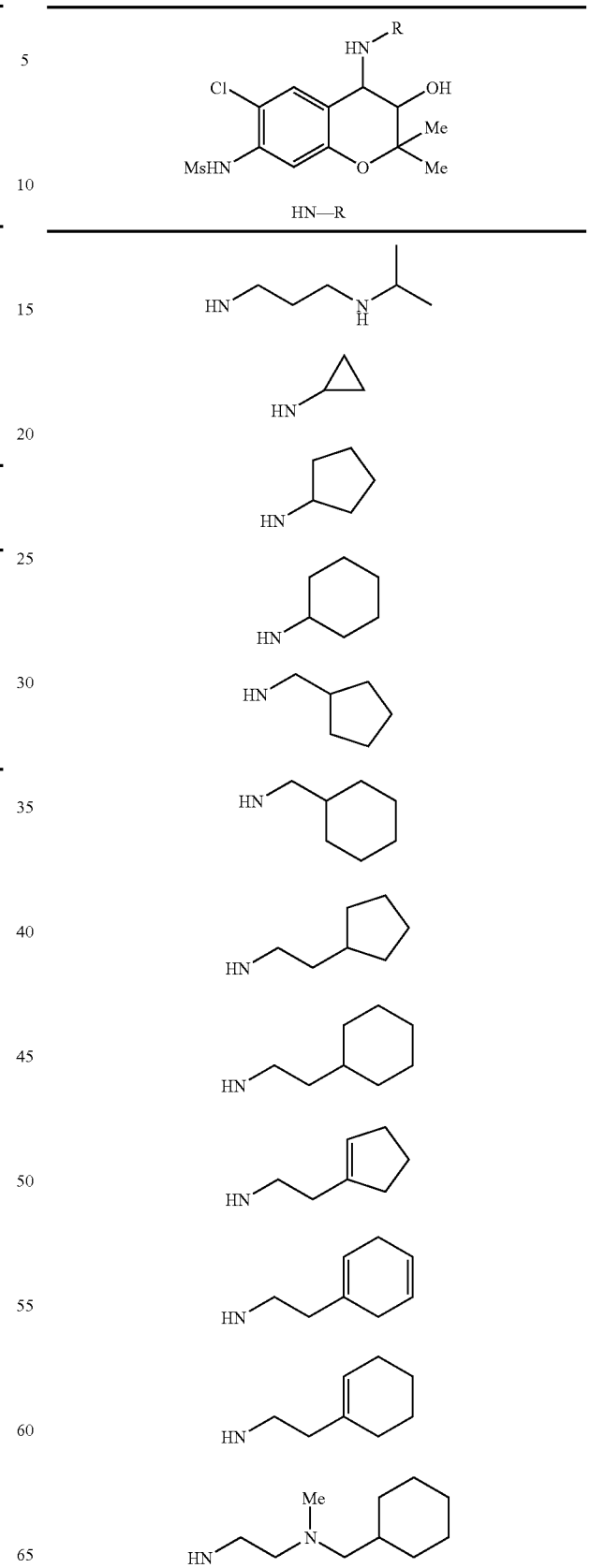

TABLE 52-continued
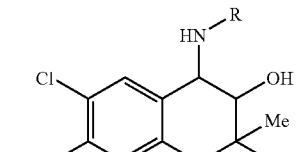
HN—R
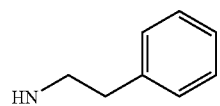
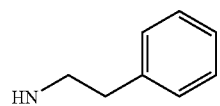
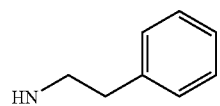
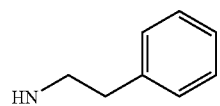
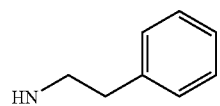
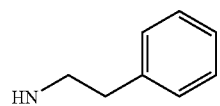
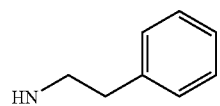
TABLE 53
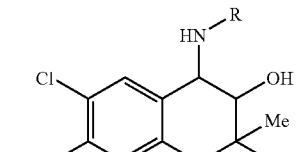
HN—R
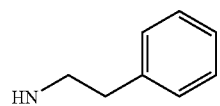
TABLE 53-continued
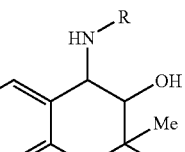
HN—R
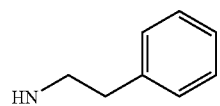
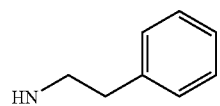
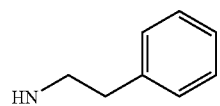
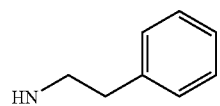
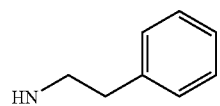
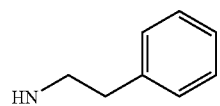
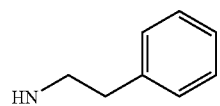
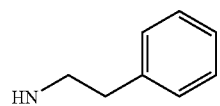
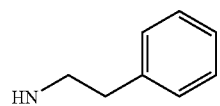

TABLE 53-continued
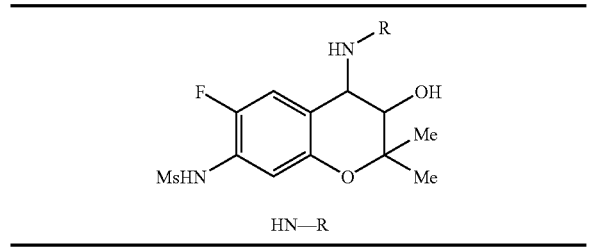
HN—R
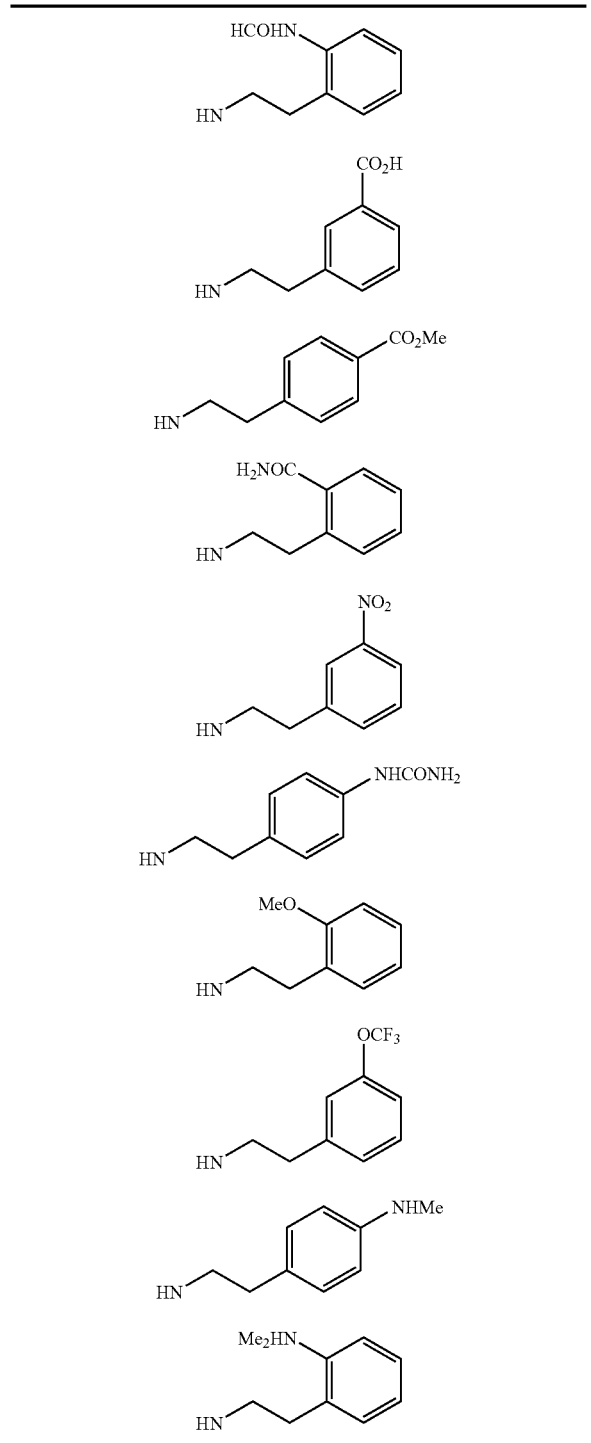
TABLE 53-continued
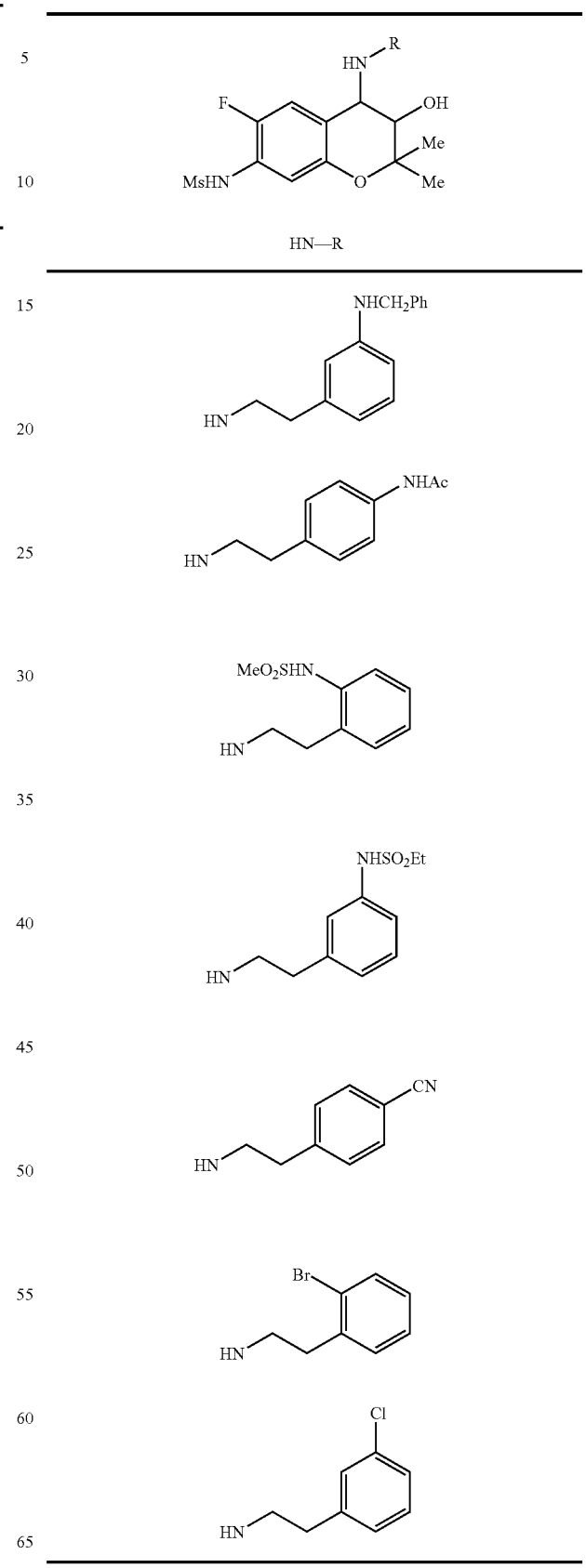

TABLE 54
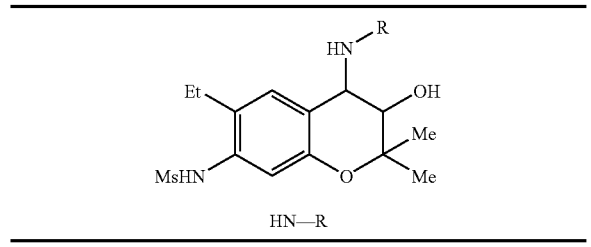
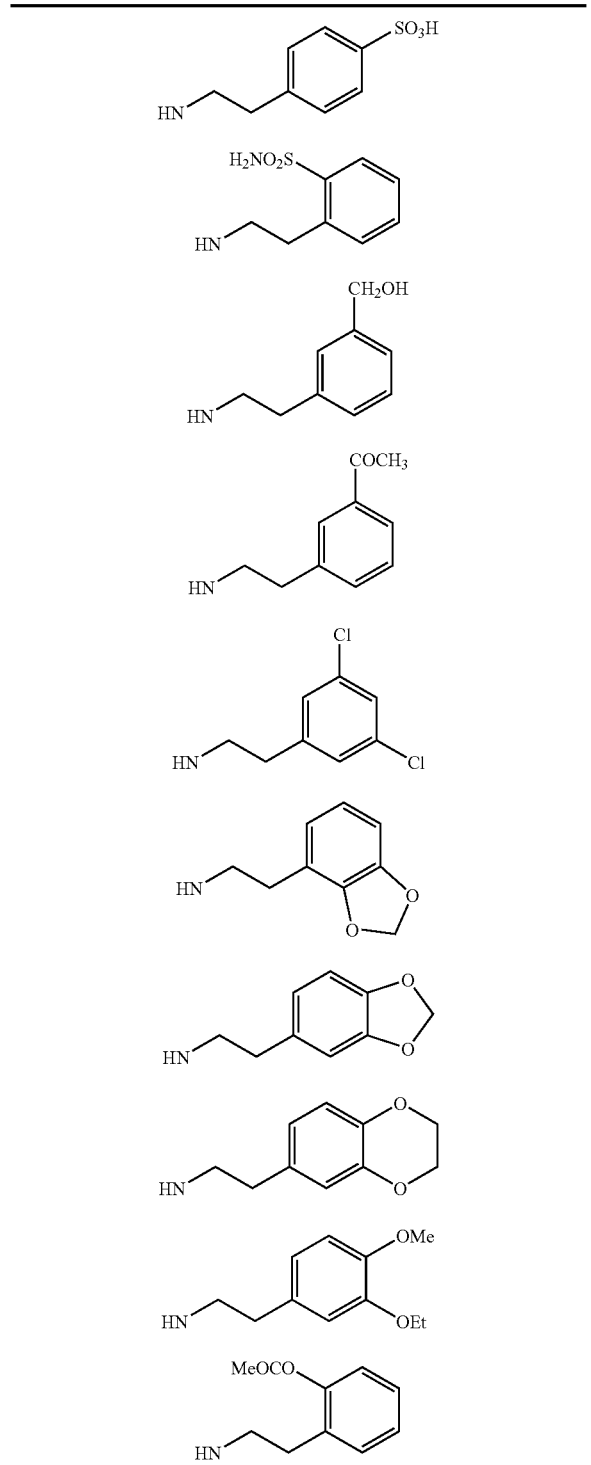
TABLE 54-continued
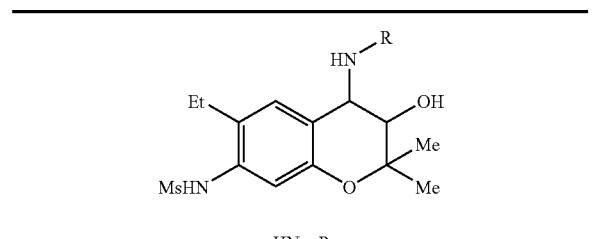
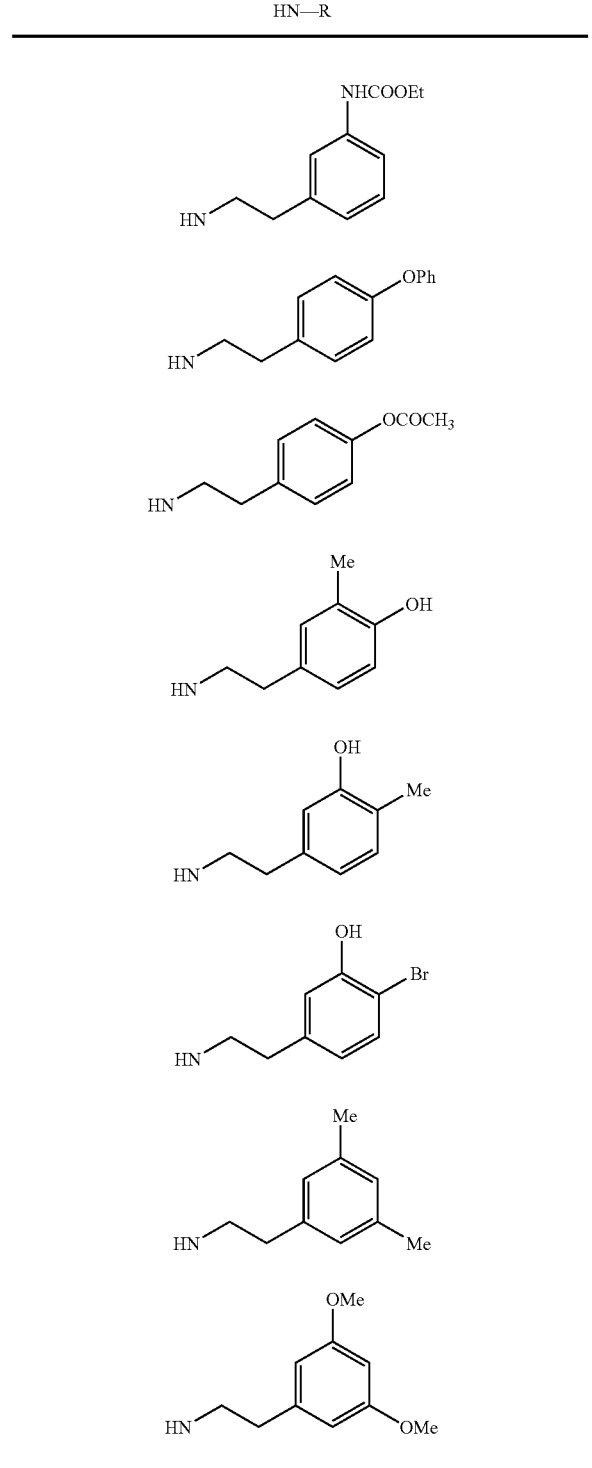

TABLE 54-continued
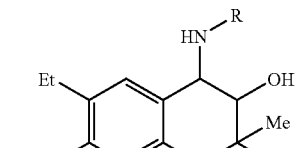
HN—R
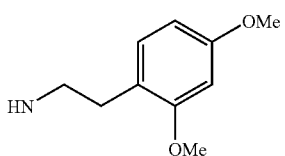
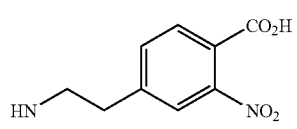
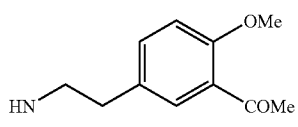
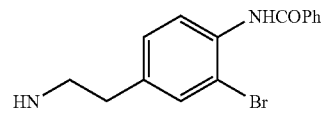
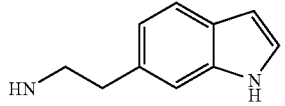
TABLE 55
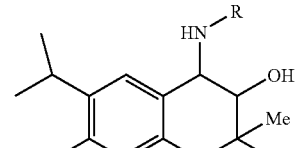
HN—R
HN—Me
HN—Et
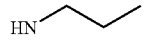
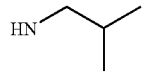
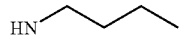
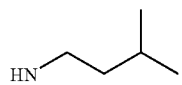
TABLE 55-continued
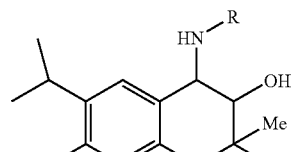
HN—R
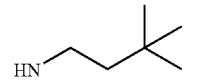
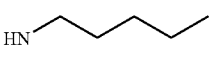
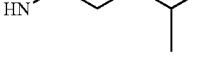
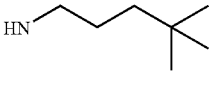
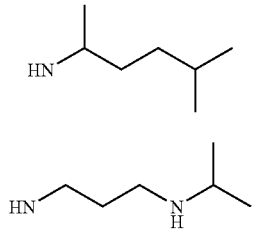
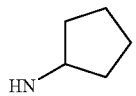
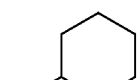
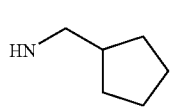
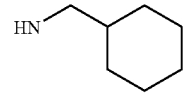
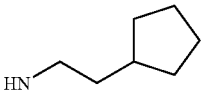
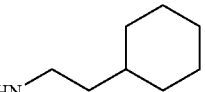

TABLE 55-continued
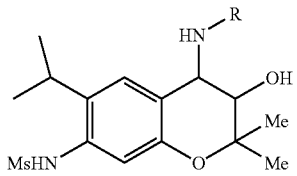
HN—R
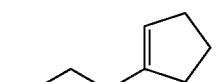
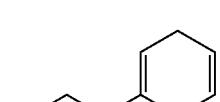
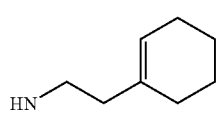
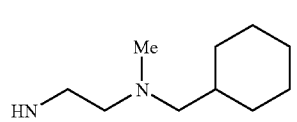
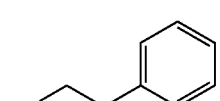
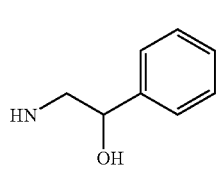
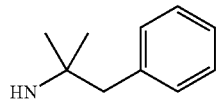
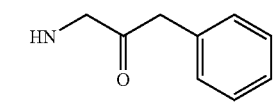
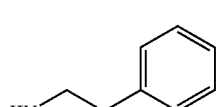
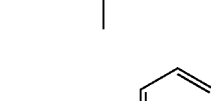
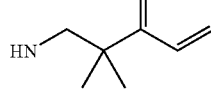
TABLE 55-continued
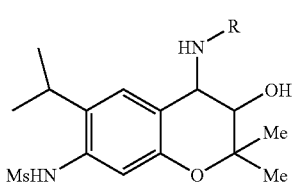
HN—R
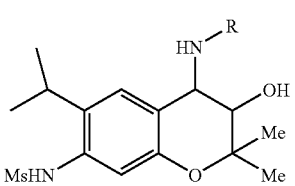
TABLE 56
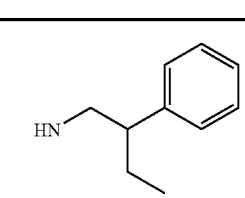
HN—R
HN—Me
HN—Et
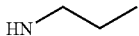
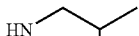
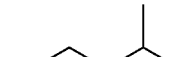
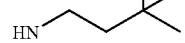
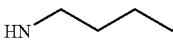
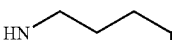

TABLE 56-continued
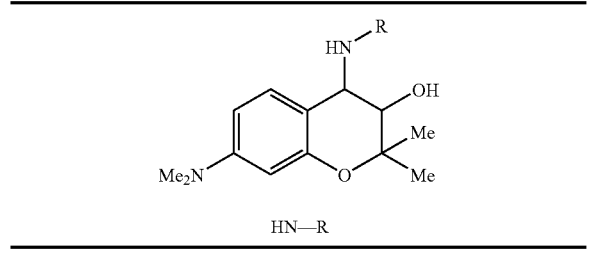
HN—R
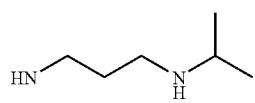
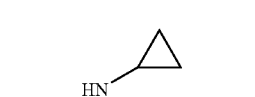
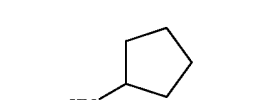
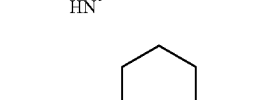
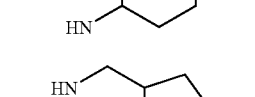
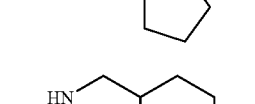
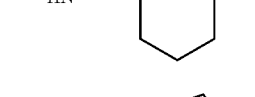
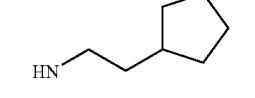
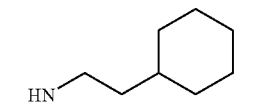
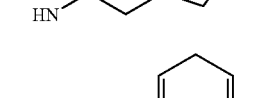
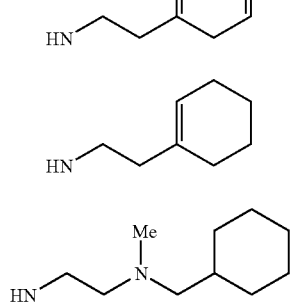
TABLE 56-continued
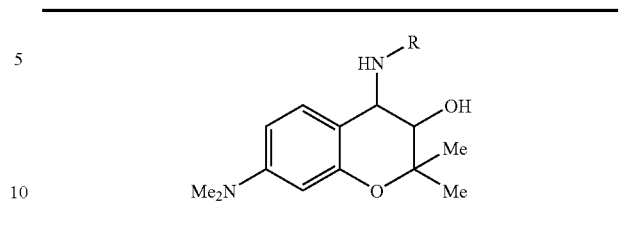
HN—R
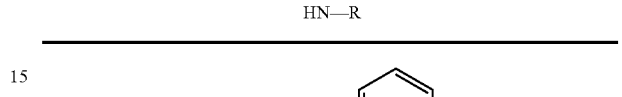
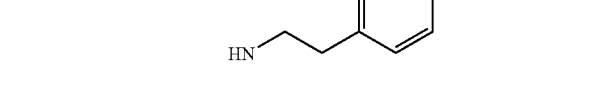
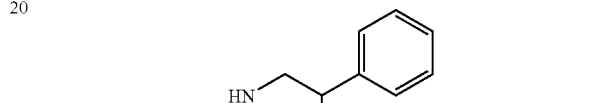
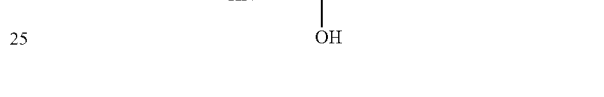
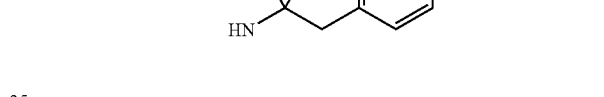
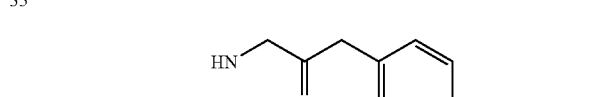
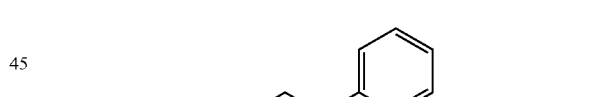
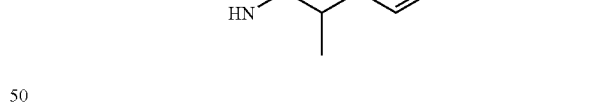
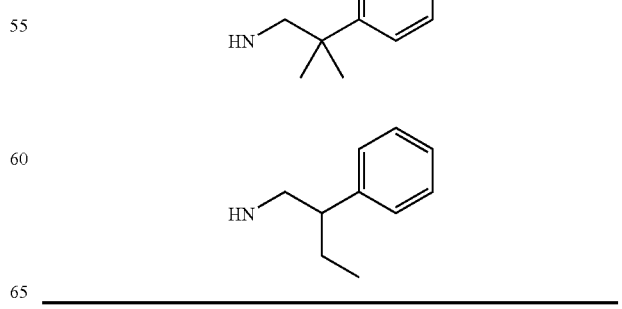

TABLE 57
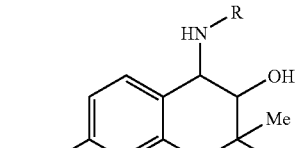
| HN—R |
|---|
| HN—Me |
| HN—Et |
|  |
| 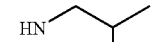 |
| 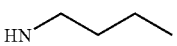 |
|  |
|  |
| 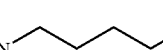 |
| 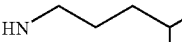 |
| 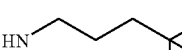 |
|  |
|  |
|  |
|  |
| 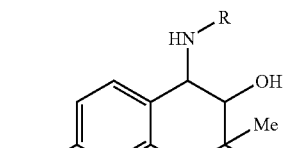 |
TABLE 57-continued
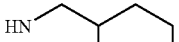
| HN—R |
|---|
|  |
|  |
| 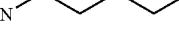 |
| 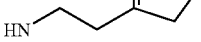 |
|  |
|  |
|  |
|  |
| 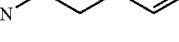 |
| 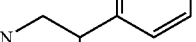 |

TABLE 57-continued
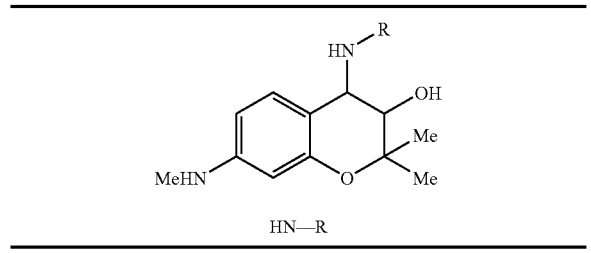
HN—R
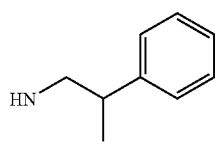
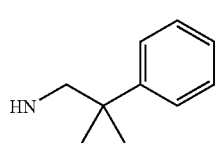
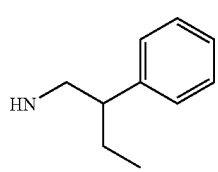
TABLE 58
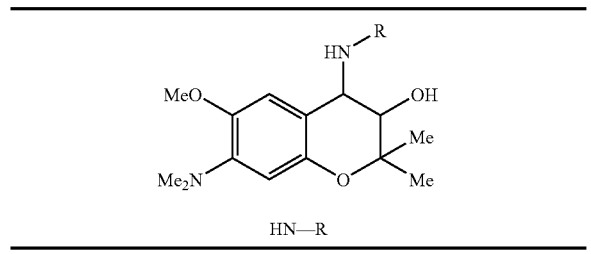
HN—R
HN—Me
HN—Et
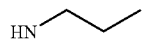
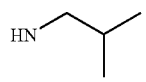
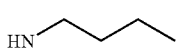
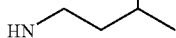
TABLE 58-continued
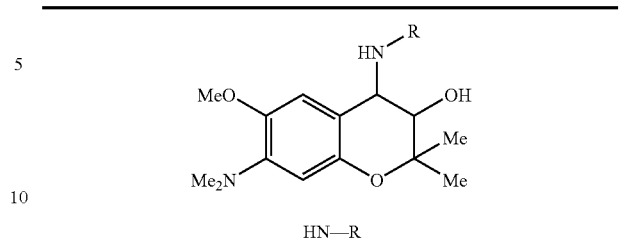
HN—R
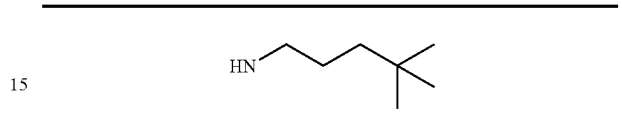
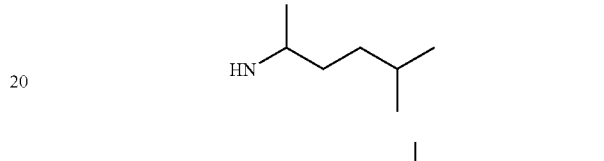
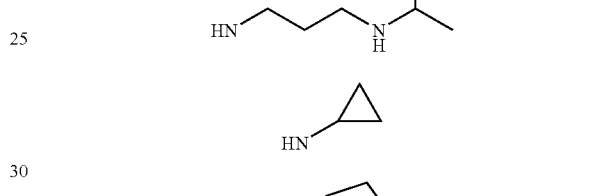
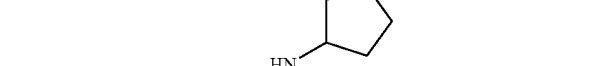
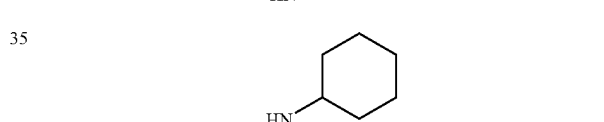
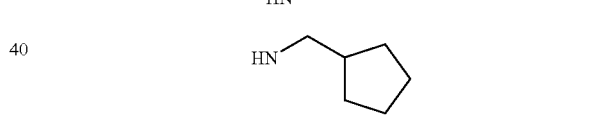
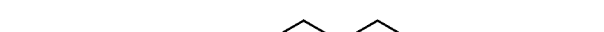
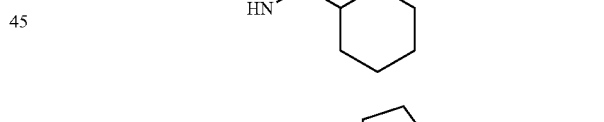
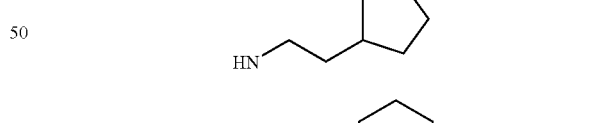
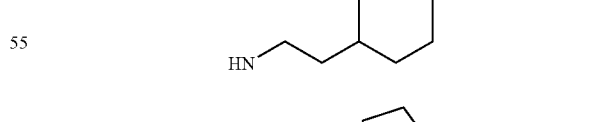
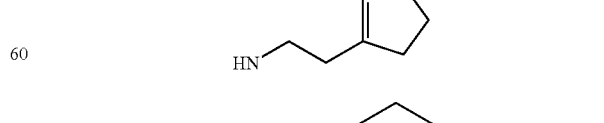

TABLE 58-continued
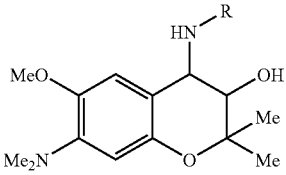
HN—R
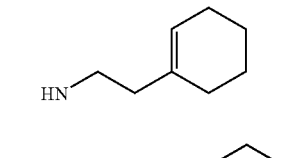
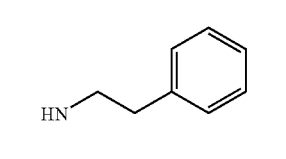
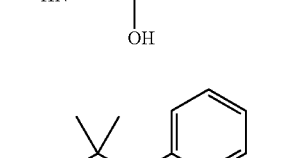
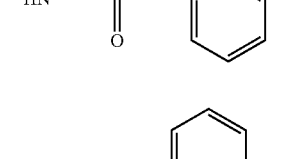
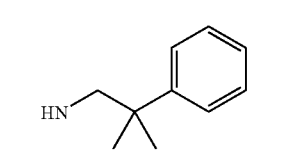
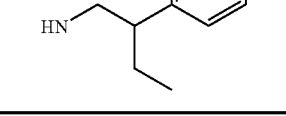
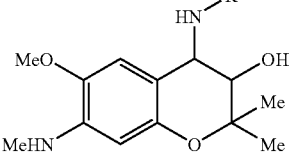
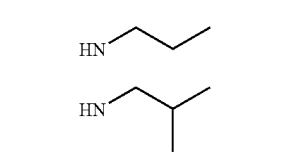
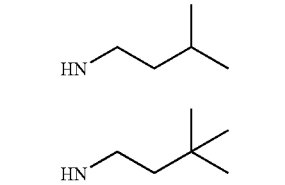
TABLE 59
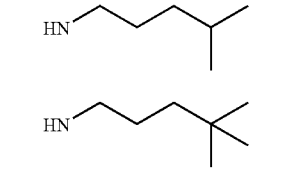
HN—Me
HN—Et
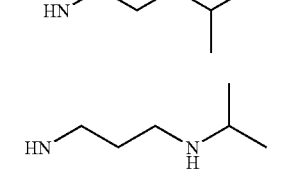
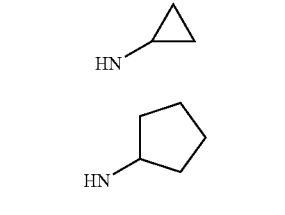
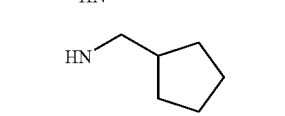

TABLE 59-continued

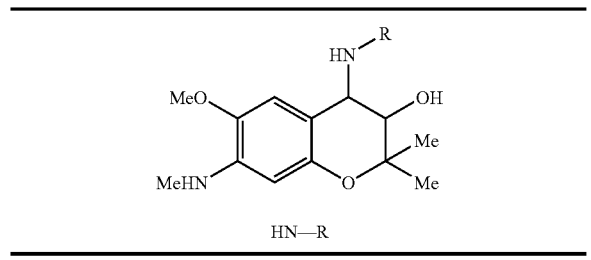

HN—R

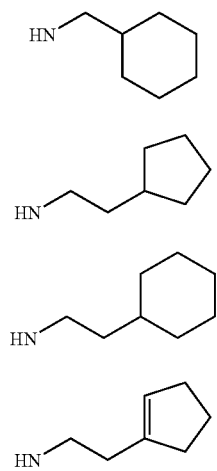

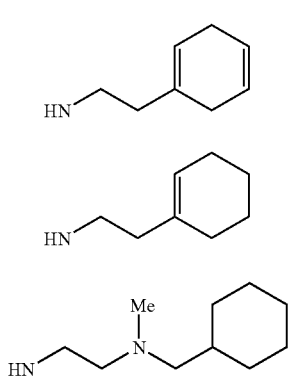

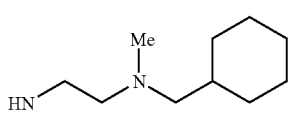

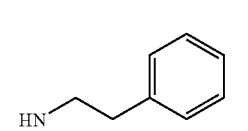

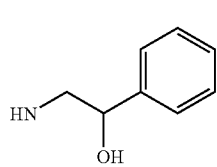

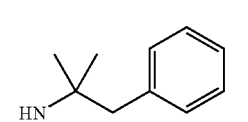

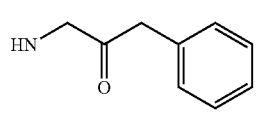

TABLE 59-continued

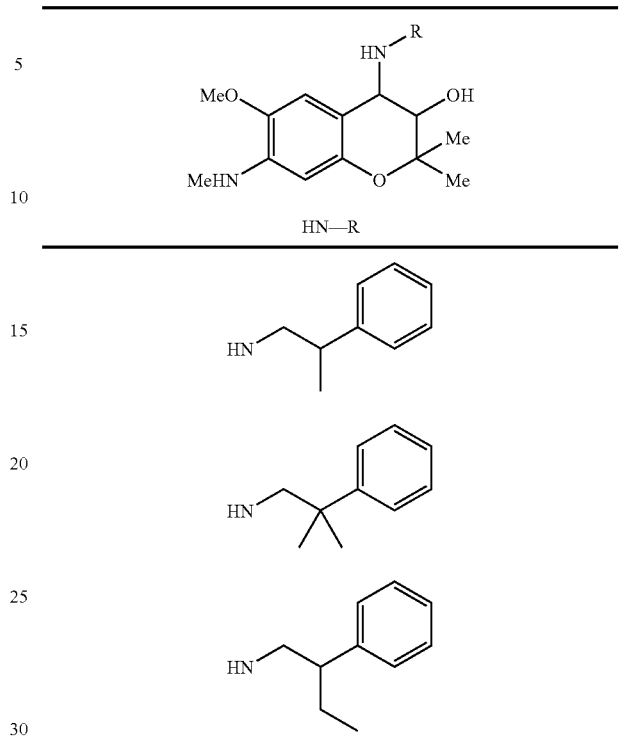

The compound according to the present invention has asymmetric carbon atoms at 3-position and 4-position, thus optical isomers thereof based on the asymmetric carbon atoms are present, and optical active substances can be also used in the application of the present invention, like racemic modifications. Further, cis- and trans-isomer based on configuration at 3-position and 4-position may be included, but trans-isomer is preferred.

Further, when the compounds can form their salts, the pharmaceutically acceptable salts thereof can also be used as active ingredients.

Examples of pharmaceutically acceptable salt are such as hydrochlorides, hydrobromides, sulfates, methanesulfonates, acetates, benzoates, tartrates, phosphates, lactates, maleates, fumarates, malates, gluconates, salicylates and the like.

Preferably, hydrochlorides, methanesulfonates and maleates may be mentioned.

The method for producing the compound according to the present invention is illustrated.

The compound of formula (I) can be obtained by using compound of formula (2) as a starting material as shown in the reaction scheme described below.

The compound of formula (2) can be synthesized according to known methods (methods described in J. M. Evans et al., J. Med. Chem. 1984, 27, 1127; J. Med. Chem. 1986, 29, 2194; J. T North et al., J. Org. Chem. 1995, 60, 3397; as well as Japanese Patent Laid-open Nos. Sho 56-57785, Sho 56-57786, Sho 58-188880, Hei 2-141, Hei 10-87650 and Hei 11-209366 and the like).

The compounds of formula (I) wherein Y is SO or $SO_2$ can be obtained according to the method shown below.

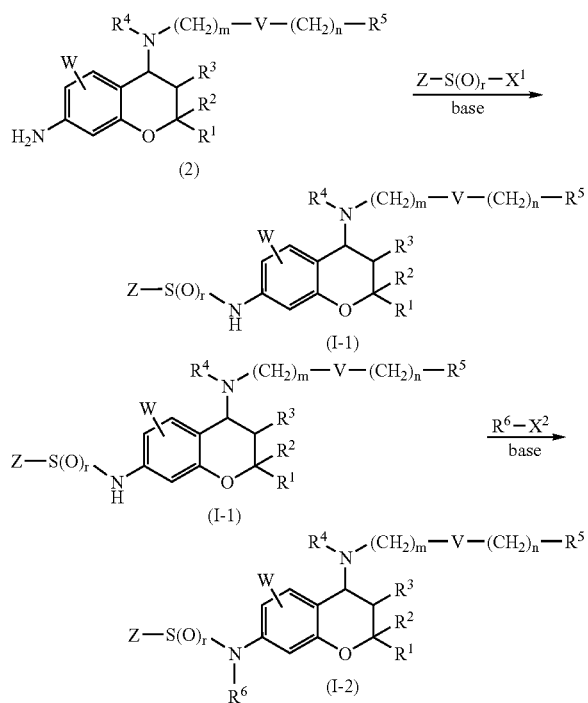

wherein $R^1$, $R^2$, $R^3$, $R^4$, $R^5$, $R^6$, m, n, V, W and Z have the above-mentioned meanings, r is 1 or 2, $X^1$ is a leaving group, such as chlorine atom, bromine atom, methanesulfonyloxy, p-toluenesulfonyloxy or trifluoromethanesulfonyloxy, etc., and $X^2$ is a leaving group, such as chlorine atom, bromine atom, iodine atom, methanesulfonyloxy, p-toluenesulfonyloxy or trifluoromethanesulfonyloxy, etc.

That is, compound (I-1) wherein $R^6$ is hydrogen atom can be obtained by reacting the compound of formula (2) with Z-S(O)$_r$—$X^1$ in the presence of a base.

In addition, compound (I-2) wherein $R^6$ is $C_{1-4}$ alkyl group can be obtained by reacting compound (I-1) with $R^6$—$X^2$ in the presence of a base.

In the meanwhile, in case where $R^4$ is hydrogen atom, prior to the reaction of the compound of formula (2) with Z-S(O)$_r$—$X^1$, a protecting group such as t-butoxycarbonyl group or the like is introduced at the position of $R^4$, and the protecting group is removed after the introduction of Z-S(O)$_r$—$X^1$ or $R^6$—$X^2$ to give compound (I-1) or (I-2).

The introduction and removal of the protecting group, such as t-butoxycarbonyl, etc. can be conducted according to any known process.

As the solvents used in the reaction of the compound of formula (2) with Z-S(O)$_r$—$X^1$, the followings may be mentioned.

Sulfoxide type solvents exemplified by dimethylsulfoxide; amide type solvents exemplified by dimethylformamide or dimethylacetamide; ether type solvents exemplified by diethyl ether, dimethoxyethane, tetrahydrofuran or cyclopentyl methyl ether; halogen type solvents exemplified by dichloromethane, chloroform or dichloroethane; nitrile type solvents exemplified by acetonitrile or propionitrile; ketone type solvents exemplified by acetone, methyl ethyl ketone or methyl isobutyl ketone; aromatic hydrocarbon type solvents exemplified by benzene and toluene; hydrocarbon type solvents exemplified by hexane or heptane; and ester type solvents exemplified by ethyl acetate may be mentioned. Further, the reaction can be carried out in the absence of any solvent. Preferably, ether type solvents may be mentioned.

The reaction temperature is generally from −80° C. to the reflux temperature of the reaction solvent, preferably from −10° C. to 80° C.

The molar ratio of the reaction materials is within the range of 0.5-20.0, preferably 1.0-10.0, for Z-S(O)$_r$—$X^1$/compound (2).

The base includes trialkylamines exemplified by triethylamine and ethyldiisopropylamine; pyridine amines exemplified by pyridine, 2,6-lutidine, 2,6-di-t-butylpyridine, 2,6-di-t-butyl-4-methylpyridine and proton sponge; and inorganic bases exemplified by sodium hydroxide, potassium hydroxide and potassium carbonate. Preferably, triethylamine, ethyldiisopropylamine and pyridine may be mentioned.

As the solvents used in the reaction of the compound of formula (I-1) with $R^6$—$X^2$, the followings may be mentioned.

Sulfoxide type solvents exemplified by dimethylsulfoxide; amide type solvents exemplified by dimethylformamide and dimethylacetamide; ether type solvents exemplified by diethyl ether, dimethoxyethane, tetrahydrofuran and cyclopentyl methyl ether; halogen type solvents exemplified by dichloromethane, chloroform and dichloroethane; nitrile type solvents exemplified by acetonitrile and propionitrile; ketone type solvents exemplified by acetone, methyl ethyl ketone and methyl isobutyl ketone; aromatic hydrocarbon type solvents exemplified by benzene and toluene; hydrocarbon type solvents exemplified by hexane and heptane; and ester type solvents exemplified by ethyl acetate may be mentioned. Further, the reaction can be carried out in the absence of any solvent. Preferably, ketone type solvents and ether type solvents may be mentioned.

The reaction temperature is generally from −80° C. to the reflux temperature of the reaction solvent, preferably from 20° C. to the reflux temperature of the reaction solvent.

The molar ratio of the reaction materials is within the range of 0.5-20.0, preferably 1.0-10.0, for $R^6$—$X^2$/compound (I-1).
tk The base includes trialkylamines exemplified by triethylamine and ethyldiisopropylamine; pyridine amines exemplified by pyridine, 2,6-lutidine, 2,6-di-t-butylpyridine, 2,6-di-t-butyl-4-methylpyridine and proton sponge; and inorganic bases exemplified by sodium hydroxide, potassium hydroxide and potassium carbonate. Preferably, inorganic bases exemplified by potassium carbonate may be mentioned.

The process mentioned below can afford compounds of formula (I) wherein Y is a single bond, and Z is $C_{1-4}$ alkyl group (wherein the $C_{1-4}$ alkyl group may be arbitrarily substituted with 1 to 5 halogen atoms or phenyl group (wherein the phenyl group may be arbitrarily substituted with $C_{1-4}$ alkyl group)).

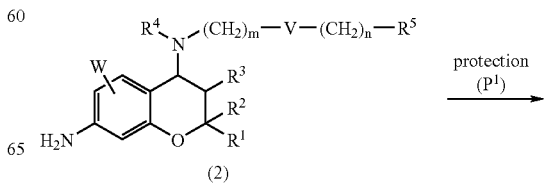

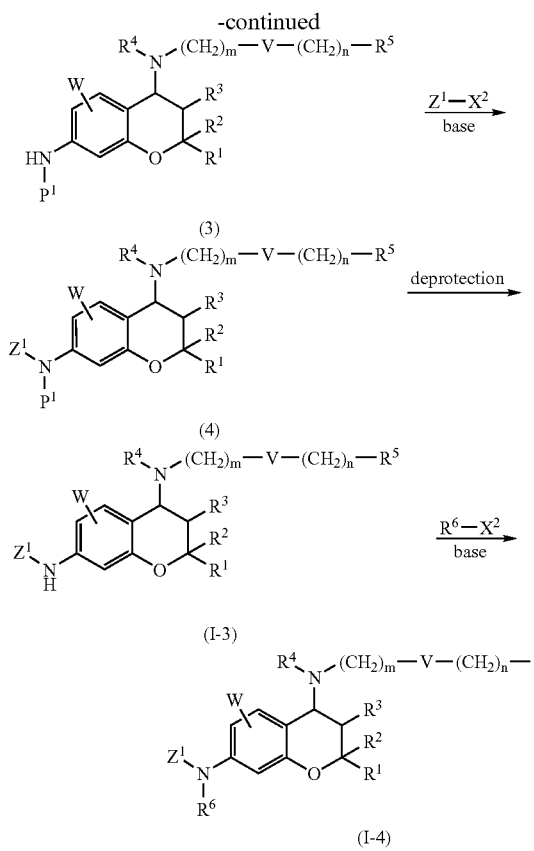

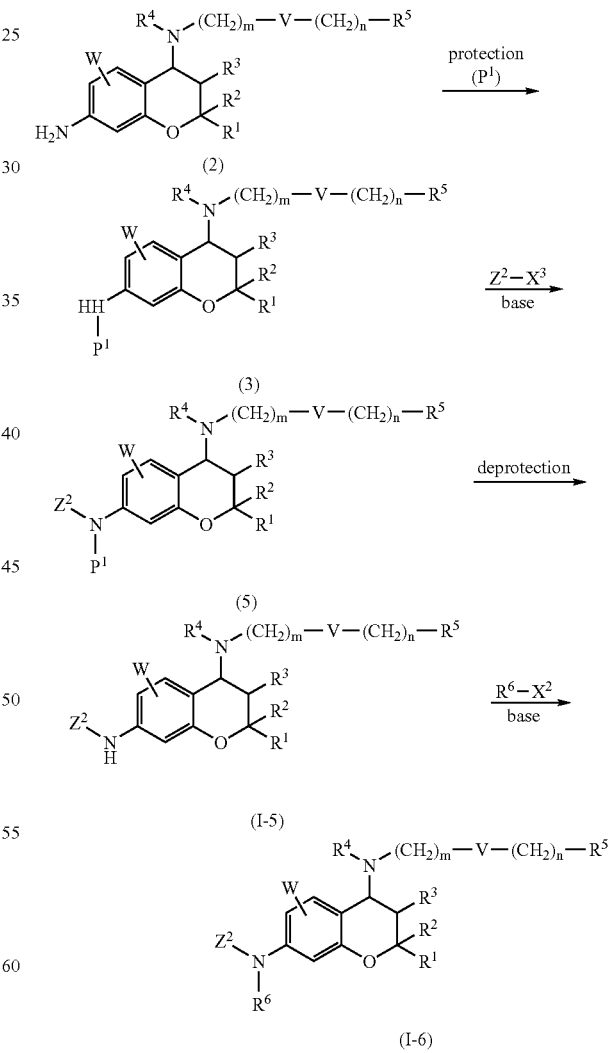

wherein $R^1$, $R^2$, $R^3$, $R^4$, $R^5$, $R^6$, m, n, V, W and $X^2$ have the above-mentioned meanings, $Z^1$ is $C_{1-4}$ alkyl group (wherein the $C_{1-4}$ alkyl group may be arbitrarily substituted with 1 to 5 halogen atoms or phenyl group (wherein the phenyl group may be arbitrarily substituted with $C_{1-4}$ alkyl group)), and $P^1$ is a protecting group, such as formyl, t-butoxycarbonyl and benzyloxycarbonyl, etc.

That is, compound (I-3) wherein $R^6$ is hydrogen atom can be obtained by introducing a protecting group ($P^1$) to the compound of formula (2) to obtain compound (3), reacting compound (3) with $Z^1$-$X^2$ in the presence of a base to obtain compound (4), and then removing the protecting group.

In addition, compound (I-4) wherein $R^6$ is $C_{1-4}$ alkyl group can be obtained by reacting compound (I-3) with $R^6$—$X^2$ in the presence of a base.

In the meanwhile, in case where $R^4$ is hydrogen atom, an agent for introducing a protecting group ($P^1$) to the compound of formula (2) is used in an amount of two equivalents or more to introduce protecting groups ($P^1$) to two nitrogen atoms at 4- and 7-positions, or prior to the introduction of a protecting group ($P^1$), a protecting group such as t-butoxycarbonyl group or the like is introduced at the position of $R^4$, and the protecting group is removed simultaneously or successively after the reaction with $Z^1$-$X^2$ to obtain compound (1-3).

Compound (I-4) where $R^4$ is hydrogen atom can be obtained by introducing a protecting group such as t-butoxycarbonyl group or the like at the position of $R^4$ prior to the reaction of compound (I-3) with $R^6$—$X^2$, and then removing the protecting group after the reaction with $R^6$—$X^2$.

The introduction and removal of the protecting group, such as t-butoxycarbonyl, etc. can be conducted according to any known process.

The introduction of a protecting group ($P^1$) is achieved by treating with formic acid-acetic acid, an acid anhydride or phenyl formate for example in case of formyl, with di-t-butyl dicarbonate in case of t-butoxycarbonyl, and with benzyl chloroformate in case of benzyloxycarbonyl, according to any known process.

The reaction condition for producing compound (4) from compound (3) and $Z^1$-$X^2$ in the presence of a base is similar to that used in the reaction of the compound of formula (I-1) with $R^6$—$X^2$.

The deprotection is achieved by treating according to any known process, such as by treatment with an acid or a base, or by hydrolysis, or the like.

The reaction condition for producing compound (I-4) from compound (I-3) and $R^6$—$X^2$ in the presence of a base is similar to that used in the reaction of the compound of formula (I-1) with $R^6$—$X^2$ The process mentioned below can afford compounds of formula (I) wherein Y is a single bond, and Z is phenyl group (wherein the phenyl group may be arbitrarily substituted with $C_{1-4}$ alkyl group).

wherein $R^1$, $R^2$, $R^3$, $R^4$, $R^5$, $R^6$, m, n, V, $P^1$, W and $X^2$ have the above-mentioned meanings, $Z^2$ is phenyl group (wherein the phenyl group may be arbitrarily substituted with $C_{1-4}$ alkyl group), and $X^3$ is a leaving group, such as fluorine atom, chlorine atom, bromine atom, iodine atom, etc.

That is, compound (I-5) wherein $R^6$ is hydrogen atom can be obtained by introducing a protecting group ($P^1$) to the compound of formula (2) to obtain compound (3), reacting compound (3) with $Z^2$-$X^3$ in the presence of a base to obtain compound (5), and then removing the protecting group.

In addition, compound (I-6) wherein $R^6$ is $C_{1-4}$ alkyl group can be obtained by reacting compound (I-5) with $R^6$—$X^2$ in the presence of a base.

In the meanwhile, in case where $R^4$ is hydrogen atom, an agent for introducing a protecting group ($P^1$) to the compound of formula (2) is used in an amount of two equivalents or more to introduce protecting groups ($P^1$) to two nitrogen atoms at 4- and 7-positions, or prior to the introduction of a protecting group ($P^1$), a protecting group such as t-butoxycarbonyl group or the like is introduced at the position of $R^4$, and the protecting group is removed simultaneously or successively after the reaction with $Z^2$-$X^3$ to obtain compound (I-5).

Compound (I-6) where $R^4$ is hydrogen atom can be obtained by introducing a protecting group such as t-butoxycarbonyl group or the like at the position of $R^4$ prior to the reaction of compound (I-5) with $R^6$—$X^2$, and then removing the protecting group after the reaction with $R^6$—$X^2$.

The introduction and removal of the protecting group, such as t-butoxycarbonyl, etc. can be conducted according to any known process.

The introduction of a protecting group ($P^1$) is achieved by treating with formic acid-acetic acid, an acid anhydride or phenyl formate for example in case of formyl, with di-t-butyl dicarbonate in case of t-butoxycarbonyl, and with benzyl chloroformate in case of benzyloxycarbonyl, according to any known process.

As the solvents used in the reaction of the compound of formula (3) with $Z^2$-$X^3$, the followings may be mentioned.

Sulfoxide type solvents exemplified by dimethylsulfoxide; amide type solvents exemplified by dimethylformamide or dimethylacetamide; ether type solvents exemplified by diethyl ether, dimethoxyethane, tetrahydrofuran or cyclopentyl methyl ether; halogen type solvents exemplified by dichloromethane, chloroform and dichloroethane; nitrile type solvents exemplified by acetonitrile and propionitrile; ketone type solvents exemplified by acetone, methyl ethyl ketone and methyl isobutyl ketone; aromatic hydrocarbon type solvents exemplified by benzene and toluene; hydrocarbon type solvents exemplified by hexane and heptane; and ester type solvents exemplified by ethyl acetate may be mentioned. Further, the reaction can be carried out in the absence of any solvent. Preferably, hydrocarbon type solvents, sulfoxide type solvents and amide type solvents may be mentioned.

The reaction temperature is generally from −80° C. to the reflux temperature of the reaction solvent, preferably from 50° C. to 120° C.

The molar ratio of the reaction materials is within the range of 0.5-20.0, preferably 1.0-10.0, for $Z^2$-$X^3$/compound (3).

The base includes trialkylamines exemplified by triethylamine and ethyldiisopropylamine; pyridine amines exemplified by pyridine, 2,6-lutidine, 2,6-di-t-butylpyridine, 2,6-di-t-butyl-4-methylpyridine and proton sponge; metal alkoxides exemplified by potassium t-butoxide, sodium t-butoxide, sodium ethoxide and potassium ethoxide and inorganic bases exemplified by sodium hydroxide, potassium hydroxide, potassium carbonate, sodium carbonate, potassium hydrogen carbonate and sodium hydrogen carbonate. Preferably, metal alkoxides and inorganic bases may be mentioned.

Metal catalysts can be added in the reaction system. The metal catalysts include copper catalysts such as copper iodide, copper chloride and copper oxide; and palladium catalysts exemplified by palladium chloride, palladium bromide, palladium iodide, dichlorobis(acetonitrile) palladium, dichlorobis(benzonitrile) palladium, dichlorobis(triphenylphosphine) palladium. dichlorobis(diphenylphosphinoethane) palladium, dichlorobis(diphenylphosphinopropane) palladium, dichlorobis(diphenylphosphinobutane) palladium, palladium acetate, tetrakistriphenylphosphine palladium, palladium benzylidene acetone, and the like.

When the metal catalyst is used, any ligands can be added. The ligands include phosphine ligand exemplified by triphenylphosphine, tributylphosphine, diphenylphosphinoethane, diphenylphosphinopropane and diphenylphosphinobutane.

The deprotection is achieved by treating according to any known process, such as by treatment with an acid or a base, or by hydrogenolysis, or the like.

The reaction condition for producing compound (I-6) from compound (I-5) and $R^6$—$X^2$ in the presence of a base is similar to that used in the reaction of the compound of formula (I-1) with $R^6$—$X^2$ Syntheses of optically active compounds among the compounds of formula (I) can be attained by utilizing optical resolution methods (Japanese Patent Laid-open No. Hei 3-141286, U.S. Pat. No. 5,097,037 and European Patent No. 409165).

Furthermore, syntheses of optically active compounds of formula (2) can be attained by utilizing asymmetric synthetic methods (PCT Japanese Translation Patent Publication No. Hei 5-507645, Japanese Patent Laid-open Nos. Hei 5-301878 and Hei 7-285983, European Patent Laid-open No. 535377 and U.S. Pat. No. 5,420,314).

As described above, the inventors of the present invention found that the compound of formula (I) has a strong prolongation effect on the refractory period. The prolongation effect on the refractory period is one of mechanisms of anti-arrhythmic action and is an important indicator that can be taken in judging the effectiveness in clinical arrhythmia. Conventional anti-arrhythmic agents having the prolongation effect on the refractory period as the main mechanism (such as d-sotalol belonging to Class III of the antiarrhythmic agent classification according to Vaughan Williams) have been the therapeutic problems in inducing highly dangerous arrhythmia leading to the sudden death from such as torsades de pointes among others due to prolongation of action potential in ventricular muscle correlated to the prolongation effect on the refractory period, and thus becoming the therapeutic problem in arrhythmia mainly of atrial muscle (such as supraventricular tachycardia, atrial flutter, atrial fibrillation and the like).

In order to solve the problems, the inventors of the present invention carried out the investigation of compounds having the prolongation effect on the refractory period selective for atrium muscle than for ventricular muscle, and found that the compound of formula (I) has a prolongation effect on the refractory period selective for atrium muscle without any influence on the refractory period and action potential in ventricular muscle. The difference between the findings by the inventors and the prior art is in providing the prolongation effect on the refractory period selective for atrium muscle to these compound group, which may be shown by the facts that there is no influence on the action potential duration period of isolated ventricular muscle and there is no influence on QT in the electrocardiogram of anesthetized animal. From above, the compounds of the present invention show no inducing action of arrhythmia in ventricular muscle, thus they can contribute to much safer use in arrhythmia mainly of atrial muscle in comparison with the prior art. The present technical knowledge is beneficial for therapeutic or preventive uses as anti-atrial fibrillation agents, anti-atrial flutter agents and anti-atrial tachycardia agents relating to paroxysmal, chronic, preoperative, intraoperative or postoperative atrial arrhythmia, prevention in the progression leading to embolus due to arrhythmia of atrial nature, prevention in the progression leading to ventricular arrhythmia or tachycardia from atrial arrhythmia or tachycardia, and averting the life threatening prognosis due to preventive action on atrial arrhythmia or tachycardia leading to ventricular arrhythmia or tachycardia.

The present invention provides a pharmaceutical composition or a veterinary pharmaceutical composition containing a compound of formula (I) in an effective amount for these treatments.

As forms of administration for the compound according to the present invention, parenteral administration forms such as injections (subcutaneous, intravenous, intramuscular and intraperitoneal injections), ointments, suppositories, aerosols and the like, and oral administration forms such as tablets, capsules, granules, pills, syrups, solutions, emulsions, suspensions and the like can be mentioned.

The pharmaceutical or veterinary pharmaceutical composition described above contains the compound according to the present invention in an amount of about 0.01-99.5%, preferably about 0.1-30%, based on the total weight of the composition.

In addition to the compound according to the present invention or the composition containing the compound, other pharmaceutically or veterinary pharmaceutically active compounds may be contained.

Further, these compositions may contain the plurality of compounds according to the present invention.

An amount of the compound according to the present invention to be used in clinical administration may vary depending on age, weight and sensitivity of the patient, symptomatic condition and the like, but an effective amount in clinical administration is generally about 0.003-1.5 g, preferably 0.01-0.6 g, per day for adult. If necessary, however, the amount outside of the aforementioned range may be used.

The compound according to the present invention is formulated for administration by conventional pharmaceutical means.

That is, tablets, capsules, granules and pills for oral administration are prepared by using excipients such as sucrose, lactose, glucose, starch and mannitol; binders such as hydroxypropyl cellulose, syrup, gum arabic, gelatin, sorbitol, tragacanth, methyl cellulose and polyvinyl pyrrolidone; disintegrators such as starch, carboxymethyl cellulose or its calcium salt, microcrystalline cellulose and polyethylene glycol; lubricants such as talc, magnesium or calcium stearate, and silica; lubricating agents such as sodium laurate and glycerol and the like.

Injections, solutions, emulsions, suspensions, syrups and aerosols are prepared by using solvents for the active components such as water, ethyl alcohol, isopropyl alcohol, propylene glycol, 1,3-butylene glycol and polyethylene glycol; surfactants such as sorbitan fatty acid ester, polyoxyethylene sorbitan fatty acid ester, polyoxyethylene fatty acid ester, polyoxyethylene ether of hydrogenated castor oil and lecithin; suspending agents such as carboxymethyl cellulose sodium salt, cellulose derivatives such as methyl cellulose or the like, and natural rubbers such as gum arabic, tragacanth or the like; and preserves such as p-hydroxybenzoic acid esters, benzalkonium chloride, sorbic acid salts and the like.

For ointments that are transdermally adsorptive pharmaceutics, for example, white vaseline, liquid paraffin, higher alcohols, Macrogol ointments, hydrophilic ointments, aqueous gel-type bases and the like are used.

Suppositories are prepared by using, for example, cocoa fats, polyethylene glycol, lanolin, fatty acid triglyceride, coconut oil, polysorbate and the like.

EXAMPLES

The present invention is illustrated in detail by the Examples as follows, but the present invention is not limited to these Examples.

Synthesis Examples

Furthermore, Ph,Ph salen manganese complex (XY) and Cyc,Ph salen manganese complex (XX) mean optically active compounds of formulae below which were synthesized according to the method similar to one described in Japanese Patent Laid-open No. Hei 7-285983.

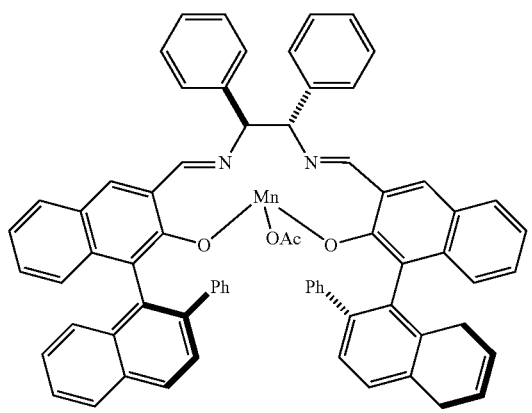

(XY)

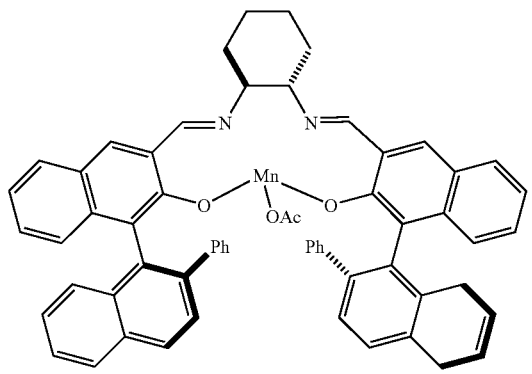

(XX)

Synthesis Example 1

N-{(3R*,4S*)-3-Hydroxy-6-methoxy-2,2-dimethyl-4-[(2-phenylethyl)amino]-3,4-dihydro-2H-1-benzopyran-7-yl}methanesulfonamide

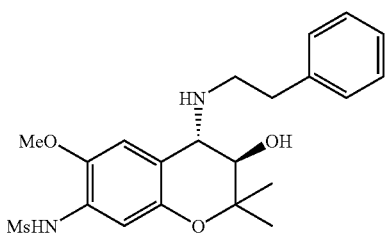

4-(1,1-dimethyl-2-propynyloxy)anisole

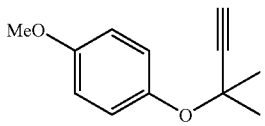

To a solution of 4-methoxyphenol (15.0 g, 121 mmol) in acetonitrile (75 mL), 1,8-diazabicyclo[5.4.0]undecene (23.9 g, 157 mmol) was added under ice cooling and the resulting mixture was stirred at 0° C. for 30 minutes (Solution 1). To a solution of 2-methyl-3-butyn-2-ol (11.7 g, 139 mmol) in acetonitrile (75 mL), 1,8-diazabicyclo[5.4.0]undecene (23.9 g, 157 mmol) was added under ice cooling, the resulting mixture was stirred at 0° C. for 30 minutes, then trifluoroacetic anhydride (25.4 g, 121 mmol) was added and the resulting mixture was stirred at 0° C. for 30 minutes (Solution 2). Copper (I) chloride (36 mg, 0.36 mmol) was added to Solution 1, and then Solution 2 was added dropwise thereto over 15 minutes. Upon the conclusion of dropwise addition, the temperature was raised to room temperature, and the mixture was stirred overnight. Upon the completion of the reaction, an aqueous solution of ammonium chloride was added to the reaction solution, and the solvent was distilled off under a reduced pressure. An aqueous solution of 1 mol/L hydrochloric acid was added to the residue, the resulting mixture was extracted with ethyl acetate, the organic phase was washed once with an aqueous solution of 1 mol/L hydrochloric acid, twice with an aqueous solution of saturated sodium hydrogen carbonate and once with saturated sodium chloride solution. Then, the organic phase was dried over anhydrous magnesium sulfate. After distilling off the solvent, the residue was directly used for the subsequent reaction.

6-methoxy-2,2-dimethyl-2H-1-benzopyran

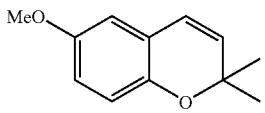

A solution of 4-(1,1-dimethyl-2-propynyloxy)anisole in 1,2-dichlorobenzene (50 mL) was stirred at 190° C. for 2 hours. Upon the completion of the reaction, the solvent was distilled off under a reduced pressure. The residue was purified by column chromatography (hexane/chloroform=3/1) and the aimed product was obtained as red oily substance (2-step, yield: 61%).

$^1$H-NMR (CDCl$_3$) δ: 1.41 (s, 6H), 3.75 (s, 3H), 5.64 (d, J=9.9 Hz, 1H), 6.28 (d, J=9.9 Hz, 1H), 6.55 (d, J=2.7 Hz, 1H), 6.64-6.73 (m, 2H)

LC/MS (ESI$^+$): 191[M$^+$+1]

6-methoxy-2,2-dimethyl-7-nitro-2H-1-benzopyran

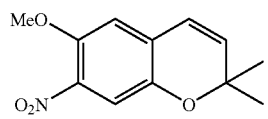

A mixed solution of acetic acid (6.2 mL) and acetic anhydride (6.2 mL) containing 6-methoxy-2,2-dimethyl-2H-1-benzopyran (3.1 g, 16.4 mmol) was cooled with ice, nitric acid (1.37 mL, 18.0 mmol) was added dropwise and then the mixture was stirred at 0° C. for 1 hour. Upon the completion of the reaction, an aqueous solution of 1 mol/L sodium hydroxide was added to the reaction solution, the resulting solution was extracted with ethyl acetate (150 mL). The organic phase was washed twice with 1 mol/L sodium hydroxide aqueous solution and once with saturated sodium chloride solution. Then, the organic phase was dried over anhydrous magnesium sulfate. After distilling off the solvent, the residue was purified by column chromatography (hexane/ethyl acetate=6/1) and the aimed product was obtained as yellow crystal (yield: 79%).

$^1$H-NMR (CDCl$_3$) δ: 1.44 (s, 6H), 3.91 (s, 3H), 5.85 (d, J=9.6 Hz, 1H), 6.33 (d, J=9.6 Hz, 1H), 6.69 (s, 1H), 7.34 (s, 1H)

LC/MS (ESI$^+$): 236 [M$^+$+1]

(3R*,4R*)-3,4-Epoxy-6-methoxy-2,2-dimethyl-7-nitro-3,4-dihydro-2H-1-benzopyran

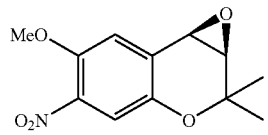

To a solution (300 mL) of acetonitrile containing 6-methoxy-2,2-dimethyl-7-nitro-2H-1-benzopyran (10.0 g, 42.5 mmol), N-methyl imidazole (0.678 mL, 8.50 mmol), (R,R,S,S)-Ph,Ph salen manganese complex (XY) (880 mg, 0.850 mmol) and iodosobenzene (18.7 mg, 85.0 mmol) were added at room temperature and the mixture was stirred for 2 hours. Upon the completion of the reaction, an aqueous solution of sodium thiosulfate was added to the reaction solution, the resulting solution was filtered through celite. The resulting filtrate extracted with ethyl acetate. The organic phase was washed with water and sodium chloride solution, and then dried over anhydrous magnesium sulfate. After distilling off the solvent, the residue was purified by column chromatography (hexane/ethyl acetate=4/1) and the aimed product was obtained as yellow crystals (yield: 75%, optical purity: 99.7% ee).

¹H-NMR (CDCl₃) δ: 1.26 (s, 3H), 1.58 (s, 3H), 3.53 (d, J=4.3 Hz, 1H), 3.90 (d, J=4.3 Hz, 1H), 3.95 (s, 3H), 7.08 (s, 1H), 7.33 (s, 1H)

MS (EI): 251 [M⁺]

HPLC: 18.6 min (enantiomer 24.1 min)

HPLC condition: chiralcel OJ-RH, MeCN/MeOH/0.01 M NaCl aq.=1/3/5, 1.0 ml/min, 40° C., 256 nm (3R*,4S*)-6-Methoxy-2,2-dimethyl-7-nitro-4-[(2-phenylethyl)amino]-3,4-dihydro-2H-1-benzopyran-3-ol

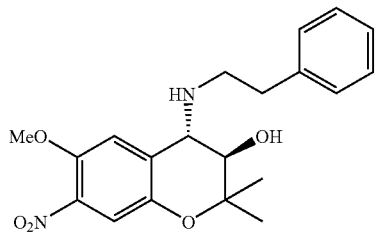

To a solution of (3R*,4R*)-3,4-epoxy-6-methoxy-2,2-dimethyl-7-nitro-3,4-dihydro-2H-1-benzopyran (2.50 g, 9.95 mmol) in 1,4-dioxane (5.0 mL), lithium perchlorate (1.06 g, 9.95 mmol) and 42-(phenylethyl)amine (1.50 mL, 11.9 mmol) were added at room temperature and the mixture was stirred at 80° C. for 1 hour. Upon the completion of the reaction, an aqueous solution of saturated ammonium chloride was added to the reaction solution, and the resulting solution was extracted with ethyl acetate. The organic phase was washed with saturated sodium chloride solution, and then dried over anhydrous sodium sulfate. After distilling off the solvent, the residue was purified by column chromatography (hexane/ethyl acetate=6/4) and the aimed product was obtained as orange amorphous substance (quantitative yield).

¹H-NMR (CDCl₃) δ: 1.15 (s, 3H), 1.47 (s, 3H), 2.73-2.95 (m, 4H), 3.60 (d, J=10.0 Hz, 1H), 3.68 (d, J=10.0 Hz, 1H), 3.73 (s, 3H), 6.78 (s, 1H), 7.21-7.35 (m, 6H)

MS (EI): 372[M⁺]

t-Butyl (2-phenylethyl) (3R*,4S*)-3-hydroxy-6-methoxy-2,2-dimethyl-7-nitro-3,4-dihydro-2H-1-benzopyran-4-yl carbamate

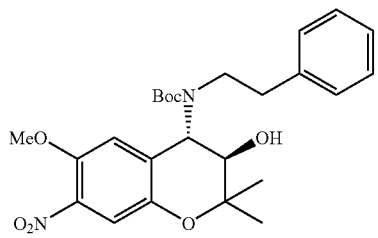

To a solution of (3R*,4S*)-6-methoxy-2,2-dimethyl-7-nitro-4-[(2-phenylethyl)amino]-3,4-dihydro-2H-1-benzopyran-3-ol (407 mg, 1.09 mmol) and di-t-butyl di-carbonate (477 mg, 2.19 mmol) in tetrahydrofuran (6.0 mL), triethylamine (305 mL, 2.19 mmol) was added at 0° C. and the mixture was stirred at room temperature overnight. Upon the completion of the reaction, an aqueous solution of saturated sodium carbonate was added to the reaction solution, and the resulting solution was extracted with ethyl acetate. The organic phase was washed with 1 mol/L hydrochloric acid aqueous solution and saturated sodium chloride solution, and then dried over anhydrous sodium sulfate. After distilling off the solvent, the residue was purified by column chromatography (hexane/ethyl acetate=4/1) and the aimed product was obtained as yellow amorphous substance (yield: 88%).

MS (EI): 473 [M⁺+1]

t-Butyl (2-phenylethyl) (3R*,4S*)-7-amino-3-hydroxy-6-methoxy-2,2-dimethyl-3,4-dihydro-2H-1-benzopyran-4-yl carbamate

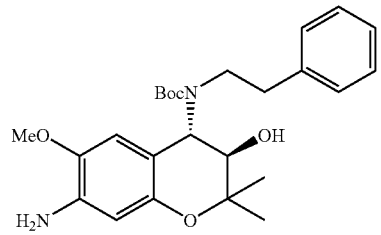

A solution of t-butyl (2-phenylethyl) (3R*,4S*)-3-hydroxy-6-methoxy-2,2-dimethyl-7-nitro-3,4-dihydro-2H-1-benzopyran-4-yl carbamate (1.32 g, 2.80 mmol) and 5% palladium-carbon (132 mg) in methanol (26 mL) was stirred under hydrogen atmosphere at room temperature overnight. Upon the completion of the reaction, the reaction solution was filtered through celite. After distilling off the solvent, the residue was purified by column chromatography (hexane/ethyl acetate=4/1) and the aimed product was obtained as colorless solid (yield: 94%).

LC/MS (ESI⁺): 443[M⁺+1]

t-Butyl (2-phenylethyl) (3R*,4S*)-3-hydroxy-6-methoxy-2,2-dimethyl-7-[(methylsulfonyl)amino]-3,4-dihydro-2H-1-benzopyran-4-yl carbamate

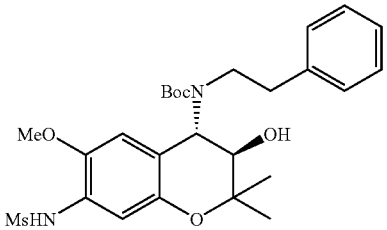

To a solution of t-butyl (2-phenylethyl) (3R*,4S*)-7-amino-3-hydroxy-6-methoxy-2,2-dimethyl-3,4-dihydro-2H-1-benzopyran-4-yl carbamate (1.16 g, 2.62 mmol) in pyridine (11.6 mL), methanesulfonyl chloride (0.223 mL, 2.88 mmol) was added, at 0° C., the temperature was raised to room temperature and the resulting mixture was stirred at room temperature overnight. Upon the completion of the reaction, an aqueous solution (ca. 30 mL) of 1 mol/L hydrochloric acid was added to the reaction solution to adjust pH to 5-9, and then the mixture was extracted with ethyl acetate. The organic phase was washed with saturated sodium chloride solution, and then dried over anhydrous sodium sulfate. After distilling off the solvent, the residue was purified by column chromatography (hexane/ethyl acetate=3/1) and the aimed product was obtained as colorless oily substance (yield: 77%).

MS (EI): 520[M+]

N-{(3R*,4S*)-3-Hydroxy-6-methoxy-2,2-dimethyl-4-[(2-phenylethyl)amino]-3,4-dihydro-2H-1-benzopyran-7-yl}methanesulfonamide

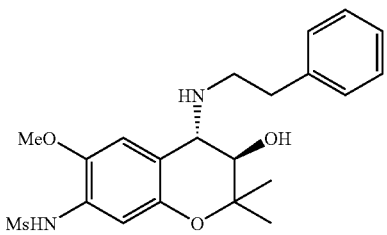

A solution of t-butyl (2-phenylethyl) (3R*,4S*)-3-hydroxy-6-methoxy-2,2-dimethyl-7-[(methylsulfonyl)amino]-3,4-dihydro-2H-1-benzopyran-4-yl carbamate (300 mg, 0.577 mmol) in dichloromethane (3.0 mL) was cooled to 0° C., trifluoroacetic acid (3.0 mL) was added thereto, and the resulting mixture was stirred at 0° C. for 1 hour. Upon the completion of the reaction, the solvent was distilled off, and the residue was purified by column chromatography (hexane/ethyl acetate=2/1) and the aimed product was obtained as gray amorphous substance (yield: 99%).

$^1$H-NMR (CDCl$_3$) δ: 1.12 (s, 3H), 1.49 (s, 3H), 2.93-3.16 (m, 4H), 3.03 (s, 3H), 3.81 (s, 3H), 3.95 (d, J=9.2 Hz, 1H), 4.55 (d, J=9.2 Hz, 1H), 7.02-7.32 (m, 7H)

MS (EI): 420[M+]

Synthesis Example 2

N-{(3R*,4S*)-3,6-Dihydroxy-2,2-dimethyl-4-[(2-phenylethyl)amino]-3,4-dihydro-2H-1-benzopyran-7-yl}methanesulfonamide

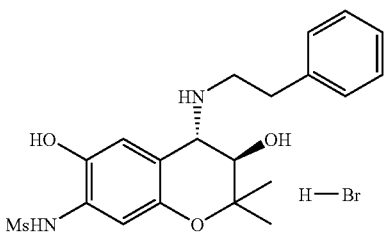

To a solution of t-butyl (2-phenylethyl) (3R*,4S*)-7-{(methylsulfonyl)amino}-3-hydroxy-6-methoxy-2,2-dimethyl-3,4-dihydro-2H-1-benzopyran-4-yl carbamate (300 mg, 0.58 mmol) in dichloromethane (3.0 mL), a solution of 1 mol/L boron tribromide-dichloromethane (2.88 mL, 2.88 mmol) was added under cooling with ice and the resulting mixture was stirred at 0° C. for 1 hour. Upon the completion of the reaction, methanol was added and the resulting mixture was stirred for 30 minutes, and the solvent was distilled off. The residue was washed ethyl acetate, and the resulting solid was dried under a reduced pressure at 50° C. for 2 hours, and thereby hydrobromide of the aimed product was obtained as yellow solid (yield: 56%).

$^1$H-NMR (DMSO-d$_6$) δ: 1.08 (s, 3H), 1.39 (s, 3H), 2.99-3.11 (m, 4H), 3.00 (s, 3H), 3.89 (dd, J=6.6, 8.8 Hz, 1H), 4.30 (d, J=8.8 Hz, 1H), 6.12 (d, J=6.6 Hz, 1H), 6.73 (s, 1H), 7.10 (s, 1H), 7.23-7.36 (m, 5H), 8.82 (s, 1H), 8.88 (brs, 1H), 9.35 (brs, 1H), 9.54 (s, 1H)

LC/MS (ESI$^+$): 407[M$^+$+1], (ESI$^-$): 405[M$^+$−1]

Synthesis Example 3

N-{(3R*,4S*)-3-Hydroxy-6-methoxy-2,2-dimethyl-4-[(2-phenylethyl)amino]-3,4-dihydro-2H-1-benzopyran-7-yl}-N-methylmethanesulfonamide

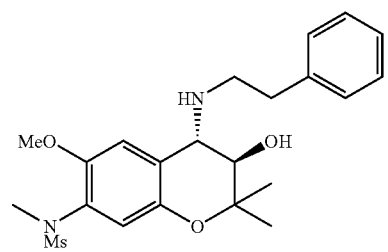

t-Butyl (2-phenylethyl) (3R*,4S*)-3-hydroxy-6-methoxy-2,2-dimethyl-7-(N-methyl-N-methylsulfonylamino)-3,4-dihydro-2H-1-benzopyran-4-yl carbamate

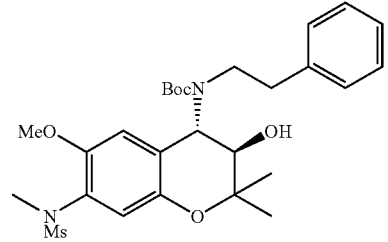

To a solution of t-butyl (2-phenylethyl) (3R*,4S*)-3-hydroxy-6-methoxy-2,2-dimethyl-7-(N-methylsulfonylamino)-3,4-dihydro-2H-1-benzopyran-4-yl carbamate (227 mg, 0.423 mmol) and potassium carbonate (76 mg, 0.550 mmol) in acetone (2.3 mL), methyl iodide (0.040 mL, 0.635 mmol) was added at room temperature and the resulting mixture was stirred overnight. Upon the completion of the reaction, the solvent was distilled off, and water was added to the residue. The resulting mixture was extracted with ethyl acetate. The organic phase was washed with saturated sodium chloride solution, dried over anhydrous magnesium sulfate and the solvent was distilled off. The residue was purified by column chromatography (hexane/ethyl acetate=3/1) and the aimed product was obtained as colorless amorphous substance (yield: 93%).

LC/MS (ESI$^+$): 535 [M$^+$+1], 557 [M$^+$+Na]

N-{(3R*,4S*)-3-Hydroxy-6-methoxy-2,2-dimethyl-4-[(2-phenylethyl)amino]-3,4-dihydro-2H-1-benzopyran-7-yl}-N-methyl-methanesulfonamide

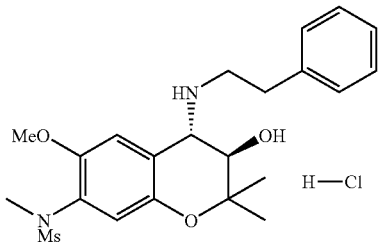

A solution of 4 mol/L hydrogen chloride in 1,4-dioxane (2.01 mL, 8.04 mmol) was added to t-butyl (2-phenylethyl)(3R*,4S*)-3-hydroxy-6-methoxy-2,2-dimethyl-7-(N-methyl-N-methylsulfonylamino)-3,4-dihydro-2H-1-benzopyran-4-yl carbamate (201 mg, 0.389 mmol) at room temperature, and the resulting mixture was stirred at 100° C. for 30 minutes. Upon the completion of the reaction, the solvent was distilled off. The resulting solid was washed with 2-propanol and thereby hydrochloride of the aimed product was obtained as pale blue solid (yield: 84%).

$^1$H-NMR (DMSO-$d_6$) δ: 1.09 (s, 3H), 1.41 (s, 3H), 3.00 (s, 3H), 3.02-3.19 (m, 4H), 3.10 (s, 3H), 3.85 (s, 3H), 4.00 (dd, J=5.8, 9.3 Hz, 1H), 4.40 (d, J=9.3 Hz, 1H), 6.28 (d, J=5.8 Hz, 1H), 6.79 (s, 1H), 7.23-7.36 (m, 5H), 7.68 (s, 1H), 9.48 (brs, 1H), 9.81 (brs, 1H)

LC/MS (ESI$^+$): 435[M$^+$+1]

Synthesis Example 4

N-{(3R*,4S*)-4-[(2-Cyclohexylethyl)amino]-3-hydroxy-6-methoxy-2,2-dimethyl-3,4-dihydro-2H-1-benzopyran-7-yl}methanesulfonamide

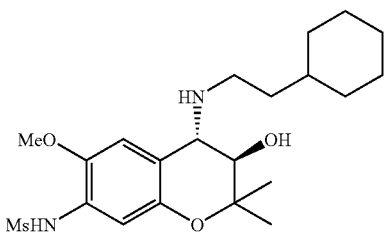

(3R*,4S*)-4-Amino-6-methoxy-2,2-dimethyl-7-nitro-3,4-dihydro-2H-1-benzopyran-3-ol

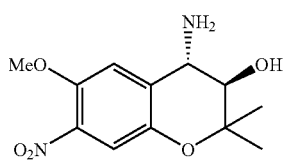

To a solution of (3R*,4R*)-3,4-epoxy-6-methoxy-2,2-dimethyl-7-nitro-3,4-dihydro-2H-1-benzopyran (2.64 g, 10.5 mmol) in ethanol (26 mL), an ammonia water (26 mL) was added, and the resulting mixture was stirred in a sealed tube at 100° C. for 2 hours. Upon the completion of the reaction, the solvent was distilled off. An aqueous solution of saturated sodium carbonate was added to the residue, and the resulting mixture was extracted with ethyl acetate. The organic phase was washed with saturated sodium chloride solution, dried over anhydrous magnesium sulfate and thereby the aimed product was obtained as red amorphous substance (yield: 84%).

$^1$H-NMR (DMSO-$d_6$) δ: 1.20 (s, 3H), 1.50 (s, 3H), 1.60 (brs, 3H), 3.38 (d, J=9.6 Hz, 1H), 3.67 (d, J=9.6 Hz, 1H), 3.93 (s, 3H), 7.20 (s, 1H), 7.31 (s, 1H)

t-Butyl {(3R*,4S*)-3-hydroxy-6-methoxy-2,2-dimethyl-7-nitro-3,4-dihydro-2H-1-benzopyran-4-yl}carbamate

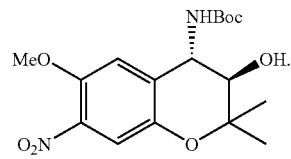

To a solution of(3R*, 4S*).4amino-6-methoxy-2,2-dimethyl-7-nitro-3,4-dihydro-2H-1-benzopyran-3-ol (2.62 g, 9.77 mmol) and di-t-butyl di-carbonate (4.26 g, 19.5 mmol) in tetrahydrofuran (52 mL), triethylamine (2.72 mL, 19.5 mmol) was added at 0° C. and the mixture was stirred at room temperature overnight. Upon the completion of the reaction, an aqueous solution of saturated sodium carbonate was added to the reaction solution, and the resulting solution was extracted with ethyl acetate. The organic phase was washed with 1 mol/L hydrochloric acid aqueous solution and saturated sodium chloride solution, and then dried over anhydrous sodium sulfate. After distilling off the solvent, the residue was purified by column chromatography (hexane/ethyl acetate =2/1) and the aimed product was obtained as yellow solid (yield: 92%).

$^1$H-NMR (CDCl$_3$) δ: 1.24 (s, 3H), 1.48 (s, 3H), 1.52 (s, 9H), 1.61 (s, 1H), 3.47-3.51 (m, 1H), 3.62-3.67 (m, 1H), 3.90 (s, 3H), 4.72 (m, 1H), 4.87-4.94 (m, 1H), 6.98 (s, 1H), 7.32 (s, 1H)

t-Butyl {(3R*,4S*)-7-amino-3-hydroxy-6-methoxy-2,2-dimethyl-3,4-dihydro-2H-1-benzopyran-4-yl}carbamate

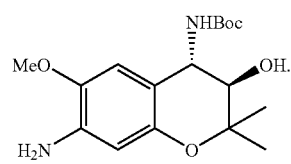

A solution of t-butyl (3R*,4S*)-3-hydroxy-6-methoxy-2,2-dimethyl-7-nitro-3,4-dihydro-2H-1-benzopyran-4-yl carbamate (3.31 g, 8.96 mmol) and 5% palladium-carbon (330 mg) in ethanol (66 mL) was stirred under hydrogen atmosphere at room temperature overnight. Upon the completion of the reaction, the reaction solution was filtered through celite. After distilling off the solvent, the residue was purified by column chromatography (chloroform/methanol=30/1) and the aimed product was obtained as colorless amorphous substance (yield: 33%).

¹H-NMR (CDCl₃) δ: 1.20 (s, 3H), 1.43 (s, 3H), 1.51 (s, 9H), 3.59 (d, J=8.8 Hz, 1H), 3.80 (s, 3H), 3.97 (s, 1H), 4.62 (dd, J=7.4, 8.8 Hz, 1H), 4.84 (d, J=7.4 Hz, 1H), 6.17 (s, 1H), 6.59 (s, 1H)

LC/MS (ESI⁺): 339[M⁺+1], 361[M⁺+Na]

t-Butyl (3R*,4S*)-3-hydroxy-6-methoxy-2,2-dimethyl-7-[(methylsulfonyl)amino]-3,4-dihydro-2H-1-benzopyran-4-yl carbamate

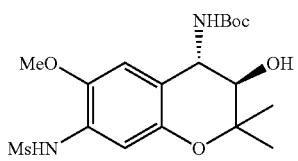

To a solution of t-butyl {(3R*,4S*)-7-amino-3-hydroxy-6-methoxy-2,2-dimethyl-3,4-dihydro-2H-1-benzopyran-4-yl}carbamate (980 mg, 2.90 mmol) in pyridine (9.8 mL), methanesulfonyl chloride (0.25 mL, 3.19 mmol) was added and the resulting mixture was stirred at room temperature overnight. Upon the completion of the reaction, an aqueous solution (ca. 30 mL) of 1 mol/L hydrochloric acid was added to the reaction solution to adjust pH to 5-9, and then the mixture was extracted with ethyl acetate. The organic phase was washed with saturated sodium chloride solution, and then dried over anhydrous sodium sulfate. After distilling off the solvent, the solidified residue was washed with a mixed solvent of methanol and diisopropyl ether and the aimed product was obtained as pink solid (yield: 79%).

¹H-NMR (CDCl₃) δ: 1.22 (s, 3H), 1.45 (s, 3H), 1.51 (s, 9H), 3.00 (s, 3H), 3.61 (dd, J=3.0, 8.9 Hz, 1H), 3.67 (s, 1H), 3.84 (s, 3H), 4.69 (dd, J=8.0, 8.9 Hz, 1H), 4.81 (d, J=8.0 Hz, 1H), 6.74 (s, 1H), 6.83 (s, 1H), 7.01 (s, 1H)

LC/MS (ESI⁺): 438[M⁺+Na], (ESI⁻): 415[M⁺−1]

N-{(3R*, 4S*)-(4-Amino-3-hydroxy-6-methoxy-2,2-dimethyl-3,4-dihydro-2H-1-benzopyran-7-yl)} methanesulfonamide hydrochloride

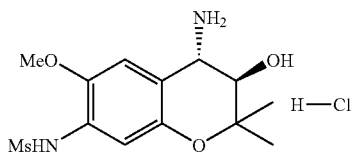

A solution of 4 mol/L hydrogen chloride-1,4-dioxane (2.52 mL, 10.1 mmol) was added to t-butyl {(3R*,4S*)-3-hydroxy-6-methoxy-2,2-dimethyl-7-[(methylsulfonyl)amino]-3,4-dihydro-2H-1-benzopyran-4-yl} carbamate (419 mg, 1.00 mmol) at room temperature, and the resulting mixture was stirred at 100° C. for 30 minutes. Upon the completion of the reaction, the solvent was distilled off. The resulting solid was washed with diisopropyl ether and thereby hydrochloride of the aimed product was obtained as colorless solid (yield: 99%).

LC/MS (ESI⁺): 339[M⁺+Na], (ESI⁻): 315[M⁺−1]

N-{(3R*, 4S*)-4-[(2 Cyclohexylethyl)amino]-3-hydroxy-6-methoxy-2,2-dimethyl-3,4-dihydro-2H-1-benzopyran-7-yl} methanesulfonamide

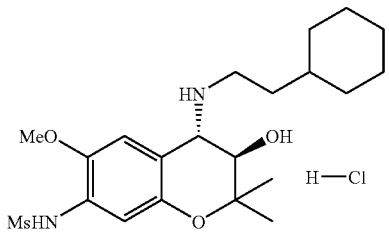

To a solution of N-((3R*, 4S*) 4-amino-3-hydroxy-6-methoxy-2,2-dimethyl-3,4-dihydro-2H-1-benzopyran-7-yl) methanesulfonamide hydrochloride (118 mg, 0.34 mmol), cyclohexyl acetaldehyde (63 mg, 0.50 mmol) and triethylamine (0.034 mL, 0.34 mmol) in methanol (2.4 mL), sodium cyanoborohydride (42 mg, 0.67 mmol) was added at room temperature and the mixture was stirred at the temperature for 2 hours. Upon the completion of the reaction, water was added to the reaction solution, and the resulting solution was extracted with ethyl acetate. The organic phase was washed with saturated sodium chloride solution, and then dried over anhydrous sodium sulfate. After distilling off the solvent, the residue was purified by column chromatography (hexane/ethyl acetate =1/2) and the aimed product was obtained as oily substance. A solution of 4 mol/L hydrogen chloride in 1,4-dioxane (0.40 mL, 2.0 mmol) was added to the oily substance as 1,4-dioxane solution (0.40 mL), and the resulting mixture was stirred at 0° C. for 30 minutes. Further, di-isopropyl ether (5 mL) was added and the resulting mixture was stirred for 30 minutes, and the resulting crystals were filtered off, and thereby hydrochloride of the aimed product was obtained as colorless solid (yield: 34%).

¹H-NMR (CDCl₃) δ: 0.87-1.69 (m, 13H), 1.24 (s, 3H), 1.47 (s, 3H), 2.49-2.57 (m, 1H), 2.63-2.72 (m, 1H), 3.00 (s, 3H), 3.60 (d, J=9.6 Hz, 1H), 3.67 (d, J=9.6 Hz, 1H), 3.83 (s, 3H), 6.84 (s, 1H), 7.00 (s, 1H)

LC/MS (ESI⁺): 427[M⁺+1], (ESI⁻): 425[M⁺−1]

Synthesis Example 5

N-{(3R*, 4S*, 4-3-Hydroxy-6-methoxy-2,2-dimethyl-4-(n-pentylamino)-3,4-dihydro-2H-1-benzopyran-7-yl} methanesulfonamide

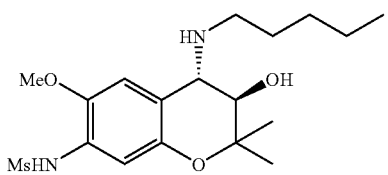

Hydrochloride of the aimed product was obtained as colorless solid (yield: 32%) by synthesizing similarly to the above-mentioned process.

¹H-NMR (CDCl₃) δ: 0.90 (t, J=6.8 Hz, 3H), 1.23-1.52 (m, 6H), 1.18 (s, 3H), 1.48 (s, 3H), 2.47-2.55 (m, 1H), 2.61-2.70 (m, 1H), 3.00 (s, 3H), 3.59 (d, J=9.8 Hz, 1H), 3.66 (d, J=9.8 Hz, 1H), 3.83 (s, 3H), 6.85 (s, 1H), 6.99 (s, 1H)

LC/MS (ESI⁺): 387[M⁺+1], (ESI⁻): 385[M⁺−1]

Synthesis Example 6

N-{(3R*,4S*)-3-Hydroxy-2,2,8-trimethyl-4-[(2-phenylethyl)amino]-3,4-dihydro-2H-1-benzopyran-7-yl}methanesulfonamide

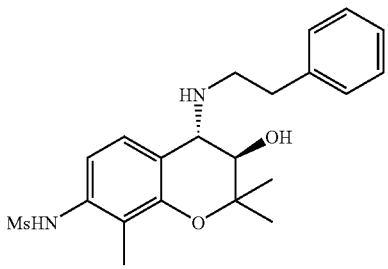

2,2,8-Trimethyl-7-nitro-2H-1-benzopyran

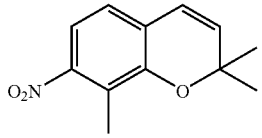

The compound was synthesized according to the method similar to one described in Synthesis Example 1 (2-step, yield: 70%).

$^1$H-NMR (CDCl$_3$) δ: 1.46 (s, 6H), 2.36 (s, 3H), 5.78 (d, J=9.6 Hz, 1H), 6.34 (d, J=9.6 Hz, 1H), 6.91 (d, J=8.3 Hz, 1H), 7.39 (d, J=8.3 Hz, 1H)

MS (EI): 219 [M$^+$]

(3R*,4R*)-3,4-Epoxy-2,2,8-trimethyl-7-nitro-3,4-dihydro-2H-1-benzopyran

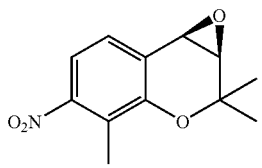

To a solution (50 mL) of ethyl acetate containing 2,2,8-trimethyl-7-nitro-2H-1-benzopyran (3.32 g, 15.1 mmol), N-methyl imidazole (0.482 mL, 6.05 mmol) and (R,R,S,S)-Ph,Ph salen manganese complex (XY) (142 mg, 0.151 mmol) were added at room temperature, and sodium hypochlorite aqueous solution (34.1 mL, 1.776 mol/kg, 60.5 mmol) was added dropwise, and the resulting mixture was stirred at room temperature for 1 hour. Upon the completion of the reaction, sodium thiosulfate aqueous solution was added to the reaction solution, the resulting solution was filtered through celite. The resulting filtrate extracted with ethyl acetate. The organic phase was washed with water and sodium chloride aqueous solution, and then dried over anhydrous magnesium sulfate. After distilling off the solvent, the residue was purified by column chromatography (hexane/ethyl acetate=7/1) and the aimed product was obtained as pale yellow crystal (yield: 78%, optical purity: 99% ee).

$^1$H-NMR (CDCl$_3$) δ: 1.25 (s, 3H), 1.64 (s, 3H), 2.32 (s, 3H), 3.55 (d, J=4.2 Hz, 1H), 3.94 (d, J=4.2 Hz, 1H), 7.31 (d, J=8.3 Hz, 1H), 7.44 (d, J=8.3 Hz, 1H)

HPLC: 18.7 min (enantiomer 21.8 min)

HPLC condition: chiralcel OJ-RH, MeCN/MeOH/0.01 M NaCl aq.=1/3/3, 1.0 ml/min, 40° C., 256 nm (3R*,4S*)-2,2,8-Trimethyl-7-nitro-4-[(2-phenylethyl)amino]-3,4-dihydro-2H-1-benzopyran-3-ol

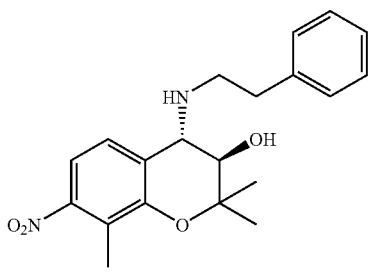

To a solution of (3R*,4R*)-3,4-epoxy-2,2,8-trimethyl-7-nitro-3,4-dihydro-2H-1-benzopyran (600 mg, 2.55 mmol) in 1,4-dioxane (1.2 mL), lithium perchlorate (271 mg, 2.55 mmol) and 2-(phenylethyl)amine (0.384 mL, 3.06 mmol) were added at room temperature and the mixture was stirred at 80° C. for 1 hour. Upon the completion of the reaction, saturated ammonium chloride was added to the reaction solution, and the resulting solution was extracted with ethyl acetate. The organic phase was washed with saturated sodium chloride solution, and then dried over anhydrous sodium sulfate. After distilling off the solvent, the residue was purified by column chromatography (hexane/ethyl acetate=4/1) and the aimed product was obtained as orange oily substance (yield: 99%).

$^1$H-NMR (CDCl$_3$) δ: 1.16 (s, 3H), 1.52 (s, 3H), 2.31 (s, 3H), 2.72-2.91 (m, 4H), 3.54 (d, J=10.0 Hz, 1H), 3.67 (d, J=10.0 Hz, 1H), 6.91 (d, J=8.5 Hz, 1H), 7.19 (m, 6H)

MS (EI): 356[M$^+$]

t-Butyl (2-phenylethyl) (3R*,4S*)-3-hydroxy-2,2,8-trimethyl-7-nitro-3,4-dihydro-2H-1-benzopyran-4-yl carbamate

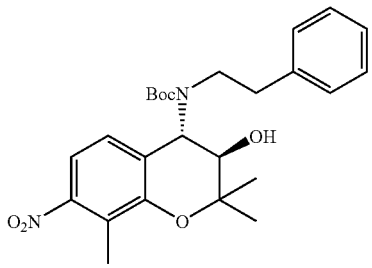

To a solution of (3R*,4S*)-2,2,8-trimethyl-7-nitro-4-[(2-phenylethyl)amino]-3,4-dihydro-2H-1-benzopyran-3-ol (896 mg, 2.51 mmol) and di-t-butyl di-carbonate (1.10 g, 5.03 mmol) in tetrahydrofuran (9.0 mL), triethylamine (700 μL, 5.03 mmol) was added at 0° C. and the mixture was stirred at room temperature overnight. Upon the completion of the reaction, saturated sodium carbonate aqueous solution was added to the reaction solution, and the resulting solution was extracted with ethyl acetate. The organic phase was washed with 1 mol/L hydrochloric acid aqueous solution and saturated sodium chloride solution, and then dried over anhydrous sodium sulfate. After distilling off the solvent, the residue was purified by column chromatography (hexane/ethyl acetate=4/1) and the aimed product was obtained as colorless amorphous substance (yield: 86%).

MS (EI): 456 [M$^+$]

t-Butyl (2-phenylethyl) (3R*,4S*)-7-amino-3-hydroxy-2,2,8-trimethyl-3,4-dihydro-2H-1-benzopyran-4-yl carbamate

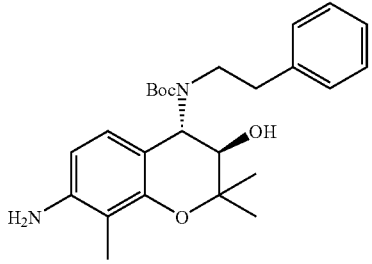

A solution of t-butyl (2-phenylethyl) (3R*,4S*)-3-hydroxy-2,2,8-trimethyl-7-nitro-3,4-dihydro-2H-1-benzopyran-4-yl carbamate (980 mg, 2.15 mmol) and 5% palladium-carbon (98 mg) in ethanol (19.6 mL) was stirred under hydrogen atmosphere at room temperature overnight. Upon the completion of the reaction, the reaction solution was filtered through celite. After distilling off the solvent, the residue was purified by column chromatography (hexane/ethyl acetate=3/1) and the aimed product was obtained as colorless solid (yield: 87%).

LC/MS (ESI$^+$): 427[M$^+$+1]

t-Butyl (2-phenylethyl) (3R*,4S*)-3-hydroxy-2,2,8-trimethyl-7-[(methylsulfonyl)amino]-3,4-dihydro-2H-1-benzopyran-4-yl carbamate

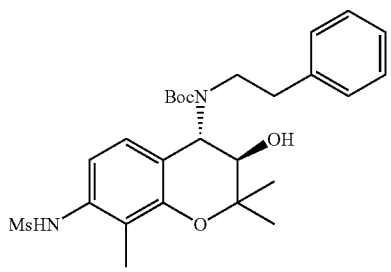

To a solution of t-butyl (2-phenylethyl) (3R*,4S*)-7-amino-3-hydroxy-2,2,8-trimethyl-3,4-dihydro-2H-1-benzopyran-4-yl carbamate (440 mg, 1.03 mmol) in pyridine (4.4 mL), methanesulfonyl chloride (0.31 mL, 3.52 mmol) was added at room temperature and the resulting mixture was stirred at room temperature for 3 hours. Upon the completion of the reaction, an aqueous solution (ca. 30 mL) of 1 mol/L hydrochloric acid was added to the reaction solution to adjust pH to 5-9, and then the mixture was extracted with ethyl acetate. The organic phase was washed with saturated sodium chloride solution, and then dried over anhydrous sodium sulfate. After distilling off the solvent, the residue was purified by column chromatography (hexane/ethyl acetate=3/1) and the aimed product was obtained as colorless oily substance (yield: 75%).

LC/MS (ESI$^+$): 527[M$^+$+Na], (ESI$^-$): 503[M$^+$−1]

N-{3-hydroxy-2,2,8-trimethyl-4-[(2-phenylethyl)amino]-3,4-dihydro-2H-1-benzopyran-7-yl}methanesulfonamide

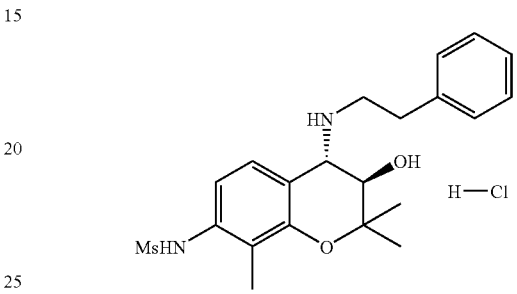

To a solution of t-butyl (2-phenylethyl) (3R*,4S*)-3-hydroxy-2,2,8-trimethyl-7-[(methylsulfonyl)amino]-3,4-dihydro-2H-1-benzopyran-4-yl carbamate (390 mg, 0.77 mmol) in 1,4-dioxane (3.9 mL), a solution (1.94 mL, 7.8 mmol) of 4 mol/L hydrogen chloride-1,4-dioxane was added at room temperature and the resulting mixture was stirred at 100° C. for 30 minutes. Upon the completion of the reaction, the solvent was distilled off, and the resulting solid was washed with a solution of ethyl acetate/hexane=1/3 and hydrochloride of the aimed product was obtained as colorless solid (yield: 92%).

$^1$H-NMR (DMSO-d$_6$) δ: 1.08 (s, 3H), 1.45 (s, 3H), 2.10 (s, 3H), 2.98 (s, 3H), 3.02-3.36 (m, 4H), 4.01 (dd, J=6.1, 8.2 Hz, 1H), 4.40 (d, J=8.2 Hz, 1H), 6.31 (d, J=6.1 Hz, 1H), 6.97 (d, J=8.5 Hz, 1H), 7.22-7.34 (m, 5H), 7.66 (d, J=8.5 Hz, 1H), 9.20 (s, 1H), 9.35 (brs, 1H), 9.80 (brs, 1H)

LC/MS (ESI$^+$): 405[M$^+$+1], (ESI$^-$): 403[M$^+$−1]

Synthesis Example 7

N-{(3R*,4S*)-3-Hydroxy-2,2-dimethyl-4-[(2-phenylethyl)amino]-3,4-dihydro-2H-1-benzopyran-7-yl}methanesulfonamide maleate t-Butyl (2-phenylethyl) (3R*,4S*)-3-hydroxy-2,2-dimethyl-7-amino-3,4-dihydro-2H-1-benzopyran-4-yl carbamate

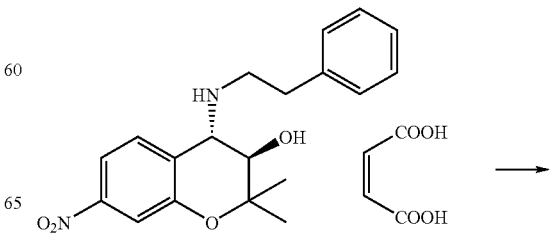

-continued

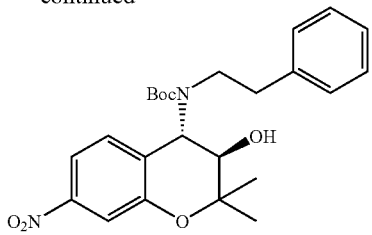

A suspension of (3R*,4S*)-2,2-dimethyl-7-nitro-4-[(2-phenylethyl)amino]-2H-1-benzopyran-3-ol maleate (5.20 g, 11.3 mmol) in ethyl acetate was neutralized with an aqueous solution of saturated sodium hydrogen carbonate. The organic phase was washed with saturated sodium chloride solution, and dried over magnesium sulfate. After concentrating under a reduced pressure, the resulting (3R*,4S*)-2,2-dimethyl-7-nitro-4-[(2-phenylethyl)amino]-2H-1-benzopyran-3-ol was diluted with tetrahydrofuran (50 mL). Di-t-butyl dicarbonate (2.96 g, 27.1 mmol) was added thereto and the resulting reaction solution was stirred at room temperature for 1 day and concentrated under a reduced pressure. Ethyl acetate was added to the resulting residue, the resulting mixture was washed with water and saturated sodium chloride solution. The organic phase was dried over magnesium sulfate and concentrated under a reduced pressure. The resulting residue was purified by silica gel column chromatography (hexane:ethyl acetate=10:1) to obtain t-butyl (2-phenylethyl) (3R*,4S*)-3-hydroxy-2,2-dimethyl-7-nitro-3,4-dihydro-2H-1-benzopyran-4-yl carbamate (yield: 91%).

MS (ESI$^+$) m/z; 443 [M$^+$+1]
MS (ESI$^-$) m/z; 441 [M$^+$−1]

t-Butyl (2-phenylethyl) (3R*,4S*)-7-amino-3-hydroxy-2,2-dimethyl-3,4-dihydro-2H-1-benzopyran-4-yl carbamate To a solution of t-butyl (2-phenylethyl) (3R*,4S*)-3-hydroxy-2,2-dimethyl-7-nitro-3,4-dihydro-2H-1-benzopyran-4-yl carbamate (4.55 g, 10.3 mmol) in ethanol (91 mL), palladium-carbon (230 mg) was added, and hydrogen was added under normal pressure, and then the mixture was stirred at room temperature for 1 day. The reaction solution was filtered through celite, and the filtrate was concentrated under a reduced pressure. The resulting residue was purified by column chromatography (hexane/ethyl acetate=5/1) to obtain t-butyl (2-phenylethyl) (3R*,4S*)-7-amino-3-hydroxy-2,2-dimethyl-3,4-dihydro-2H-1-benzopyran-4-yl carbamate (yield: 93%).

MS (ESI$^+$) m/z; 413 [M$^+$+1]
MS (ESI$^-$) m/z; 457 [M$^+$+45, HCO$_2$H adduct]

t-Butyl (2-phenylethyl) (3R*,4S*)-3-hydroxy-2,2-dimethyl-7-[(methanesulfonyl)amino]-3,4-dihydro-2H-1-benzopyran-4-yl carbamate

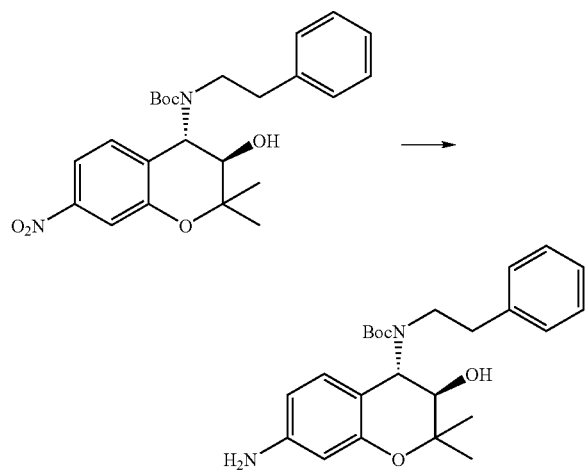

To a solution of t-butyl (2-phenylethyl) (3R*,4S*)-7-amino-3-hydroxy-2,2-dimethyl-3,4-dihydro-2H-benzopyran-4-yl carbamate (321 mg, 0.779 mmol) in tetrahydrofuran (3.2 mL), triethylamine (239 μL, 1.71 mmol) was added, and mesyl chloride (60.3 μL, 0.779 mmol) was added dropwise at 0° C. The resulting mixture was stirred at room temperature for 2 hours, and then mesyl chloride (60.3 mL, 0.779 mmol) was further added at 0° C. After stirring at room temperature, the mixture was neutralized with saturated sodium hydrogen carbonate aqueous solution. Ethyl acetate was added to the reaction solution, the reaction solution was washed with saturated sodium hydrogen carbonate aqueous solution and saturated sodium chloride solution, the resulting organic phase was dried over magnesium sulfate and concentrated under a reduced pressure. The resulting residue was purified by silica gel column chromatography (hexane:ethyl acetate=3:1) to obtain t-butyl (2-phenylethyl) (3R*,4S*)-3-hydroxy-2,2-dimethyl-7-[(methanesulfonyl)amino]-3,4-dihydro-2H-benzopyran-4-yl carbamate (yield: 65%).

MS (ESI$^+$) m/z; 491 [M$^+$+1]
MS (ESI$^-$) m/z; 489 [M$^+$−1]

N-{(3R*,4S*)-3-hydroxy-2,2-dimethyl-4-[(2-phenylethyl)amino]-3,4-dihydro-2H-benzopyran-7-yl}methanesulfonamide

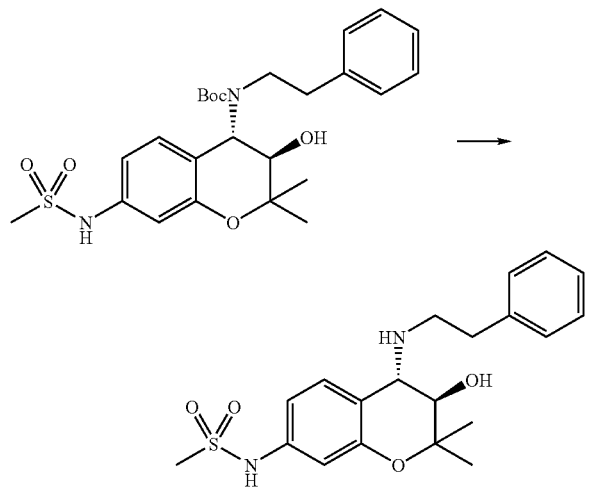

A solution (24 mL) of 4 mol/L hydrochloric acid-dioxane containing t-butyl (2-phenylethyl) {(3R*,4S*)-3-hydroxy-2,2-dimethyl-7-[(methanesulfonyl)amino]-3,4-dihydro-2H-1-benzopyran-4-yl}carbamate (1.2 g, 2.4 mmol) was stirred at room temperature for 1 hour. Ethyl acetate was added to the reaction solution, the reaction solution was washed with 1 mol/L sodium hydroxide aqueous solution and saturated sodium chloride solution. The organic phase was dried over magnesium sulfate and concentrated under a reduced pressure. The resulting residue was purified by silica gel column chromatography (hexane:ethyl acetate =1:1) to obtain N-{(3R*,4S*)-3-hydroxy-2,2-dimethyl-4-[(2-phenylethyl)amino]-3,4-dihydro-2H-1-benzopyran-7-yl}methanesulfonamide (yield: 58%).

N-{(3R*,4S*)-3-hydroxy-2,2-dimethyl-4-[(2-phenylethyl)amino]-3,4-dihydro-2H-1-benzopyran-7-yl}methanesulfonamide maleate

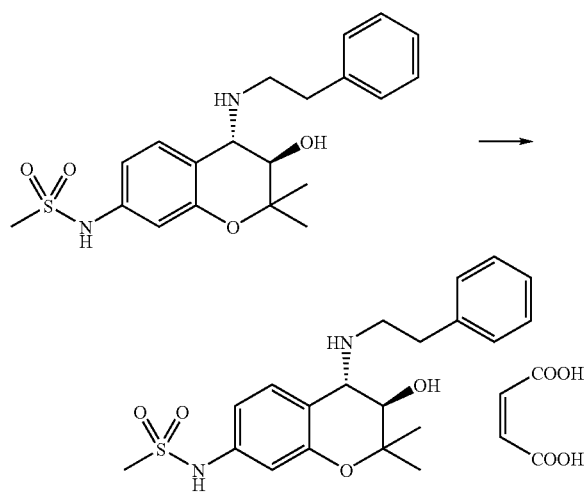

To a solution of N-{(3R*,4S*)-3-hydroxy-2,2-dimethyl-4-[(2-phenylethyl)amino]-3,4-dihydro-2H-1-benzopyran-7-yl}methanesulfonamide, (66.8 mg, 0.171 mmol) in ethanol, a solution of maleic acid (22 mg, 0.19 mmol) in ethanol was added dropwise. After concentrating under a reduced pressure, the resulting solid was suspended in ethyl acetate. The suspension was stirred and solid was filtered off. The solid was washed with ethyl acetate, dried and thus N-{(3R*,4S*)-3-hydroxy-2,2-dimethyl-4-[(2-phenylethyl)amino]-3,4-dihydro-2H-1-benzopyran-7-yl}-methanesulfonamide maleate (yield: 85%) was obtained.

White solid:

$^1$H-NMR (DMSO-$d_6$) δ: 1.10 (s, 3H), 1.42 (s, 3H), 2.80-3.50 (m, 7H), 3.90 (m, 1H), 4.31 (m, 1H), 6.04 (s, 2H), 6.16 (m, 1H), 6.65 (m, 1H), 6.85 (m, 1H), 7.15-7.40 (m, 5H), 7.50 (m, 1H), 9.93 (br, 1H).

MS (ESI$^+$) m/z; 391 [M$^+$+1]

MS (ESI$^-$) m/z; 389 [M$^+$−1]

Synthesis Example 8

N-{(3R*,4S*)-3-hydroxy-2,2-dimethyl-4-[(2-henylethyl)amino]-3,4-dihydro-2H-1-benzopyran-7-yl}ethanesulfonamide hydrochloride t-Butyl (2-phenylethyl) (3R*,4S*)-7-amino-3-hydroxy-2,2-dimethyl-3,4-dihydro-2H-1-benzopyran-4-yl carbamate

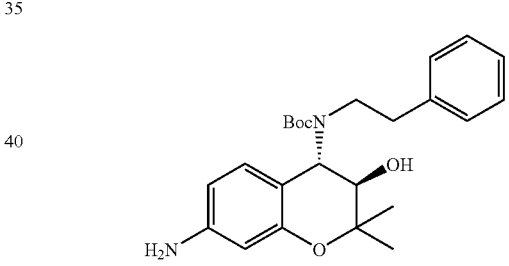

The compound was synthesized according to the synthesis method of Synthesis Example 7.

t-Butyl (2-phenylethyl) (3R*,4S*)-7-[(ethylsulfonyl)amino]-3-hydroxy-2,2-dimethyl-3,4-dihydro-2H-benzopyran-4-yl carbamate

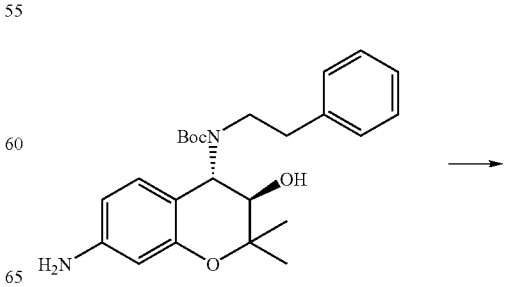

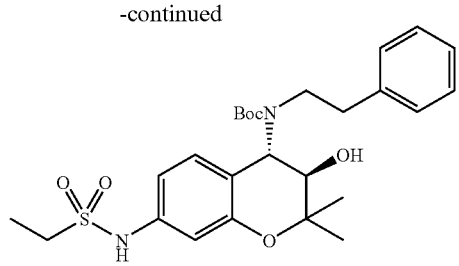

To a solution of t-butyl (2-phenylethyl) (3R*,4S*)-7-amino-3-hydroxy-2,2-dimethyl-3,4-dihydro-2H-benzopyran-4-yl carbamate (190 mg, 0.459 mmol) in pyridine (2 mL), ethylsulfonyl chloride (48 μL, 0.46 mmol) was added dropwise at 0° C., and the resulting mixture was stirred at room temperature for 14 hours. Ethyl acetate was added to the reaction solution, the solution was washed with 1 mol/L hydrochloric acid aqueous solution and saturated sodium chloride solution, thereafter the organic phase was dried over magnesium sulfate and concentrated under a reduced pressure. The resulting residue was purified by silica gel column chromatography (hexane:ethyl acetate=3:1) to quantitatively obtain t-butyl (2-phenylethyl) (3R*,4S*)-7-[(ethylsulfonyl)amino]-3-hydroxy-2,2-dimethyl-3,4-dihydro-2H-benzopyran-4-yl carbamate.

MS (ESI⁻) m/z; 503 [M⁺−1]

N-{(3R*,4S*)-3-hydroxy-2,2-dimethyl-4-[(2-phenylethyl)amino]-3,4-dihydro-2H-benzopyran-7-yl}ethanesulfonamide hydrochloride

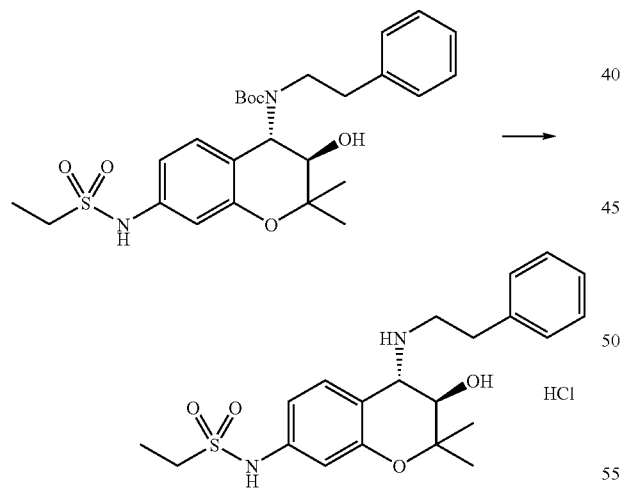

t-Butyl (2-phenylethyl) (3R*,4S*)-7-[(ethylsulfonyl)amino]-3-hydroxy-2,2-dimethyl-3,4-dihydro-2H-benzopyran-4-yl carbamate (239 mg, 0.473 mmol) was suspended in 4 mol/L hydrogen chloride in dioxane solution (4 mL), and the resulting suspension was stirred at room temperature for 1.5 hour, then solid was filtered off. The solid was washed with ethyl acetate to obtain N-{(3R*,4S*)-3-hydroxy-2,2-dimethyl-4-[2-phenylethyl)amino]-3,4-dihydro-2H-benzopyran-7-yl}-ethanesulfonamide hydrochloride (yield: 66%).

White solid:
¹H-NMR (DMSO-d₆) δ: 1.11 (s, 3H), 1.91 (t, J=7.4 Hz, 3H), 2.90-3.40 (m, 6H), 3.13 (q, J=7.4 Hz, 2H), 3.97 (m, 1H), 4.36 (m, 1H), 6.32 (m, 1H), 6.68 (m, 1H), 6.86 (m, 1H), 7.20-7.40 (m, 5H), 7.75 (m, 1H), 10.03 (s, 1H).

MS (ESI⁺) m/z; 405 [M⁺+1]

MS (ESI⁻) m/z; 403 [M⁺−1]

Synthesis Example 9

N-{(3R*,4S*)-3-hydroxy-2,2-dimethyl-4-[(2-phenylethyl)amino]-3,4-dihydro-2H-benzopyran-7-yl}-4-methylbenzenesulfonamide t-Butyl (2-phenylethyl) (3R*,4S*)-3-hydroxy-2,2-dimethyl-7-{(4-methylphenyl)sulfonylamino}-3,4-dihydro-2H-benzopyran-4-yl carbamate

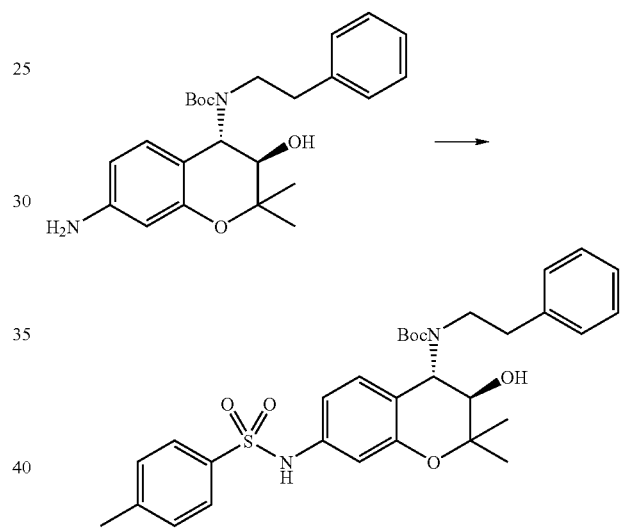

The compound was synthesized according to the synthesis method of Synthesis Example 7.

MS (ESI⁺) m/z; 567 [M⁺+1]

MS (ESI⁻) m/z; 565 [M⁺−1]

N-{(3R*,4S*)-3-hydroxy-2,2-dimethyl-4-[(2-phenylethyl)amino]-3,4-dihydro-2H-benzopyran-7-yl}-4-methylbenzenesulfonamide

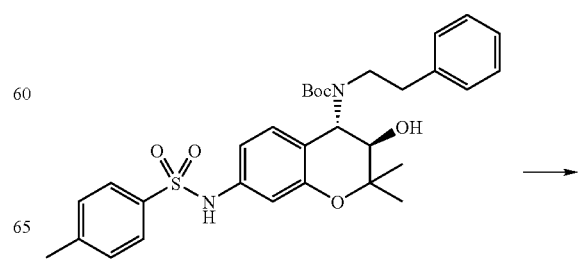

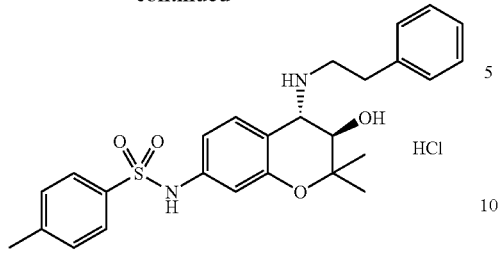

The compound was synthesized according to the synthesis method of Synthesis Example 8.

White solid:
¹H-NMR (CDCl₃) δ: 1.10 (s, 3H), 1.42 (s, 3H), 2.37 (s, 3H), 2.65-3.00 (m, 4H), 3.35-3.60 (m, 2H), 6.47 (d, J=1.9 Hz, 1H), 6.59 (dd, J=1.9 Hz, 8.3 Hz, 1H), 6.84 (d, J=8.3 Hz, 1H), 7.10-7.35 (m, 7H), 7.68 (m, 2H).

(The NMR data were obtained by using the free form of the hydrochloride obtained above.)

Synthesis Example 10

1,1,1-trifluoro-N-{(3R*,4S*)-3-hydroxy-2,2-dimethyl-4-[(2-phenylethyl)amino]-3,4-dihydro-2H-benzopyran-7-yl}methanesulfonamide maleate t-Butyl (2-phenylethyl) (3R*,4S*)-7-amino-3-hydroxy-2,2-dimethyl-3,4-dihydro-2H-benzopyran-4-yl carbamate

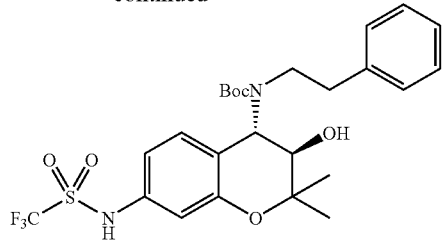

To a solution of t-butyl (2-phenylethyl) (3R*,4S*)-7-amino-3-hydroxy-2,2-dimethyl-3,4-dihydro-2H-benzopyran-4-yl carbamate (1.04 g, 2.52 mmol) in dichloromethane (20 mL) triethylamine (879 μL, 6.30 mmol) was added, and trifluoromethanesulfonyl chloride (424 μL, 2.52 mmol) was added dropwise at −78° C. After stirring for 1 hour, the resulting mixture was quenched with saturated sodium hydrogen carbonate aqueous solution, heated to room temperature and stirred. Ethyl acetate was added to the reaction solution, the solution was washed with saturated sodium hydrogen carbonate aqueous solution and saturated sodium chloride solution, thereafter the organic phase was dried over magnesium sulfate and concentrated under a reduced pressure. The resulting residue was purified by silica gel column chromatography (hexane:ethyl acetate=2:1) to obtain t-butyl (2-phenylethyl) (3R*,4S*)-3-hydroxy-2,2-dimethyl-7-{(trifluoromethyl)sulfonylamino}-3,4-dihydro-2H-benzopyran-4-yl carbamate (yield: 33%).

MS (ESI⁻) m/z; 543 [M⁺−1]

1,1,1-trifluoro-N-{(3R*,4S*)-3-hydroxy-2,2-dimethyl-4-[(2-phenylethyl)amino]-3,4-dihydro-2H-benzopyran-7-yl}methanesulfonamide

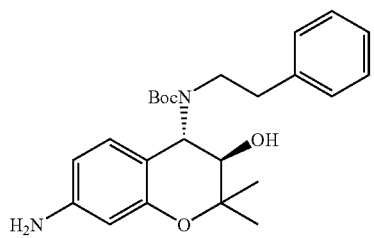

The compound was synthesized according to the synthesis method of Synthesis Example 7.

t-Butyl (2-phenylethyl) (3R*,4S*)-3-hydroxy-2,2-dimethyl-7-{(trifluoromethyl)sulfonyl amino}-3,4-dihydro-2H-benzopyran-4-yl carbamate

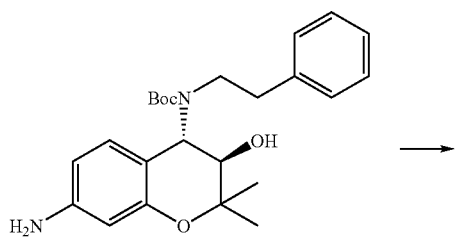 →

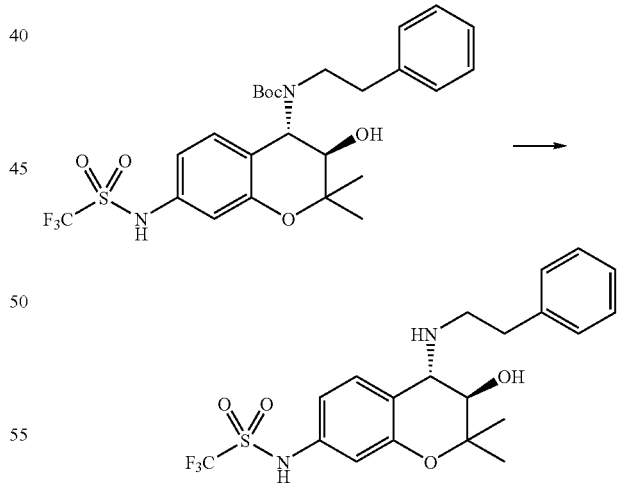

A solution of t-butyl (2-phenylethyl) (3R*,4S*)-3-hydroxy-2,2-dimethyl-7-{(trifluoromethyl)sulfonylamino}-3,4-dihydro-2H-benzopyran-4-yl carbamate (459 mg, 0.844 mmol) in 4 mol/L hydrogen chloride in dioxane (9 mL) was stirred at room temperature. Ethyl acetate was added to the reaction solution, and the solution was washed with 1 mol/L sodium hydroxide aqueous solution and saturated sodium chloride solution. After drying the organic phase on magnesium sulfate, it was concentrated under a reduced pressure to obtain 1,1,1-trifluoro-N-{(3R*,4S*)-3-hydroxy-2,2-dimethyl-4-[(2-phenylethyl) amino]-3,4-dihydro-2H-benzopyran-7-yl}-methanesulfonamide (yield: 91%) as colorless syrup.

1,1,1-trifluoro-N-{(3R*,4S*)-3-hydroxy-2,2-dimethyl-4-[(2-phenylethyl)amino]-3,4-dihydro-2H-benzopyran-7-yl}methanesulfonamide maleate

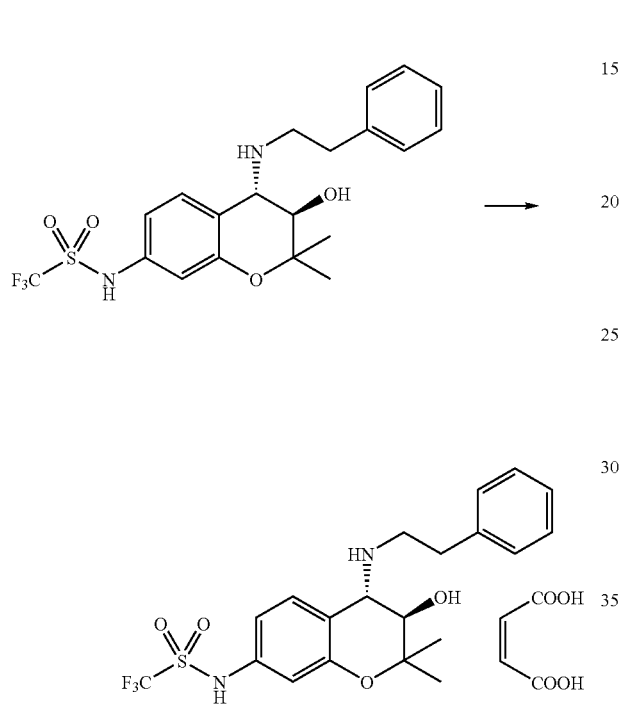

To a solution of 1,1,1-trifluoro-N-{(3R*,4S*)-3-hydroxy-2,2-dimethyl-4-[(2-phenylethyl)amino]-3,4-dihydro-2H-benzopyran-7-yl}methanesulfonamide (343 mg, 0.773 mmol) in ethanol (6 mL), a solution of maleic acid (100 mg, 0.862 mmol) in ethanol (1 mL) was added dropwise, and the resulting reaction solution was concentrated under a reduced pressure. The resulting solid was suspended in ethyl acetate, and the resulting suspension was stirred at room temperature and solid was filtered off to obtain 1,1,1-trifluoro-N-{(3R*, 4S*)-3-hydroxy-2,2-dimethyl-4-[(2-phenylethyl)amino]-3, 4-dihydro-2H-benzopyran-7-yl}methanesulfonamide maleate (yield: 65%).

White solid:
$^1$H-NMR (DMSO-$d_6$) δ: 1.08 (s, 3H), 1.40 (s, 3H), 2.85-3.40 (m, 4H), 3.89 (dd, J=4.0 Hz, 6.0 Hz, 1H), 4.30 (d, J=6.0 Hz, 1H), 6.11 (d, J=4.0 Hz, 1H), 6.16 (s, 2H), 6.55 (m, 1H), 6.70 (m, 1H), 7.15-7.40 (m, 6H).

MS (ESI$^+$) m/z; 445 [M$^+$+1]

MS (ESI$^-$) m/z; 443 [M$^+$−1]

Synthesis Example 11

N-{(3R*,4S*)-3-hydroxy-2,2-dimethyl-6-[(methylsulfonyl)amino]-4-[(2-phenylethyl)-amino]-3,4-dihydro-2H-benzopyran-7-yl}methanesulfonamide (3R*,4S*)-6,7-diamino-2,2-dimethyl-4-[(2-phenylethyl)amino]benzopyran-3-ol

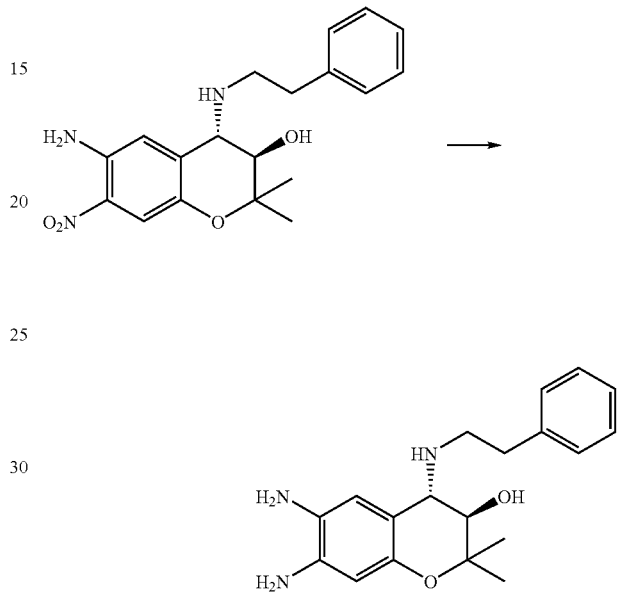

Under hydrogen gas flow at 1 atm, an ethanol solution (200 mL) containing (3R*,4S*)-6-amino-2,2-dimethyl-7-nitro-4-[(2-phenylethyl)amino]benzopyran-3-ol (10.0 g, 28.0 mmol) and 5% palladium carbon (AER type, 1 g) was stirred at room temperature for 6 hours. The reaction solution was filtered through celite, and the resulting filtrate was concentrated under a reduced pressure to obtain (3R*,4S*)-6,7-diamino-2,2-dimethyl-4-[(2-phenylethyl)amino]benzopyran-3-ol (yield: 98%).

N-{(3R*,4S*)-3-hydroxy-2,2-dimethyl-6-[(methylsulfonyl)amino]-4-[(2-phenylethyl)-amino]-3,4-dihydro-2H-benzopyran-7-yl}methanesulfonamide

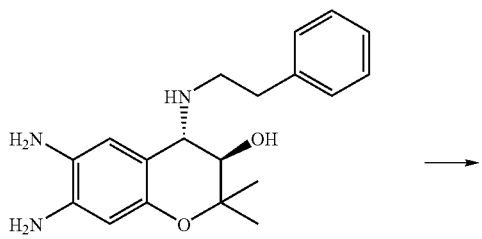

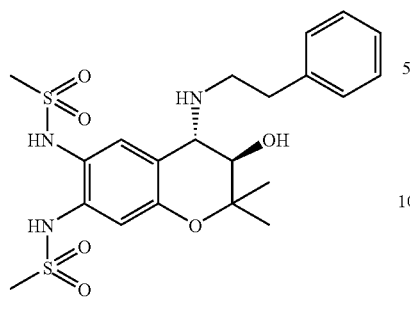

To a solution of t-butyl (2-phenylethyl) (3R*,4S*)-7-amino-3-hydroxy-2,2-dimethyl-3,4-dihydro-2H-benzopyran-4-yl carbamate (186 mg, 0.569 mmol) in pyridine (2 mL), mesyl chloride (88.2 μL, 1.14 mmol) was added dropwise at 0° C., and the resulting mixture was stirred at room temperature for 14 hours. Ethyl acetate was added to the reaction solution, the solution was washed with 1 mol/L hydrochloric acid aqueous solution. The aqueous phase was extracted with ethyl acetate, and the combined organic phases were washed with saturated sodium chloride solution, then dried over magnesium sulfate and concentrated under a reduced pressure. The resulting residue was purified by reversed-phase column chromatography (acetonitrile:water=1:1) to obtain N-{(3R*,4S*)-3-hydroxy-2,2-dimethyl-6-[(methylsulfonyl)amino]-4-[(2-phenylethyl)amino]-3,4-dihydro-2H-benzopyran-7-yl}methanesulfonamide (yield: 15%).

$^1$H-NMR (DMSO-$d_6$) δ: 1.14 (s, 3H), 1.42 (s, 3H), 2.90-3.30 (m, 10H), 3.96 (dd, J=6.0 Hz, 9.0 Hz, 1H), 4.38 (d, J=9.0 Hz, 1H), 6.34 (d, J=6.0 Hz, 1H), 6.93 (s, 1H), 7.20-7.35 (m, 5H), 7.84 (s, 1H), 9.07 (m, 2H).

MS (ESI$^-$) m/z; 482 [M$^+$−1]

Synthesis Example 12

N-{(3R*,4S*)-3-hydroxy-2,2-dimethyl-4-[(2-phenylethyl)amino]-3,4-dihydro-2H-benzopyran-7-yl}-N-methylmethanesulfonamide hydrochloride t-Butyl (2-phenylethyl) (3R*,4S*)-3-hydroxy-2,2-dimethyl-7-[(methylsulfonyl)amino]-3,4-dihydro-2H-benzopyran-4-yl carbamate

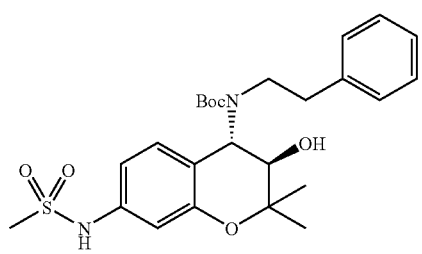

The compound was synthesized according to the synthesis method of Synthesis Example 7.

t-Butyl (2-phenylethyl) (3R*,4S*)-3-hydroxy-2,2-dimethyl-7-[N-methyl-N-(methylsulfonyl)amino]-3,4-dihydro-2H-benzopyran-4-yl carbamate

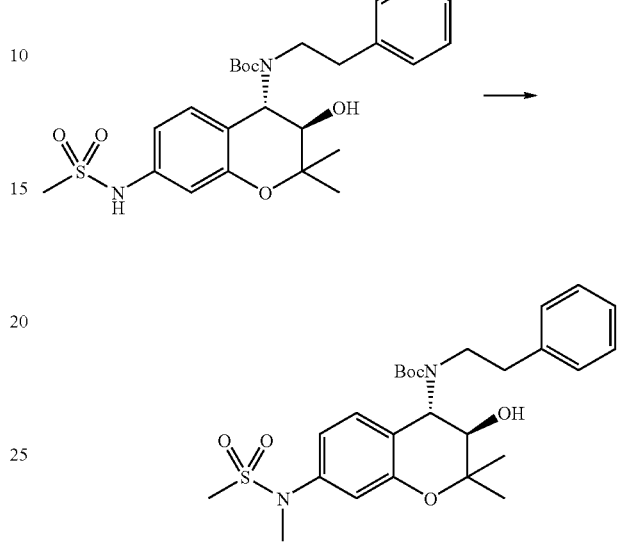

To a solution of t-butyl (2-phenylethyl) (3R*,4S*)-3-hydroxy-2,2-dimethyl-7-(methanesulfonyl)amino-3,4-dihydro-2H-benzopyran-4-yl carbamate (500 mg, 1.02 mmol) in acetone (5.4 mL), potassium carbonate (an excess amount) was suspended, methyl iodide (152 μL, 2.04 mmol) was added to the resulting suspension, and the resulting mixture was stirred at room temperature for some days. Ethyl acetate was added to the reaction solution, the solution was washed with water and saturated sodium chloride solution, thereafter the organic phase was dried over magnesium sulfate and concentrated under a reduced pressure. The resulting residue was purified by silica gel column chromatography (hexane:ethyl acetate=3:1) to obtain t-butyl (2-phenylethyl) (3R*,4S*)-3-hydroxy-2,2-dimethyl-7-[N-methyl-N-(methylsulfonyl)amino]-3,4-dihydro-2H-benzopyran-4-yl carbamate (yield: 81%).

MS (ESI$^-$) m/z; 505 [M$^+$+1]

N-{(3R*,4S*)-3-hydroxy-2,2-dimethyl-4-[(2-phenylethyl)amino]-3,4-dihydro-2H-benzopyran-7-yl}-N-methyl-N-methanesulfonamide hydrochloride

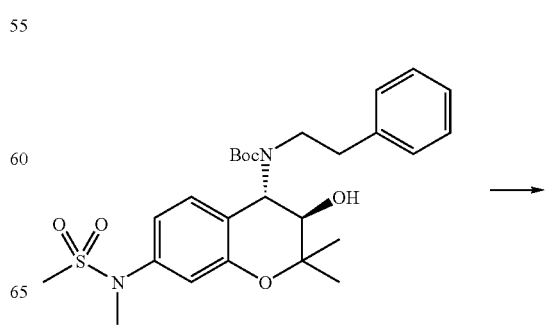

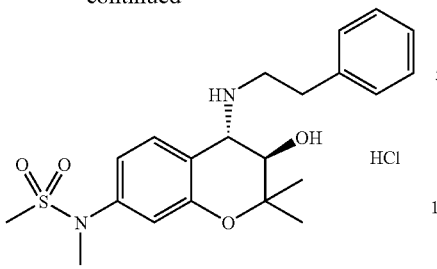

4 mol/L hydrochloric acid-dioxane solution containing t-butyl (2-phenylethyl) (3R*,4S*)-3-hydroxy-2,2-dimethyl-7-[N-methyl-N-(methylsulfonyl)amino]-3,4-dihydro-2H-benzopyran-4-yl carbamate (418 mg, 0.828 mmol) was stirred at room temperature for 1.5 hour, then solid was filtered off. The solid was washed with ethyl acetate to obtain N-{(3R*,4S*)-3-hydroxy-2,2-dimethyl-4-[(2-phenylethyl)-amino]-3,4-dihydro-2H-benzopyran-7-yl}-N-methyl-N-methanesulfonamide hydrochloride (yield: 75%).

White solid:
$^1$H-NMR (DMSO-$d_6$) δ: 1.12 (s, 3H), 1.43 (s, 3H), 2.92-3.19 (m, 4H), 2.94 (s, 3H), 3.21 (s, 3H), 4.00 (m, 1H), 4.41 (m, 1H), 6.30 (m, 1H), 6.92 (m, 1H), 7.07 (m, 1H), 7.2-7.4 (m, 5H), 7.75 (m, 1H).
MS (ESI$^+$) m/z; 405 [M$^+$+1]

Synthesis Example 13

N-{(3R*,4S*)-6-bromo-3-hydroxy-2,2-dimethyl-4-[(2-phenylethyl)amino]-3,4-dihydro-2H-benzopyran-7-yl}methanesulfonamide (3R*,4S*)-6-bromo-2,2-dimethyl-7-nitro-4-[(2-phenylethyl)amino]benzopyran-3-ol

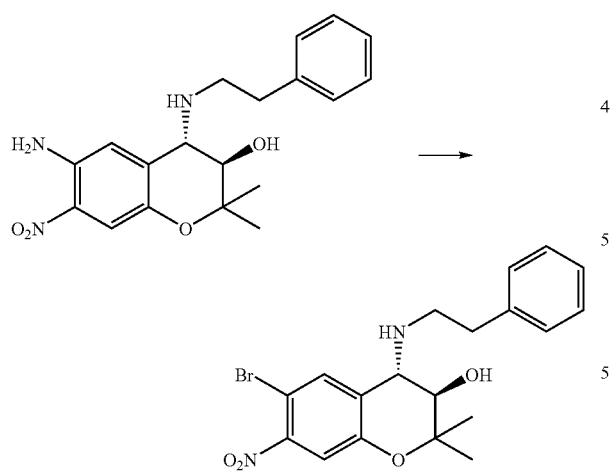

To a solution of (3R*,4S*)-6-amino-2,2-dimethyl-7-nitro-4-[(2-phenylethyl)amino]benzopyran-3-ol in acetic acid-hydrobromic acid (1:1, 60 mL), sodium nitrite aqueous solution (965 mg, 14.0 mmol/7 mL of water) was added dropwise over 45 minutes at −20° C., and the resulting solution was stirred at the temperature for 5 minutes. The reaction solution was added to a solution of copper (I) bromide (3.01 g, 21.0 mmol) in hydrobromic acid (30 mL) cooled at −20° C., and after stirring at the temperature for 2 hours, the solution was heated to room temperature and further stirred until bubbling ceased. Ethyl acetate was added to the reaction solution, the resulting reaction solution was washed with water, ammonia water and saturated sodium chloride solution. The organic phase was dried over magnesium sulfate and then concentrated under a reduced pressure. The resulting residue was purified by silica gel column chromatography (hexane:ethyl acetate=3:1) to obtain (3R*,4S*)-6-bromo-2,2-dimethyl-7-nitro-4-[(2-phenylethyl)amino]benzopyran-3-ol (yield: 85%).

(3R*,4S*)-6-bromo-2,2-dimethyl-7-nitro-4-[(2-phenylethyl)amino]benzopyran-3-ol maleate

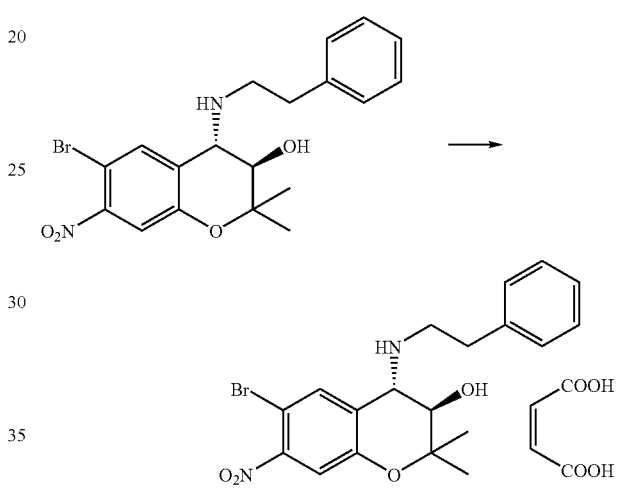

To a solution of (3R*,4S*)-6-bromo-2,2-dimethyl-7-nitro-4-[(2-phenylethyl)amino]benzopyran-3-ol (5.0 g, 12 mmol) in ethanol (50 mL), a solution of maleic acid (1.5 g, 13 mmol) in ethanol was added dropwise at room temperature. The resulting solid was filtered off, washed with ethanol, and then dried to obtain (3R*,4S*)-6-bromo-2,2-dimethyl-7-nitro-4-[(2-phenylethyl)amino]benzopyran-3-ol maleate (yield: 73%).
MS (ESI$^+$) m/z; 421 [M$^+$+1]

(3R*,4S*)-7-amino-6-bromo-2,2-dimethyl-4-[(2-phenylethyl)amino]benzopyran-3-ol

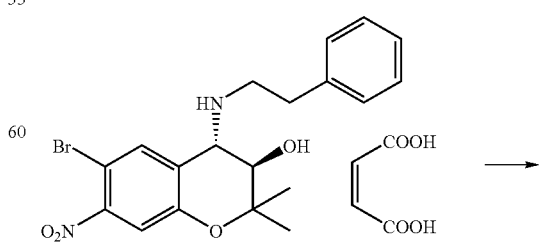

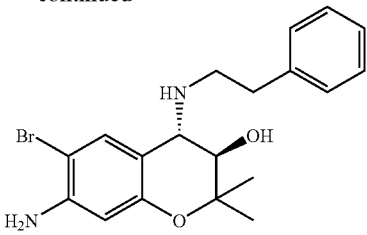

(3R*,4S*)-6-bromo-2,2-dimethyl-7-nitro-4-[(2-phenylethyl)amino]-benzopyran-3-ol maleate was suspended in ethyl acetate, the resulting suspension was neutralized with 1 mol/L sodium hydroxide aqueous solution, and then washed with 1 mol/L sodium hydroxide aqueous solution and saturated sodium chloride solution. The resulting organic phase was dried over magnesium sulfate and concentrated under a reduced pressure. To a solution of the resulting (3R*,4S*)-6-bromo-2,2-dimethyl-7-nitro-4-[(2-phenylethyl)amino]benzopyran-3-ol (2.46 g, 5.84 mmol) in ethanol (25 mL), water (5 mL) and iron powder (1.08 g, 19.3 mmol) were added, and concentrated hydrochloric acid (246 μL) was added dropwise at room temperature. After stirring at 70° C. for 3 hours, the solution was stood to cool to room temperature. Ethyl acetate was added to the reaction solution, and the resulting solution was washed with 1 mol/L sodium hydroxide aqueous solution and saturated sodium chloride solution (in the course of this procedure, emulsion was removed by filtration through celite). The organic phase was dried over magnesium sulfate and then concentrated under a reduced pressure. The resulting residue was purified by silica gel column chromatography (hexane:ethyl acetate=5:1 to 4:1) to obtain (3R*,4S*)-7-amino-6-bromo-2,2-dimethyl-4-[(2-phenylethyl)amino]-benzopyran-3-ol (yield: 65%).

MS (ESI$^+$) m/z; 391 [M$^+$+1]

N-{(3R*,4S*)-6-bromo-3-hydroxy-2,2-dimethyl-4-[(2-phenylethyl)amino]-3,4-dihydro-2H-benzopyran-7-yl}methanesulfonamide

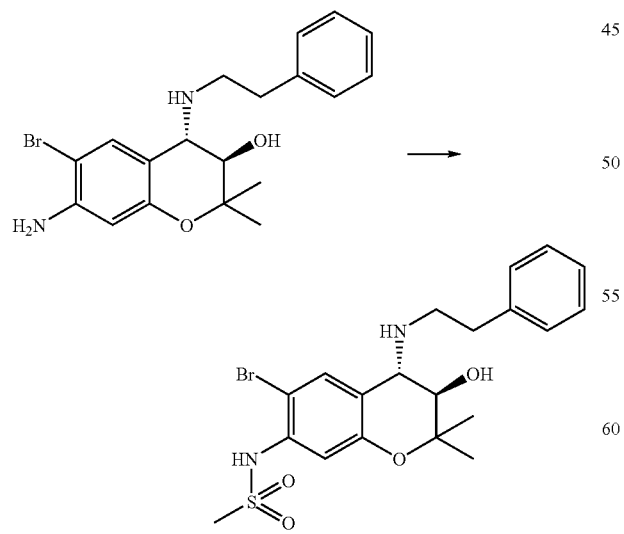

To a solution of (3R*,4S*)-7-amino-6-bromo-2,2-dimethyl-4-[(2-phenylethyl)amino]benzopyran-3-ol (1.48 g, 3.78 mmol) in pyridine (15 mL), mesyl chloride (29 μL, 3.78 mmol) was added dropwise at 0° C. After stirring at room temperature for some minutes, the resulting mixture was quenched with 1 mol/L hydrochloric acid aqueous solution. Ethyl acetate was added to the reaction solution, the solution was washed with 1 mol/L hydrochloric acid aqueous solution and saturated sodium chloride solution. The organic phase was dried over magnesium sulfate and concentrated under a reduced pressure. The resulting residue was purified by silica gel column chromatography (hexane:ethyl acetate=1:1) to obtain N-{(3R*,4S*)-6-bromo-3-hydroxy-2,2-dimethyl-4-[(2-phenylethyl)amino]-3,4-dihydro-2H-benzopyran-7-yl}methanesulfonamide (yield: 7%) as white crystal (crude crystal). The resulting crude crystal of N-{(3R*,4S*)-6-bromo-3-hydroxy-2,2-dimethyl-4-[(2-phenylethyl)amino]-3,4-dihydro-2H-benzopyran-7-yl}methanesulfonamide was recrystallized in ethyl acetate to obtain N-{(3R*,4S*)-6-bromo-3-hydroxy-2,2-dimethyl-4-[(2-phenylethyl)amino]-3,4-dihydro-2H-benzopyran-7-yl}methanesulfonamide as white crystal (yield from the crude crystal: 89%).

White crystal:

$^1$H-NMR (CDCl$_3$) δ: 1.24 (s, 3H), 1.46 (s, 3H), 2.65-3.00 (m, 4H), 3.13 (s, 3H), 3.91 (d, J=8.4 Hz, 1H), 4.04 (br, 2H), 4.75 (d, J=8.4 Hz, 1H), 6.21 (s, 1H), 7.06 (s, 1H), 7.15-7.40 (m, 5H).

MS (ESI$^+$) m/z; 469 [M$^+$+1]

Synthesis Example 14

(3R*,4S*)-2,2-dimethyl-7-dimethylamino-4-[(2-phenylethyl)amino]-3-chromanol hydrochloride

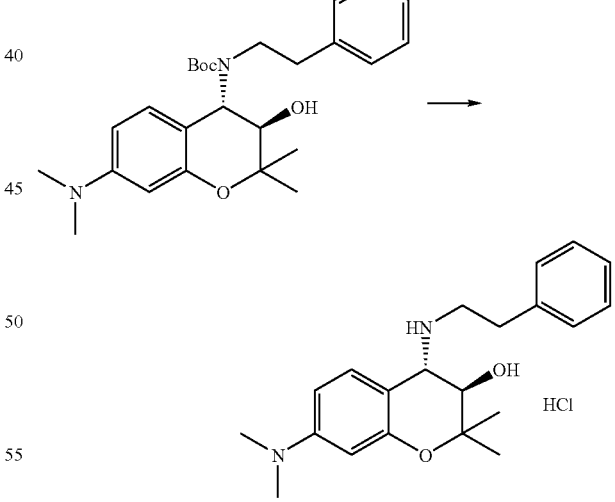

t-Butyl (2-phenylethyl) (3R*,4S*)-3-hydroxy-2,2-dimethyl-7-dimethylamino-3,4-dihydro-2H-chromen-4-yl carbamate (79.5 mg, 0.175 mmol) was dissolved in 4 mol/L hydrogen chloride in dioxane (1.6 mL) solution, and the resulting solution was stirred at room temperature. The resulting solid was filtered off, washed with ethyl acetate and then dried to quantitatively obtain (3R*,4S*)-2,2-dimethyl-7-dimethylamino-4-[(2-phenylethyl)amino]-3-chromanol hydrochloride.

White solid:

The hydrochloride was extracted and the free form thereof was used for spectrum measurement.

$^1$H-NMR (CDCl$_3$) δ: 1.17 (s, 3H), 1.47 (s, 3H), 2.79-3.00 (m, 10H), 3.47 (d, J=9.9 Hz, 1H), 3.59 (d, J=9.9 Hz, 1H), 6.13 (d, J=2.7 Hz, 1H), 6.29 (dd, J=2.7 Hz, 8.4 Hz, 1H), 6.87 (d, J=8.4 Hz, 1H), 7.20-7.31 (m, 5H).

MS (ESI$^+$) m/z; 341 [M$^+$+1]

t-Butyl (2-phenylethyl) (3R*,4S*)-3-hydroxy-2,2-dimethyl-7-dimethylamino-3,4-dihydro-2H-chromen-4-yl carbamate (Compound A)

t-Butyl (2-phenylethyl) (3R*,4S*)-3-hydroxy 2,2-dimethyl-7-methylamino-3,4-dihydro-2H-chromen-4-yl carbamate (Compound B)

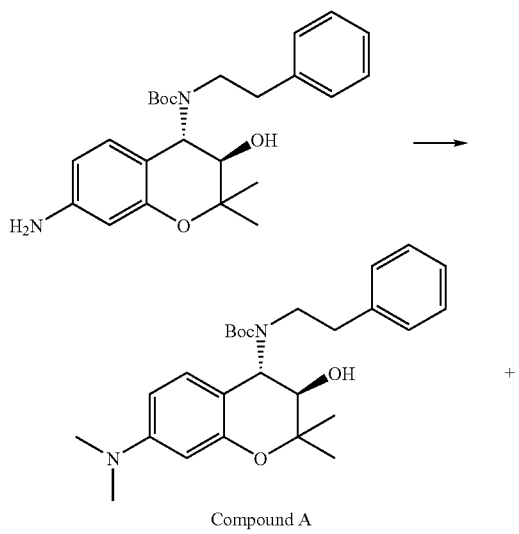

Compound A

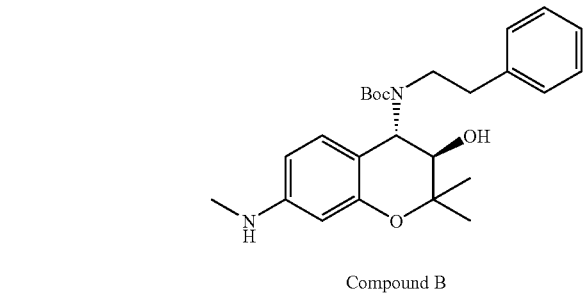

Compound B

To a solution of t-butyl (2-phenylethyl) (3R*,4S*)-7-amino-3-hydroxy-2,2-dimethyl-3,4-dihydro-2H-chromen-4-yl carbamate (240 mg, 0.581 mmol) in N,N-dimethylformamide (2.4 mL), potassium carbonate (402 mg, 2.91 mmol) was suspended, methyl iodide (109 μL, 1.74 mmol) was added to the resulting suspension. After stirring the resulting mixture at room temperature, the reaction solution was diluted with ethyl acetate, and the solution was washed with water and saturated sodium chloride solution. The organic phase was dried over magnesium sulfate and concentrated under a reduced pressure. The resulting residue was purified by silica gel column chromatography (hexane:ethyl acetate=3:1) to obtain Compound A (yield: 31%) and Compound B (yield: 15%).

Compound A: MS (ESI$^+$) m/z; 441 [M+1]$^+$

Compound B: MS (ESI$^+$) m /z; 427 [M+1]$^+$

Synthesis Example 15

(3R*,4S*)-2,2-dimethyl-7-methylamino-4-[(2-phenylethyl)amino]-3-chromanol hydrochloride

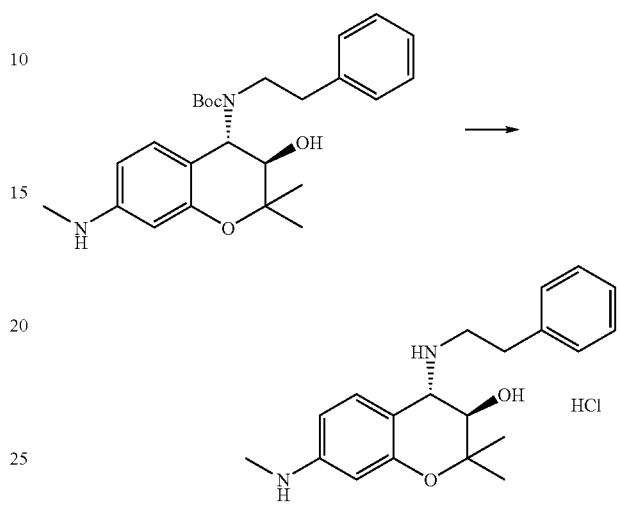

t-Butyl (2-phenylethyl) (3R*,4S*)-3-hydroxy-2,2-dimethyl-7-methylamino-3,4-dihydro-2H-chromen-4-yl carbamate (41.5 mg, 0.0973 mmol) was dissolved in 4 mol/L hydrogen chloride in dioxane (1.5 mL), some drops of methanol was added thereto and the resulting solution was stirred at room temperature. The resulting solid was filtered off, washed with ethyl acetate and then dried to quantitatively obtain (3R*,4S*)-2,2-dimethyl-7-methylamino-4-[(2-phenylethyl)amino]-3-chromanol hydrochloride.

White solid:

The hydrochloride was extracted and the free form thereof was used for spectrum measurement.

$^1$H-NMR (CDCl$_3$) δ: 1.17 (s, 3H), 1.46 (s, 3H), 2.77-3.01 (m, 7H), 3.46 (d, J=9.8 Hz, 1H), 3.55 (d, J=9.8 Hz, 1H), 6.03 (d, J=2.1 Hz, 1H), 6.16 (dd, J=2.1 Hz, 8.1 Hz, 1H), 6.79 (d, J=8.1 Hz, 1H), 7.20-7.33 (m, 5H).

MS (ESI$^+$) m/z; 327 [M+1]$^+$ t-Butyl (2-phenylethyl) (3R*,4S*)-3-hydroxy-2,2-dimethyl-7-methylamino-3,4-dihydro-2H-chromen-4-yl carbamate

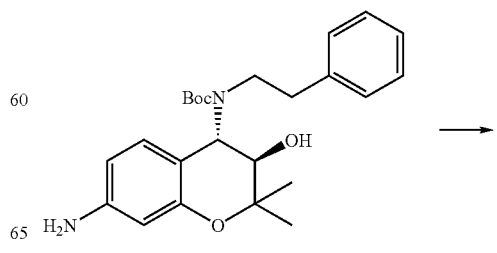

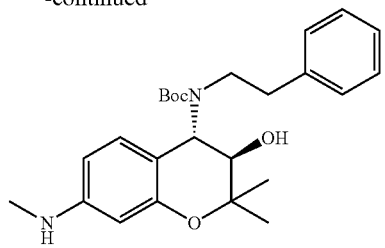

To a solution of t-butyl (2-phenylethyl) (3R*,4S*)-7-amino-3-hydroxy-2,2-dimethyl-3,4-dihydro-2H-chromen-4-yl carbamate (215 mg, 0.521 mmol) in N,N-dimethylformamide (2 mL), potassium carbonate (360 mg, 2.61 mmol) was suspended, methyl iodide (32 μL, 0.52 mmol) was added dropwise to the resulting suspension. After stirring the resulting mixture at room temperature, the reaction solution was diluted with ethyl acetate, and the solution was washed with water and saturated sodium chloride solution. The organic phase was dried over magnesium sulfate and concentrated under a reduced pressure. The resulting residue was purified by silica gel column chromatography (hexane:ethyl acetate=3:1) to obtain t-butyl (2-phenylethyl) (3R*,4S*)-3-hydroxy-2,2-dimethyl-7-methylamino-3,4-dihydro-2H-chromen-4-yl carbamate (yield: 19%).

Synthesis Example 16

(3R*,4S*)-4-{[2-(4-fluorophenyl)ethyl]amino}-2,2-dimethyl-7-dimethylamino-3-chromanol hydrochloride

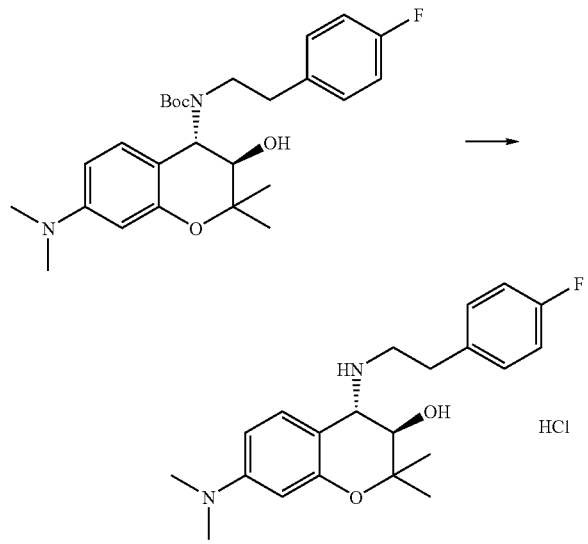

t-Butyl (3R*,4S*)-3-hydroxy-2,2-dimethyl-7-dimethylamino-3,4-dihydro-2H-chromen-4-yl [(2-(4-fluorophenyl)ethyl)]carbamate (72.2 mg, 0.157 mmol) was dissolved in 4 mol/L hydrogen chloride in dioxane (2 mL), and the resulting solution was stirred at 50° C. The resulting solid was filtered off, washed with ethyl acetate and then dried to obtain (3R*,4S*)-4-{[2-(4-fluorophenyl)ethyl]amino}-2,2-dimethyl-7-dimethylamino-3-chromanol hydrochloride (yield: 97%).

White solid:

The hydrochloride was extracted and the free form thereof was used for spectrum measurement.

$^1$H-NMR (CDCl$_3$) δ: 1.19 (s, 3H), 1.48 (s, 3H), 2.73-2.97 (m, 10H), 3.47 (d, J=9.9 Hz, 1H), 3.58 (d, J=9.9 Hz, 1H), 6.14 (d, J=2.4 Hz, 1H), 6.30 (dd, J=2.4 Hz, 8.7 Hz, 1H), 6.87 (d, J=8.7 Hz, 1H), 6.97-7.03 (m, 2H), 7.15-7.20 (m, 2H).

MS (ESI$^+$) m/z; 359 [M+1]$^+$ t-Butyl (3R*,4S*)-3-hydroxy-2,2-dimethyl-7-dimethylamino-3,4-dihydro-2H-chromen-4-yl[2-(4-fluorophenyl)ethyl]carbamate

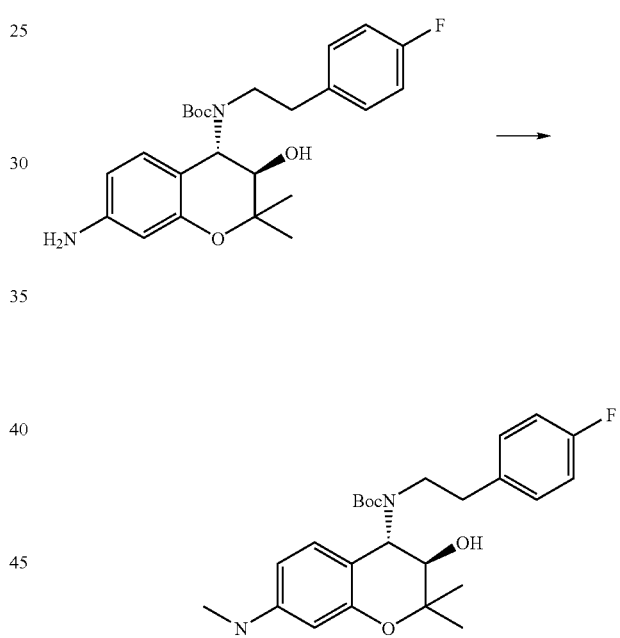

To a solution of t-butyl (3R*,4S*)-7-amino-3-hydroxy-2,2-dimethyl-3,4-dihydro-2H-chromen-4-yl[2-(4-fluorophenyl)ethyl]carbamate (177 mg, 0.412 mmol) in N,N-dimethylformamide (2 mL), potassium carbonate (285 mg, 2.06 mmol) was suspended, methyl iodide (64 μL, 1.0 mmol) was added dropwise to the resulting suspension. After stirring the resulting mixture at 40° C., the reaction solution was diluted with ethyl acetate, and the solution was washed with water and saturated sodium chloride solution. The organic phase was dried over magnesium sulfate and concentrated under a reduced pressure. The resulting residue was purified by silica gel column chromatography (hexane:ethyl acetate=5:1) to obtain t-butyl (3R*,4S*)-3-hydroxy-2,2-dimethyl-7-dimethylamino-3,4-dihydro-2H-chromen-4-yl[2-(4-fluorophenyl)ethyl]carbamate (yield: 38%).

Colorless amorphous.

t-Butyl (3R*,4S*)-7-amino-3-hydroxy-2,2-dimethyl-3,4-dihydro-2H-chromen-4-yl[2-(4-fluorophenyl)ethyl]carbamate

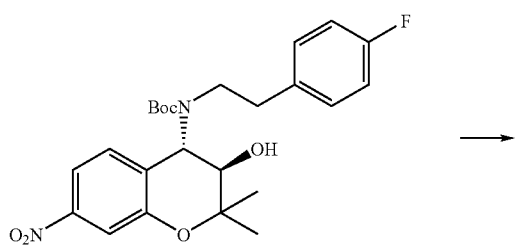

To a solution of t-butyl (3R*,4S*)-7-amino-3-hydroxy-2,2-dimethyl-3,4-dihydro-2H-chromen-4-yl[2-(4-fluorophenyl)ethyl]carbamate (3.35 g, 7.28 mmol) in methanol (30 mL), palladium/carbon (480 mg) was suspended, hydrogen was added at normal pressure and the resulting solution was stirred at room temperature for 12 hours. The reaction solution was filtered through celite, and the resulting filtrate was concentrated under a reduced pressure. The resulting residue was purified by silica gel column chromatography (hexane:ethyl acetate=4:1) to obtain t-butyl (3R*,4S*)-7-amino-3-hydroxy-2,2-dimethyl-3,4-dihydro-2H-chromen-4-yl[2-(4-fluorophenyl)ethyl]carbamate (yield: 57%).

Colorless amorphous.

t-Butyl (3R*,4S*)-3-hydroxy-2,2-dimethyl-3,4-dihydro-7nitro-2H-chromen-4-yl[2-(4-fluorophenyl)ethyl]carbamate

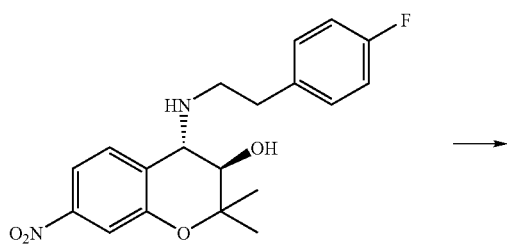

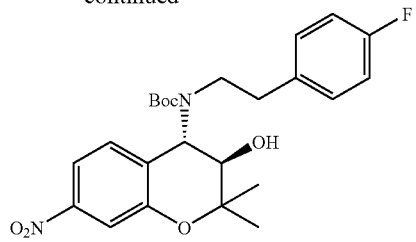

To a solution of (3R*,4S*)-4-{[2-(4-fluorophenyl)ethyl]amino}-2,2-dimethyl-7-nitro-3-chromanol (3.25 g, 9.02 mmol) in tetrahydrofuran (30 mL), t-butoxycarbonyl anhydride (2.96 g, 27.1 mmol) and triethyl amine (2.5 mL, 18 mmol) were added, and the resulting solution was stirred at room temperature and concentrated under a reduced pressure. The resulting residue was diluted with ethyl acetate, washed with saturated ammonium chloride aqueous solution and saturated sodium chloride solution. Then, the organic phase was dried over magnesium sulfate and concentrated under a reduced pressure. The resulting residue was purified by silica gel column chromatography (hexane:ethyl acetate=4:1) to obtain t-butyl (3R*,4S*)-7-nitro-3-hydroxy-2,2-dimethyl-3,4-dihydro-2H-chromen-4-yl[2-(4-fluorophenyl)ethyl]carbamate (yield: 81%).

Amorphous crystal.

(3R*,4S*)-4-{[2-(4-Fluorophenyl)ethyl]amino}-2,2-dimethyl-7-nitro-3-chromanol

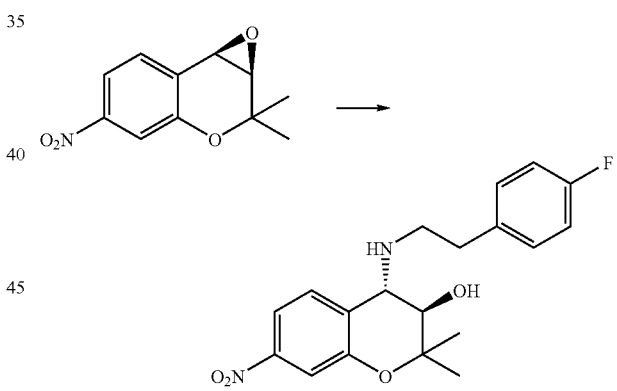

To a solution of (3R*,4R*)-3,4-epoxy-2,2-dimethyl-7-nitro-3-chromanol (2.07 g, 9.37 mmol) in dioxane (4 mL), lithium perchlorate (997 mg, 9.37 mmol) and 4-fluorophenethyl amine (1.47 mL, 11.3 mmol) were added, and the resulting solution was stirred at 70° C. for 3.5 hours under nitrogen atmosphere. The reaction solution was diluted with ethyl acetate, washed with saturated sodium hydrogen carbonate solution and saturated sodium chloride solution. Then, the organic phase was dried over magnesium sulfate and concentrated under a reduced pressure. The resulting residue was diluted with ethanol, and a solution of maleic acid (1.20 g, 10.3 mmol) in ethanol was added dropwise thereto. The resulting solid was filtered off, and washed with ethyl acetate. The resulting solid was suspended in ethyl acetate, the resulting suspension was neutralized with 1 mol/L sodium hydroxide aqueous solution and washed with saturated sodium chloride solution. After drying the organic phase over magnesium sulfate, it was dried under a reduced pressure. The resulting residue was purified by silica gel column chromatography (hexane:ethyl acetate=4:1) to obtain (3R*,4S*)-4-{[2-(4-fluorophenyl)ethyl]amino}-2,2-dimethyl-7-nitro-3-chromanol (yield: 81%).

Amorphous crystal.

MS (ESI+) m/z; 361 [M+1]

(3R*,4R*)-3,4-Epoxy-2,2-dimethyl-7-nitro-3-chromanol

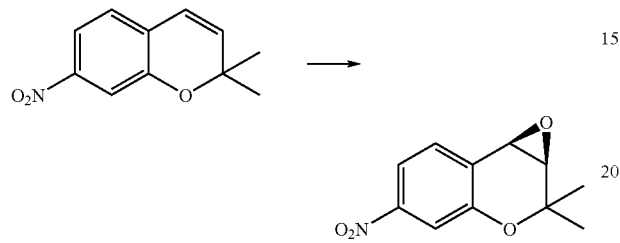

To a solution of 2,2-dimethyl-7-nitrobenzopyran (11.1 g, 53.9 mmol) in ethyl acetate (165 mL), (Cyc, Ph)-salen manganese complex (XX) (405 mg, 0.431 mmol) and N-methyl imidazole (858 μL, 10.8 mmol) were added, and sodium hypochlorite aqueous solution (101 g, 162 mmol) was added dropwise at 20° C. thereto over 15 minutes. After stirring the resulting mixture at room temperature for 3 hours, saturated sodium thiosulfate aqueous solution was added thereto under cooling with water. The resulting reaction solution was filtered through celite, the organic phase was washed with saturated sodium thiosulfate aqueous solution and saturated sodium chloride solution, and then dried over magnesium sulfate, and concentrated under a reduced pressure. The resulting solid was recrystallized in ethanol to obtain (3R*, 4R*)-3,4-epoxy-2,2-dimethyl-7-nitro-3-chromanol (yield: 66%).

Yellowish white needle crystal:

¹H-NMR (CDCl₃) δ: 1.29 (s, 3H), 1.62 (s, 3H), 3.57 (d, J=3.5 Hz, 1H), 3.97 (d, J=3.5 Hz, 1H), 7.50 (d, J=6.3 Hz, 1H), 7.67 (d, J=1.8 Hz, 1H), 7.80 (dd, J=1.8 Hz, 6.3 Hz, 1H)

100% ee (CHIRALCEL OJ, hexane/isopropanol=6:4, 1 mL/min, 40° C., 254 nm)

2,2-Dimethyl-7-nitro-1-benzopyran

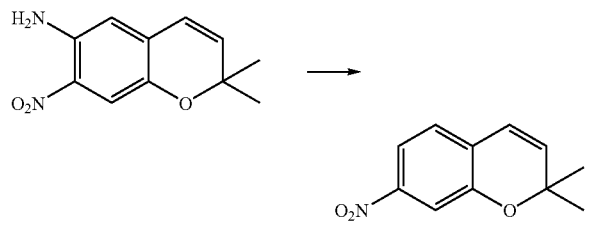

To a mixed solution of 6-amino-2,2-dimethyl-7-nitro-1-benzopyran (19.5 g, 88.7 mmol) in methanol-concentrated hydrochloric acid (1:1 v/v, 280 mL) and hypophosphorous acid aqueous solution (100 mL), an aqueous solution of sodium nitrite (12.2 g, 178 mmol) was added dropwise over 30 minutes at −3° C., and the resulting solution was stirred at room temperature until bubbling ceased. The reaction solution was diluted with ethyl acetate, washed with water and saturated sodium chloride solution. The organic phase was dried over magnesium sulfate and then concentrated under a reduced pressure. The resulting solid was recrystallized in methanol to obtain 2,2-dimethyl-7-nitro-1-benzopyran (yield: 61%).

Orange crystal

¹H-NMR (CDCl₃) δ: 1.47 (s, 6H), 5.83 (d, J=7.5 Hz, 1H), 6.83 (d, J=7.5 Hz, 1H), 7.08 (d, J=6.3 Hz, 1H), 7.61 (d, J=1.5 Hz, 1H), 7.71 (dd, J=1.5 Hz, 6.3 Hz, 1H)

Synthesis Example 17

(3R*,4S*)-6-Methoxy-2,2-dimethyl-7-dimethylamino-4-[(2-phenylethyl)amino]-3-chromanol

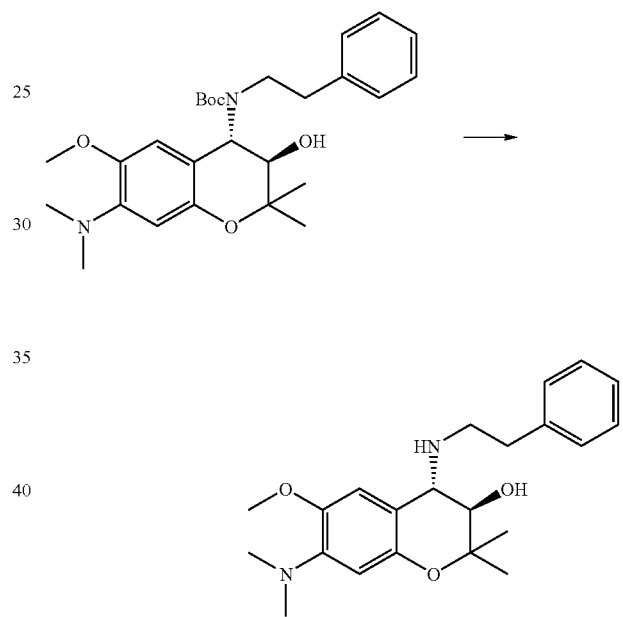

t-Butyl (2-phenylethyl) (3R*,4S*)-3-hydroxy-6-methoxy-2,2-dimethyl-7-dimethylamino-3,4-dihydro-2H-chromen-4-yl carbamate (133 mg, 0.283 mmol) was dissolved in 4 mol/L hydrogen chloride in dioxane (2 mL), some drops of methanol were added thereto, and the resulting solution was stirred at room temperature. The reaction solution was diluted with ethyl acetate, washed with 1 mol/L sodium hydroxide aqueous solution and saturated sodium chloride solution, then the resulting organic phase was dried over magnesium sulfate and concentrated under a reduced pressure to obtain (3R*, 4S*)-6-methoxy-2,2-dimethyl-7-dimethylamino-4-[(2-phenylethyl)amino]-3-chromanol (yield: 79%).

Transparent oil

¹H-NMR (CDCl₃) δ: 1.17 (s, 3H), 1.46 (s, 3H), 2.73 (s, 6H), 2.79-2.99 (m, 4H), 3.54 (d, J=9.8 Hz, 1H), 3.61 (d, J=9.8 Hz, 1H), 3.70 (s, 3H), 6.37 (s, 1H), 6.49 (s, 1H), 7.19-7.32 (m, 5H).

MS (ESI+) m/z; 371 [M++1]

223 t-Butyl (2-phenylethyl) (3R*,4S*)-3-hydroxy-6-methoxy-2,2-dimethyl-7-dimethylamino-3,4-dihydro-2H-chromen-4-yl carbamate (Compound C)

t-Butyl (2-phenylethyl) (3R*,4S*)-3-hydroxy-6-methoxy-2,2-dimethyl-7-methylamino-3,4-dihydro-2H-chromen-4-yl carbamate (Compound D)

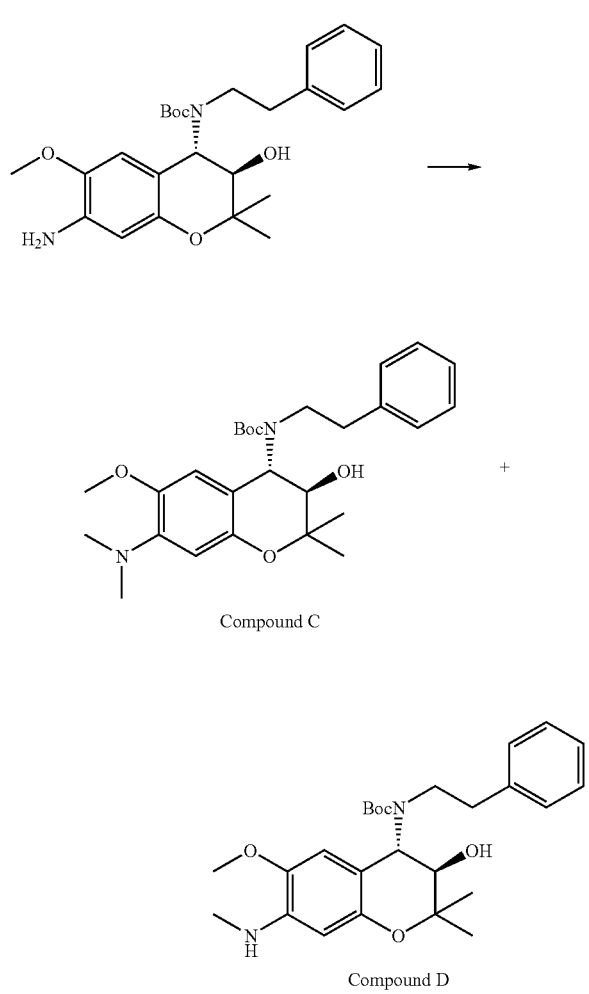

Compound C

Compound D

To a solution of t-butyl (2-phenylethyl) (3R*,4S*)-7-amino-3-hydroxy-6-methoxy-2,2-dimethyl-3,4-dihydro-2H-chromen-4-yl carbamate (1.05 g, 2.37 mmol) in N,N-dimethylformamide (10 mL), potassium carbonate (1.64 mg, 11.8 mmol) was suspended, methyl iodide (368 µL, 5.92 mmol) was added dropwise to the resulting suspension. After stirring the resulting mixture at room temperature for 1 hour, the reaction solution was diluted with ethyl acetate, and the solution was washed with water and saturated sodium chloride solution. The organic phase was dried over magnesium sulfate and concentrated under a reduced pressure. The resulting residue was purified by silica gel column chromatography (hexane:ethyl acetate=4:1) to obtain Compound C (yield: 12%) and Compound D (yield: 10%).

Compound C: Colorless amorphous

Compound D: Colorless amorphous

224

Synthesis Example 18

(3R*,4S*)-6-Methoxy-2,2-dimethyl-7-methylamino-4-[(2-phenylethyl)amino]-3-chromanol hydrochloride

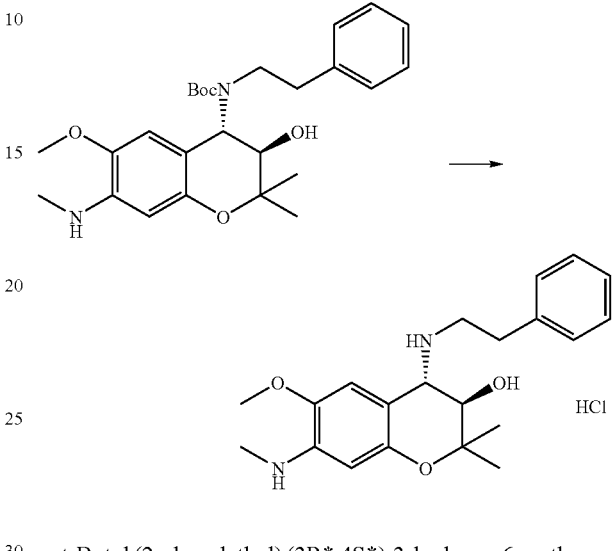

t-Butyl (2-phenylethyl) (3R*,4S*)-3-hydroxy-6-methoxy-2,2-dimethyl-7-methylamino-3,4-dihydro-2H-chromen-4-yl carbamate (108 mg, 0.237 mmol) was dissolved in 4 mol/L hydrochloric acid-dioxane (2 mL), and the resulting solution was stirred at room temperature. The resulting solid was filtered off, washed with ethyl acetate and then dried to quantitatively obtain (3R*,4S*)-6-methoxy-2,2-dimethyl-7-methylamino-4-[(2-phenylethyl)amino]-3-chromanol hydrochloride.

White solid:

$^1$H-NMR (DMSO-d$_6$) δ: 1.07 (s, 3H), 1.38 (s, 3H), 2.69 (s, 3H), 3.01-3.08 (m, 2H), 3.16-3.23 (m, 2H), 3.80 (s, 3H), 3.92 (d, J=8.8 Hz, 1H), 4.82 (d, J=8.8 Hz, 1H), 6.20 (br, 1H), 7.22-7.34 (m, 5H), 7.53 (br, 1H).

Synthesis Example 19

(3R*,4S*)-2,2-dimethyl-7-isopropylamino-4-[(2-phenylethyl)amino]-3-chromanol hydrochloride

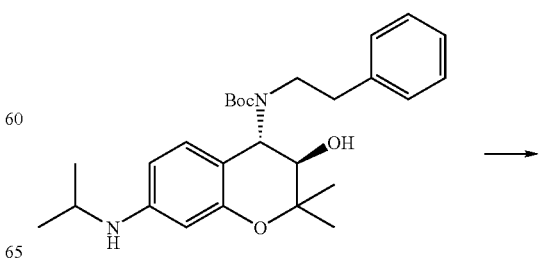

-continued

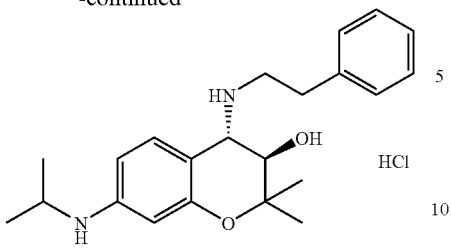

t-Butyl (2-phenylethyl) (3R*,4S*)-3-hydroxy-2,2-dimethyl-7-isopropylamino-3,4-dihydro-2H-chromen-4-yl carbamate (69 mg, 0.15 mmol) was dissolved in 4 mol/L hydrogen chloride in dioxane (1 mL), and the resulting solution was stirred at room temperature. The resulting solid was filtered off, washed with ethyl acetate and then dried to quantitatively obtain (3R*,4S*)-2,2-dimethyl-7-isopropylamino-4-[(2-phenylethyl)amino]-3-chromanol hydrochloride.

White solid:

The hydrochloride was extracted and the free form thereof was used for spectrum measurement.

$^1$H-NMR (CDCl$_3$) δ: 1.11-1.13 (m, 9H), 1.41 (s, 3H), 2.75-2.91 (m, 4H), 3.38-3.52 (m, 3H), 5.95 (d, J=2.2 Hz, 1H), 6.06 (d, J=2.2 Hz, 8.3 Hz, 1H), 6.72 (d, J=8.3 Hz, 1H), 7.15-7.26 (m, 5H)

MS (ESI$^+$) m/z; 355 [M$^+$+1]

t-Butyl (2-phenylethyl) (3R*,4S*)-3-hydroxy-2,2-dimethyl-7-isopropylamino-3,4-dihydro-2H-chromen-4-yl carbamate

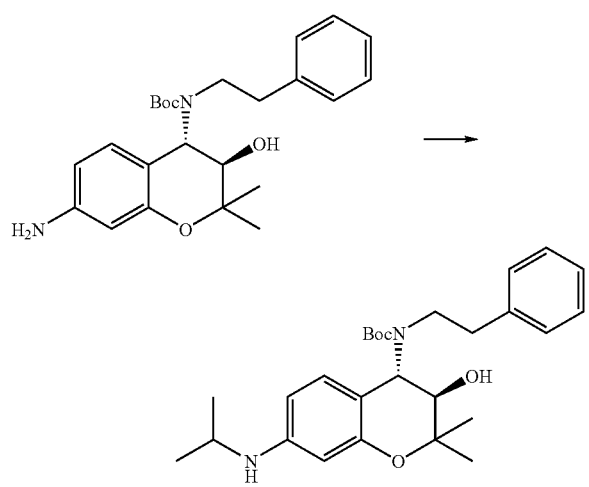

To a solution of t-butyl (2-phenylethyl) (3R*,4S*)-7-amino-3-hydroxy-2,2-dimethyl-3,4-dihydro-2H-chromen-4-yl carbamate (176 mg, 0.427 mmol) in N,N-dimethylformamide (2 mL), potassium carbonate (295 mg, 2.13 mmol) was suspended, and isopropyl iodide (56 μL, 0.56 mmol) was added dropwise. After stirring at room temperature, the reaction solution was diluted with ethyl acetate, and washed with water and saturated sodium chloride solution. The organic phase was dried over magnesium sulfate, concentrated under a reduced pressure and the resulting residue was purified by silica gel column chromatography (hexane:ethyl acetate=5:1) to obtain t-butyl (2-phenylethyl) (3R*,4S*)-3-hydroxy-2,2-dimethyl-7-isopropylamino-3,4-dihydro-2H-chromen-4-yl carbamate (yield: 36%).

MS (ESI$^+$) m/z; 455 [M$^+$+1]

Synthesis Example 20

N-{(3R*,4S*)-3-Hydroxy-2,2-dimethyl-4-[(2-phenylethyl)amino]-3,4-dihydro-2H-chromen-7-yl}-N-isopropylmethanesulfonamide hydrochloride

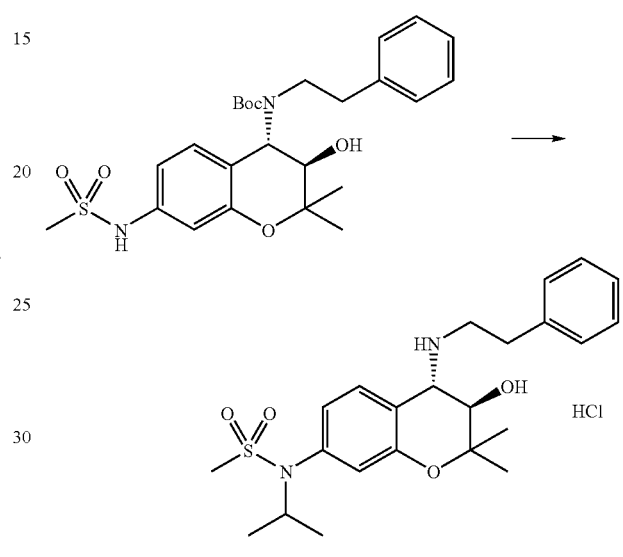

To a solution of t-butyl (2-phenylethyl) (3R*,4S*)-3-hydroxy-2,2-dimethyl-7-[(methylsulfonyl)amino]-3,4-dihydro-2H-chromen-4-yl carbamate (512 mg, 1.04 mmol) in N,N-dimethylformamide (5 mL), potassium carbonate (an excess amount) was suspended, isopropyl iodide (208 μL, 2.09 mmol) was added to the resulting suspension, and the resulting mixture was stirred at room temperature. The reaction solution was diluted in ethyl acetate and water, and then washed with water and saturated sodium chloride solution, thereafter the organic phase was dried over magnesium sulfate and concentrated under a reduced pressure. The resulting residue was purified by silica gel column chromatography (hexane:ethyl acetate=3:1) to obtain amorphous (yield: 94%).

The resulting amorphous (523 mg, 0.982 mmol) was dissolved in 4N hydrogen chloride in dioxane solution and the resulting solution was stirred at room temperature. The reaction solution was concentrated under a reduced pressure, and the resulting solid was filtered off. The solid was washed with ethyl acetate to obtain N-{(3R*,4S*)-3-hydroxy-2,2-dimethyl-4-[(2-phenylethyl)amino]-3,4-dihydro-2H-chromen-7-yl}-N-isopropylmethanesulfonamide hydrochloride (yield: 31%).

White solid:

$^1$H-NMR (CDCl$_3$) δ: 1.14 (s, 3H), 1.17 (s, 3H), 1.19 (s, 3H), 1.48 (s, 3H), 2.75-3.10 (m, 7H), 3.49 (d, J=9.9 Hz, 1H), 3.64 (d, J=9.9 Hz; 1H), 6.67 (d, J=1.8 Hz, 1H), 6.76 (dd, J=1.8 Hz, 8.3 Hz, 1H), 7.05 (d, J=8.3 Hz, 1H), 7.1-7.4 (m, 5H). (Data as free form)

MS (EI$^+$) m/z; 433 [M$^+$+1]$^+$

Preparation Examples

Preparation Example 1

Tablet

| | |
|---|---|
| A compound according to the invention | 10 g |
| Lactose | 260 g |
| Microcrystalline cellulose | 600 g |
| Corn starch | 350 g |
| Hydroxypropyl cellulose | 100 g |
| CMC-Ca | 150 g |
| Magnesium stearate | 30 g |
| Total weight | 1,500 g |

The aforementioned ingredients were mixed by a conventional method and then 10,000 sugar-coated tablets each containing 1 mg of the active ingredient per tablet were prepared.

Preparation Example 2

Capsule

| | |
|---|---|
| A compound according to the invention | 10 g |
| Lactose | 440 g |
| Microcrystalline cellulose | 1,000 g |
| Magnesium stearate | 50 g |
| Total weight | 1,500 g |

The aforementioned ingredients were mixed by a conventional method and then filled into gelatin capsules to prepare 10,000 capsules each containing 1 mg of the active ingredient per capsule.

Preparation Example 3

Soft Capsule

| | |
|---|---|
| A compound according to the invention | 10 g |
| PEG 400 | 479 g |
| Saturated fatty acid triglyceride | 1,500 g |
| Peppermint oil | 1 g |
| Polysorbate 80 | 10 g |
| Total weight | 2,000 g |

The aforementioned ingredients were mixed by a conventional method and then filled into No. 3 soft gelatin capsules to prepare 10,000 soft capsules each containing 1 mg of the active ingredient per capsule.

Preparation Example 4

Ointment

| | |
|---|---|
| A compound according to the invention | 1.0 g |
| Liquid paraffin | 10.0 g |
| Cetanol | 20.0 g |
| White vaseline | 68.4 g |
| Ethylparaben | 0.1 g |
| 1-menthol | 0.5 g |
| Total weight | 100.0 g |

The aforementioned ingredients were mixed by a conventional method to obtain 1% ointment.

Preparation Example 5

Suppository

| | |
|---|---|
| A compound according to the invention | 1 g |
| Witepsol H15* | 478 g |
| Witepsol W35* | 520 g |
| Polysorbate 80 | 1 g |
| Total weight | 1,000 g |

(*trade name for triglyceride type compounds)

The aforementioned ingredients were melt-mixed by a conventional method, poured into suppository containers and cooled to solidify, and 1,000 suppositories (1 g) each containing 1 mg of the active ingredient per suppository were prepared.

Preparation Example 6

Injection

| | |
|---|---|
| A compound according to the invention | 1 mg |
| Distilled water for injection | 5 mL |

It is used by dissolving when applied.

Pharmacological Test Example

Effects on the Effective Refractory Period

Method

Beagles were anesthetized with pentobarbital sodium and thoracotomy was done along the median line under a respirator and the incision was made on the pericardium to expose the heart. An electrocardiogram (ECG) was recorded using bipolar electrodes attached to the surface of the right atrial free wall, right atrial auricle, and right ventricular free wall. The vagal nerves were stimulated using an electrostimulation device with Nichrome wires inserted into the vagal nerves in the neck bilaterally. The conditions for electrostimulation to the vagal nerves were set such that the RR intervals on ECG were prolonged by about 100 msec compared with those before the stimulation was started.

Atrial and ventricular effective refractory periods were determined by S1-S2 extrastimulus technique at basic cycle length of 300 msec during bilateral vagal nerve stimulation, using programmable electric stimulator. A train of 10 basic stimuli (S1) was followed by a premature extrastimulus (S2) at 2 times diastolic threshold. The S1-S2 interval was successively decreased by 2 msec, and the effective refractory period was defined as the point at which S2 failed to produced a propagated response.

For evaluation of drug effects, the atrial and ventricular effective refractory periods were determined before drug administration, then respective compound was administrated intravenously at the dose of 0.3 mg/kg, and the atrial and ventricular effective refractory periods were determined from 5 min after the administration.

The results were shown as the prolongation time on the atrial and ventricular effective refractory periods, i.e. [effective refractory period after drug administration]–[effective refractory period before drug administration] (msec).

Results

The compounds of the present invention exhibited the prolongation effect on the effective refractory period selective for atrium as shown in Table 60.

TABLE 60

| Compound (Synthesis Example No.) | Prolongation time on the effective refractory period (msec) Atrium |
|---|---|
| 1 | 24 |
| 2 | 26 |
| 3 | 20 |
| 4 | 26 |
| 7 | 32 |
| 12 | 28 |

EFFECTS OF THE INVENTION

The compounds according to the present invention exhibit the prolongation effect on the effective refractory period selective for atrium, thus can be used as an anti-atrial fibrillation agents and an supraventricular antiarrhythmic agent, and are useful as pharmaceuticals. Further, since the compounds according to the present invention have small influence on ventricle, they can contribute to safe treatments of aforementioned arrhythmic conditions.

The invention claimed is:
1. A benzopyran compound of formula (I)

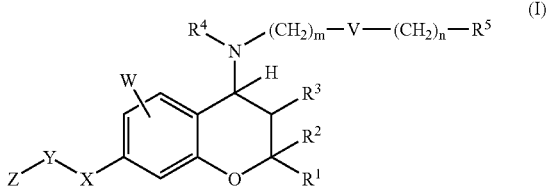

or a pharmaceutically acceptable salt thereof,
wherein
X is $NR^6$ wherein $R^6$ is hydrogen atom or $C_{1-4}$ alkyl group;
Y is a bond, SO or $SO_2$;
Z is $C_{1-4}$ alkyl group (wherein the $C_{1-4}$ alkyl group may be arbitrarily substituted with 1 to 5 halogen atoms);
W is hydrogen atom, hydroxy group, $C_{1-6}$ alkoxy group (wherein the $C_{1-6}$ alkoxy group may be arbitrarily substituted with halogen atom), halogen atom, $C_{1-4}$ alkyl group or $C_{1-6}$ alkylsulfonylamino group;
$R^1$ and $R^2$ are independently of each other $C_{1-3}$ alkyl group (wherein the $C_{1-3}$ alkyl group may be arbitrarily substituted with hydroxy group, methoxy group, halogen atom or trifluoromethoxy group);
$R^3$ is hydrogen atom, hydroxy group or methoxy group;
m is an integer of 0 to 4;
n is an integer of 0 to 4;
V is a single bond, $CR^7R^8$ wherein $R^7$ is
$C_{1-6}$ alkyl group (wherein the $C_{1-6}$ alkyl group may be arbitrarily substituted with halogen atom, hydroxy group, $C_{1-6}$ alkoxy group (wherein the $C_{1-6}$ alkoxy group may be arbitrarily substituted with halogen atom), $C_{6-14}$ aryl group or $C_{2-9}$ heteroaryl group (wherein each of the $C_{6-14}$ aryl group or $C_{2-9}$ heteroaryl group may be arbitrarily substituted with 1 to 3 $R^{10}$ wherein $R^{10}$ is halogen atom; hydroxy group; $C_{1-6}$ alkyl group (wherein the $C_{1-6}$ alkyl group may be arbitrarily substituted with halogen atom, hydroxy group or $C_{1-6}$ alkoxy group (wherein the $C_{1-6}$ alkoxy group may be arbitrarily substituted with halogen atom)); $C_{1-6}$ alkoxy group (wherein the $C_{1-6}$ alkoxy group may be arbitrarily substituted with halogen atom); nitro group; cyano group; formyl group; formamide group; sulfonylamino group; sulfonyl group; amino group; $C_{1-6}$ alkylamino group; di-$C_{1-6}$ alkylamino group; $C_{1-6}$ alkylcarbonylamino group; $C_{1-6}$ alkylsulfonylamino group; aminocarbonyl group; $C_{1-6}$ alkylaminocarbonyl group; di-$C_{1-6}$ alkylaminocarbonyl group; $C_{1-6}$ alkylcarbonyl group; $C_{1-6}$ alkoxycarbonyl group; aminosulfonyl group; $C_{1-6}$ alkylsulfonyl group; carboxy group or $C_{6-14}$ arylcarbonyl group, and when a plurality of $R^{10}$ are present, they may be identical or different from each other)),
$C_{6-14}$ aryl group or $C_{2-9}$ heteroaryl group (wherein each of the $C_{6-14}$ aryl group or $C_{2-9}$ heteroaryl group may be arbitrarily substituted with 1 to 3 $R^{10}$ wherein $R^{10}$ has the above-mentioned meaning);
hydroxy group or
$C_{1-6}$ alkoxy group (wherein the $C_{1-6}$ alkoxy group may be arbitrarily substituted with halogen atom), and $R^8$ is
hydrogen atom,
$C_{1-6}$ alkyl group (wherein the $C_{1-6}$ alkyl group may be arbitrarily substituted with halogen atom, hydroxy group, $C_{1-6}$ alkoxy group (wherein the $C_{1-6}$ alkoxy group may be arbitrarily substituted with halogen atom)),
$C_{6-14}$ aryl group or $C_{2-9}$ heteroaryl group (wherein each of the $C_{6-14}$ aryl group or $C_{2-9}$ heteroaryl group may be arbitrarily substituted with 1 to 3 $R^{11}$ wherein $R^{11}$ is halogen atom; hydroxy group; $C_{1-6}$ alkyl group (wherein the $C_{1-6}$ alkyl group may be arbitrarily substituted with halogen atom, hydroxy group or $C_{1-6}$ alkoxy group (wherein the $C_{1-6}$ alkoxy group may be arbitrarily substituted with halogen atom)); $C_{1-6}$ alkoxy group (wherein the $C_{1-6}$ alkoxy group may be arbitrarily substituted with halogen atom); nitro group; cyano group; formyl group; formamide group; sulfonylamino group; sulfonyl group; amino group; $C_{1-6}$ alkylamino group; di-$C_{1-6}$ alkylamino group; $C_{1-6}$ alkylcarbonylamino group; $C_{1-6}$ alkylsulfonylamino group; aminocarbonyl group; $C_{1-6}$ alkylaminocarbonyl group; di-$C_{1-6}$ alkylaminocarbonyl group; $C_{1-6}$ alkylcarbonyl group; $C_{1-6}$ alkoxycarbonyl group; aminosulfonyl group; $C_{1-6}$ alkylsulfonyl group; carboxy group or $C_{6-14}$ arylcarbonyl group, and when a plurality of $R^{11}$ are present, they may be identical or different from each other),
hydroxy group or
$C_{1-6}$ alkoxy group (wherein the $C_{1-6}$ alkoxy group may be arbitrarily substituted with halogen atom), or $R^7$ together with $R^8$ may represent O or S, or
V is $NR^9$ wherein $R^9$ is hydrogen or $C_{1-6}$ alkyl group (wherein the $C_{1-6}$ alkyl group may be arbitrarily substituted with halogen atom, $C_{1-6}$ alkoxy group (wherein the $C_{1-6}$ alkoxy group may be arbitrarily substituted with halogen atom), hydroxy group, $C_{6-14}$ aryl group or $C_{2-9}$ heteroaryl group (wherein each of the $C_{6-14}$ aryl group or $C_{2-9}$ heteroaryl group may be arbitrarily substituted with 1 to 3 $R^{11}$ wherein $R^{11}$ has the above-mentioned meaning)); or O, S, SO or $SO_2$;

$R^4$ is hydrogen or $C_{1-6}$ alkyl group (wherein the $C_{1-6}$ alkyl group may be arbitrarily substituted with halogen atom, $C_{1-6}$ alkoxy group (wherein the $C_{1-6}$ alkoxy group may be arbitrarily substituted with halogen atom), or hydroxy group); and $R^5$ is hydrogen atom, $C_{1-6}$ alkyl group (wherein the $C_{1-6}$ alkyl group may be arbitrarily substituted with halogen atom, $C_{1-6}$ alkoxy group (wherein the $C_{1-6}$ alkoxy group may be arbitrarily substituted with halogen atom), amino group, carboxy group or hydroxy group), $C_{3-8}$ cycloalkyl group or $C_{3-8}$ cycloalkenyl group (wherein the $C_{3-8}$ cycloalkyl group or $C_{3-8}$ cycloalkenyl group may be arbitrarily substituted with halogen atom, $C_{1-6}$ alkyl group (wherein the $C_{1-6}$ alkyl group may be arbitrarily substituted with halogen atom, $C_{1-6}$ alkoxy group (wherein the $C_{1-6}$ alkoxy group may be arbitrarily substituted with halogen atom), amino group, carboxy group or hydroxy group), $C_{1-6}$ alkoxy group (wherein the $C_{1-6}$ alkoxy group may be arbitrarily substituted with halogen atom), amino, carboxy group or hydroxy group), or $C_{6-14}$ aryl group or $C_{2-9}$ heteroaryl group (wherein each of the $C_{6-14}$ aryl group or $C_{2-9}$ heteroaryl group may be arbitrarily substituted with 1 to 3 $R^{12}$ wherein $R^{12}$ is halogen atom; hydroxy group; $C_{1-6}$ alkyl group (wherein the $C_{1-6}$ alkyl group may be arbitrarily substituted with halogen atom, hydroxy group or $C_{1-6}$ alkoxy group (wherein the $C_{1-6}$ alkoxy group may be arbitrarily substituted with halogen atom)); $C_{1-6}$ alkoxy group (wherein the $C_{1-6}$ alkoxy group may be arbitrarily substituted with halogen atom); nitro group; cyano group; formyl group; formamide group; sulfonylamino group; sulfonyl group; amino group; $C_{1-6}$ alkylamino group; di-$C_{1-6}$ alkylamino group; $C_{1-6}$ alkylcarbonylamino group; $C_{1-6}$ alkylsulfonylamino group; aminocarbonyl group; $C_{1-6}$ alkylaminocarbonyl group; di-$C_{1-6}$ alkylaminocarbonyl group; $C_{1-6}$ alkylcarbonyl group; $C_{1-6}$ alkoxycarbonyl group; aminosulfonyl group; $C_{1-6}$ alkylsulfonyl group; carboxy group, $C_{6-14}$ arylcarbonyl group, ureido group, $C_{1-6}$ alkylureilene group, $C_{6-14}$ aryl $C_{1-6}$ alkylamino group, $C_{1-6}$ alkoxycarbonylamino group, $C_{6-14}$ aryloxy group or $C_{6-14}$ arylcarbonylamino group, when a plurality of $R^{12}$ are present, they may be identical or different from each other).

2. The benzopyran compound or a pharmaceutically acceptable salt thereof according to claim 1, wherein both $R^1$ and $R^2$ are methyl group, $R^3$ is hydroxy group, and V is a single bond.

3. The benzopyran compound or a pharmaceutically acceptable salt thereof according to claim 1, wherein both $R^1$ and $R^2$ are methyl group, $R^3$ is hydroxy group, and V is $CR^7R^8$.

4. The benzopyran compound or a pharmaceutically acceptable salt thereof according to claim 1, wherein both $R^1$ and $R^2$ are methyl group, $R^3$ is hydroxy group, and V is $NR^9$.

5. The benzopyran compound or a pharmaceutically acceptable salt thereof according to claim 2, wherein $R^5$ is $C_{1-6}$ alkyl group, $C_{3-8}$ cycloalkyl group or $C_{6-14}$ aryl group.

6. The benzopyran compound or a pharmaceutically acceptable salt thereof according to claim 3, wherein $R^5$ is $C_{1-6}$ alkyl group, $C_{3-8}$ cycloalkyl group or $C_{6-14}$ aryl group.

7. The benzopyran compound or a pharmaceutically acceptable salt thereof according to claim 4, wherein $R^5$ is $C_{1-6}$ alkyl group, $C_{3-8}$ cycloalkyl group or $C_{6-14}$ aryl group.

8. The benzopyran compound or a pharmaceutically acceptable salt thereof according to claim 5, wherein W is hydrogen atom, hydroxy group, methoxy group, chlorine atom, bromine atom, methyl group, ethyl group or methylsulfonylamino group.

9. The benzopyran compound or a pharmaceutically acceptable salt thereof according to claim 6, wherein W is hydrogen atom, hydroxy group, methoxy group, chlorine atom, bromine atom, methyl group, ethyl group or methylsulfonylamino group.

10. The benzopyran compound or a pharmaceutically acceptable salt thereof according to claim 8, wherein $R^5$ is $C_{1-6}$ alkyl group or $C_{6-14}$ aryl group, $R^6$ is hydrogen atom or methyl group, Y is $SO_2$, and Z is $C_{1-4}$ alkyl group.

11. The benzopyran compound or a pharmaceutically acceptable salt thereof according to claim 8, wherein $R^5$ is $C_{1-6}$ alkyl group or $C_{6-14}$ aryl, $R^6$ is hydrogen atom or methyl group, Y is a bond, and Z is $C_{1-4}$ alkyl group.

12. A benzopyran compound which is N-{(3R*, 4S*)-3-hydroxy-6-methoxy-2,2-dimethyl-4-[(2-phenylethyl)amino]-3,4-dihydro-2H-1-benzopyran-7-yl}-methanesulfonamide or a pharmaceutically acceptable salt thereof.

13. A benzopyran compound which is N-{(3R*, 4S*)-3,6-dihydroxy-2,2-dimethyl-4-[(2-phenylethyl)amino]-3,4-dihydro-2H-1-benzopyran-7-yl} methanesulfonamide or a pharmaceutically acceptable salt thereof.

14. A benzopyran compound which is N—{(3R*, 4S*)-3-hydroxy-6-methoxy-2,2-dimethyl-4-[(2-phenylethyl)amino]-3,4-dihydro-2H-1-benzopyran-7-yl}-N-methyl-methanesulfonamide or a pharmaceutically acceptable salt thereof.

15. A benzopyran compound which is N-{(3R*, 4S*)-44-[(2-cyclohexylethyl)amino]-3-hydroxy-6-methoxy-2,2-dimethyl-3,4-dihydro-2H-1-benzopyran-7-yl} methanesulfonamide or a pharmaceutically acceptable salt thereof.

16. A benzopyran compound which is N-{(3R*, 4S*)-3-hydroxy-6-methoxy-2,2-dimethyl-4-(pentylamino)-3,4-dihydro-2H-1-1-benzopyran-7-yl} methanesulfonamide or a pharmaceutically acceptable salt thereof.

17. A benzopyran compound which N-{(3R*, 4S*)-3-hydroxy-2,2,8-trimethyl-4-[(2-phenylethyl)amino]-3,4-dihydro-2H-1-benzopyran-7-yl} methanesulfonamide or a pharmaceutically acceptable salt thereof.

18. A benzopyran compound which is N-{(3R*, 4S*)-3-hydroxy-2,2-dimethyl-4-[(2-phenylethyl)amino]-3,4-dihydro-2H-benzopyran-7-yl} methanesulfonamide or a pharmaceutically acceptable salt thereof.

19. A benzopyran compound which is N-{(3R*, 4S*)-3-hydroxy-2,2-dimethyl-4-[(2-phenylethyl)amino]-3,4-dihydro-2H-benzopyran-7-yl} ethanesulfonamide or a pharmaceutically acceptable salt thereof.

20. A benzopyran compound which is 1,1,1-trifluoro-N-{(3R*, 4S*)-3-hydroxy-2,2-dimethyl-4-[(2-phenylethyl)amino]-3,4-dihydro-2H-benzopyran-7-yl}-methanesulfonamide or a pharmaceutically acceptable salt thereof.

21. A benzopyran compound which is N-{(3R*, 4S*)-3-hydroxy-2,2-dimethyl-4-[(2-phenylethyl)amino]-3,4-dihydro-2H-benzopyran-7-yl}-N-methylmethanesulfonamide or a pharmaceutically acceptable salt thereof.

22. A benzopyran compound which is N-{(3R*, 4S*)-6-bromo-3-hydroxy-2,2-dimethyl-4-[(2-phenylethyl)amino]-3,4-dihydro-2H-benzopyran-7-yl}-methanesulfonamide or a pharmaceutically acceptable salt thereof.

23. A benzopyran compound which is (3R*, 4S*)-2,2-dimethyl-7-dimethylamino-4-[(2-phenylethyl)amino]-3-chromanol or a pharmaceutically acceptable salt thereof.

24. A benzopyran compound which is (3R*, 4S*)-2,2-dimethyl-7-methylamino-4-[(2-phenylethyl)amino]-3-chromanol or a pharmaceutically acceptable salt thereof.

25. A benzopyran compound which is (3R*, 4S*)-4-{[2-(4-fluorophenyl)ethyl]amino}-2,2-dimethyl-7-dimethylamino-3-chromanol or a pharmaceutically acceptable salt thereof.

26. A benzopyran compound which is (3R*, 4S*)-6-methoxy-2,2-dimethyl-7-dimethylamino-4-[(2-phenylethyl)amino]-3-chromanol or a pharmaceutically acceptable salt thereof.

27. A benzopyran compound which is (3R*, 4S*)-6-methoxy-2,2-dimethyl-7-methylamino-4-[(2-phenylethyl)amino]-3-chromanol or a pharmaceutically acceptable salt thereof.

28. A benzopyran compound which is N-{(3R*, 4S*)-3-hydroxy-2,2-dimethyl-4-[(2-phenylethyl)amino]-3,4-dihydro-2H-benzopyran-7-yl}-4-methylbenzenesulfonamide or a pharmaceutically acceptable salt thereof.

29. A benzopyran compound which is N-{(3R*, 4S*)-3-hydroxy-2,2-dimethyl-6-[(methylsulfonyl)amino]-4-[(2-phenylethyl)amino]-3,4-dihydro-2H-benzopyran-7-yl}-methanesulfonamide or a pharmaceutically acceptable salt thereof.

30. A benzopyran compound which is (3R*, 4S*)-2,2-dimethyl-7-methylethylamino-4-[(2-phenyl)amino]-3-chromanol or a pharmaceutically acceptable salt thereof.

31. A benzopyran compound which is N-{(3R*, 4S*)-3-hydroxy-2,2-dimethyl-4-[(2-phenylethyl)amino]-3,4-dihydro-2H-chromen-7-yl}-N-isopropylmethanesulfonamide or a pharmaceutically acceptable salt thereof.

32. A pharmaceutical comprising the benzopyran compound of claim 1 or pharmaceutically acceptable salt thereof as an active ingredient, and a pharmaceutically acceptable excipient.

33. A pharmaceutical for treating arrhythmia comprising the benzopyran compound of claim 1 or pharmaceutically acceptable salt thereof as an active ingredient, and a pharmaceutically acceptable excipient.

34. The benzopyran compound of claim 18, wherein the pharmaceutically acceptable salt is N-{(3R*, 4S*)-3-hydroxy-2,2-dimethyl-4-[(2-phenylethyl)amino]-3,4-dihydro-2H-benzopyran-7-yl} methanesulfonamide maleate.

35. The benzopyran compound of claim 19, wherein the pharmaceutically acceptable salt is N-{(3R*, 4S*)-3-hydroxy-2,2-dimethyl-4-[(2-phenylethyl)amino]-3,4-dihydro-2H-benzopyran-7-yl} ethanesulfonamide hydrochloride.

36. The benzopyran compound of claim 20, wherein the pharmaceutically acceptable salt is 1,1,1-trifluoro-N-{(3R*, 4S*)-3-hydroxy-2,2-dimethyl-4-[(2-phenylethyl)amino]-3,4-dihydro-2H-benzopyran-7-yl}-methanesulfonamide maleate.

37. The benzopyran compound of claim 21, wherein the pharmaceutically acceptable salt is N-{(3R*, 4S*)-3-hydroxy-2,2-dimethyl-4-[(2-phenylethyl)amino]-3,4-dihydro-2H-benzopyran-7-yl}-N-methylmethanesulfonamide hydrochloride.

38. The benzopyran compound of claim 23, wherein the pharmaceutically acceptable salt is (3R*, 4S*)-2,2-dimethyl-7-dimethylamino-4-[(2-phenylethyl)amino]-3-chromanol hydrochloride.

39. The benzopyran compound of claim 24, wherein the pharmaceutically acceptable salt is (3R*, 4S*)-2,2-dimethyl-7-methylamino-4-[(2-phenylethyl)amino]-3-chromanol hydrochloride.

40. The benzopyran compound of claim 25, wherein the pharmaceutically acceptable salt is (3R*, 4S*)-4-{[2-(4-fluorophenyl)ethyl]amino}-2,2-dimethyl-7-dimethylamino-3-chromanol hydrochloride.

41. The benzopyran compound of claim 27, wherein the pharmaceutically acceptable salt is (3R*, 4S*)-6-methoxy-2,2-dimethyl-7-methylamino-4-[(2-phenylethyl)amino]-3-chromanol hydrochloride.

42. The benzopyran compound of claim 30, wherein the pharmaceutically acceptable salt is (3R*, 4S*)-2,2-dimethyl-7-methylethylamino-4-[(2-phenylethyl)amino]-3-chromanol hydrochloride.

43. The benzopyran compound of claim 31, wherein the pharmaceutically acceptable salt is (N-{(3R*, 4S*)-3-hydroxy-2,2-dimethyl-4-[(2-phenylethyl)amino]-3,4-dihydro-2H-chromen-7-yl}-N-isopropylmethanesulfonamid hydrochloride.

* * * * *